(12) United States Patent
Lotta et al.

(10) Patent No.: US 11,759,476 B2
(45) Date of Patent: *Sep. 19, 2023

(54) METHODS OF TREATING METABOLIC DISORDERS AND CARDIOVASCULAR DISEASE WITH INHIBIN SUBUNIT BETA E (INHBE) INHIBITORS

(71) Applicant: Regeneron Pharmaceuticals, Inc., Tarrytown, NY (US)

(72) Inventors: Luca Andrea Lotta, Tarrytown, NY (US); Parsa Akbari, Tarrytown, NY (US); Olukayode Sosina, Tarrytown, NY (US); Manuel Allen Revez Ferreira, Tarrytown, NY (US); Aris Baras, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/711,137

(22) Filed: Apr. 1, 2022

(65) Prior Publication Data

US 2022/0313726 A1 Oct. 6, 2022

Related U.S. Application Data

(63) Continuation of application No. 17/549,692, filed on Dec. 13, 2021.

(60) Provisional application No. 63/274,595, filed on Nov. 2, 2021, provisional application No. 63/233,258, filed on Aug. 14, 2021, provisional application No. 63/159,019, filed on Mar. 10, 2021, provisional application No. 63/124,949, filed on Dec. 14, 2020.

(51) Int. Cl.
| | |
|---|---|
| *A61K 31/7105* | (2006.01) |
| *A61P 9/10* | (2006.01) |
| *A61P 1/16* | (2006.01) |
| *A61P 3/04* | (2006.01) |
| *A61P 3/10* | (2006.01) |
| *A61K 38/46* | (2006.01) |
| *A61K 31/7088* | (2006.01) |
| *A61K 31/713* | (2006.01) |

(52) U.S. Cl.
CPC ...... *A61K 31/7105* (2013.01); *A61K 31/7088* (2013.01); *A61K 31/713* (2013.01); *A61K 38/465* (2013.01); *A61P 1/16* (2018.01); *A61P 3/04* (2018.01); *A61P 3/10* (2018.01); *A61P 9/10* (2018.01)

(58) Field of Classification Search
CPC .. A61K 31/713; A61K 45/06; A61K 2300/00; A61P 1/16; A61P 3/04; A61P 3/00; C12Q 1/6883; C12Q 2600/156
USPC .............. 435/6.1, 91.1, 91.31, 455, 458; 514/44 A, 44 R; 536/23.1, 24.5
See application file for complete search history.

(56) References Cited

U.S. PATENT DOCUMENTS

| | | |
|---|---|---|
| 7,507,787 B2 | 3/2009 | Hancock et al. |
| 7,687,454 B2 | 3/2010 | Hancock et al. |
| 8,137,970 B2 | 3/2012 | Jhon et al. |
| 8,236,527 B2 | 8/2012 | Chen et al. |
| 8,269,061 B2 | 9/2012 | Williams |
| 9,121,032 B2 | 9/2015 | Williams et al. |
| 9,526,800 B2 | 12/2016 | Hynes et al. |
| 9,651,565 B2 | 5/2017 | Wetzel et al. |
| 9,994,903 B2 | 6/2018 | Chan et al. |
| 10,024,860 B2 | 7/2018 | Hynes et al. |
| 10,619,211 B2 | 4/2020 | Kelsey et al. |
| 10,620,224 B2 | 4/2020 | Wetzel et al. |
| 11,078,247 B2 | 8/2021 | Fotin-Mleczek et al. |
| 11,191,775 B2 | 12/2021 | Han et al. |
| 2007/0134261 A1 | 6/2007 | Hancock et al. |
| 2007/0190533 A1 | 8/2007 | Hancock et al. |
| 2008/0189801 A1 | 8/2008 | Williams et al. |
| 2010/0111983 A1 | 5/2010 | Sen |
| 2010/0144838 A1 | 6/2010 | Beck et al. |
| 2010/0291580 A1 | 11/2010 | Parimoo et al. |
| 2012/0141603 A1 | 6/2012 | Tsao et al. |
| 2012/0258878 A1 | 10/2012 | Saad |
| 2013/0095062 A1 | 4/2013 | Chen et al. |
| 2013/0202564 A1 | 8/2013 | Han et al. |
| 2014/0178348 A1 | 6/2014 | Kelsey et al. |
| 2014/0287948 A1 | 9/2014 | Boniface et al. |
| 2014/0287950 A1 | 9/2014 | Hickok et al. |
| 2015/0099295 A1 | 4/2015 | Chen et al. |
| 2015/0284455 A1 | 10/2015 | Springer et al. |
| 2016/0154003 A1 | 6/2016 | Boniface et al. |

(Continued)

FOREIGN PATENT DOCUMENTS

| | | |
|---|---|---|
| EP | 3260130 | 12/2017 |
| WO | 2003048383 | 6/2003 |

(Continued)

OTHER PUBLICATIONS

Sugiyama et al (PLOS ONE, pp. 1-20 (Mar. 29, 2018)) (Year: 2018).*

(Continued)

*Primary Examiner* — Jane J Zara
(74) *Attorney, Agent, or Firm* — Armstrong Teasdale LLP

(57) ABSTRACT

The present disclosure provides methods of treating a subject having metabolic disorders and/or cardiovascular diseases, methods of identifying subjects having an increased risk of developing a metabolic disorder and/or a cardiovascular disease, and methods of detecting human Inhibin Subunit Beta E variant nucleic acid molecules and variant polypeptides.

16 Claims, 10 Drawing Sheets

Specification includes a Sequence Listing.

(56) References Cited

U.S. PATENT DOCUMENTS

| | | |
|---|---|---|
| 2017/0051073 A1 | 2/2017 | Hynes et al. |
| 2017/0146548 A1 | 5/2017 | Hickok et al. |
| 2017/0182080 A1 | 6/2017 | Han |
| 2017/0306027 A1 | 10/2017 | Knopf et al. |
| 2018/0172696 A1 | 6/2018 | Boniface et al. |
| 2018/0291455 A1 | 10/2018 | Chan et al. |
| 2019/0216846 A1 | 7/2019 | Javanbakht et al. |
| 2019/0317107 A1 | 10/2019 | Boniface et al. |
| 2019/0376978 A1 | 12/2019 | Hickok et al. |
| 2020/0024339 A1 | 1/2020 | Springer et al. |
| 2020/0138976 A1 | 5/2020 | Murphy et al. |
| 2020/0147118 A1 | 5/2020 | Rayner et al. |
| 2020/0297752 A1 | 9/2020 | Gong et al. |
| 2020/0347359 A1 | 11/2020 | Magin et al. |
| 2020/0392454 A1 | 12/2020 | Chai et al. |
| 2021/0002296 A1 | 1/2021 | Mainolfi et al. |
| 2022/0002364 A1 | 1/2022 | Selvaraj et al. |
| 2022/0025369 A1 | 1/2022 | Fotin-Mleczek et al. |

FOREIGN PATENT DOCUMENTS

| | | |
|---|---|---|
| WO | 2011053281 | 5/2011 |
| WO | 2012022634 | 2/2012 |
| WO | 2012162660 | 11/2012 |
| WO | 2014089121 | 6/2014 |
| WO | 2017075037 | 5/2017 |
| WO | 2021092474 | 5/2021 |
| WO | 2021216460 | 10/2021 |

OTHER PUBLICATIONS

Hashimoto et al (Cell Reports, vol. 25, pp. 1193-1203 (2018)) (Year: 2018).*

U.S. Appl. No. 17/549,692 (Year: 2021).*

Sugiyama et al., "Inhibin [beta]E (INHBE) is a possible insulin resistance-associated hepatokine identified by comprehensive gene expression analysis in human liver biopsy samples", PLoS ONE, 2018, 13(3), pp. e0194798.

Hashimoto et al., "Activin E Controls Energy Homeostasis in Both Brown and White Adipose Tissue as a Hepatokine", Cell Reports, 2018, 25(5), pp. 1193-1203.

International Search Report and Written Opinion dated Jun. 2, 2022 for International Patent Application No. PCT/US2021/063150.

Non-Final Office Action dated Apr. 3, 2023 in U.S. Appl. No. 17/823,586.

Damase et al., "The Limitless Future of RNA Therapeutics", Frontiers in Bioengineering and Biotechnology, 2021, 9, pp. 1-24.

Roberts et al., "Advances in oligonucleotide drug delivery", Nature Reviews Drug Discovery, 2020, 19, pp. 673-694.

Non-Final Office Action dated Apr. 5, 2023 in U.S. Appl. No. 17/549,692.

Mayo Clinic, "Metformin (Oral Route)—Type 2 diabetes diagnosis and treatment", 2015, pp. 1-8.

* cited by examiner

12:57456093:G:C (splice acceptor SNP, c.299-1G>C )

ORIGINAL EXON 2
AGACTCCACTTCAGCCTACAGCT

PREDICTED EXON 2
ACACTCCACTTCAGCCTACAGCT

Exon 2 Shortened by 12 bp from the 5' end of exon which will lead to an inframe deletion of 4 amino acids

Figure 3

INHBE Reference Sequence

MRLPDVQLWLVLLWALVRAQGTGSVCPSCGGSKLAPQAERALVLELAKQQILDGLHLTSR
PRITHPPQAALTRALRRLQPGSVAPGNGEEVISFATVTDSTSAYSSLLTFHLSTPRSHH
LYHARLWLHVLPTLPGTLCLRIFRWGPRRRQGSRTLLAEHHITNLGWHTLTLPSSGLRG
EKSGVLKLQLDCRPLEGNSTVTGQPRRLLDTAGHQQPFLELKIRANEPGAGRARRRTPTC
EPATPLCCRRDHYVDFQELGWRDWILQPEGYQLNYCSGQCPPHLAGSPGIAASFHSAVFS
LLKANNPWPASTSCCVPTARRPLSLLYLDHNGNVVKTDVPDMVEACGCS

INHBE Predicted Sequence (splice acceptor variant)

MRLPDVQLWLVLLWALVRAQGTGSVCPSCGGSKLAPQAERALVLELAKQQILDGLHLTSR
PRITHPPQAALTRALRRLQPGSVAPGNGEEVISFATVTDSTSAYSSLLTFHLSTPRSHH
LYHARLWLHVLPTLPGTLCLRIFRWGPRRRQGSRTLLAEHHITNLGWHTLTLPSSGLRG
EKSGVLKLQLDCRPLEGNSTVTGQPRRLLDTAGHQQPFLELKIRANEPGAGRARRRTPTC
EPATPLCCRRDHYVDFQELGWRDWILQPEGYQLNYCSGQCPPHLAGSPGIAASFHSAVFS
LLKANNPWPASTSCCVPTARRPLSLLYLDHNGNVVKTDVPDMVEACGCS

Figure 4

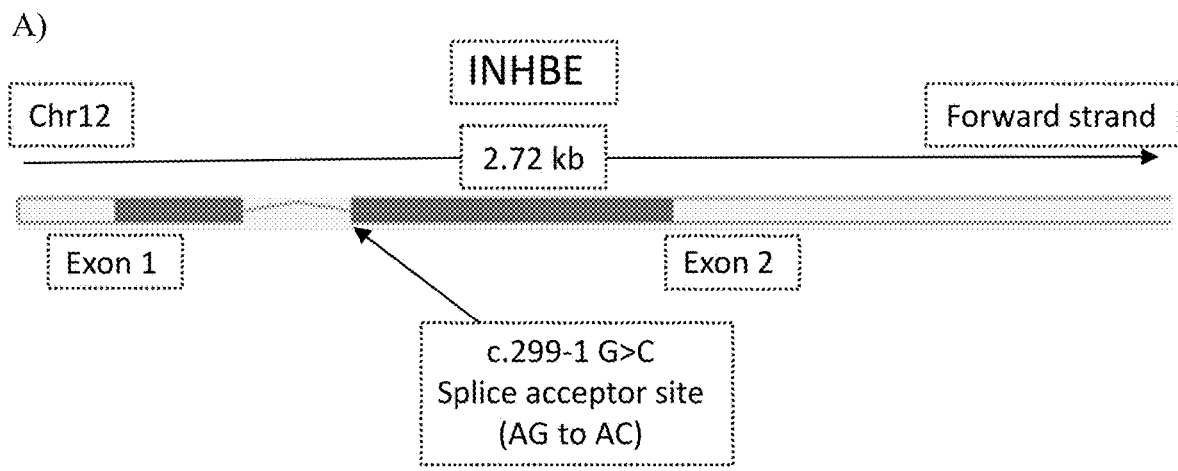
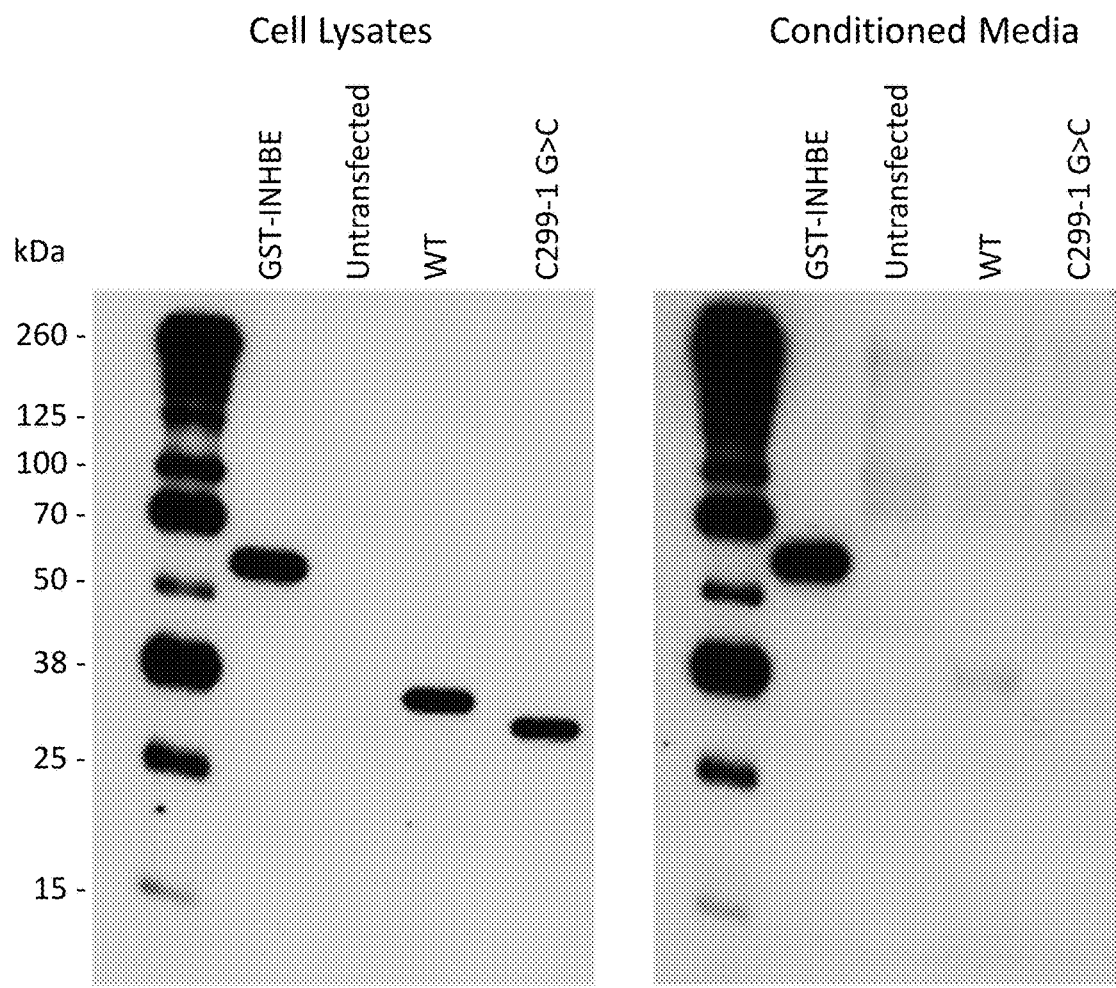
Figure 5

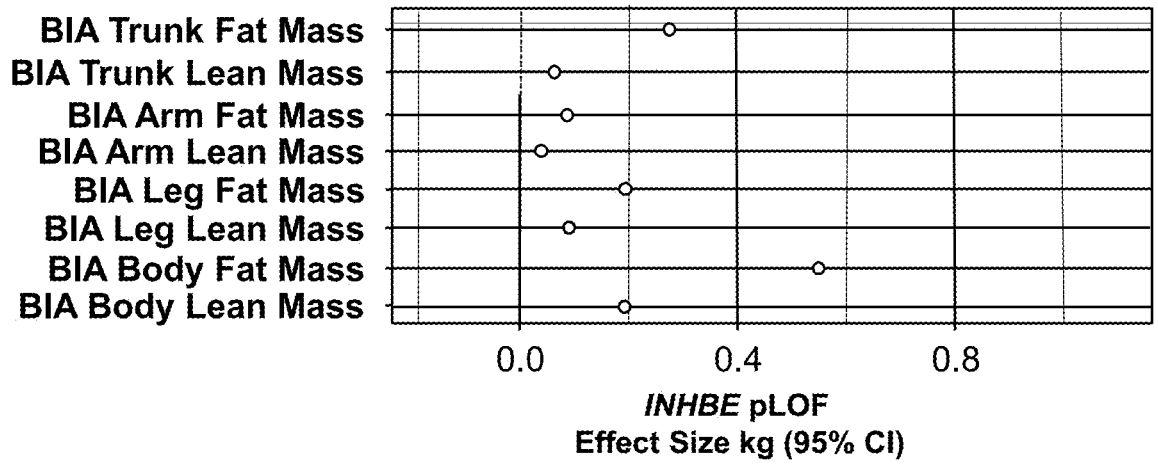
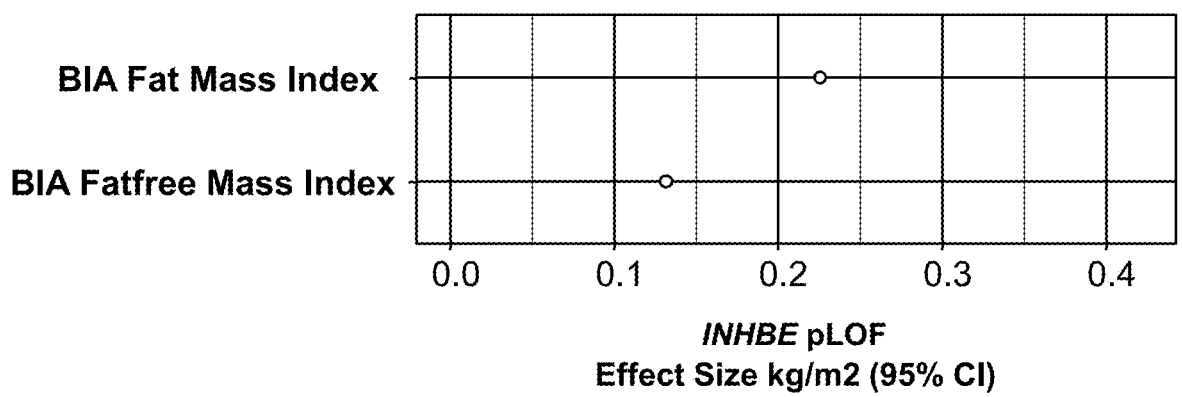
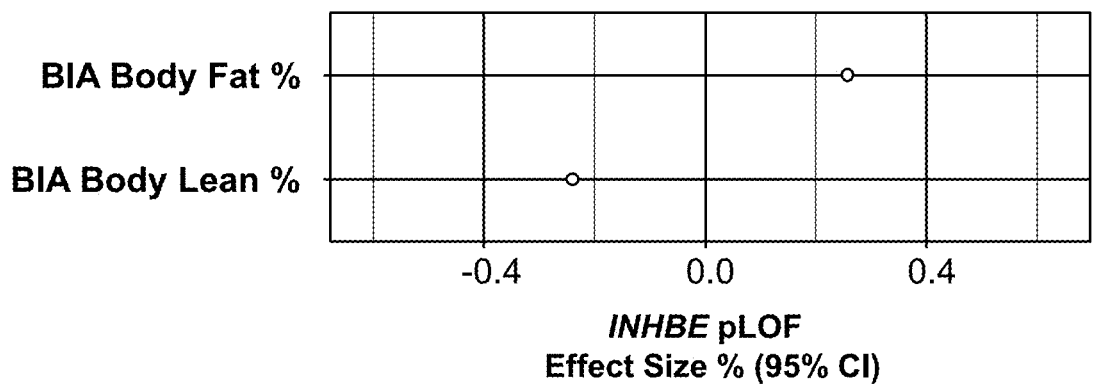
Figure 6

| Comparison | Fold-difference | P-value |
|---|---|---|
| Simple steatosis vs healthy liver | 1.25 | $4.1 \times 10^{-16}$ |
| NASH vs healthy liver | 1.60 | $2.0 \times 10^{-63}$ |
| NASH vs simple steatosis | 1.28 | $5.4 \times 10^{-23}$ |

Figure 8 (cont.)

METHODS OF TREATING METABOLIC DISORDERS AND CARDIOVASCULAR DISEASE WITH INHIBIN SUBUNIT BETA E (INHBE) INHIBITORS

REFERENCE TO SEQUENCE LISTING

This application includes a Sequence Listing submitted electronically as a text file named 18923805711SEQ, created on Apr. 1, 2022, with a size of 974 kilobytes. The Sequence Listing is incorporated herein by reference.

FIELD

The present disclosure relates generally to the treatment of subjects having metabolic disorders and/or cardiovascular disease with Inhibin Subunit Beta E inhibitors, methods of identifying subjects having an increased risk of developing a metabolic disorder and/or cardiovascular disease, and methods of detecting INHBE variant nucleic acid molecules and variant polypeptides.

BACKGROUND

Body fat distribution is an important risk factor for cardiovascular and metabolic disease independent of overall adiposity. A body fat distribution characterized by higher accumulation of fat around the waist (such as greater abdominal fat or larger waist circumference) and/or lower accumulation of fat around the hips (such as lower gluteofemoral fat or smaller hip circumference), resulting in a greater waist-to-hip ratio (WHR), is associated with higher cardio-metabolic risk independent of body mass index (BMI). Metabolic conditions associated with body fat distribution include, but are not limited to: type 2 diabetes, hyperlipidemia or dyslipidemia (high or altered circulating levels of low-density lipoprotein cholesterol (LDL-C), triglycerides, very low-density lipoprotein cholesterol (VLDL-C), apolipoprotein B or other lipid fractions), obesity (particularly abdominal obesity), lipodystrophy (such as an inability to deposit fat in adipose depots regionally (partial lipodystrophy) or in the whole body (lipoatrophy)), insulin resistance or higher or altered insulin levels at fasting or during a metabolic challenge, liver fat deposition or fatty liver disease and their complications (such as, for example, cirrhosis, fibrosis, or inflammation of the liver), nonalcoholic steatohepatitis, other types of liver inflammation, higher or elevated or altered liver enzyme levels or other markers of liver damage, inflammation or fat deposition in the liver, higher blood pressure and/or hypertension, higher blood sugar or glucose or hyperglycemia, metabolic syndrome, coronary artery disease, and other atherosclerotic conditions, and the complications of each of the aforementioned conditions. Identifying genetic variants associated with a more favorable fat distribution (such as a lower WHR, particularly when adjusted for BMI) can be a pathway to identify mechanisms that can be exploited therapeutically for benefit in these cardio-metabolic diseases.

Inhibin Subunit Beta E (INHBE) is a member of the TGF-beta (transforming growth factor-beta) superfamily of proteins. Inhibins have been implicated in regulating numerous cellular processes including cell proliferation, apoptosis, immune response and hormone secretion. Inhibins and activins inhibit and activate, respectively, the secretion of follitropin by the pituitary gland. Inhibins/activins are involved in regulating a number of diverse functions such as hypothalamic and pituitary hormone secretion, gonadal hormone secretion, germ cell development and maturation, erythroid differentiation, insulin secretion, nerve cell survival, embryonic axial development or bone growth, depending on their subunit composition. Inhibins appear to oppose the functions of activins. In addition, INHBE may be upregulated under conditions of endoplasmic reticulum stress, and this protein may inhibit cellular proliferation and growth in pancreas and liver.

SUMMARY

The present disclosure provides methods of treating a subject having a metabolic disorder or at risk of developing a metabolic disorder, the methods comprising administering an INHBE inhibitor to the subject.

The present disclosure also provides methods of treating a subject having type 2 diabetes or at risk of developing type 2 diabetes, the methods comprising administering an INHBE inhibitor to the subject.

The present disclosure also provides methods of treating a subject having obesity or at risk of developing obesity, the methods comprising administering an INHBE inhibitor to the subject.

The present disclosure also provides methods of treating a subject having elevated triglyceride level (hypertriglyceridemia) or at risk of developing elevated triglyceride level (hypertriglyceridemia), the methods comprising administering an INHBE inhibitor to the subject.

The present disclosure also provides methods of treating a subject having lipodystrophy or at risk of developing lipodystrophy, the methods comprising administering an INHBE inhibitor to the subject.

The present disclosure also provides methods of treating a subject having liver inflammation or at risk of developing liver inflammation, the methods comprising administering an INHBE inhibitor to the subject.

The present disclosure also provides methods of treating a subject having fatty liver disease or at risk of developing fatty liver disease, the methods comprising administering an INHBE inhibitor to the subject.

The present disclosure also provides methods of treating a subject having hypercholesterolemia or at risk of developing hypercholesterolemia, the methods comprising administering an INHBE inhibitor to the subject.

The present disclosure also provides methods of treating a subject having elevated liver enzymes (such as, for example, alanine transaminase (ALT) and/or aspartate transaminase (AST)) or at risk of developing elevated liver enzymes (such as, for example, ALT and/or AST), the methods comprising administering an INHBE inhibitor to the subject.

The present disclosure also provides methods of treating a subject having nonalcoholic steatohepatitis (NASH) or at risk of developing NASH, the methods comprising administering an INHBE inhibitor to the subject.

The present disclosure also provides methods of treating a subject having a cardiovascular disease or at risk of developing a cardiovascular disease, the methods comprising administering an INHBE inhibitor to the subject.

The present disclosure also provides methods of treating a subject having cardiomyopathy or at risk of developing cardiomyopathy, the methods comprising administering an INHBE inhibitor to the subject.

The present disclosure also provides methods of treating a subject having heart failure or at risk of developing heart failure, the methods comprising administering an INHBE inhibitor to the subject.

The present disclosure also provides methods of treating a subject having high blood pressure or at risk of developing high blood pressure, the methods comprising administering an INHBE inhibitor to the subject.

The present disclosure also provides methods of treating a subject with a therapeutic agent that treats or inhibits a metabolic disorder, wherein the subject is suffering from a metabolic disorder, the methods comprise the steps of: determining whether the subject has an INHBE variant nucleic acid molecule encoding an INHBE predicted loss-of-function polypeptide by: obtaining or having obtained a biological sample from the subject; and performing or having performed a genotyping assay on the biological sample to determine if the subject has a genotype comprising the INHBE variant nucleic acid molecule; and when the subject is INHBE reference, then administering or continuing to administer to the subject the therapeutic agent that treats or inhibits the metabolic disorder in a standard dosage amount, and administering to the subject an INHBE inhibitor; and when the subject is heterozygous for an INHBE variant nucleic acid molecule, then administering or continuing to administer to the subject the therapeutic agent that treats or inhibits the metabolic disorder in an amount that is the same as or lower than a standard dosage amount, and administering to the subject an INHBE inhibitor; when the subject is homozygous for an INHBE variant nucleic acid molecule, then administering or continuing to administer to the subject the therapeutic agent that treats or inhibits the metabolic disorder in an amount that is the same as or lower than a standard dosage amount; wherein the presence of a genotype having the INHBE variant nucleic acid molecule encoding the INHBE predicted loss-of-function polypeptide indicates the subject has a decreased risk of developing the metabolic disorder.

The present disclosure also provides methods of treating a subject with a therapeutic agent that treats or inhibits a cardiovascular disease, wherein the subject is suffering from a cardiovascular disease, the methods comprise the steps of: determining whether the subject has an INHBE variant nucleic acid molecule encoding an INHBE predicted loss-of-function polypeptide by: obtaining or having obtained a biological sample from the subject; and performing or having performed a genotyping assay on the biological sample to determine if the subject has a genotype comprising the INHBE variant nucleic acid molecule; and when the subject is INHBE reference, then administering or continuing to administer to the subject the therapeutic agent that treats or inhibits the cardiovascular disease in a standard dosage amount, and administering to the subject an INHBE inhibitor; and when the subject is heterozygous for an INHBE variant nucleic acid molecule, then administering or continuing to administer to the subject the therapeutic agent that treats or inhibits the cardiovascular disease in an amount that is the same as or lower than a standard dosage amount, and administering to the subject an INHBE inhibitor; when the subject is homozygous for an INHBE variant nucleic acid molecule, then administering or continuing to administer to the subject the therapeutic agent that treats or inhibits the cardiovascular disease in an amount that is the same as or lower than a standard dosage amount; wherein the presence of a genotype having the INHBE variant nucleic acid molecule encoding the INHBE predicted loss-of-function polypeptide indicates the subject has a decreased risk of developing the cardiovascular disease.

The present disclosure also provides methods of identifying a subject having an increased risk for developing a metabolic disorder, wherein the methods comprise: determining or having determined the presence or absence of an INHBE variant nucleic acid molecule encoding an INHBE predicted loss-of-function polypeptide in a biological sample obtained from the subject; wherein: when the subject is INHBE reference, then the subject has an increased risk for developing the metabolic disorder; and when the subject is heterozygous for an INHBE variant nucleic acid molecule or homozygous for an INHBE variant nucleic acid molecule, then the subject has a decreased risk for developing the metabolic disorder.

The present disclosure also provides methods of identifying a subject having an increased risk for developing a cardiovascular disease, wherein the methods comprise: determining or having determined the presence or absence of an INHBE variant nucleic acid molecule encoding an INHBE predicted loss-of-function polypeptide in a biological sample obtained from the subject; wherein: when the subject is INHBE reference, then the subject has an increased risk for developing the cardiovascular disease; and when the subject is heterozygous for an INHBE variant nucleic acid molecule or homozygous for an INHBE variant nucleic acid molecule, then the subject has a decreased risk for developing the cardiovascular disease.

The present disclosure also provides therapeutic agents that treat or inhibit a metabolic disorder for use in the treatment of the metabolic disorder in a subject having: an INHBE variant genomic nucleic acid molecule encoding an INHBE predicted loss-of-function polypeptide; an INHBE variant mRNA molecule encoding an INHBE predicted loss-of-function polypeptide; or an INHBE variant cDNA molecule encoding an INHBE predicted loss-of-function polypeptide.

The present disclosure also provides therapeutic agents that treat or inhibit a cardiovascular disease for use in the treatment of the cardiovascular disease in a subject having: an INHBE variant genomic nucleic acid molecule encoding an INHBE predicted loss-of-function polypeptide; an INHBE variant mRNA molecule encoding an INHBE predicted loss-of-function polypeptide; or an INHBE variant cDNA molecule encoding an INHBE predicted loss-of-function polypeptide.

The present disclosure also provides INHBE inhibitors that treat or inhibit a metabolic disorder for use in the treatment of the metabolic disorder in a subject having: an INHBE variant genomic nucleic acid molecule encoding an INHBE predicted loss-of-function polypeptide; an INHBE variant mRNA molecule encoding an INHBE predicted loss-of-function polypeptide; or an INHBE variant cDNA molecule encoding an INHBE predicted loss-of-function polypeptide.

The present disclosure also provides INHBE inhibitors that treat or inhibit a cardiovascular disease for use in the treatment of the cardiovascular disease in a subject having: an INHBE variant genomic nucleic acid molecule encoding an INHBE predicted loss-of-function polypeptide; an INHBE variant mRNA molecule encoding an INHBE predicted loss-of-function polypeptide; or an INHBE variant cDNA molecule encoding an INHBE predicted loss-of-function polypeptide.

BRIEF DESCRIPTION OF THE FIGURES

The accompanying figures, which are incorporated in and constitute a part of this specification, illustrate several aspects and together with the description serve to explain the principles of the present disclosure.

FIG. 3 shows the in silico predicted functional consequences of the INHBE c.299-1G:C (12:57456093:G:C) splice variant; top sequence=original exon 2 (SEQ ID NO:28); bottom sequence=predicted exon 2 (SEQ ID NO:29).

FIG. 4 shows the wild type INHBE protein sequence (top; SEQ ID NO:8) and the in silico predicted protein sequence for the c.299-1G:C acceptor splice variant (bottom; SEQ ID NO:8 with change in amino acids "STS" after underlined and bolded amino acid "D").

FIG. 5 shows Chinese hamster ovary (CHO) cells experiments for the c.299-1G>C: variant. The variant occurs in the splice acceptor site for the first and only splice junction in the INHBE gene (Panel A). In CHO cells, the c.299-1G>C variant results in the expression of a lower molecular weight variant which is present in cell lysates but not in the media, consistent with a loss-of-function (Panel B).

FIG. 6 shows associations of INHBE pLOF variants with body fat and lean mass, percentage and body-surface adjusted indices as measured by electrical bioimpedance in 423,418 participants from the UKB study.

DESCRIPTION

Figure 1:
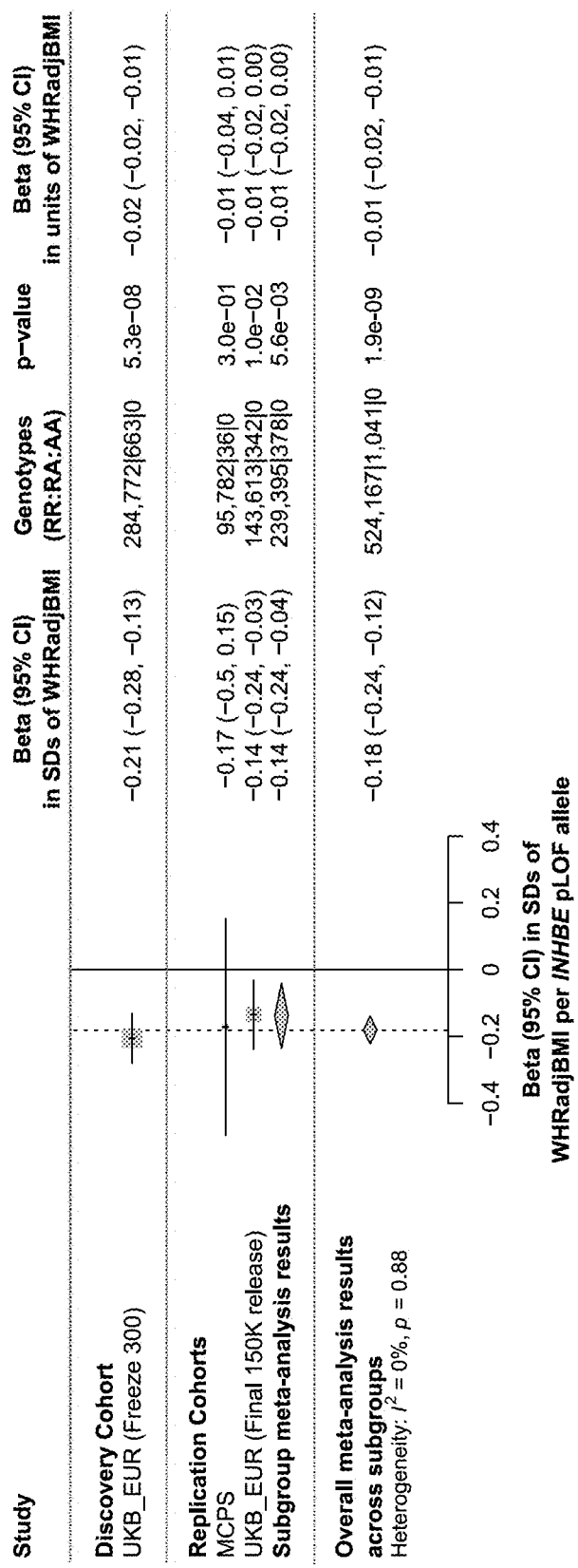
FIG. 1 shows association of INHBE predicted loss-of-function (pLOF) variants with a favorable fat distribution (i.e., lower BMI adjusted WHR) in an exome sequencing analysis of over 525,000 people from multiple studies; association analyses were estimated by fitting mixed-effects linear regression models accounting for relatedness and population stratification using the REGENIE software; abbreviations: confidence interval, CI; standard deviation, SD; body mass index, BMI; waist-hip ratio adjusted for BMI, WHRadjBMI; reference-reference allele, RR; reference-alternative allele, RA; alternative-alternative allele, AA; UK Biobank cohort, UKB; European ancestry, EUR; Mexico city prospective study cohort, MCPS; predicted loss-of-function, pLOF.

Various terms relating to aspects of the present disclosure are used throughout the specification and claims. Such terms are to be given their ordinary meaning in the art, unless otherwise indicated. Other specifically defined terms are to be construed in a manner consistent with the definitions provided herein.

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-expressed basis for interpretation, including matters of logic with respect to arrangement of steps or operational flow, plain meaning derived from grammatical organization or punctuation, or the number or type of aspects described in the specification.

As used herein, the singular forms "a," "an" and "the" include plural referents unless the context clearly dictates otherwise.

As used herein, the term "about" means that the recited numerical value is approximate and small variations would not significantly affect the practice of the disclosed embodiments. Where a numerical value is used, unless indicated otherwise by the context, the term "about" means the numerical value can vary by ±10% and remain within the scope of the disclosed embodiments.

As used herein, the term "comprising" may be replaced with "consisting" or "consisting essentially of" in particular embodiments as desired.

As used herein, the term "isolated", in regard to a nucleic acid molecule or a polypeptide, means that the nucleic acid molecule or polypeptide is in a condition other than its native environment, such as apart from blood and/or animal tissue. In some embodiments, an isolated nucleic acid molecule or polypeptide is substantially free of other nucleic acid molecules or other polypeptides, particularly other nucleic acid molecules or polypeptides of animal origin. In some embodiments, the nucleic acid molecule or polypeptide can be in a highly purified form, i.e., greater than 95% pure or greater than 99% pure. When used in this context, the term "isolated" does not exclude the presence of the same nucleic acid molecule or polypeptide in alternative physical forms, such as dimers or Alternately phosphorylated or derivatized forms.

As used herein, the terms "nucleic acid", "nucleic acid molecule", "nucleic acid sequence", "polynucleotide", or "oligonucleotide" can comprise a polymeric form of nucleotides of any length, can comprise DNA and/or RNA, and can be single-stranded, double-stranded, or multiple stranded. One strand of a nucleic acid also refers to its complement.

As used herein, the term "subject" includes any animal, including mammals. Mammals include, but are not limited to, farm animals (such as, for example, horse, cow, pig), companion animals (such as, for example, dog, cat), laboratory animals (such as, for example, mouse, rat, rabbits), and non-human primates. In some embodiments, the subject is a human. In some embodiments, the human is a patient under the care of a physician.

It has been observed in accordance with the present disclosure that loss-of-function variants in INHBE (whether these variations are homozygous or heterozygous in a particular subject) associate with a decreased risk of developing a metabolic disorder, such as type 2 diabetes, obesity, lipodystrophy, liver inflammation, fatty liver disease, hypercholesterolemia, elevated liver enzymes (such as, for example, ALT and/or AST), NASH, and/or elevated triglyceride level, and/or a cardiovascular disease, such as cardiomyopathy, heart failure, and high blood pressure. It is believed that loss-of-function variants in the INHBE gene or protein have not been associated with metabolic disorders and/or cardiovascular disease in genome-wide or exome-wide association studies. Therefore, subjects that are homozygous or heterozygous for reference INHBE variant nucleic acid molecules may be treated with an INHBE inhibitor such that a metabolic disorder and/or cardiovascular disease is inhibited, the symptoms thereof are reduced, and/or development of symptoms is repressed. It is also believed that such subjects having metabolic disorders and/or cardiovascular disease may further be treated with therapeutic agents that treat or inhibit a metabolic disorder, such as type 2 diabetes, obesity, high blood pressure, lipodystrophy, liver inflammation, fatty liver disease, hypercholesterolemia, elevated liver enzymes (such as, for example, ALT and/or AST), NASH, and/or elevated triglyceride level, and/or cardiovascular disease such as cardiomyopathy, heart failure, and high blood pressure.

For purposes of the present disclosure, any particular subject, such as a human, can be categorized as having one of three INHBE genotypes: i) INHBE reference; ii) heterozygous for an INHBE variant nucleic acid molecule encoding an INHBE predicted loss-of-function polypeptide; or iii) homozygous for an INHBE variant nucleic acid molecule encoding an INHBE predicted loss-of-function polypeptide. A subject is INHBE reference when the subject does not have a copy of an INHBE variant nucleic acid molecule encoding an INHBE predicted loss-of-function polypeptide. A subject is heterozygous for an INHBE variant nucleic acid molecule when the subject has a single copy of an INHBE variant nucleic acid molecule encoding an INHBE predicted loss-of-function polypeptide. An INHBE variant nucleic acid molecule is any nucleic acid molecule (such as, a genomic nucleic acid molecule, an mRNA molecule, or a cDNA molecule) encoding an INHBE polypeptide having a partial loss-of-function, a complete loss-of-function, a predicted partial loss-of-function, or a predicted complete loss-of-function. A subject who has an INHBE polypeptide having a partial loss-of-function (or predicted partial loss-of-function) is hypomorphic for INHBE. A subject is homozygous for an INHBE variant nucleic acid molecule encoding an INHBE predicted loss-of-function polypeptide when the subject has two copies (same or different) of an INHBE variant nucleic acid molecule encoding an INHBE predicted loss-of-function polypeptide.

For subjects that are genotyped or determined to be INHBE reference, such subjects have an increased risk of developing a metabolic disorder, such as type 2 diabetes, lipodystrophy, liver inflammation, fatty liver disease, hypercholesterolemia, elevated liver enzymes (such as, for example, ALT and/or AST), obesity, high blood pressure, and/or elevated triglyceride level (hypertriglyceridemia), and/or a cardiovascular disease, such as cardiomyopathy, heart failure, and high blood pressure. For subjects that are genotyped or determined to be either INHBE reference or heterozygous for an INHBE variant nucleic acid molecule, such subjects or subjects can be treated with an INHBE inhibitor.

In any of the embodiments described herein, the INHBE variant nucleic acid molecule can be any nucleic acid molecule (such as, for example, genomic nucleic acid molecule, mRNA molecule, or cDNA molecule) encoding an INHBE polypeptide having a partial loss-of-function, a complete loss-of-function, a predicted partial loss-of-function, or a predicted complete loss-of-function. In some embodiments, the INHBE variant nucleic acid molecule is associated with a reduced in vitro response to INHBE ligands compared with reference INHBE. In some embodiments, the INHBE variant nucleic acid molecule is an INHBE variant that results or is predicted to result in a premature truncation of an INHBE polypeptide compared to the human reference genome sequence. In some embodiments, the INHBE variant nucleic acid molecule is a variant that is predicted to be damaging by in vitro prediction algorithms such as Polyphen, SIFT, or similar algorithms. In some embodiments, the INHBE variant nucleic acid molecule is a variant that causes or is predicted to cause a nonsynonymous amino-acid substitution in INHBE and whose allele frequency is less than 1/100 alleles in the population from which the subject is selected. In some embodiments, the INHBE variant nucleic acid molecule is any rare missense variant (allele frequency <0.1%; or 1 in 1,000 alleles), or any splice-site, stop-gain, start-loss, stop-loss, frameshift, or in-frame indel, or other frameshift INHBE variant.

In any of the embodiments described herein, the INHBE predicted loss-of-function polypeptide can be any INHBE polypeptide having a partial loss-of-function, a complete loss-of-function, a predicted partial loss-of-function, or a predicted complete loss-of-function.

In any of the embodiments described herein, the INHBE variant nucleic acid molecules encoding variations in the protein sequence can include variations at positions of chromosome 12 using the nucleotide sequence of the INHBE reference genomic nucleic acid molecule (SEQ ID NO:1; ENST00000266646.3 chr12:57455307-57458025 in the GRCh38/hg38 human genome assembly) as a reference sequence.

Numerous genetic variants in INHBE exist which cause subsequent changes in the INHBE polypeptide sequence including, but not limited to: Gln7fs, Arg18STOP, Gln37STOP, Arg40STOP, Leu55fs, Cys139fs, Arg144STOP, Cys192fs, Arg224fs, Arg224STOP, Arg233fs, Arg250STOP, Asp251fs, Tyr253STOP, Tyr275STOP, Ser293fs, Trp308fs, Pro309fs, Arg320STOP, Leu323fs, and Ter351Tyrext*?. Additional variant genomic nucleic acid molecules of INHBE exist, including, but not limited to (using the human genome reference build GRch38): C298+1G:T (12:57455835:G:T), c.299-2A:G, c.299-1G:C (12:57456093:G:C), and 12:57259799:A:C. Additional variant INHBE polypeptides exist, including, but not limited to INHBE polypeptide having the methionine at position 1 removed.

Any one or more (i.e., any combination) of the INHBE pLOF variants can be used within any of the methods described herein to determine whether a subject has an increased risk for developing a metabolic disorder and/or a cardiovascular disease. The combinations of particular variants can form a mask used for statistical analysis of the particular correlation of INHBE and increased type 2 diabetes/BMI risk and/or a cardiovascular disease.

In any of the embodiments described herein, the metabolic disorder is type 2 diabetes, obesity, NASH, and/or elevated triglyceride level. In any of the embodiments described herein, the metabolic disorder is type 2 diabetes. In any of the embodiments described herein, the metabolic disorder is obesity. In any of the embodiments described herein, the metabolic disorder is NASH. In any of the embodiments described herein, the metabolic disorder is elevated triglyceride level. In any of the embodiments described herein, the metabolic disorder is lipodystrophy. In any of the embodiments described herein, the metabolic disorder is liver inflammation. In any of the embodiments described herein, the metabolic disorder is fatty liver disease. In any of the embodiments described herein, the metabolic disorder is hypercholesterolemia. In any of the embodiments described herein, the metabolic disorder is elevated liver enzymes (such as, for example, ALT and/or AST).

Metabolic disorders/conditions associated with body fat distribution also include, but are not limited to: type 2 diabetes, hyperlipidemia or dyslipidemia (high or altered circulating levels of low-density lipoprotein cholesterol (LDL-C), triglycerides, very low-density lipoprotein cholesterol (VLDL-C), apolipoprotein B or other lipid fractions), obesity (particularly abdominal obesity), lipodystrophy (such as an inability to deposit fat in adipose depots regionally (partial lipodystrophy) or in the whole body (lipoatrophy)), insulin resistance or higher or altered insulin levels at fasting or during a glucose or insulin challenge, liver fat deposition or fatty liver disease and their complications (such as, for example, cirrhosis, fibrosis, or inflammation of the liver), higher or elevated or altered liver enzyme levels or other markers of liver damage, inflammation or fat deposition, higher blood pressure and/or hypertension, higher blood sugar or glucose or hyperglycemia, metabolic syndrome, coronary artery disease, and other atherosclerotic conditions, and the complications of each of the aforementioned conditions.

In any of the embodiments described herein, the cardiovascular disease is cardiomyopathy, heart failure, or high blood pressure. In any of the embodiments described herein, the cardiovascular disease is cardiomyopathy. In any of the embodiments described herein, the cardiovascular disease is heart failure. In any of the embodiments described herein, the cardiovascular disease is high blood pressure.

The present disclosure provides methods of treating a subject having or at risk of developing a metabolic disorder, the methods comprising administering an INHBE inhibitor to the subject.

The present disclosure also provides methods of treating a subject having or at risk of developing type 2 diabetes, the methods comprising administering an INHBE inhibitor to the subject.

The present disclosure also provides methods of treating a subject having or at risk of developing obesity, the methods comprising administering an INHBE inhibitor to the subject.

The present disclosure also provides methods of treating a subject having or at risk of developing elevated triglyceride level, the methods comprising administering an INHBE inhibitor to the subject.

The present disclosure also provides methods of treating a subject having or at risk of developing NASH, the methods comprising administering an INHBE inhibitor to the subject.

The present disclosure also provides methods of treating a subject having or at risk of developing lipodystrophy, the methods comprising administering an INHBE inhibitor to the subject.

The present disclosure also provides methods of treating a subject having or at risk of developing liver inflammation, the methods comprising administering an INHBE inhibitor to the subject.

The present disclosure also provides methods of treating a subject having or at risk of developing fatty liver disease, the methods comprising administering an INHBE inhibitor to the subject.

The present disclosure also provides methods of treating a subject having or at risk of developing hypercholesterolemia, the methods comprising administering an INHBE inhibitor to the subject.

The present disclosure also provides methods of treating a subject having or at risk of developing elevated liver enzymes (such as, for example, ALT and/or AST), the methods comprising administering an INHBE inhibitor to the subject.

The present disclosure also provides methods of treating a subject having or at risk of developing a cardiovascular disease, the methods comprising administering an INHBE inhibitor to the subject.

The present disclosure also provides methods of treating a subject having or at risk of developing cardiomyopathy, the methods comprising administering an INHBE inhibitor to the subject.

The present disclosure also provides methods of treating a subject having or at risk of developing heart failure, the methods comprising administering an INHBE inhibitor to the subject.

The present disclosure also provides methods of treating a subject having or at risk of developing high blood pressure, the methods comprising administering an INHBE inhibitor to the subject.

In some embodiments, the INHBE inhibitor comprises an inhibitory nucleic acid molecule. Examples of inhibitory nucleic acid molecules include, but are not limited to, antisense nucleic acid molecules, small interfering RNAs (siRNAs), and short hairpin RNAs (shRNAs). Such inhibitory nucleic acid molecules can be designed to target any region of an INHBE mRNA. In some embodiments, the antisense RNA, siRNA, or shRNA hybridizes to a sequence within an INHBE genomic nucleic acid molecule or mRNA molecule and decreases expression of the INHBE polypeptide in a cell in the subject. In some embodiments, the INHBE inhibitor comprises an antisense RNA that hybridizes to an INHBE genomic nucleic acid molecule or mRNA molecule and decreases expression of the INHBE polypeptide in a cell in the subject. In some embodiments, the INHBE inhibitor comprises an siRNA that hybridizes to an INHBE genomic nucleic acid molecule or mRNA molecule and decreases expression of the INHBE polypeptide in a cell in the subject. In some embodiments, the INHBE inhibitor comprises an shRNA that hybridizes to an INHBE genomic nucleic acid molecule or mRNA molecule and decreases expression of the INHBE polypeptide in a cell in the subject.

In some embodiments, the antisense nucleic acid molecules comprise or consist of the nucleotide sequences shown in Table 1.

TABLE 1

| Sequence | SEQ ID NO: |
|---|---|
| ACAGCUCAUGUCUGGCUACU | 30 |
| UGACCCUCACAGCUCAUGUC | 31 |
| UUGACCCUCACAGCUCAUGU | 32 |
| UGCUUGACCCUCACAGCUCA | 33 |
| GUGCUUGACCCUCACAGCUC | 34 |
| UAGCUGUGCUUGACCCUCAC | 35 |
| AUAGCUGUGCUUGACCCUCA | 36 |
| GAUAGCUGUGCUUGACCCUC | 37 |
| GGAUAGCUGUGCUUGACCCU | 38 |
| UGGAUAGCUGUGCUUGACCC | 39 |
| AUGGAUAGCUGUGCUUGACC | 40 |
| GAUGGAUAGCUGUGCUUGAC | 41 |
| UGAUGGAUAGCUGUGCUUGA | 42 |
| AUCUGAUGGAUAGCUGUGCU | 43 |
| CAUCUGAUGGAUAGCUGUGC | 44 |
| AUCAUCUGAUGGAUAGCUGU | 45 |
| GAUCAUCUGAUGGAUAGCUG | 46 |
| AGAUCAUCUGAUGGAUAGCU | 47 |
| UAGAUCAUCUGAUGGAUAGC | 48 |
| GUAGAUCAUCUGAUGGAUAG | 49 |
| GAAAGUAGAUCAUCUGAUGG | 50 |
| GCUGAAAGUAGAUCAUCUGA | 51 |
| AGGCUGAAAGUAGAUCAUCU | 52 |
| AAGGCUGAAAGUAGAUCAUC | 53 |
| GAAGGCUGAAAGUAGAUCAU | 54 |
| GGAAGGCUGAAAGUAGAUCA | 55 |
| AGGAAGGCUGAAAGUAGAUC | 56 |
| GUCUGGGACUCAGGAAGGCU | 57 |
| UAUUGUCUGGGACUCAGGAA | 58 |
| CUAUUGUCUGGGACUCAGGA | 59 |
| UCUAUUGUCUGGGACUCAGG | 60 |
| CUUCUAUUGUCUGGGACUCA | 61 |
| UCUUCUAUUGUCUGGGACUC | 62 |
| CACCUGUCUUCUAUUGUCUG | 63 |
| CCACCUGUCUUCUAUUGUCU | 64 |
| GCCACCUGUCUUCUAUUGUC | 65 |
| AGCCACCUGUCUUCUAUUGU | 66 |
| AUGAGGGCACAGUGACAGCA | 67 |
| CAAUGAGGGCACAGUGACAG | 68 |

TABLE 1-continued

| Sequence | SEQ ID NO: |
|---|---|
| CCAAUGAGGGCACAGUGACA | 69 |
| CGUCUGUUGAGCUGAUUGC | 70 |
| CCGUCUGUUGAGUCUGAUUG | 71 |
| UCCGUCUGUUGAGUCUGAUU | 72 |
| CUCCGUCUGUUGAGUCUGAU | 73 |
| GCUCCGUCUGUUGAGUCUGA | 74 |
| UGCUCCGUCUGUUGAGUCUG | 75 |
| UUGCUCCGUCUGUUGAGUCU | 76 |
| AGUUGCUCCGUCUGUUGAGU | 77 |
| GCAGUUGCUCCGUCUGUUGA | 78 |
| GGCAGUUGCUCCGUCUGUUG | 79 |
| GAUGGCAGUUGCUCCGUCUG | 80 |
| GGAUGGCAGUUGCUCCGUCU | 81 |
| AGCCUCGGAUGGCAGUUGCU | 82 |
| AGGAGCCUCGGAUGGCAGUU | 83 |
| UUCAGGAGCCUCGGAUGGCA | 84 |
| UGGUUCAGGAGCCUCGGAUG | 85 |
| CUGGUUCAGGAGCCUCGGAU | 86 |
| CUGGUGAAUGGCCCUGGUUC | 87 |
| CCUGGUGAAUGGCCCUGGUU | 88 |
| UCCUGGUGAAUGGCCCUGGU | 89 |
| UGGACAUCAGGGAGCCGCAU | 90 |
| AGGAUUUGCUGCUUGGCUAG | 91 |
| CAGGAUUUGCUGCUUGGCUA | 92 |
| UCCAGGAUUUGCUGCUUGGC | 93 |
| ACCCAUCCAGGAUUUGCUGC | 94 |
| AACCCAUCCAGGAUUUGCUG | 95 |
| CAACCCAUCCAGGAUUUGCU | 96 |
| UGCAACCCAUCCAGGAUUUG | 97 |
| GUGCAACCCAUCCAGGAUUU | 98 |
| GGUGCAACCCAUCCAGGAUU | 99 |
| AGGUGCAACCCAUCCAGGAU | 100 |
| CAGGUGCAACCCAUCCAGGA | 101 |
| UCAGGUGCAACCCAUCCAGG | 102 |
| GUCAGGUGCAACCCAUCCAG | 103 |
| GGUCAGGUGCAACCCAUCCA | 104 |
| UGGUCAGGUGCAACCCAUCC | 105 |
| CUGGUCAGGUGCAACCCAUC | 106 |

TABLE 1-continued

| Sequence | SEQ ID NO: |
|---|---|
| ACUGGUCAGGUGCAACCCAU | 107 |
| GACUGGUCAGGUGCAACCCA | 108 |
| ACGACUGGUCAGGUGCAACC | 109 |
| GACGACUGGUCAGGUGCAAC | 110 |
| GGACGACUGGUCAGGUGCAA | 111 |
| UCUGGGACGACUGGUCAGGU | 112 |
| UUCUGGGACGACUGGUCAGG | 113 |
| AUUCUGGGACGACUGGUCAG | 114 |
| UAUUCUGGGACGACUGGUCA | 115 |
| UUAUUCUGGGACGACUGGUC | 116 |
| GUUAUUCUGGGACGACUGGU | 117 |
| AGUUAUUCUGGGACGACUGG | 118 |
| GAGUUAUUCUGGGACGACUG | 119 |
| UGAGUUAUUCUGGGACGACU | 120 |
| AUGAGUUAUUCUGGGACGAC | 121 |
| GAUGAGUUAUUCUGGGACGA | 122 |
| GGAUGAGUUAUUCUGGGACG | 123 |
| UGGAGGAUGAGUUAUUCUGG | 124 |
| GUGGAGGAUGAGUUAUUCUG | 125 |
| GGUGGAGGAUGAGUUAUUCU | 126 |
| GGGUGGAGGAUGAGUUAUUC | 127 |
| AAAGCUGAUGACCUCCUCCC | 128 |
| CAAAGCUGAUGACCUCCUCC | 129 |
| AGCAAAGCUGAUGACCUCCU | 130 |
| UAGCAAAGCUGAUGACCUCC | 131 |
| GUAGCAAAGCUGAUGACCUC | 132 |
| AGUAGCAAAGCUGAUGACCU | 133 |
| ACAGUAGCAAAGCUGAUGAC | 134 |
| UGACAGUAGCAAAGCUGAUG | 135 |
| GUGACAGUAGCAAAGCUGAU | 136 |
| GUCUGUGACAGUAGCAAAGC | 137 |
| AGUCUGUGACAGUAGCAAAG | 138 |
| GAGUCUGUGACAGUAGCAAA | 139 |
| UGGAGUCUGUGACAGUAGCA | 140 |
| GUGGAGUCUGUGACAGUAGC | 141 |
| AGUGGAGUCUGUGACAGUAG | 142 |
| AAGUGGAGUCUGUGACAGUA | 143 |
| UGAAGUGGAGUCUGUGACAG | 144 |
| CUGAAGUGGAGUCUGUGACA | 145 |

TABLE 1-continued

| Sequence | SEQ ID NO: |
|---|---|
| GCUGAAGUGGAGUCUGUGAC | 146 |
| GGCUGAAGUGGAGUCUGUGA | 147 |
| AGGCUGAAGUGGAGUCUGUG | 148 |
| UAGGCUGAAGUGGAGUCUGU | 149 |
| GUAGGCUGAAGUGGAGUCUG | 150 |
| GCUGUAGGCUGAAGUGGAGU | 151 |
| AGCUGUAGGCUGAAGUGGAG | 152 |
| GAGCUGUAGGCUGAAGUGGA | 153 |
| GGGAGCUGUAGGCUGAAGUG | 154 |
| AGGGAGCUGUAGGCUGAAGU | 155 |
| AAGUGAGCAGGGAGCUGUAG | 156 |
| UGGACAGGUGAAAAGUGAGC | 157 |
| GUGGACAGGUGAAAAGUGAG | 158 |
| AGUGGACAGGUGAAAAGUGA | 159 |
| GAGUGGACAGGUGAAAAGUG | 160 |
| GGAGUGGACAGGUGAAAAGU | 161 |
| AGGAGUGGACAGGUGAAAAG | 162 |
| GAGGAGUGGACAGGUGAAAA | 163 |
| CGAGGAGUGGACAGGUGAAA | 164 |
| CCGAGGAGUGGACAGGUGAA | 165 |
| ACCGAGGAGUGGACAGGUGA | 166 |
| CAUGGUACAGGUGGUGGGAC | 167 |
| GCAUGGUACAGGUGGUGGGA | 168 |
| CAAAGAGUGCCAGGAAGGGU | 169 |
| GCAAAGAGUGCCAGGAAGGG | 170 |
| AAGCAAAGAGUGCCAGGAAG | 171 |
| UCAAGCAAAGAGUGCCAGGA | 172 |
| CUCAAGCAAAGAGUGCCAGG | 173 |
| CCUCAAGCAAAGAGUGCCAG | 174 |
| AUCCUCAAGCAAAGAGUGCC | 175 |
| GAUCCUCAAGCAAAGAGUGC | 176 |
| GAAGAUCCUCAAGCAAAGAG | 177 |
| GGAAGAUCCUCAAGCAAAGA | 178 |
| CGGAAGAUCCUCAAGCAAAG | 179 |
| AUCGGAAGAUCCUCAAGCAA | 180 |
| CAUCGGAAGAUCCUCAAGCA | 181 |
| CCAUCGGAAGAUCCUCAAGC | 182 |
| CCCAUCGGAAGAUCCUCAAG | 183 |

TABLE 1-continued

| Sequence | SEQ ID NO: |
|---|---|
| AUGUGGUGCUCAGCCAGGAG | 184 |
| UUGGUGAUGUGGUGCUCAGC | 185 |
| GGUUGGUGAUGUGGUGCUCA | 186 |
| AGGUUGGUGAUGUGGUGCUC | 187 |
| CAGGUUGGUGAUGUGGUGCU | 188 |
| AGCCCAGGUUGGUGAUGUGG | 189 |
| CAGCCCAGGUUGGUGAUGUG | 190 |
| UGCCAGCCCAGGUUGGUGAU | 191 |
| AUGCCAGCCCAGGUUGGUGA | 192 |
| GUAUGCCAGCCCAGGUUGGU | 193 |
| AGGUAUGCCAGCCCAGGUUG | 194 |
| AAGGUAUGCCAGCCCAGGUU | 195 |
| UAAGGUAUGCCAGCCCAGGU | 196 |
| UUAAGGUAUGCCAGCCCAGG | 197 |
| GUUAAGGUAUGCCAGCCCAG | 198 |
| AGUUAAGGUAUGCCAGCCCA | 199 |
| GAGUUAAGGUAUGCCAGCCC | 200 |
| AGAGUUAAGGUAUGCCAGCC | 201 |
| CAGAGUUAAGGUAUGCCAGC | 202 |
| GCAGAGUUAAGGUAUGCCAG | 203 |
| AGGGCAGAGUUAAGGUAUGC | 204 |
| AGAGGGCAGAGUUAAGGUAU | 205 |
| UAGAGGGCAGAGUUAAGGUA | 206 |
| CUAGAGGGCAGAGUUAAGGU | 207 |
| CACUAGAGGGCAGAGUUAAG | 208 |
| GCCACUAGAGGGCAGAGUUA | 209 |
| GGACACCAGACUUCUCACCC | 210 |
| AGGACACCAGACUUCUCACC | 211 |
| CAGGACACCAGACUUCUCAC | 212 |
| UUUCAGGACACCAGACUUCU | 213 |
| GUUUCAGGACACCAGACUUC | 214 |
| UAGUUGCAGUUUCAGGACAC | 215 |
| CUAGUUGCAGUUUCAGGACA | 216 |
| UCUAGUUGCAGUUUCAGGAC | 217 |
| GUCUAGUUGCAGUUUCAGGA | 218 |
| AGUCUAGUUGCAGUUUCAGG | 219 |
| CAGUCUAGUUGCAGUUUCAG | 220 |
| AACUGUGCUGUUGCCUUCUA | 221 |
| UAACUGUGCUGUUGCCUUCU | 222 |

TABLE 1-continued

| Sequence | SEQ ID NO: |
|---|---|
| GUAACUGUGCUGUUGCCUUC | 223 |
| CCAGUAACUGUGCUGUUGCC | 224 |
| GUCCAGUAACUGUGCUGUUG | 225 |
| UGUCCAGUAACUGUGCUGUU | 226 |
| UUGUCCAGUAACUGUGCUGU | 227 |
| GGUUGUCCAGUAACUGUGCU | 228 |
| CGGUUGUCCAGUAACUGUGC | 229 |
| UCGGUUGUCCAGUAACUGUG | 230 |
| CUCGGUUGUCCAGUAACUGU | 231 |
| CCUCGGUUGUCCAGUAACUG | 232 |
| GCCUCGGUUGUCCAGUAACU | 233 |
| CGCCUCGGUUGUCCAGUAAC | 234 |
| CCGCCUCGGUUGUCCAGUAA | 235 |
| UGCUGGUGUCCUGCUGUGUC | 236 |
| CUGCUGGUGUCCUGCUGUGU | 237 |
| UCUAGGAAGGGCUGCUGGUG | 238 |
| UUAAGCUCUAGGAAGGGCUG | 239 |
| CUCAUUGGCUCGGAUCUUAA | 240 |
| GCUCAUUGGCUCGGAUCUUA | 241 |
| GGCUCAUUGGCUCGGAUCUU | 242 |
| AGGCUCAUUGGCUCGGAUCU | 243 |
| CAGGCUCAUUGGCUCGGAUC | 244 |
| UCCAGGCUCAUUGGCUCGGA | 245 |
| UCUCGCCUGCAACAUAAGGG | 246 |
| CAGAAUGGAAAGAGGCAGCA | 247 |
| GCAGAAUGGAAAGAGGCAGC | 248 |
| AAGACGGCAGAAUGGAAAGA | 249 |
| GAAGACGGCAGAAUGGAAAG | 250 |
| UGAAGACGGCAGAAUGGAAA | 251 |
| CUGAAGACGGCAGAAUGGAA | 252 |
| GCUGAAGACGGCAGAAUGGA | 253 |
| GGCUGAAGACGGCAGAAUGG | 254 |
| AGGCUGAAGACGGCAGAAUG | 255 |
| GGAGGCUGAAGACGGCAGAA | 256 |
| AGGAGGCUGAAGACGGCAGA | 257 |
| UGUUGGCUUUGAGGAGGCUG | 258 |
| CAAGGAUUGUUGGCUUUGAG | 259 |
| UGGCAGGCCAAGGAUUGUUG | 260 |

TABLE 1-continued

| Sequence | SEQ ID NO: |
|---|---|
| CUGGCAGGCCAAGGAUUGUU | 261 |
| ACUGGCAGGCCAAGGAUUGU | 262 |
| AGGAGGUACUGGCAGGCCAA | 263 |
| AACAGGAGGUACUGGCAGGC | 264 |
| CAACAGGAGGUACUGGCAGG | 265 |
| ACACAACAGGAGGUACUGGC | 266 |
| AGGGACACAACAGGAGGUAC | 267 |
| UCGGGCAGUAGGGACACAAC | 268 |
| UUCGGGCAGUAGGGACACAA | 269 |
| CUUCGGGCAGUAGGGACACA | 270 |
| AUGAUCCAGGUAGAGGAGAG | 271 |
| UAUGAUCCAGGUAGAGGAGA | 272 |
| UUAUGAUCCAGGUAGAGGAG | 273 |
| AUUAUGAUCCAGGUAGAGGA | 274 |
| CAUUAUGAUCCAGGUAGAGG | 275 |
| CCAUUAUGAUCCAGGUAGAG | 276 |
| UGCCAUUAUGAUCCAGGUAG | 277 |
| UUGCCAUUAUGAUCCAGGUA | 278 |
| AUUGCCAUUAUGAUCCAGGU | 279 |
| CAUUGCCAUUAUGAUCCAGG | 280 |
| ACAUUGCCAUUAUGAUCCAG | 281 |
| CCACAUUGCCAUUAUGAUCC | 282 |
| GACCACAUUGCCAUUAUGAU | 283 |
| UGACCACAUUGCCAUUAUGA | 284 |
| UUGACCACAUUGCCAUUAUG | 285 |
| UCUUGACCACAUUGCCAUUA | 286 |
| GUCUUGACCACAUUGCCAUU | 287 |
| CGUCUUGACCACAUUGCCAU | 288 |
| CCGUCUUGACCACAUUGCCA | 289 |
| UCCGUCUUGACCACAUUGCC | 290 |
| AUCCGUCUUGACCACAUUGC | 291 |
| CAUCCGUCUUGACCACAUUG | 292 |
| ACAUCCGUCUUGACCACAUU | 293 |
| CACAUCCGUCUUGACCACAU | 294 |
| GCACAUCCGUCUUGACCACA | 295 |
| GGCACAUCCGUCUUGACCAC | 296 |
| UGGCACAUCCGUCUUGACCA | 297 |
| CUGGCACAUCCGUCUUGACC | 298 |
| UCUGGCACAUCCGUCUUGAC | 299 |

TABLE 1-continued

| Sequence | SEQ ID NO: |
|---|---|
| AUCUGGCACAUCCGUCUUGA | 300 |
| UAUCUGGCACAUCCGUCUUG | 301 |
| AUAUCUGGCACAUCCGUCUU | 302 |
| CAUAUCUGGCACAUCCGUCU | 303 |
| CCAUAUCUGGCACAUCCGUC | 304 |
| CACCAUAUCUGGCACAUCCG | 305 |
| CUCCACCACCAUAUCUGGCA | 306 |
| UGGUCUCUUCACUCCAAAGC | 307 |
| CUUCAUCUUGGUCUCUUCAC | 308 |
| ACUUCAUCUUGGUCUCUUCA | 309 |
| AACUUCAUCUUGGUCUCUUC | 310 |
| GGAAACUUCAUCUUGGUCUC | 311 |
| CCUCCAGUCACAGAUGCCCU | 312 |
| GAUGCCUCCAGUCACAGAUG | 313 |
| UGAUGCCUCCAGUCACAGAU | 314 |
| CAGGUGGUUGUUGGGUUGGG | 315 |
| CCAGGUGGUUGUUGGGUUGG | 316 |
| GCCAGGUGGUUGUUGGGUUG | 317 |
| UGCCAGGUGGUUGUUGGGUU | 318 |
| CAUAUUGCCAGGUGGUUGUU | 319 |
| UCAUAUUGCCAGGUGGUUGU | 320 |
| GUCAUAUUGCCAGGUGGUUG | 321 |
| AGUCAUAUUGCCAGGUGGUU | 322 |
| GAGUCAUAUUGCCAGGUGGU | 323 |
| AGUGAGUCAUAUUGCCAGGU | 324 |
| AAGUGAGUCAUAUUGCCAGG | 325 |
| CAAGUGAGUCAUAUUGCCAG | 326 |
| GUCAAGUGAGUCAUAUUGCC | 327 |
| GGUCAAGUGAGUCAUAUUGC | 328 |
| GGGUCAAGUGAGUCAUAUUG | 329 |
| CCCAUUUGGGUCCCAUAGGG | 330 |
| GCCCAUUUGGGUCCCAUAGG | 331 |
| UGCCCAUUUGGGUCCCAUAG | 332 |
| GUGCCCAUUUGGGUCCCAUA | 333 |
| AGUGCCCAUUUGGGUCCCAU | 334 |
| AAGUGCCCAUUUGGGUCCCA | 335 |
| AAAGUGCCCAUUUGGGUCCC | 336 |
| GAAAGUGCCCAUUUGGGUCC | 337 |

TABLE 1-continued

| Sequence | SEQ ID NO: |
|---|---|
| AGAAAGUGCCCAUUUGGGUC | 338 |
| CAAGAAAGUGCCCAUUUGGG | 339 |
| ACAAGAAAGUGCCCAUUUGG | 340 |
| GACAAGAAAGUGCCCAUUUG | 341 |
| GAGUCUCAGACAAGAAAGUG | 342 |
| CCAGAGUCUCAGACAAGAAA | 343 |
| GCCAGAGUCUCAGACAAGAA | 344 |
| AGCCAGAGUCUCAGACAAGA | 345 |
| UAAGCCAGAGUCUCAGACAA | 346 |
| AUAAGCCAGAGUCUCAGACA | 347 |
| AGCCAACCUGGAAUAAGCCA | 348 |
| UCAGCCAACCUGGAAUAAGC | 349 |
| CAUCAGCCAACCUGGAAUAA | 350 |
| CACAUCAGCCAACCUGGAAU | 351 |
| ACACAUCAGCCAACCUGGAA | 352 |
| AACACAUCAGCCAACCUGGA | 353 |
| CAACACAUCAGCCAACCUGG | 354 |
| CUCCAACACAUCAGCCAAC | 355 |
| CGCUUUACCCAUCUCCCAAC | 356 |
| AACGCUUUACCCAUCUCCCA | 357 |
| AAACGCUUUACCCAUCUCCC | 358 |
| AGAAACGCUUUACCCAUCUC | 359 |
| AAGAAACGCUUUACCCAUCU | 360 |
| GAAGAAACGCUUUACCCAUC | 361 |
| AGAAGAAACGCUUUACCCAU | 362 |
| UAGAAGAAACGCUUUACCCA | 363 |
| UUAGAAGAAACGCUUUACCC | 364 |
| AAUCAUGCUUUCUGGGUAGA | 365 |
| CUUAGGGCAGGAAAUCAUGC | 366 |
| ACUUAGGGCAGGAAAUCAUG | 367 |
| GACUUAGGGCAGGAAAUCAU | 368 |
| AGGACUUAGGGCAGGAAAUC | 369 |
| CAGGACUUAGGGCAGGAAAU | 370 |
| ACAGGACUUAGGGCAGGAAA | 371 |
| UCUCACAGGACUUAGGGCAG | 372 |
| UUCUCACAGGACUUAGGGCA | 373 |
| AUCUUCUCACAGGACUUAGG | 374 |
| CAUCUUCUCACAGGACUUAG | 375 |
| UAGUCCCUGACAUCUUCUCA | 376 |

TABLE 1-continued

| Sequence | SEQ ID NO: |
|---|---|
| CUAGUCCCUGACAUCUUCUC | 377 |
| CCUAGUCCCUGACAUCUUCU | 378 |
| CCCUAGUCCCUGACAUCUUC | 379 |
| UCCCUAGUCCCUGACAUCUU | 380 |
| CUCCCUAGUCCCUGACAUCU | 381 |
| AUCUAUCUGCUUCCUCCUCC | 382 |
| CCAUCUAUCUGCUUCCUCCU | 383 |
| ACCAUCUAUCUGCUUCCUCC | 384 |
| GACCAUCUAUCUGCUUCCUC | 385 |
| GGACCAUCUAUCUGCUUCCU | 386 |
| UGGACCAUCUAUCUGCUUCC | 387 |
| CUGGACCAUCUAUCUGCUUC | 388 |
| CUGCUGGACCAUCUAUCUGC | 389 |
| GCCUGCUGGACCAUCUAUCU | 390 |
| UUCAAGCCUGCUGGACCAUC | 391 |
| UGCUUCAAGCCUGCUGGACC | 392 |
| CCUCAACAGCCCUUACCCUG | 393 |
| UCCCUCUUGACCUUCCCUUA | 394 |
| CUCCCUCUUGACCUUCCCUU | 395 |
| UCUCCCUCUUGACCUUCCCU | 396 |
| CAUCUCCCUCUUGACCUUCC | 397 |
| CCAUCUCCCUCUUGACCUUC | 398 |
| CCCAUCUCCCUCUUGACCUU | 399 |
| GCCCAUCUCCCUCUUGACCU | 400 |
| UUGCCCAUCUCCCUCUUGAC | 401 |
| CUUGCCCAUCUCCCUCUUGA | 402 |
| CCCUAAGCAUCCUCCCUCAG | 403 |
| AACUUCUUAGGCUUAGUGCC | 404 |
| GGAACUUCUUAGGCUUAGUG | 405 |
| GGGAACUUCUUAGGCUUAGU | 406 |
| AGGGAACUUCUUAGGCUUAG | 407 |
| UGUCUCCCAGUGGGUCCUGU | 408 |
| AGUAUAAAUGCUUGUCUCCC | 409 |
| GACAGAGCGAGACUCGAUCU | 410 |
| UGACAGAGCGAGACUCGAUC | 411 |
| GUGACAGAGCGAGACUCGAU | 412 |
| GGUGACAGAGCGAGACUCGA | 413 |
| UGGUGACAGAGCGAGACUCG | 414 |

TABLE 1-continued

| Sequence | SEQ ID NO: |
|---|---|
| CUGGUGACAGAGCGAGACUC | 415 |
| CCUGGUGACAGAGCGAGACU | 416 |
| AGCCUGGUGACAGAGCGAGA | 417 |
| UGCACUCCAGCCUGGUGACA | 418 |
| ACUGCACUCCAGCCUGGUGA | 419 |
| UCACUGCACUCCAGCCUGGU | 420 |
| UGUCACUGCACUCCAGCCUG | 421 |
| GUGUCACUGCACUCCAGCCU | 422 |
| AGACGGAGGUUGCAGUGAGC | 423 |
| GAGACGGAGGUUGCAGUGAG | 424 |
| GGAGACGGAGGUUGCAGUGA | 425 |
| ACUUGAACCCAGGAGACGGA | 426 |
| CACUUGAACCCAGGAGACGG | 427 |
| UCACUUGAACCCAGGAGACG | 428 |
| AUCACUUGAACCCAGGAGAC | 429 |
| AAUCACUUGAACCCAGGAGA | 430 |
| GAAUCACUUGAACCCAGGAG | 431 |
| AGAAUCACUUGAACCCAGGA | 432 |
| AAGAAUCACUUGAACCCAGG | 433 |
| GAAGAAUCACUUGAACCCAG | 434 |
| AGAAGAAUCACUUGAACCCA | 435 |
| CAGAAGAAUCACUUGAACCC | 436 |
| GCAGAAGAAUCACUUGAACC | 437 |
| GGCAGAAGAAUCACUUGAAC | 438 |
| AGGCAGAAGAAUCACUUGAA | 439 |
| GAGGCAGAAGAAUCACUUGA | 440 |
| UGAGGCAGAAGAAUCACUUG | 441 |
| CUGAGGCAGAAGAAUCACUU | 442 |
| GCUGAGGCAGAAGAAUCACU | 443 |
| GGCUGAGGCAGAAGAAUCAC | 444 |
| AGGCUGAGGCAGAAGAAUCA | 445 |
| GAGGCUGAGGCAGAAGAAUC | 446 |
| GGAGGCUGAGGCAGAAGAAU | 447 |
| GGGAGGCUGAGGCAGAAGAA | 448 |
| AGAUUGAGACCAUCCUGGCC | 449 |
| GAGAUUGAGACCAUCCUGGC | 450 |
| AGAGAUUGAGACCAUCCUGG | 451 |
| AAGAGAUUGAGACCAUCCUG | 452 |
| CAAGAGAUUGAGACCAUCCU | 453 |

TABLE 1-continued

| Sequence | SEQ ID NO: |
|---|---|
| GGUGGCUCACGCCUAUAAUC | 454 |
| CGGUGGCUCACGCCUAUAAU | 455 |
| GCGGUGGCUCACGCCUAUAA | 456 |
| CCCUAACCCUUCUUUAUGAC | 457 |
| CACCCUAACCCUUCUUUAUG | 458 |
| AUCACCCUAACCCUUCUUUA | 459 |
| CAUCACCCUAACCCUUCUUU | 460 |
| CCAUCACCCUAACCCUUCUU | 461 |
| GACCAUCACCCUAACCCUUC | 462 |
| GGACCAUCACCCUAACCCUU | 463 |
| UGGACCAUCACCCUAACCCU | 464 |
| CUGGACCAUCACCCUAACCC | 465 |
| UCUGGACCAUCACCCUAACC | 466 |
| CUCUGGACCAUCACCCUAAC | 467 |
| GCUCUGGACCAUCACCCUAA | 468 |
| UGCUCUGGACCAUCACCCUA | 469 |
| GUUGCUCUGGACCAUCACCC | 470 |
| UGUUGCUCUGGACCAUCACC | 471 |
| ACUGUUGCUCUGGACCAUCA | 472 |
| AACUGUUGCUCUGGACCAUC | 473 |
| GAACUGUUGCUCUGGACCAU | 474 |
| GAAGAACUGUUGCUCUGGAC | 475 |
| UUGAAGAACUGUUGCUCUGG | 476 |
| ACUUGAAGAACUGUUGCUCU | 477 |
| CACUUGAAGAACUGUUGCUC | 478 |
| UACACUUGAAGAACUGUUGC | 479 |
| GAGUACACUUGAAGAACUGU | 480 |
| AGAGUACACUUGAAGAACUG | 481 |
| CAGAGUACACUUGAAGAACU | 482 |
| ACAGAGUACACUUGAAGAAC | 483 |
| CUACAGAGUACACUUGAAGA | 484 |
| CCUACAGAGUACACUUGAAG | 485 |
| GCCUACAGAGUACACUUGAA | 486 |
| AGCCUACAGAGUACACUUGA | 487 |
| AAGCCUACAGAGUACACUUG | 488 |
| CAGAAGCCUACAGAGUACAC | 489 |
| CCAGAAGCCUACAGAGUACA | 490 |
| AAAAGGGACCUCCCAGAAGC | 491 |

TABLE 1-continued

| Sequence | SEQ ID NO: |
| --- | --- |
| GAAAAGGGACCUCCCAGAAG | 492 |
| UGAAAAGGGACCUCCCAGAA | 493 |
| CUUUGACUUUGUGGACACCC | 494 |
| GCUUUGACUUUGUGGACACC | 495 |
| UAGCUUUGACUUUGUGGACA | 496 |
| AUAGCUUUGACUUUGUGGAC | 497 |
| GUCACACGGCCUCUGGAAAA | 498 |
| UGUCACACGGCCUCUGGAAA | 499 |
| AUGUCACACGGCCUCUGGAA | 500 |

In some embodiments, the antisense nucleic acid molecules comprise or consist of the nucleotide sequences shown in Table 2.

TABLE 2

| Sequence | SEQ ID NO: |
| --- | --- |
| CUUAGUCACUUUUCCCAAGA | 501 |
| UCUUAGUCACUUUUCCCAAG | 502 |
| CUCUUAGCAUCUUAGUCACU | 503 |
| GCUCUUAGCAUCUUAGUCAC | 504 |
| UACGCUCUUAGCAUCUUAGU | 505 |
| AUACGCUCUUAGCAUCUUAG | 506 |
| CUCAGCUAUAAAUACGCUCU | 507 |
| GCUCAGCUAUAAAUACGCUC | 508 |
| AGCUCAGCUAUAAAUACGCU | 509 |
| ACCCUCACUGUCAGAUGCCC | 510 |
| CACCCUCACUGUCAGAUGCC | 511 |
| CCCACCCUCACUGUCAGAUG | 512 |
| GGGAAGUGACAAGAAGUGGC | 513 |
| GUAUCAGUAGGCAGUCAGGG | 514 |
| GGUAUCAGUAGGCAGUCAGG | 515 |
| GUUGGUAUCAGUAGGCAGUC | 516 |
| UGUUGGUAUCAGUAGGCAGU | 517 |
| CCUGUUGGUAUCAGUAGGCA | 518 |
| ACCUGUUGGUAUCAGUAGGC | 519 |
| CAGACGGCUUACCUGUUGGU | 520 |
| UCAGACGGCUUACCUGUUGG | 521 |
| CUCAGACGGCUUACCUGUUG | 522 |
| CCUCAGACGGCUUACCUGUU | 523 |
| GCCUCAGACGGCUUACCUGU | 524 |

TABLE 2-continued

| Sequence | SEQ ID NO: |
| --- | --- |
| UGCCUCAGACGGCUUACCUG | 525 |
| GUGCCUCAGACGGCUUACCU | 526 |
| UGGUGCCUCAGACGGCUUAC | 527 |
| GUGGUGCCUCAGACGGCUUA | 528 |
| AGCAAAGUGGAGGUAUCUAU | 529 |
| GUCAGCAAAGUGGAGGUAUC | 530 |
| GGUCAGCAAAGUGGAGGUAU | 531 |
| UUGGUCAGCAAAGUGGAGGU | 532 |
| AUUGGUCAGCAAAGUGGAGG | 533 |
| CAUUGGUCAGCAAAGUGGAG | 534 |
| ACAUUGGUCAGCAAAGUGGA | 535 |
| AACAUUGGUCAGCAAAGUGG | 536 |
| UGGAACAUUGGUCAGCAAAG | 537 |
| UCUGGAACAUUGGUCAGCAA | 538 |
| GGUCUGGAACAUUGGUCAGC | 539 |
| GGGUCUGGAACAUUGGUCAG | 540 |
| CGGGUCUGGAACAUUGGUCA | 541 |
| UCGGGUCUGGAACAUUGGUC | 542 |
| CUCGGGUCUGGAACAUUGGU | 543 |
| GGAAAUGACAGCCCUCUACC | 544 |
| GGGAAAUGACAGCCCUCUAC | 545 |
| UGGGAAAUGACAGCCCUCUA | 546 |
| GGUUGGGCUGGGAAAUGACA | 547 |
| UUGGUUGGGCUGGGAAAUGA | 548 |
| UGUUGGUUGGGCUGGGAAAU | 549 |
| UCUGUUGGUUGGGCUGGGAA | 550 |
| AUUCUGUUGGUUGGGCUGGG | 551 |
| CUCCCAGCAACCAUUCUGUU | 552 |
| GCUCCCAGCAACCAUUCUGU | 553 |
| AGCUCCCAGCAACCAUUCUG | 554 |
| AGCUCUGUCCAGUGUUCUCC | 555 |
| CUGUCCACCCUGCAUUUCUC | 556 |
| AUUAGACCCUCCUGUCCACC | 557 |
| GAUUAGACCCUCCUGUCCAC | 558 |
| CGAUUAGACCCUCCUGUCCA | 559 |
| ACGAUUAGACCCUCCUGUCC | 560 |
| GACGAUUAGACCCUCCUGUC | 561 |
| AGACGAUUAGACCCUCCUGU | 562 |
| GAGACGAUUAGACCCUCCUG | 563 |

TABLE 2-continued

| Sequence | SEQ ID NO: |
|---|---|
| UGAGACGAUUAGACCCUCCU | 564 |
| CUGAGACGAUUAGACCCUCC | 565 |
| ACUGAGACGAUUAGACCCUC | 566 |
| CACUGAGACGAUUAGACCCU | 567 |
| GCACUGAGACGAUUAGACCC | 568 |
| CGCACUGAGACGAUUAGACC | 569 |
| GCGCACUGAGACGAUUAGAC | 570 |
| GGCGCACUGAGACGAUUAGA | 571 |
| ACCUCAGGGCACUCUUUGGU | 572 |
| AACCUCAGGGCACUCUUUGG | 573 |
| GAACCUCAGGGCACUCUUUG | 574 |
| AGAACCUCAGGGCACUCUUU | 575 |
| UAGAACCUCAGGGCACUCUU | 576 |
| CUAGAACCUCAGGGCACUCU | 577 |
| CCUAGAACCUCAGGGCACUC | 578 |
| UCCUAGAACCUCAGGGCACU | 579 |
| GCUCUUCCUAGAACCUCAGG | 580 |
| CCAGGCUCUUCCUAGAACCU | 581 |
| ACCAGGCUCUUCCUAGAACC | 582 |
| UACCAGGCUCUUCCUAGAAC | 583 |
| GUACCAGGCUCUUCCUAGAA | 584 |
| UGUACCAGGCUCUUCCUAGA | 585 |
| AUGUACCAGGCUCUUCCUAG | 586 |
| UGAUGUACCAGGCUCUUCCU | 587 |
| GGUGAUGUACCAGGCUCUUC | 588 |
| AUGGAGCUUGGUGAUGUACC | 589 |
| UGGCAAUGGAGCUUGGUGAU | 590 |
| GUGGCAAUGGAGCUUGGUGA | 591 |
| CGUGGCAAUGGAGCUUGGUG | 592 |
| ACGUGGCAAUGGAGCUUGGU | 593 |
| ACCUUUGGUUUUGGACCUCA | 594 |
| UACCUUUGGUUUUGGACCUC | 595 |
| CUACCUUUGGUUUUGGACCU | 596 |
| GCUACCUUUGGUUUUGGACC | 597 |
| ACUGCUACCUUUGGUUUUGG | 598 |
| CACUGCUACCUUUGGUUUUG | 599 |
| UCACUGCUACCUUUGGUUUU | 600 |
| AUCACUGCUACCUUUGGUUU | 601 |
| GAGAGACUGUCUUCAGGAUC | 602 |
| ACACUGCCAGAGAAGAGAGA | 603 |
| CACACUGCCAGAGAAGAGAG | 604 |
| AGCUGGUUCCUUUGUUCUUU | 605 |
| GGGACAAGCUGGUUCCUUUG | 606 |
| AGGGACAAGCUGGUUCCUUU | 607 |
| CAGGGACAAGCUGGUUCCUU | 608 |
| GACAGGGACAAGCUGGUUCC | 609 |
| AGACAGGGACAAGCUGGUUC | 610 |
| AAGACAGGGACAAGCUGG | 611 |
| CAAGAGACAGGGACAAGCUG | 612 |
| ACAAGAGACAGGGACAAGCU | 613 |
| AUGGAGUGAUGAGGAGUGCC | 614 |
| CUGGCUUGUAGCUGGCUGGA | 615 |
| CCACCAGUGUCCACCAUGUG | 616 |
| AGUACCACCAGUGUCCACCA | 617 |
| CAGUACCACCAGUGUCCACC | 618 |
| CCUCAGUACCACCAGUGUCC | 619 |
| GACCUCAGUACCACCAGUGU | 620 |
| UGGACCUCAGUACCACCAGU | 621 |
| GCUGGACCUCAGUACCACCA | 622 |
| AAGGCUGGACCUCAGUACCA | 623 |
| GAAGGCUGGACCUCAGUACC | 624 |
| GGAAGGCUGGACCUCAGUAC | 625 |
| UUGGAAGGCUGGACCUCAGU | 626 |
| AUUGGAAGGCUGGACCUCAG | 627 |
| AAUUGGAAGGCUGGACCUCA | 628 |
| CUAAUUGGAAGGCUGGACCU | 629 |
| CCUAAUUGGAAGGCUGGACC | 630 |
| UCCUAAUUGGAAGGCUGGAC | 631 |
| CUGUCAAGAGAGACUAUUAG | 632 |
| GCUGUCAAGAGAGACUAUUA | 633 |
| GGCUGUCAAGAGAGACUAUU | 634 |
| GGGCUGUCAAGAGAGACUAU | 635 |
| CCCUCUGUUUAGAUGAUGGG | 636 |
| CUCCACUUUGCUCAUCUCCC | 637 |
| UACUCCACUUUGCUCAUCUC | 638 |
| UUACUCCACUUUGCUCAUCU | 639 |
| UUUACUCCACUUUGCUCAUC | 640 |

TABLE 2-continued

| Sequence | SEQ ID NO: |
|---|---|
| CUUUACUCCACUUUGCUCAU | 641 |
| UCUUUACUCCACUUUGCUCA | 642 |
| GUCUUUACUCCACUUUGCUC | 643 |
| GAAAUGUGUCUUUACUCCAC | 644 |
| GUGUGAUUUGGAAAUGUGUC | 645 |
| GUGGGUGUGAUUUGGAAAUG | 646 |
| AGUGGGUGUGAUUUGGAAAU | 647 |
| GAAGGUGGGCCUCAUGCUAG | 648 |
| CACCACACCCAGUCCUCACU | 649 |
| AUGAGCCACCACACCCAGUC | 650 |
| CAUGAGCCACCACACCCAGU | 651 |
| ACAUGAGCCACCACACCCAG | 652 |
| GACAUGAGCCACCACACCCA | 653 |
| AGACAUGAGCCACCACACCC | 654 |
| UAGACAUGAGCCACCACACC | 655 |
| AUAGACAUGAGCCACCACAC | 656 |
| GCUCAAGCGAUCCUCUCACC | 657 |
| GGCUCAAGCGAUCCUCUCAC | 658 |
| GGGCUCAAGCGAUCCUCUCA | 659 |
| UGGGCUCAAGCGAUCCUCUC | 660 |
| CUGGGCUCAAGCGAUCCUCU | 661 |
| UCUUUUGUAGAGACAGGGUC | 662 |
| UUCUUUUGUAGAGACAGGGU | 663 |
| AUUCUUUUGUAGAGACAGGG | 664 |
| ACACCACACAGGCUAAUUUA | 665 |
| UGCCACCACACCAACCACAC | 666 |
| GUGCCACCACACCAACCACA | 667 |
| GCUAAGUCUACAGGUGCGUG | 668 |
| UUGACCUCCUGGGUUAAGUG | 669 |
| CUUGACCUCCUGGGUUAAGU | 670 |
| GCCUUGACCUCCUGGGUUAA | 671 |
| UACAGGCAUGAGCCACCGCA | 672 |
| UUACAGGCAUGAGCCACCGC | 673 |
| AUUACAGGCAUGAGCCACCG | 674 |
| GAUUACAGGCAUGAGCCACC | 675 |
| GGAUUACAGGCAUGAGCCAC | 676 |
| GGGAUUACAGGCAUGAGCCA | 677 |
| UGGGAUUACAGGCAUGAGCC | 678 |
| CUGGGAUUACAGGCAUGAGC | 679 |
| GCUGGGAUUACAGGCAUGAG | 680 |
| UGCUGGGAUUACAGGCAUGA | 681 |
| GUGCUGGGAUUACAGGCAUG | 682 |
| AGUGCUGGGAUUACAGGCAU | 683 |
| AAGUGCUGGGAUUACAGGCA | 684 |
| AAAGUGCUGGGAUUACAGGC | 685 |
| CAAAGUGCUGGGAUUACAGG | 686 |
| CCAAAGUGCUGGGAUUACAG | 687 |
| GUUAGCCAGGAUGGUCUCCA | 688 |
| UGUUAGCCAGGAUGGUCUCC | 689 |
| GUGUUAGCCAGGAUGGUCUC | 690 |
| UGUGUUAGCCAGGAUGGUCU | 691 |
| CUGUGUUAGCCAGGAUGGUC | 692 |
| ACUGUGUUAGCCAGGAUGGU | 693 |
| CACUGUGUUAGCCAGGAUGG | 694 |
| UCACUGUGUUAGCCAGGAUG | 695 |
| UUCACUGUGUUAGCCAGGAU | 696 |
| UUUCACUGUGUUAGCCAGGA | 697 |
| GUUUCACUGUGUUAGCCAGG | 698 |
| GGUUUCACUGUGUUAGCCAG | 699 |
| GGGUUUCACUGUGUUAGCCA | 700 |
| UUCUUCUGCCUCAGCCUCCC | 701 |
| AUUCUUCUGCCUCAGCCUCC | 702 |
| CAUUCUUCUGCCUCAGCCUC | 703 |
| CCAUUCUUCUGCCUCAGCCU | 704 |
| ACCAUUCUUCUGCCUCAGCC | 705 |
| CACCAUUCUUCUGCCUCAGC | 706 |
| ACACCAUUCUUCUGCCUCAG | 707 |
| CUCACUGCAAGCUCCACCUC | 708 |
| GCUCACUGCAAGCUCCACCU | 709 |
| UCGGCUCACUGCAAGCUCCA | 710 |
| UCUCGGCUCACUGCAAGCUC | 711 |
| AUCUCGGCUCACUGCAAGCU | 712 |
| AAUCUCGGCUCACUGCAAGC | 713 |
| CAAUCUCGGCUCACUGCAAG | 714 |
| ACAAUCUCGGCUCACUGCAA | 715 |
| CACAAUCUCGGCUCACUGCA | 716 |
| GCACAAUCUCGGCUCACUGC | 717 |

TABLE 2-continued

| Sequence | SEQ ID NO: |
|---|---|
| GGCACAAUCUCGGCUCACUG | 718 |
| UGGCACAAUCUCGGCUCACU | 719 |
| GUGGCACAAUCUCGGCUCAC | 720 |
| AGUGGCACAAUCUCGGCUCA | 721 |
| CAGUGGCACAAUCUCGGCUC | 722 |
| GCAGUGGCACAAUCUCGGCU | 723 |
| UGCAGUGGCACAAUCUCGGC | 724 |
| AGGCUGAGUCUCGCUCUGUC | 725 |
| CCACAUUUUCUCACUGUCUU | 726 |
| CUCCUGACCACAUUUUCUCA | 727 |
| CCUCCUGACCACAUUUUCUC | 728 |
| CCCUCCUGACCACAUUUUCU | 729 |
| GCCCUCCUGACCACAUUUUC | 730 |
| UCUUGGUUCCCAGCUCAGC | 731 |
| GCAGUCUUGGUUCCCAGUCU | 732 |
| CAGCAGUCUUGGUUCCCAGU | 733 |
| UACAGCAGUCUUGGUUCCCA | 734 |
| AUACAGCAGUCUUGGUUCCC | 735 |
| CAAAUACAGCAGUCUUGGUU | 736 |
| GCAAAUACAGCAGUCUUGGU | 737 |
| GGCAAAUACAGCAGUCUUGG | 738 |
| AAGGCAAAUACAGCAGUCUU | 739 |
| CAAGGCAAAUACAGCAGUCU | 740 |
| GCAAGGCAAAUACAGCAGUC | 741 |
| AGCAAGGCAAAUACAGCAGU | 742 |
| AAAGCAAGGCAAAUACAGCA | 743 |
| CAAAGCAAGGCAAAUACAGC | 744 |
| UUGCAACAAAGCAAGGCAA | 745 |
| CUCUAAGAGCUUUUGACAAC | 746 |
| UUGCCUCAGCCUCCUAAAGU | 747 |
| CUUGCCUCAGCCUCCUAAAG | 748 |
| ACUUGCCUCAGCCUCCUAAA | 749 |
| CACUUGCCUCAGCCUCCUAA | 750 |
| CCACUUGCCUCAGCCUCCUA | 751 |
| UCCACUUGCCUCAGCCUCCU | 752 |
| AUCCACUUGCCUCAGCCUCC | 753 |
| UGGGCUCAAGCAAUCCACUU | 754 |
| CUGGGCUCAAGCAAUCCACU | 755 |

TABLE 2-continued

| Sequence | SEQ ID NO: |
|---|---|
| CCUGGGCUCAAGCAAUCCAC | 756 |
| UCCUGGGCUCAAGCAAUCCA | 757 |
| CUCCUGGGCUCAAGCAAUCC | 758 |
| ACUCCUGGGCUCAAGCAAUC | 759 |
| AACUCCUGGGCUCAAGCAAU | 760 |
| GAACUCCUGGGCUCAAGCAA | 761 |
| UGAACUCCUGGGCUCAAGCA | 762 |
| GUCUUGAACUCCUGGGCUCA | 763 |
| GGUCUUGAACUCCUGGGCUC | 764 |
| UGGUCUUGAACUCCUGGGCU | 765 |
| CUGGUCUUGAACUCCUGGGC | 766 |
| GCUGGUCUUGAACUCCUGGG | 767 |
| GGCUGGUCUUGAACUCCUGG | 768 |
| AGGCUGGUCUUGAACUCCUG | 769 |
| CAGGCUGGUCUUGAACUCCU | 770 |
| CCAGGCUGGUCUUGAACUCC | 771 |
| AUUUCCCACAGAGACAGGGU | 772 |
| CACCACACCUGGCUAAUUUU | 773 |
| CCACCACACCUGGCUAAUUU | 774 |
| ACCACCACACCUGGCUAAUU | 775 |
| CACCACCACACCUGGCUAAU | 776 |
| GCACCACCACACCUGGCUAA | 777 |
| AGUUGGGACUACAGGUGCGC | 778 |
| CUGCCUCAGCCUCCUUAGUA | 779 |
| UCUGCCUCAGCCUCCUUAGU | 780 |
| UUCUGCCUCAGCCUCCUUAG | 781 |
| CUUCUGCCUCAGCCUCCUUA | 782 |
| CCUUCUGCCUCAGCCUCCUU | 783 |
| UCCUUCUGCCUCAGCCUCCU | 784 |
| AUCCUUCUGCCUCAGCCUCC | 785 |
| AAUCCUUCUGCCUCAGCCUC | 786 |
| CAAUCCUUCUGCCUCAGCCU | 787 |
| CACAAUCAUAGCUCACUGCA | 788 |
| GCACAAUCAUAGCUCACUGC | 789 |
| CUCAAUCUGUUGUUCAGGCU | 790 |
| UCUCAAUCUGUUGUUCAGGC | 791 |
| GUCUCAAUCUGUUGUUCAGG | 792 |
| GGUCUCAAUCUGUUGUUCAG | 793 |
| CCUAGAAGUAGUGCCAGGCC | 794 |

TABLE 2-continued

| Sequence | SEQ ID NO: |
|---|---|
| UCCUAGAAGUAGUGCCAGGC | 795 |
| AUCCUAGAAGUAGUGCCAGG | 796 |
| GCAUCCUAGAAGUAGUGCCA | 797 |
| GACUGUGAGAGUUGCCUAAA | 798 |
| GGGACUGUGAGAGUUGCCUA | 799 |
| AGGGACUGUGAGAGUUGCCU | 800 |
| AAGGGACUGUGAGAGUUGCC | 801 |
| CAAGGGACUGUGAGAGUUGC | 802 |
| UCAAGGGACUGUGAGAGUUVG | 803 |
| UUCAAGGGACUGUGAGAGUU | 804 |
| CUUUCAAGGGACUGUGAGAG | 805 |
| UCUUUCAAGGGACUGUGAGA | 806 |
| CUCUUUCAAGGGACUGUGAG | 807 |
| UCUCUUUCAAGGGACUGUGA | 808 |
| CUUCUCUUUCAAGGGACUGU | 809 |
| ACUUCUCUUUCAAGGGACUG | 810 |
| CACUUCUCUUUCAAGGGACU | 811 |
| UGCCACUUCUCUUUCAAGGG | 812 |
| ACUUGGGAGGGCCUAUACCC | 813 |
| CACUUGGGAGGGCCUAUACC | 814 |
| ACACUUGGGAGGGCCUAUAC | 815 |
| CAUGACACUUGGGAGGGCCU | 816 |
| UCUUACACAGGGCAGAGUCC | 817 |
| AUCUUACACAGGGCAGAGUC | 818 |
| AAUCUUACACAGGGCAGAGU | 819 |
| AUGCAAUCUUACACAGGGCA | 820 |
| GUGAUGCAAUCUUACACAGG | 821 |
| GGUGAUGCAAUCUUACACAG | 822 |
| UGGUGAUGCAAUCUUACACA | 823 |
| GUGGUGAUGCAAUCUUACAC | 824 |
| GGUGGUGAUGCAAUCUUACA | 825 |
| UGGUGGUGAUGCAAUCUUAC | 826 |
| UGGUGGUGAUGCAAUCU | 827 |
| GUGGUGGUGGUGAUGCAAUC | 828 |
| GUGGUGGUGGUGGUGAUVGCA | 829 |
| AGGUGGUGGUGGUGGUGAUVG | 830 |
| GAGGUGGUGGUGGUGGUGAU | 831 |
| AGAGGUGGUGGUGGUGGUGA | 832 |
| AGAGAGGUGGUGGUGGUGGU | 833 |
| ACGUGUUCCUGUGAUGUCUG | 834 |
| AACGUGUUCCUGUGAUGUCU | 835 |
| GAACGUGUUCCUGUGAUGUC | 836 |
| UGAUGUGGAGGAGGGCCAGA | 837 |
| AUGAUGUGGAGGAGGGCCAG | 838 |
| CAUGAUGUGGAGGAGGGCCA | 839 |
| GGAGCAUGAUGUGGAGGAGG | 840 |
| UGGAGCAUGAUGUGGAGGAG | 841 |
| GUGGAGCAUGAUGUGGAGGA | 842 |
| UGUGGAGCAUGAUGUGGAGG | 843 |
| AUGUGGAGCAUGAUGUGGAG | 844 |
| GAUGUGGAGCAUGAUGUGGA | 845 |
| UGAUGUGGAGCAUGAUGUGG | 846 |
| AUGAUGUGGAGCAUGAUGUG | 847 |
| UGGAGCAUGAUGUGGAGCAU | 848 |
| GCCUGGAGCAUGAUGUGGAG | 849 |
| GGCCUGGAGCAUGAUGUGGA | 850 |
| UGGCCUGGAGCAUGAUGUGG | 851 |
| UUGGCCUGGAGCAUGAUGUG | 852 |
| GUUGGCCUGGAGCAUGAUGU | 853 |
| AGUUGGCCUGGAGCAUGAUG | 854 |
| CAGUUGGCCUGGAGCAUGAU | 855 |
| GCCACGAGGCACAGAAGUCA | 856 |
| GAGAAUGGAGCCCUCUUGCU | 857 |
| GGUAGGAGAAUGGAGCCCUC | 858 |
| GGGUAGGAGAAUGGAGCCCU | 859 |
| ACAGGGAUGAGGGUUUGGGC | 860 |
| UAGGACAGGGAUGAGGGUUU | 861 |
| CUAGGACAGGGAUGAGGGUU | 862 |
| UUCCAGUGGGUAUUCCUCUG | 863 |
| GUUCCAGUGGGUAUUCCUCU | 864 |
| AGUUCCAGUGGGUAUUCCUC | 865 |
| GCAGUUUCCAUGAGGCAGCU | 866 |
| UGCAGCAGUUUCCAUGAGGC | 867 |
| CUAGCUUCACCACUGCUGCA | 868 |
| CUUUCUAGCUUCACCACUGC | 869 |
| UAGUCUUUCUAGCUUCACCA | 870 |
| CUCAUACCUCUAGUCUUUCU | 871 |

TABLE 2-continued

| Sequence | SEQ ID NO: |
|---|---|
| CCUCAUACCUCUAGUCUUUC | 872 |
| CCCUCAUACCUCUAGUCUUU | 873 |
| UCCCUCAUACCUCUAGUCUU | 874 |
| UUCCCUCAUACCUCUAGUCU | 875 |
| UUUCCCUCAUACCUCUAGUC | 876 |
| UUUUCCCUCAUACCUCUAGU | 877 |
| AUUUUCCCUCAUACCUCUAG | 878 |
| GCAAUUUUCCCUCAUACCUC | 879 |
| ACGCCUUAUGAGCCAGGUGG | 880 |
| AACGCCUUAUGAGCCAGGUG | 881 |
| GAACGCCUUAUGAGCCAGGU | 882 |
| GGGAACGCCUUAUGAGCCAG | 883 |
| AGGGAACGCCUUAUGAGCCA | 884 |
| GAGGGAACGCCUUAUGAGCC | 885 |
| GGAGGGAACGCCUUAUGAGC | 886 |
| GGGAGGGAACGCCUUAUGAG | 887 |
| GAUGAUUUCACAUGCUCAGU | 888 |
| AGGAUGAUUUCACAUGCUCA | 889 |
| GAGGAUGAUUUCACAUGCUC | 890 |
| AGAGGAUGAUUUCACAUGCU | 891 |
| CAUGAUGCAAGAAAGAGGAU | 892 |
| GCAUGAUGCAAGAAAGAGGA | 893 |
| CACGCAUGAUGCAAGAAAGA | 894 |
| ACACGCAUGAUGCAAGAAAG | 895 |
| GACACGCAUGAUGCAAGAAA | 896 |
| GGACACGCAUGAUGCAAGAA | 897 |
| UGGACACGCAUGAUGCAAGA | 898 |
| GUGGACACGCAUGAUGCAAG | 899 |
| UGUGGACACGCAUGAUGCAA | 900 |
| AUGUGGACACGCAUGAUGCA | 901 |
| CAAUGUGGACACGCAUGAUG | 902 |
| GCAAUGUGGACACGCAUGAU | 903 |
| GUGCAAUGUGGACACGCAUG | 904 |
| GGUGCAAUGUGGACACGCAU | 905 |
| GGGUGCAAUGUGGACACGCA | 906 |
| UGACUGGGCCUGAAGUAGGG | 907 |
| CAUGGUGACUGGGCCUGAAG | 908 |
| CUCAGGUUUCACCAUCUGGC | 909 |

TABLE 2-continued

| Sequence | SEQ ID NO: |
|---|---|
| CAGCUCAGGUUUCACCAUCU | 910 |
| UCAGCUCAGGUUUCACCAUC | 911 |
| AUCAGCUCAGGUUUCACCAU | 912 |
| CAUCAGCUCAGGUUUCACCA | 913 |
| UCUGAGUCCCAGGAUUGGCC | 914 |
| CCUCUGAGUCCCAGGAUUGG | 915 |
| CCCUCUGAGUCCCAGGAUUG | 916 |
| ACCCUCUGAGUCCCAGGAUU | 917 |
| UACCCUCUGAGUCCCAGGAU | 918 |
| CUACCCUCUGAGUCCCAGGA | 919 |
| AGCCGACCUACCCUCUGAGU | 920 |
| AACCUAGUGGUCAGCCAGCC | 921 |
| AAACCUAGUGGUCAGCCAGC | 922 |
| CCAAACCUAGUGGUCAGCCA | 923 |
| UCCAAACCUAGUGGUCAGCC | 924 |
| UUCCAAACCUAGUGGUCAGC | 925 |
| UCUUCCAAACCUAGUGGUCA | 926 |
| GUCUUCCAAACCUAGUGGUC | 927 |
| GGUCUUCCAAACCUAGUGGU | 928 |
| GGGUCUUCCAAACCUAGUGG | 929 |
| UGGGUCUUCCAAACCUAGUG | 930 |
| CUGGGUCUUCCAAACCUAGU | 931 |
| CCUGGGUCUUCCAAACCUAG | 932 |
| GCUGCCUGGGUCUUCCAAAC | 933 |
| GGGCCUCUUUAGAGCCAGCU | 934 |
| AUGUCUGGCUACUGACCUGG | 935 |
| UCAUGUCUGGCUACUGACCU | 936 |
| CUCAUGUCUGGCUACUGACC | 937 |
| GCUCAUGUCUGGCUACUGAC | 938 |
| AGCUCAUGUCUGGCUACUGA | 939 |
| CAGCUCAUGUCUGGCUACUG | 940 |
| ACAGCUCAUGUCUGGCUACU | 941 |
| UGACCCUCACAGCUCAUGUC | 942 |
| UUGACCCUCACAGCUCAUGU | 943 |
| UGCUUGACCCUCACAGCUCA | 944 |
| GUGCUUGACCCUCACAGCUC | 945 |
| UAGCUGUGCUUGACCCUCAC | 946 |
| AUAGCUGUGCUUGACCCUCA | 947 |
| GAUAGCUGUGCUUGACCCUC | 948 |

TABLE 2-continued

| Sequence | SEQ ID NO: |
|---|---|
| GGAUAGCUGUGCUUGACCCU | 949 |
| UGGAUAGCUGUGCUUGACCC | 950 |
| AUGGAUAGCUGUGCUUGACC | 951 |
| GAUGGAUAGCUGUGCUUGAC | 952 |
| UGAUGGAUAGCUGUGCUUGA | 953 |
| AUCUGAUGGAUAGCUGUGCU | 954 |
| CAUCUGAUGGAUAGCUGUGC | 955 |
| AUCAUCUGAUGGAUAGCUGU | 956 |
| GAUCAUCUGAUGGAUAGCUG | 957 |
| AGAUCAUCUGAUGGAUAGCU | 958 |
| UAGAUCAUCUGAUGGAUAGC | 959 |
| GUAGAUCAUCUGAUGGAUAG | 960 |
| GAAAGUAGAUCAUCUGAUGG | 961 |
| GCUGAAAGUAGAUCAUCUGA | 962 |
| AGGCUGAAAGUAGAUCAUCU | 963 |
| AAGGCUGAAAGUAGAUCAUC | 964 |
| GAAGGCUGAAAGUAGAUCAU | 965 |
| GGAAGGCUGAAAGUAGAUCA | 966 |
| AGGAAGGCUGAAAGUAGAUC | 967 |
| GUCUGGGACUCAGGAAGGCU | 968 |
| UAUUGUCUGGGACUCAGGAA | 969 |
| CUAUUGUCUGGGACUCAGGA | 970 |
| UCUAUUGUCUGGGACUCAGG | 971 |
| CUUCUAUUGUCUGGGACUCA | 972 |
| UCUUCUAUUGUCUGGGACUC | 973 |
| CACCUGUCUUCUAUUGUCUG | 974 |
| CCACCUGUCUUCUAUUGUCU | 975 |
| GCCACCUGUCUUCUAUUGUC | 976 |
| AGCCACCUGUCUUCUAUUGU | 977 |
| AUGAGGGCACAGUGACAGCA | 978 |
| CAAUGAGGGCACAGUGACAG | 979 |
| CCAAUGAGGGCACAGUGACA | 980 |
| CGUCUGUUGAGUCUGAUUGC | 981 |
| CCGUCUGUUGAGUCUGAUUG | 982 |
| UCCGUCUGUUGAGUCUGAUU | 983 |
| CUCCGUCUGUUGAGUCUGAU | 984 |
| GCUCCGUCUGUUGAGUCUGA | 985 |
| UGCUCCGUCUGUUGAGUCUG | 986 |

TABLE 2-continued

| Sequence | SEQ ID NO: |
|---|---|
| UUGCUCCGUCUGUUGAGUCU | 987 |
| AGUUGCUCCGUCUGUUGAGU | 988 |
| GCAGUUGCUCCGUCUGUUGA | 989 |
| GGCAGUUGCUCCGUCUGUUG | 990 |
| GAUGGCAGUUGCUCCGUCUG | 991 |
| GGAUGGCAGUUGCUCCGUCU | 992 |
| AGCCUCGGAUGGCAGUUGCU | 993 |
| AGGAGCCUCGGAUGGCAGUU | 994 |
| UUCAGGAGCCUCGGAUGGCA | 995 |
| UGGUUCAGGAGCCUCGGAUG | 996 |
| CUGGUUCAGGAGCCUCGGAU | 997 |
| CUGGUGAAUGGCCCUGGUUC | 998 |
| CCUGGUGAAUGGCCCUGGUU | 999 |
| UCCUGGUGAAUGGCCCUGGU | 1000 |
| UGGACAUCAGGGAGCCGCAU | 1001 |
| AGGAUUUGCUGCUUGGCUAG | 1002 |
| CAGGAUUUGCUGCUUGGCUA | 1003 |
| UCCAGGAUUUGCUGCUUGGC | 1004 |
| ACCCAUCCAGGAUUUGCUGC | 1005 |
| AACCCAUCCAGGAUUUGCUG | 1006 |
| CAACCCAUCCAGGAUUUGCU | 1007 |
| UGCAACCCAUCCAGGAUUUG | 1008 |
| GUGCAACCCAUCCAGGAUUU | 1009 |
| GGUGCAACCCAUCCAGGAUU | 1010 |
| AGGUGCAACCCAUCCAGGAU | 1011 |
| CAGGUGCAACCCAUCCAGGA | 1012 |
| UCAGGUGCAACCCAUCCAGG | 1013 |
| GUCAGGUGCAACCCAUCCAG | 1014 |
| GGUCAGGUGCAACCCAUCCA | 1015 |
| UGGUCAGGUGCAACCCAUCC | 1016 |
| CUGGUCAGGUGCAACCCAUC | 1017 |
| ACUGGUCAGGUGCAACCCAU | 1018 |
| GACUGGUCAGGUGCAACCCA | 1019 |
| ACGACUGGUCAGGUGCAACC | 1020 |
| GACGACUGGUCAGGUGCAAC | 1021 |
| GGACGACUGGUCAGGUGCAA | 1022 |
| UCUGGGACGACUGGUCAGGU | 1023 |
| UUCUGGGACGACUGGUCAGG | 1024 |
| AUUCUGGGACGACUGGUCAG | 1025 |

TABLE 2-continued

| Sequence | SEQ ID NO: |
| --- | --- |
| UAUUCUGGGACGACUGGUCA | 1026 |
| UUAUUCUGGGACGACUGGUC | 1027 |
| GUUAUUCUGGGACGACUGGU | 1028 |
| AGUUAUUCUGGGACGACUGG | 1029 |
| GAGUUAUUCUGGGACGACUG | 1030 |
| UGAGUUAUUCUGGGACGACU | 1031 |
| AUGAGUUAUUCUGGGACGAC | 1032 |
| GAUGAGUUAUUCUGGGACGA | 1033 |
| GGAUGAGUUAUUCUGGGACG | 1034 |
| UGGAGGAUGAGUUAUUCUGG | 1035 |
| GUGGAGGAUGAGUUAUUCUG | 1036 |
| GGUGGAGGAUGAGUUAUUCU | 1037 |
| GGGUGGAGGAUGAGUUAUUC | 1038 |
| AAAGCUGAUGACCUCCUCCC | 1039 |
| CAAAGCUGAUGACCUCCUCC | 1040 |
| AGCAAAGCUGAUGACCUCCU | 1041 |
| UAGCAAAGCUGAUGACCUCC | 1042 |
| GUAGCAAAGCUGAUGACCUC | 1043 |
| AGUAGCAAAGCUGAUGACCU | 1044 |
| ACAGUAGCAAAGCUGAUGAC | 1045 |
| UGACAGUAGCAAAGCUGAUG | 1046 |
| GUGACAGUAGCAAAGCUGAU | 1047 |
| ACCUGUGACAGUAGCAAAGC | 1048 |
| CACCUGUGACAGUAGCAAAG | 1049 |
| CCACCUGUGACAGUAGCAAA | 1050 |
| CCCACCUGUGACAGUAGCAA | 1051 |
| ACCCACCUGUGACAGUAGCA | 1052 |
| CACCCACCUGUGACAGUAGC | 1053 |
| GUUGCUCUCUCCCUCACCCA | 1054 |
| CCUGUUGCUCUCUCCCUCAC | 1055 |
| GCCUGUUGCUCUCUCCCUCA | 1056 |
| UGCCUGUUGCUCUCUCCCUC | 1057 |
| CCCUGUCUGCUCUUUGCCUG | 1058 |
| UUUCCCUGUCUGCUCUUUGC | 1059 |
| UCCUCUGCAACCAGUCCCUG | 1060 |
| GUCCUCUGCAACCAGUCCCU | 1061 |
| GUGUCCUCUGCAACCAGUCC | 1062 |
| UGUGUCCUCUGCAACCAGUC | 1063 |

TABLE 2-continued

| Sequence | SEQ ID NO: |
| --- | --- |
| UUGUGUCCUCUGCAACCAGU | 1064 |
| ACUGCUUUGUGUCCUCUGCA | 1065 |
| GACUGCUUUGUGUCCUCUGC | 1066 |
| GAGACUGCUUUGUGUCCUCU | 1067 |
| AGAGACUGCUUUGUGUCCUC | 1068 |
| UAGAGACUGCUUUGUGUCCU | 1069 |
| UCCCUCGAACCUACCUCUAG | 1070 |
| CUCCCUCGAACCUACCUCUA | 1071 |
| UCUCCCUCGAACCUACCUCU | 1072 |
| CUCUCCCUCGAACCUACCUC | 1073 |
| ACUGCUCUCCCUCGAACCUA | 1074 |
| AGAUGAAGCUCUCCUCUGAG | 1075 |
| AUGUGAGUAGAGAUGAAGCU | 1076 |
| UGCCCGAAAGACAGAAAAGG | 1077 |
| CUGCCCGAAAGACAGAAAAG | 1078 |
| AGUGGAGUCUGCCCGAAAGA | 1079 |
| AAGUGGAGUCUGCCCGAAAG | 1080 |
| GAAGUGGAGUCUGCCCGAAA | 1081 |
| AGGCUGAAGUGGAGUCUGCC | 1082 |
| UAGGCUGAAGUGGAGUCUGC | 1083 |
| GUAGGCUGAAGUGGAGUCUG | 1084 |
| GCUGUAGGCUGAAGUGGAGU | 1085 |
| AGCUGUAGGCUGAAGUGGAG | 1086 |
| GAGCUGUAGGCUGAAGUGGA | 1087 |
| GGGAGCUGUAGGCUGAAGUG | 1088 |
| AGGGAGCUGUAGGCUGAAGU | 1089 |
| AAGUGAGCAGGGAGCUGUAG | 1090 |
| UGGACAGGUGAAAAGUGAGC | 1091 |
| GUGGACAGGUGAAAAGUGAG | 1092 |
| AGUGGACAGGUGAAAAGUGA | 1093 |
| GAGUGGACAGGUGAAAAGUG | 1094 |
| GGAGUGGACAGGUGAAAAGU | 1095 |
| AGGAGUGGACAGGUGAAAAG | 1096 |
| GAGGAGUGGACAGGUGAAAA | 1097 |
| CGAGGAGUGGACAGGUGAAA | 1098 |
| CCGAGGAGUGGACAGGUGAA | 1099 |
| ACCGAGGAGUGGACAGGUGA | 1100 |
| CAUGGUACAGGUGGUGGGAC | 1101 |
| GCAUGGUACAGGUGGUGGGA | 1102 |

TABLE 2-continued

| Sequence | SEQ ID NO: |
|---|---|
| CAAAGAGUGCCAGGAAGGGU | 1103 |
| GCAAAGAGUGCCAGGAAGGG | 1104 |
| AAGCAAAGAGUGCCAGGAAG | 1105 |
| UCAAGCAAAGAGUGCCAGGA | 1106 |
| CUCAAGCAAAGAGUGCCAGG | 1107 |
| CCUCAAGCAAAGAGUGCCAG | 1108 |
| AUCCUCAAGCAAAGAGUGCC | 1109 |
| GAUCCUCAAGCAAAGAGUGC | 1110 |
| GAAGAUCCUCAAGCAAAGAG | 1111 |
| GGAAGAUCCUCAAGCAAAGA | 1112 |
| CGGAAGAUCCUCAAGCAAAG | 1113 |
| AUCGGAAGAUCCUCAAGCAA | 1114 |
| CAUCGGAAGAUCCUCAAGCA | 1115 |
| CCAUCGGAAGAUCCUCAAGC | 1116 |
| CCCAUCGGAAGAUCCUCAAG | 1117 |
| AUGUGGUGCUCAGCCAGGAG | 1118 |
| UUGGUGAUGUGGUGCUCAGC | 1119 |
| GGUUGGUGAUGUGGUGCUCA | 1120 |
| AGGUUGGUGAUGUGGUGCUC | 1121 |
| CAGGUUGGUGAUGUGGUGCU | 1122 |
| AGCCCAGGUUGGUGAUGUGG | 1123 |
| CAGCCCAGGUUGGUGAUGUG | 1124 |
| UGCCAGCCCAGGUUGGUGAU | 1125 |
| AUGCCAGCCCAGGUUGGUGA | 1126 |
| GUAUGCCAGCCCAGGUUGGU | 1127 |
| AGGUAUGCCAGCCCAGGUUG | 1128 |
| AAGGUAUGCCAGCCCAGGUU | 1129 |
| UAAGGUAUGCCAGCCCAGGU | 1130 |
| UUAAGGUAUGCCAGCCCAGG | 1131 |
| GUUAAGGUAUGCCAGCCCAG | 1132 |
| AGUUAAGGUAUGCCAGCCCA | 1133 |
| GAGUUAAGGUAUGCCAGCCC | 1134 |
| AGAGUUAAGGUAUGCCAGCC | 1135 |
| CAGAGUUAAGGUAUGCCAGC | 1136 |
| GCAGAGUUAAGGUAUGCCAG | 1137 |
| AGGGCAGAGUUAAGGUAUGC | 1138 |
| AGAGGGCAGAGUUAAGGUAU | 1139 |
| UAGAGGGCAGAGUUAAGGUA | 1140 |
| CUAGAGGGCAGAGUUAAGGU | 1141 |
| CACUAGAGGGCAGAGUUAAG | 1142 |
| GCCACUAGAGGGCAGAGUUA | 1143 |
| GGACACCAGACUUCUCACCC | 1144 |
| AGGACACCAGACUUCUCACC | 1145 |
| CAGGACACCAGACUUCUCAC | 1146 |
| UUUCAGGACACCAGACUUCU | 1147 |
| GUUUCAGGACACCAGACUUC | 1148 |
| UAGUUGCAGUUUCAGGACAC | 1149 |
| CUAGUUGCAGUUUCAGGACA | 1150 |
| UCUAGUUGCAGUUUCAGGAC | 1151 |
| GUCUAGUUGCAGUUUCAGGA | 1152 |
| AGUCUAGUUGCAGUUUCAGG | 1153 |
| CAGUCUAGUUGCAGUUUCAG | 1154 |
| AACUGUGCUGUUGCCUUCUA | 1155 |
| UAACUGUGCUGUUGCCUUCU | 1156 |
| GUAACUGUGCUGUUGCCUUC | 1157 |
| CCAGUAACUGUGCUGUUGCC | 1158 |
| GUCCAGUAACUGUGCUGUUG | 1159 |
| UGUCCAGUAACUGUGCUGUU | 1160 |
| UUGUCCAGUAACUGUGCUGU | 1161 |
| GGUUGUCCAGUAACUGUGCU | 1162 |
| CGGUUGUCCAGUAACUGUGC | 1163 |
| UCGGUUGUCCAGUAACUGUG | 1164 |
| CUCGGUUGUCCAGUAACUGU | 1165 |
| CCUCGGUUGUCCAGUAACUG | 1166 |
| GCCUCGGUUGUCCAGUAACU | 1167 |
| CGCCUCGGUUGUCCAGUAAC | 1168 |
| CCGCCUCGGUUGUCCAGUAA | 1169 |
| UGCUGGUGUCCUGCUGUGUC | 1170 |
| CUGCUGGUGUCCUGCUGUGU | 1171 |
| UCUAGGAAGGGCUGCUGGUG | 1172 |
| UUAAGCUCUAGGAAGGGCUG | 1173 |
| CUCAUUGGCUCGGAUCUUAA | 1174 |
| GCUCAUUGGCUCGGAUCUUA | 1175 |
| GGCUCAUUGGCUCGGAUCUU | 1176 |
| AGGCUCAUUGGCUCGGAUCU | 1177 |
| CAGGCUCAUUGGCUCGGAUC | 1178 |
| UCCAGGCUCAUUGGCUCGGA | 1179 |

TABLE 2-continued

| Sequence | SEQ ID NO: |
| --- | --- |
| UCUCGCCUGCAACAUAAGGG | 1180 |
| CAGAAUGGAAAGAGGCAGCA | 1181 |
| GCAGAAUGGAAAGAGGCAGC | 1182 |
| AAGACGGCAGAAUGGAAAGA | 1183 |
| GAAGACGGCAGAAUGGAAAG | 1184 |
| UGAAGACGGCAGAAUGGAAA | 1185 |
| CUGAAGACGGCAGAAUGGAA | 1186 |
| GCUGAAGACGGCAGAAUGGA | 1187 |
| GGCUGAAGACGGCAGAAUGG | 1188 |
| AGGCUGAAGACGGCAGAAUG | 1189 |
| GGAGGCUGAAGACGGCAGAA | 1190 |
| AGGAGGCUGAAGACGGCAGA | 1191 |
| UGUUGGCUUUGAGGAGGCUG | 1192 |
| CAAGGAUUGUUGGCUUUGAG | 1193 |
| UGGCAGGCCAAGGAUUGUUG | 1194 |
| CUGGCAGGCCAAGGAUUGUU | 1195 |
| ACUGGCAGGCCAAGGAUUGU | 1196 |
| AGGAGGUACUGGCAGGCCAA | 1197 |
| AACAGGAGGUACUGGCAGGC | 1198 |
| CAACAGGAGGUACUGGCAGG | 1199 |
| ACACAACAGGAGGUACUGGC | 1200 |
| AGGGACACAACAGGAGGUAC | 1201 |
| UCGGGCAGUAGGGACACAAC | 1202 |
| UUCGGGCAGUAGGGACACAA | 1203 |
| CUUCGGGCAGUAGGGACACA | 1204 |
| AUGAUCCAGGUAGAGGAGAG | 1205 |
| UAUGAUCCAGGUAGAGGAGA | 1206 |
| UUAUGAUCCAGGUAGAGGAG | 1207 |
| AUUAUGAUCCAGGUAGAGGA | 1208 |
| CAUUAUGAUCCAGGUAGAGG | 1209 |
| CCAUUAUGAUCCAGGUAGAG | 1210 |
| UGCCAUUAUGAUCCAGGUAG | 1211 |
| UUGCCAUUAUGAUCCAGGUA | 1212 |
| AUUGCCAUUAUGAUCCAGGU | 1213 |
| CAUUGCCAUUAUGAUCCAGG | 1214 |
| ACAUUGCCAUUAUGAUCCAG | 1215 |
| CCACAUUGCCAUUAUGAUCC | 1216 |
| GACCACAUUGCCAUUAUGAU | 1217 |
| UGACCACAUUGCCAUUAUGA | 1218 |
| UUGACCACAUUGCCAUUAUG | 1219 |
| UCUUGACCACAUUGCCAUUA | 1220 |
| GUCUUGACCACAUUGCCAUU | 1221 |
| CGUCUUGACCACAUUGCCAU | 1222 |
| CCGUCUUGACCACAUUGCCA | 1223 |
| UCCGUCUUGACCACAUUGCC | 1224 |
| AUCCGUCUUGACCACAUUGC | 1225 |
| CAUCCGUCUUGACCACAUUG | 1226 |
| ACAUCCGUCUUGACCACAUU | 1227 |
| CACAUCCGUCUUGACCACAU | 1228 |
| GCACAUCCGUCUUGACCACA | 1229 |
| GGCACAUCCGUCUUGACCAC | 1230 |
| UGGCACAUCCGUCUUGACCA | 1231 |
| CUGGCACAUCCGUCUUGACC | 1232 |
| UCUGGCACAUCCGUCUUGAC | 1233 |
| AUCUGGCACAUCCGUCUUGA | 1234 |
| UAUCUGGCACAUCCGUCUUG | 1235 |
| AUAUCUGGCACAUCCGUCUU | 1236 |
| CAUAUCUGGCACAUCCGUCU | 1237 |
| CCAUAUCUGGCACAUCCGUC | 1238 |
| CACCAUAUCUGGCACAUCCG | 1239 |
| CUCCACCACCAUAUCUGGCA | 1240 |
| UGGUCUCUUCACUCCAAAGC | 1241 |
| CUUCAUCUUGGUCUCUUCAC | 1242 |
| ACUUCAUCUUGGUCUCUUCA | 1243 |
| AACUUCAUCUUGGUCUCUUC | 1244 |
| GGAAACUUCAUCUUGGUCUC | 1245 |
| CCUCCAGUCACAGAUGCCCU | 1246 |
| GAUGCCUCCAGUCACAGAUG | 1247 |
| UGAUGCCUCCAGUCACAGAU | 1248 |
| CAGGUGGUUGUUGGGUUGGG | 1249 |
| CCAGGUGGUUGUUGGGUUGG | 1250 |
| GCCAGGUGGUUGUUGGGUUG | 1251 |
| UGCCAGGUGGUUGUUGGGUU | 1252 |
| CAUAUUGCCAGGUGGUUGUU | 1253 |
| UCAUAUUGCCAGGUGGUUGU | 1254 |
| GUCAUAUUGCCAGGUGGUUG | 1255 |
| AGUCAUAUUGCCAGGUGGUU | 1256 |

TABLE 2-continued

| Sequence | SEQ ID NO: |
|---|---|
| GAGUCAUAUUGCCAGGUGGU | 1257 |
| AGUGAGUCAUAUUGCCAGGU | 1258 |
| AAGUGAGUCAUAUUGCCAGG | 1259 |
| CAAGUGAGUCAUAUUGCCAG | 1260 |
| GUCAAGUGAGUCAUAUUGCC | 1261 |
| GGUCAAGUGAGUCAUAUUGC | 1262 |
| GGGUCAAGUGAGUCAUAUUG | 1263 |
| CCCAUUUGGGUCCCAUAGGG | 1264 |
| GCCCAUUUGGGUCCCAUAGG | 1265 |
| UGCCCAUUUGGGUCCCAUAG | 1266 |
| GUGCCCAUUUGGGUCCCAUA | 1267 |
| AGUGCCCAUUUGGGUCCCAU | 1268 |
| AAGUGCCCAUUUGGGUCCCA | 1269 |
| AAAGUGCCCAUUUGGGUCCC | 1270 |
| GAAAGUGCCCAUUUGGGUCC | 1271 |
| AGAAAGUGCCCAUUUGGGUC | 1272 |
| CAAGAAAGUGCCCAUUUGGG | 1273 |
| ACAAGAAAGUGCCCAUUUGG | 1274 |
| GACAAGAAAGUGCCCAUUUG | 1275 |
| GAGUCUCAGACAAGAAAGUG | 1276 |
| CCAGAGUCUCAGACAAGAAA | 1277 |
| GCCAGAGUCUCAGACAAGAA | 1278 |
| AGCCAGAGUCUCAGACAAGA | 1279 |
| UAAGCCAGAGUCUCAGACAA | 1280 |
| AUAAGCCAGAGUCUCAGACA | 1281 |
| AGCCAACCUGGAAUAAGCCA | 1282 |
| UCAGCCAACCUGGAAUAAGC | 1283 |
| CAUCAGCCAACCUGGAAUAA | 1284 |
| CACAUCAGCCAACCUGGAAU | 1285 |
| ACACAUCAGCCAACCUGGAA | 1286 |
| AACACAUCAGCCAACCUGGA | 1287 |
| CAACACAUCAGCCAACCUGG | 1288 |
| CUCCCAACACAUCAGCCAAC | 1289 |
| CGCUUUACCCAUCUCCCAAC | 1290 |
| AACGCUUUACCCAUCUCCCA | 1291 |
| AAACGCUUUACCCAUCUCCC | 1292 |
| AGAAACGCUUUACCCAUCUC | 1293 |
| AAGAAACGCUUUACCCAUCU | 1294 |
| GAAGAAACGCUUUACCCAUC | 1295 |
| AGAAGAAACGCUUUACCCAU | 1296 |
| UAGAAGAAACGCUUUACCCA | 1297 |
| UUAGAAGAAACGCUUUACCC | 1298 |
| AAUCAUGCUUUCUGGGUAGA | 1299 |
| CUUAGGGCAGGAAAUCAUGC | 1300 |
| ACUUAGGGCAGGAAAUCAUG | 1301 |
| GACUUAGGGCAGGAAAUCAU | 1302 |
| AGGACUUAGGGCAGGAAAUC | 1303 |
| CAGGACUUAGGGCAGGAAAU | 1304 |
| ACAGGACUUAGGGCAGGAAA | 1305 |
| UCUCACAGGACUUAGGGCAG | 1306 |
| UUCUCACAGGACUUAGGGCA | 1307 |
| AUCUUCUCACAGGACUUAGG | 1308 |
| CAUCUUCUCACAGGACUUAG | 1309 |
| UAGUCCCUGACAUCUUCUCA | 1310 |
| CUAGUCCCUGACAUCUUCUC | 1311 |
| CCUAGUCCCUGACAUCUUCU | 1312 |
| CCCUAGUCCCUGACAUCUUC | 1313 |
| UCCCUAGUCCCUGACAUCUU | 1314 |
| CUCCCUAGUCCCUGACAUCU | 1315 |
| AUCUAUCUGCUUCCUCCUCC | 1316 |
| CCAUCUAUCUGCUUCCUCCU | 1317 |
| ACCAUCUAUCUGCUUCCUCC | 1318 |
| GACCAUCUAUCUGCUUCCUC | 1319 |
| GGACCAUCUAUCUGCUUCCU | 1320 |
| UGGACCAUCUAUCUGCUUCC | 1321 |
| CUGGACCAUCUAUCUGCUUC | 1322 |
| CUGCUGGACCAUCUAUCUGC | 1323 |
| GCCUGCUGGACCAUCUAUCU | 1324 |
| UUCAAGCCUGCUGGACCAUC | 1325 |
| UGCUUCAAGCCUGCUGGACC | 1326 |
| CCUCAACAGCCCUUACCCUG | 1327 |
| UCCCUCUUGACCUUCCCUUA | 1328 |
| CUCCCUCUUGACCUUCCCUU | 1329 |
| UCUCCCUCUUGACCUUCCCU | 1330 |
| CAUCUCCCUCUUGACCUUCC | 1331 |
| CCAUCUCCCUCUUGACCUUC | 1332 |
| CCCAUCUCCCUCUUGACCUU | 1333 |

TABLE 2-continued

| Sequence | SEQ ID NO: |
|---|---|
| GCCCAUCUCCCUCUUGACCU | 1334 |
| UUGCCCAUCUCCCUCUUGAC | 1335 |
| CUUGCCCAUCUCCCUCUUGA | 1336 |
| CCCUAAGCAUCCUCCCUCAG | 1337 |
| AACUUCUUAGGCUUAGUGCC | 1338 |
| GGAACUUCUUAGGCUUAGUG | 1339 |
| GGGAACUUCUUAGGCUUAGU | 1340 |
| AGGGAACUUCUUAGGCUUAG | 1341 |
| UGUCUCCCAGUGGGUCCUGU | 1342 |
| AGUAUAAAUGCUUGUCUCCC | 1343 |
| GACAGAGCGAGACUCGAUCU | 1344 |
| UGACAGAGCGAGACUCGAUC | 1345 |
| GUGACAGAGCGAGACUCGAU | 1346 |
| GGUGACAGAGCGAGACUCGA | 1347 |
| UGGUGACAGAGCGAGACUCG | 1348 |
| CUGGUGACAGAGCGAGACUC | 1349 |
| CCUGGUGACAGAGCGAGACU | 1350 |
| AGCCUGGUGACAGAGCGAGA | 1351 |
| UGCACUCCAGCCUGGUGACA | 1352 |
| ACUGCACUCCAGCCUGGUGA | 1353 |
| UCACUGCACUCCAGCCUGGU | 1354 |
| UGUCACUGCACUCCAGCCUG | 1355 |
| GUGUCACUGCACUCCAGCCU | 1356 |
| AGACGGAGGUUGCAGUGAGC | 1357 |
| GAGACGGAGGUUGCAGUGAG | 1358 |
| GGAGACGGAGGUUGCAGUGA | 1359 |
| ACUUGAACCCAGGAGACGGA | 1360 |
| CACUUGAACCCAGGAGACGG | 1361 |
| UCACUUGAACCCAGGAGACG | 1362 |
| AUCACUUGAACCCAGGAGAC | 1363 |
| AAUCACUUGAACCCAGGAGA | 1364 |
| GAAUCACUUGAACCCAGGAG | 1365 |
| AGAAUCACUUGAACCCAGGA | 1366 |
| AAGAAUCACUUGAACCCAGG | 1367 |
| GAAGAAUCACUUGAACCCAG | 1368 |
| AGAAGAAUCACUUGAACCCA | 1369 |
| CAGAAGAAUCACUUGAACCC | 1370 |
| GCAGAAGAAUCACUUGAACC | 1371 |
| GGCAGAAGAAUCACUUGAAC | 1372 |
| AGGCAGAAGAAUCACUUGAA | 1373 |
| GAGGCAGAAGAAUCACUUGA | 1374 |
| UGAGGCAGAAGAAUCACUUG | 1375 |
| CUGAGGCAGAAGAAUCACUU | 1376 |
| GCUGAGGCAGAAGAAUCACU | 1377 |
| GGCUGAGGCAGAAGAAUCAC | 1378 |
| AGGCUGAGGCAGAAGAAUCA | 1379 |
| GAGGCUGAGGCAGAAGAAUC | 1380 |
| GGAGGCUGAGGCAGAAGAAU | 1381 |
| GGGAGGCUGAGGCAGAAGAA | 1382 |
| AGAUUGAGACCAUCCUGGCC | 1383 |
| GAGAUUGAGACCAUCCUGGC | 1384 |
| AGAGAUUGAGACCAUCCUGG | 1385 |
| AAGAGAUUGAGACCAUCCUG | 1386 |
| CAAGAGAUUGAGACCAUCCU | 1387 |
| GGUGGCUCACGCCAUAAUC | 1388 |
| CGGUGGCUCACGCCAUAAU | 1389 |
| GCGGUGGCUCACGCCAUAA | 1390 |
| CCCUAACCCUUCUUUAUGAC | 1391 |
| CACCCUAACCCUUCUUUAUG | 1392 |
| AUCACCCUAACCCUUCUUUA | 1393 |
| CAUCACCCUAACCCUUCUUU | 1394 |
| CCAUCACCCUAACCCUUCUU | 1395 |
| GACCAUCACCCUAACCCUUC | 1396 |
| GGACCAUCACCCUAACCCUU | 1397 |
| UGGACCAUCACCCUAACCCU | 1398 |
| CUGGACCAUCACCCUAACCC | 1399 |
| UCUGGACCAUCACCCUAACC | 1400 |
| CUCUGGACCAUCACCCUAAC | 1401 |
| GCUCUGGACCAUCACCCUAA | 1402 |
| UGCUCUGGACCAUCACCCUA | 1403 |
| GUUGCUCUGGACCAUCACCC | 1404 |
| UGUUGCUCUGGACCAUCACC | 1405 |
| ACUGUUGCUCUGGACCAUCA | 1406 |
| AACUGUUGCUCUGGACCAUC | 1407 |
| GAACUGUUGCUCUGGACCAU | 1408 |
| GAAGAACUGUUGCUCUGGAC | 1409 |
| UUGAAGAACUGUUGCUCUGG | 1410 |

TABLE 2-continued

| Sequence | SEQ ID NO: |
|---|---|
| ACUUGAAGAACUGUUGCUCU | 1411 |
| CACUUGAAGAACUGUUGCUC | 1412 |
| UACACUUGAAGAACUGUUGC | 1413 |
| GAGUACACUUGAAGAACUGU | 1414 |
| AGAGUACACUUGAAGAACUG | 1415 |
| CAGAGUACACUUGAAGAACU | 1416 |
| ACAGAGUACACUUGAAGAAC | 1417 |
| CUACAGAGUACACUUGAAGA | 1418 |
| CCUACAGAGUACACUUGAAG | 1419 |
| GCCUACAGAGUACACUUGAA | 1420 |
| AGCCUACAGAGUACACUUGA | 1421 |
| AAGCCUACAGAGUACACUUG | 1422 |
| CAGAAGCCUACAGAGUACAC | 1423 |
| CCAGAAGCCUACAGAGUACA | 1424 |
| AAAAGGGACCUCCCAGAAGC | 1425 |
| GAAAAGGGACCUCCCAGAAG | 1426 |
| UGAAAAGGGACCUCCCAGAA | 1427 |
| CUUUGACUUUGUGGACACCC | 1428 |
| GCUUUGACUUUGUGGACACC | 1429 |
| UAGCUUUGACUUUGUGGACA | 1430 |
| AUAGCUUUGACUUUGUGGAC | 1431 |
| GUCACACGGCCUCUGGAAAA | 1432 |
| UGUCACACGGCCUCUGGAAA | 1433 |
| AUGUCACACGGCCUCUGGAA | 1434 |
| AAGACCAUACAAGCACACAU | 1435 |
| ACAAGACCAUACAAGCACAC | 1436 |
| CACAAGACCAUACAAGCACA | 1437 |
| AACACAAGACCAUACAAGCA | 1438 |
| UAACACAAGACCAUACAAGC | 1439 |
| ACUGUAACACAAGACCAUAC | 1440 |
| AGACUGUAACACAAGACCAU | 1441 |
| AAGACUGUAACACAAGACCA | 1442 |
| GCCGAGAUUGUGCCACUGCA | 1443 |
| AGCCGAGAUUGUGCCACUGC | 1444 |
| GAGCCGAGAUUGUGCCACUG | 1445 |
| UGAGCCGAGAUUGUGCCACU | 1446 |
| GUGAGCCGAGAUUGUGCCAC | 1447 |
| AGUGAGCCGAGAUUGUGCCA | 1448 |

TABLE 2-continued

| Sequence | SEQ ID NO: |
|---|---|
| CAGUGAGCCGAGAUUGUGCC | 1449 |
| GCAGUGAGCCGAGAUUGUGC | 1450 |
| UGCAGUGAGCCGAGAUUGUG | 1451 |
| UUGCAGUGAGCCGAGAUUGU | 1452 |
| GUUGCAGUGAGCCGAGAUUG | 1453 |
| GGUUGCAGUGAGCCGAGAUU | 1454 |
| AGGUUGCAGUGAGCCGAGAU | 1455 |
| GAGGUUGCAGUGAGCCGAGA | 1456 |
| UGGAGGUUGCAGUGAGCCGA | 1457 |
| AGGUGGAGGUUGCAGUGAGC | 1458 |
| GAGGUGGAGGUUGCAGUGAG | 1459 |
| GGAGGUGGAGGUUGCAGUGA | 1460 |
| UGGGAGGUGGAGGUUGCAGU | 1461 |
| UCCCAGCUACUCAGGAGGCU | 1462 |
| AGUCCCAGCUACUCAGGAGG | 1463 |
| UAGUCCCAGCUACUCAGGAG | 1464 |
| AAAUAGCUGGGCAUGGUGGC | 1465 |
| AAAAUAGCUGGGCAUGGUGG | 1466 |
| GCAGGCGGAUCACCUCAAGU | 1467 |
| AGGCAGGCGGAUCACCUCAA | 1468 |
| AAGGCAGGCGGAUCACCUCA | 1469 |
| CUGUAAUCCCAGCACUUUGG | 1470 |
| CCUGUAAUCCCAGCACUUUG | 1471 |
| ACCUGUAAUCCCAGCACUUU | 1472 |
| GACCUGUAAUCCCAGCACUU | 1473 |
| AGACCUGUAAUCCCAGCACU | 1474 |
| CAGACCUGUAAUCCCAGCAC | 1475 |
| UCAGACCUGUAAUCCCAGCA | 1476 |
| CUCAGACCUGUAAUCCCAGC | 1477 |
| AGGCACAGUGGCUCAGACCU | 1478 |
| UAGGCACAGUGGCUCAGACC | 1479 |
| UUAGGCACAGUGGCUCAGAC | 1480 |
| GUUAGGCACAGUGGCUCAGA | 1481 |
| GGUUAGGCACAGUGGCUCAG | 1482 |
| AGGUUAGGCACAGUGGCUCA | 1483 |
| AUUAGGUUAGGCACAGUGGC | 1484 |
| GUCAUUAGGUUAGGCACAGU | 1485 |
| AGUCAUUAGGUUAGGCACAG | 1486 |
| AAGUCAUUAGGUUAGGCACA | 1487 |

TABLE 2-continued

| Sequence | SEQ ID NO: |
|---|---|
| AAAGUCAUUAGGUUAGGCAC | 1488 |
| GAACACCUUACUUUCUUCUC | 1489 |
| AGCUCUCUUAGAACACCUUA | 1490 |
| GGUGCCCAGCAAGAAGAGCU | 1491 |
| GGUUUAAGCGGUCUUCCGGC | 1492 |
| GGGUUUAAGCGGUCUUCCGG | 1493 |
| UGGGUUUAAGCGGUCUUCCG | 1494 |
| CUGGGUUUAAGCGGUCUUCC | 1495 |
| CAUAGCCUCGAACUCCUGGG | 1496 |
| UCAUAGCCUCGAACUCCUGG | 1497 |
| AUCAUAGCCUCGAACUCCUG | 1498 |
| GAUCAUAGCCUCGAACUCCU | 1499 |
| GCAGAGGCUAUUCACAAGUG | 1500 |
| UGCAGAGGCUAUUCACAAGU | 1501 |
| GUGCAGAGGCUAUUCACAAG | 1502 |
| AGUGCAGAGGCUAUUCACAA | 1503 |
| AGGCUGGAGUGCAGAGGCUA | 1504 |
| UUUGCCCAGGCUGGAGUGCA | 1505 |
| AUUUGCCCAGGCUGGAGUGC | 1506 |
| UAUUUGCCCAGGCUGGAGUG | 1507 |
| CUAUUUGCCCAGGCUGGAGU | 1508 |
| ACUAUUUGCCCAGGCUGGAG | 1509 |
| CCAGAGGAGCUAUUUAUGUA | 1510 |
| AGACUAAUGGGCACUGAAAA | 1511 |
| GACCAGACUAAUGGGCACUG | 1512 |
| CAGACCAGACUAAUGGGCAC | 1513 |
| GUCAGACCAGACUAAUGGGC | 1514 |
| CCAGCUCAGUCAGACCAGAC | 1515 |
| CCCAGCUCAGUCAGACCAGA | 1516 |
| GACCCAGCUCAGUCAGACCA | 1517 |
| AGACCCAGCUCAGUCAGACC | 1518 |
| AGAGACCCAGCUCAGUCAGA | 1519 |
| UCAGAGACCCAGCUCAGUCA | 1520 |
| UGACCCAGGCUAGUUAUCCC | 1521 |
| UUGACCCAGGCUAGUUAUCC | 1522 |
| UUUGACCCAGGCUAGUUAUC | 1523 |
| CUUUGACCCAGGCUAGUUAU | 1524 |
| ACUUUGACCCAGGCUAGUUA | 1525 |

TABLE 2-continued

| Sequence | SEQ ID NO: |
|---|---|
| GACUUUGACCCAGGCUAGUU | 1526 |
| GGACUUUGACCCAGGCUAGU | 1527 |
| UUCAGUCUGAGGGUCAAGGG | 1528 |
| GUUCAGUCUGAGGGUCAAGG | 1529 |
| UGUUCAGUCUGAGGGUCAAG | 1530 |
| CUGUUCAGUCUGAGGGUCAA | 1531 |
| ACUGUUCAGUCUGAGGGUCA | 1532 |
| AACUGUUCAGUCUGAGGGUC | 1533 |
| UAACUGUUCAGUCUGAGGGU | 1534 |
| UUAACUGUUCAGUCUGAGGG | 1535 |
| GUGGAAGGUCAGUGGGUUAA | 1536 |
| GUGUGGAAGGUCAGUGGGUU | 1537 |
| GGUGUGGAAGGUCAGUGGGU | 1538 |
| UGGGUGUGGAAGGUCAGUGG | 1539 |
| UUGGGUGUGGAAGGUCAGUG | 1540 |
| UCUGCUUCCAAGAACCACCC | 1541 |
| GCUCUGCUUCCAAGAACCAC | 1542 |
| AGCUCUGCUUCCAAGAACCA | 1543 |
| UAGCUCUGCUUCCAAGAACC | 1544 |
| CCUAGCUCUGCUUCCAAGAA | 1545 |
| ACAUCCUAGCUCUGCUUCCA | 1546 |
| ACCUCCCACAUCCUAGCUCU | 1547 |
| GACCUCCCACAUCCUAGCUC | 1548 |
| AGACCUCCCACAUCCUAGCU | 1549 |
| CAGACCUCCCACAUCCUAGC | 1550 |
| GCAGACCUCCCACAUCCUAG | 1551 |
| GGCAGACCUCCCACAUCCUA | 1552 |
| AGGCAGACCUCCCACAUCCU | 1553 |
| ACAGGCAGACCUCCCACAUC | 1554 |
| CACAGGCAGACCUCCCACAU | 1555 |
| GGAGGAAGCAUGACAAGGAA | 1556 |
| AAGAGGAGGAAGCAUGACAA | 1557 |
| GGGCAGCAUUUCAGUCUCUG | 1558 |
| GAUUUGCAUUGCCAUCGUGA | 1559 |
| AGAUUUGCAUUGCCAUCGUG | 1560 |
| CUCUUUAGAUUUGCAUUGCC | 1561 |
| CCUCUUUAGAUUUGCAUUGC | 1562 |
| GCCUCUUUAGAUUUGCAUUG | 1563 |
| AAGUGCCCUGCCUCUUUAGA | 1564 |

TABLE 2-continued

| Sequence | SEQ ID NO: |
| --- | --- |
| GAAGUGCCCUGCCUCUUUAG | 1565 |
| GGGAAGUGCCCUGCCUCUUU | 1566 |
| ACUGCCUGACAGGGAAGUGC | 1567 |
| GUACUGCCUGACAGGGAAGU | 1568 |
| GGUACUGCCUGACAGGGAAG | 1569 |
| CGGUACUGCCUGACAGGGAA | 1570 |
| UAUGCCCAGCGGUACUGCCU | 1571 |
| UGCUAUGCCCAGCGGUACUG | 1572 |
| UUGCUAUGCCCAGCGGUACU | 1573 |
| GUUGCUAUGCCCAGCGGUAC | 1574 |
| GGUUGCUAUGCCCAGCGGUA | 1575 |
| AGGUUGCUAUGCCCAGCGGU | 1576 |
| AGAGGUUGCUAUGCCCAGCG | 1577 |
| AGAGGCAGAGGUUGCUAUGC | 1578 |
| GAGAGGCAGAGGUUGCUAUG | 1579 |
| GGAGAGGCAGAGGUUGCUAU | 1580 |
| CGGAGAGGCAGAGGUUGCUA | 1581 |
| AACGGAGAGGCAGAGGUUGC | 1582 |
| GAGAAACGGAGAGGCAGAGG | 1583 |
| UGAGAAACGGAGAGGCAGAG | 1584 |
| UCUGAGAAACGGAGAGGCAG | 1585 |
| AGGAGGUGGAUAUGUGAGCU | 1586 |
| CCCAGGAGGUGGAUAUGUGA | 1587 |
| AGCCCAGGAGGUGGAUAUGU | 1588 |
| AAGCCCAGGAGGUGGAUAUG | 1589 |
| AAAGCCCAGGAGGUGGAUAU | 1590 |
| AAAAGCCCAGGAGGUGGAUA | 1591 |
| UAAAAGCCCAGGAGGUGGAU | 1592 |
| UUAAAAGCCCAGGAGGUGGA | 1593 |
| GCCCACUUAAAAGCCCAGGA | 1594 |
| AGCCCACUUAAAAGCCCAGG | 1595 |
| AAGCCCACUUAAAAGCCCAG | 1596 |
| AAAGCCCACUUAAAAGCCCA | 1597 |
| UAAAGCCCACUUAAAAGCCC | 1598 |
| CUAAAGCCCACUUAAAAGCC | 1599 |
| CACUAAAGCCCACUUAAAAG | 1600 |
| CCUCACUAAAGCCCACUUAA | 1601 |
| CCCUCACUAAAGCCCACUUA | 1602 |

TABLE 2-continued

| Sequence | SEQ ID NO: |
| --- | --- |
| GGAGCCCAGUUGAAGGAGGA | 1603 |
| AGGAGCCCAGUUGAAGGAGG | 1604 |
| GGAGGAGCCCAGUUGAAGGA | 1605 |
| AGGAGGAGCCCAGUUGAAGG | 1606 |
| AGUCGAAGCAGAAGAGCUGG | 1607 |
| GAGUCGAAGCAGAAGAGCUG | 1608 |
| GGAGUCGAAGCAGAAGAGCU | 1609 |
| CGGAGUCGAAGCAGAAGAGC | 1610 |
| UCGGAGUCGAAGCAGAAGAG | 1611 |
| CUCGGAGUCGAAGCAGAAGA | 1612 |
| GCUCGGAGUCGAAGCAGAAG | 1613 |
| CGCUCGGAGUCGAAGCAGAA | 1614 |
| ACAUGACACCCGCUCGGAGU | 1615 |
| ACACAUGACACCCGCUCGGA | 1616 |
| UCACACAUGACACCCGCUCG | 1617 |
| CUCACACAUGACACCCGCUC | 1618 |
| UCUCACACAUGACACCCGCU | 1619 |
| UUCUCACACAUGACACCCGC | 1620 |
| GUACUGCCUGACAGGGAAGU | 1568 |
| GGUACUGCCUGACAGGGAAG | 1569 |
| CGGUACUGCCUGACAGGGAA | 1570 |
| UAUGCCCAGCGGUACUGCCU | 1571 |
| UGCUAUGCCCAGCGGUACUG | 1572 |
| UUGCUAUGCCCAGCGGUACU | 1573 |
| GUUGCUAUGCCCAGCGGUAC | 1574 |
| GGUUGCUAUGCCCAGCGGUA | 1575 |
| AGGUUGCUAUGCCCAGCGGU | 1576 |
| AGAGGUUGCUAUGCCCAGCG | 1577 |
| AGAGGCAGAGGUUGCUAUGC | 1578 |
| GAGAGGCAGAGGUUGCUAUG | 1579 |
| GGAGAGGCAGAGGUUGCUAU | 1580 |
| CGGAGAGGCAGAGGUUGCUA | 1581 |
| AACGGAGAGGCAGAGGUUGC | 1582 |
| GAGAAACGGAGAGGCAGAGG | 1583 |
| UGAGAAACGGAGAGGCAGAG | 1584 |
| UCUGAGAAACGGAGAGGCAG | 1585 |
| AGGAGGUGGAUAUGUGAGCU | 1586 |
| CCCAGGAGGUGGAUAUGUGA | 1587 |
| AGCCCAGGAGGUGGAUAUGU | 1588 |

TABLE 2-continued

| Sequence | SEQ ID NO: |
|---|---|
| AAGCCCAGGAGGUGGAUAUG | 1589 |
| AAAGCCCAGGAGGUGGAUAU | 1590 |
| AAAAGCCCAGGAGGUGGAUA | 1591 |
| UAAAAGCCCAGGAGGUGGAU | 1592 |
| UUAAAAGCCCAGGAGGUGGA | 1593 |
| GCCCACUUAAAAGCCCAGGA | 1594 |
| AGCCCACUUAAAAGCCCAGG | 1595 |
| AAGCCCACUUAAAAGCCCAG | 1596 |
| AAAGCCCACUUAAAAGCCCA | 1597 |
| UAAAGCCCACUUAAAAGCCC | 1598 |
| CUAAAGCCCACUUAAAAGCC | 1599 |
| CACUAAAGCCCACUUAAAAG | 1600 |
| CCUCACUAAAGCCCACUUAA | 1601 |
| CCCUCACUAAAGCCCACUUA | 1602 |
| GGAGCCCAGUUGAAGGAGGA | 1603 |
| AGGAGCCCAGUUGAAGGAGG | 1604 |
| GGAGGAGCCCAGUUGAAGGA | 1605 |
| AGGAGGAGCCCAGUUGAAGG | 1606 |
| AGUCGAAGCAGAAGAGCUGG | 1607 |
| GAGUCGAAGCAGAAGAGCUG | 1608 |
| GGAGUCGAAGCAGAAGAGCU | 1609 |
| CGGAGUCGAAGCAGAAGAGC | 1610 |
| GUUCUCACACAUGACACCCG | 1621 |
| CGUUCUCACACAUGACACCC | 1622 |
| UGGCCGUUCUCACACAUGAC | 1623 |
| CUGGCCGUUCUCACACAUGA | 1624 |
| GCUGGCCGUUCUCACACAUG | 1625 |
| UGCUGGCCGUUCUCACACAU | 1626 |
| CUGCUGGCCGUUCUCACACA | 1627 |
| UCUGCUGGCCGUUCUCACAC | 1628 |
| CUCUGCUGGCCGUUCUCACA | 1629 |

In some embodiments, the siRNA molecules comprise or consist of the nucleotide sequences (sense and antisense strands) shown in Table 3.

TABLE 3

| Sense Sequence | SEQ ID NO: | Antisense Sequence | SEQ ID NO: |
|---|---|---|---|
| GUAGCCAGACAUGAGCUGU | 1630 | ACAGCUCAUGUCUGGCUAC | 1631 |
| AGACAUGAGCUGUGAGGGU | 1632 | ACCCUCACAGCUCAUGUCU | 1633 |
| AUGAGCUGUGAGGGUCAAG | 1634 | CUUGACCCUCACAGCUCAU | 1635 |
| UGAGCUGUGAGGGUCAAGC | 1636 | GCUUGACCCUCACAGCUCA | 1637 |
| GAGCUGUGAGGGUCAAGCA | 1638 | UGCUUGACCCUCACAGCUC | 1639 |
| AGCUGUGAGGGUCAAGCAC | 1640 | GUGCUUGACCCUCACAGCU | 1641 |
| GUGAGGGUCAAGCACAGCU | 1642 | AGCUGUGCUUGACCCUCAC | 1643 |
| UGAGGGUCAAGCACAGCUA | 1644 | UAGCUGUGCUUGACCCUCA | 1645 |
| GAGGGUCAAGCACAGCUAU | 1646 | AUAGCUGUGCUUGACCCUC | 1647 |
| AGGGUCAAGCACAGCUAUC | 1648 | GAUAGCUGUGCUUGACCCU | 1649 |
| GGGUCAAGCACAGCUAUCC | 1650 | GGAUAGCUGUGCUUGACCC | 1651 |
| CAAGCACAGCUAUCCAUCA | 1652 | UGAUGGAUAGCUGUGCUUG | 1653 |
| CACAGCUAUCCAUCAGAUG | 1654 | CAUCUGAUGGAUAGCUGUG | 1655 |
| ACAGCUAUCCAUCAGAUGA | 1656 | UCAUCUGAUGGAUAGCUGU | 1657 |
| CAGCUAUCCAUCAGAUGAU | 1658 | AUCAUCUGAUGGAUAGCUG | 1659 |
| AGCUAUCCAUCAGAUGAUC | 1660 | GAUCAUCUGAUGGAUAGCU | 1661 |
| GCUAUCCAUCAGAUGAUCU | 1662 | AGAUCAUCUGAUGGAUAGC | 1663 |
| CUAUCCAUCAGAUGAUCUA | 1664 | UAGAUCAUCUGAUGGAUAG | 1665 |
| CAUCAGAUGAUCUACUUUC | 1666 | GAAAGUAGAUCAUCUGAUG | 1667 |
| AGAUGAUCUACUUUCAGCC | 1668 | GGCUGAAAGUAGAUCAUCU | 1669 |
| GAUCUACUUUCAGCCUUCC | 1670 | GGAAGGCUGAAAGUAGAUC | 1671 |
| AUCUACUUUCAGCCUUCCU | 1672 | AGGAAGGCUGAAAGUAGAU | 1673 |
| CAAUAGAAGACAGGUGGCU | 1674 | AGCCACCUGUCUUCUAUUG | 1675 |
| AAUAGAAGACAGGUGGCUG | 1676 | CAGCCACCUGUCUUCUAUU | 1677 |
| CAGGUGGCUGUACCCUUGG | 1678 | CCAAGGGUACAGCCACCUG | 1679 |
| AGGUGGCUGUACCCUUGGC | 1680 | GCCAAGGGUACAGCCACCU | 1681 |
| GGCUGUACCCUUGGCCAAG | 1682 | CUUGGCCAAGGGUACAGCC | 1683 |
| UGGUGUCUGCUGUCACUGU | 1684 | ACAGUGACAGCAGACACCA | 1685 |
| GUCUGCUGUCACUGUGCCC | 1686 | GGGCACAGUGACAGCAGAC | 1687 |
| CUGCUGUCACUGUGCCCUC | 1688 | GAGGGCACAGUGACAGCAG | 1689 |
| UGCUGUCACUGUGCCCUCA | 1690 | UGAGGGCACAGUGACAGCA | 1691 |
| GCUGUCACUGUGCCCUCAU | 1692 | AUGAGGGCACAGUGACAGC | 1693 |
| CUGUCACUGUGCCCUCAUU | 1694 | AAUGAGGGCACAGUGACAG | 1695 |
| UGUCACUGUGCCCUCAUUG | 1696 | CAAUGAGGGCACAGUGACA | 1697 |
| GUCACUGUGCCCUCAUUGG | 1698 | CCAAUGAGGGCACAGUGAC | 1699 |
| ACUGUGCCCUCAUUGGCCC | 1700 | GGGCCAAUGAGGGCACAGU | 1701 |
| CCCAGCAAUCAGACUCAAC | 1702 | GUUGAGUCUGAUUGCUGGG | 1703 |
| GGAGCAACUGCCAUCCGAG | 1704 | CUCGGAUGGCAGUUGCUCC | 1705 |

TABLE 3-continued

| Sense Sequence | SEQ ID NO: | Antisense Sequence | SEQ ID NO: |
|---|---|---|---|
| GAGCAACUGCCAUCCGAGG | 1706 | CCUCGGAUGGCAGUUGCUC | 1707 |
| AGCAACUGCCAUCCGAGGC | 1708 | GCCUCGGAUGGCAGUUGCU | 1709 |
| GCAACUGCCAUCCGAGGCU | 1710 | AGCCUCGGAUGGCAGUUGC | 1711 |
| CAACUGCCAUCCGAGGCUC | 1712 | GAGCCUCGGAUGGCAGUUG | 1713 |
| GCCAUCCGAGGCUCCUGAA | 1714 | UUCAGGAGCCUCGGAUGGC | 1715 |
| AACCAGGGCCAUUCACCAG | 1716 | CUGGUGAAUGGCCCUGGUU | 1717 |
| ACCAGGGCCAUUCACCAGG | 1718 | CCUGGUGAAUGGCCCUGGU | 1719 |
| CCAGGGCCAUUCACCAGGA | 1720 | UCCUGGUGAAUGGCCCUGG | 1721 |
| CAGGGCCAUUCACCAGGAG | 1722 | CUCCUGGUGAAUGGCCCUG | 1723 |
| GGCCAUUCACCAGGAGCAU | 1724 | AUGCUCCUGGUGAAUGGCC | 1725 |
| GCCAUUCACCAGGAGCAUG | 1726 | CAUGCUCCUGGUGAAUGGC | 1727 |
| CCAUUCACCAGGAGCAUGC | 1728 | GCAUGCUCCUGGUGAAUGG | 1729 |
| CAUUCACCAGGAGCAUGCG | 1730 | CGCAUGCUCCUGGUGAAUG | 1731 |
| AUUCACCAGGAGCAUGCGG | 1732 | CCGCAUGCUCCUGGUGAAU | 1733 |
| UUCACCAGGAGCAUGCGGC | 1734 | GCCGCAUGCUCCUGGUGAA | 1735 |
| UCACCAGGAGCAUGCGGCU | 1736 | AGCCGCAUGCUCCUGGUGA | 1737 |
| AGCAUGCGGCUCCCUGAUG | 1738 | CAUCAGGGAGCCGCAUGCU | 1739 |
| GCAUGCGGCUCCCUGAUGU | 1740 | ACAUCAGGGAGCCGCAUGC | 1741 |
| CAUGCGGCUCCCUGAUGUC | 1742 | GACAUCAGGGAGCCGCAUG | 1743 |
| AUGCGGCUCCCUGAUGUCC | 1744 | GGACAUCAGGGAGCCGCAU | 1745 |
| UGCGGCUCCCUGAUGUCCA | 1746 | UGGACAUCAGGGAGCCGCA | 1747 |
| GCUCCCUGAUGUCCAGCUC | 1748 | GAGCUGGACAUCAGGGAGC | 1749 |
| CUCCCUGAUGUCCAGCUCU | 1750 | AGAGCUGGACAUCAGGGAG | 1751 |
| UCCCUGAUGUCCAGCUCUG | 1752 | CAGAGCUGGACAUCAGGGA | 1753 |
| CCCUGAUGUCCAGCUCUGG | 1754 | CCAGAGCUGGACAUCAGGG | 1755 |
| CCUGAUGUCCAGCUCUGGC | 1756 | GCCAGAGCUGGACAUCAGG | 1757 |
| CUGAUGUCCAGCUCUGGCU | 1758 | AGCCAGAGCUGGACAUCAG | 1759 |
| UCUGGUGCUGGAGCUAGCC | 1760 | GGCUAGCUCCAGCACCAGA | 1761 |
| UGGUGCUGGAGCUAGCCAA | 1762 | UUGGCUAGCUCCAGCACCA | 1763 |
| GGUGCUGGAGCUAGCCAAG | 1764 | CUUGGCUAGCUCCAGCACC | 1765 |
| GUGCUGGAGCUAGCCAAGC | 1766 | GCUUGGCUAGCUCCAGCAC | 1767 |
| GCUGGAGCUAGCCAAGCAG | 1768 | CUGCUUGGCUAGCUCCAGC | 1769 |
| CUGGAGCUAGCCAAGCAGC | 1770 | GCUGCUUGGCUAGCUCCAG | 1771 |
| UGGAGCUAGCCAAGCAGCA | 1772 | UGCUGCUUGGCUAGCUCCA | 1773 |
| GGAGCUAGCCAAGCAGCAA | 1774 | UUGCUGCUUGGCUAGCUCC | 1775 |
| GAGCUAGCCAAGCAGCAAA | 1776 | UUUGCUGCUUGGCUAGCUC | 1777 |
| AGCUAGCCAAGCAGCAAAU | 1778 | AUUUGCUGCUUGGCUAGCU | 1779 |
| GCUAGCCAAGCAGCAAAUC | 1780 | GAUUUGCUGCUUGGCUAGC | 1781 |
| CAGCAAAUCCUGGAUGGGU | 1782 | ACCCAUCCAGGAUUUGCUG | 1783 |
| AGCAAAUCCUGGAUGGGUU | 1784 | AACCCAUCCAGGAUUUGCU | 1785 |
| GCAAAUCCUGGAUGGGUUG | 1786 | CAACCCAUCCAGGAUUUGC | 1787 |
| CAAAUCCUGGAUGGGUUGC | 1788 | GCAACCCAUCCAGGAUUUG | 1789 |
| AAAUCCUGGAUGGGUUGCA | 1790 | UGCAACCCAUCCAGGAUUU | 1791 |
| GGUUGCACCUGACCAGUCG | 1792 | CGACUGGUCAGGUGCAACC | 1793 |
| GUUGCACCUGACCAGUCGU | 1794 | ACGACUGGUCAGGUGCAAC | 1795 |
| UUGCACCUGACCAGUCGUC | 1796 | GACGACUGGUCAGGUGCAA | 1797 |
| UGCACCUGACCAGUCGUCC | 1798 | GGACGACUGGUCAGGUGCA | 1799 |
| UGACCAGUCGUCCCAGAAU | 1800 | AUUCUGGGACGACUGGUCA | 1801 |
| GACCAGUCGUCCCAGAAUA | 1802 | UAUUCUGGGACGACUGGUC | 1803 |
| ACCAGUCGUCCCAGAAUAA | 1804 | UUAUUCUGGGACGACUGGU | 1805 |
| CCAGUCGUCCCAGAAUAAC | 1806 | GUUAUUCUGGGACGACUGG | 1807 |
| CAGUCGUCCCAGAAUAACU | 1808 | AGUUAUUCUGGGACGACUG | 1809 |
| AGUCGUCCCAGAAUAACUC | 1810 | GAGUUAUUCUGGGACGACU | 1811 |
| GUCGUCCCAGAAUAACUCA | 1812 | UGAGUUAUUCUGGGACGAC | 1813 |
| UCGUCCCAGAAUAACUCAU | 1814 | AUGAGUUAUUCUGGGACGA | 1815 |
| CGUCCCAGAAUAACUCAUC | 1816 | GAUGAGUUAUUCUGGGACG | 1817 |
| GUCCCAGAAUAACUCAUCC | 1818 | GGAUGAGUUAUUCUGGGAC | 1819 |
| UCCCAGAAUAACUCAUCCU | 1820 | AGGAUGAGUUAUUCUGGGA | 1821 |
| CCCAGAAUAACUCAUCCUC | 1822 | GAGGAUGAGUUAUUCUGGG | 1823 |
| GACUACAGCCAGGGAGUGU | 1824 | ACACUCCCUGGCUGUAGUC | 1825 |
| ACUACAGCCAGGGAGUGUG | 1826 | CACACUCCCUGGCUGUAGU | 1827 |
| CUACAGCCAGGGAGUGUGG | 1828 | CCACACUCCCUGGCUGUAG | 1829 |
| GAGUGUGGCUCCAGGGAAU | 1830 | AUUCCCUGGAGCCACACUC | 1831 |
| GGGAGGAGGUCAUCAGCUU | 1832 | AAGCUGAUGACCUCCUCCC | 1833 |
| GAGGUCAUCAGCUUUGCUA | 1834 | UAGCAAAGCUGAUGACCUC | 1835 |
| AGGUCAUCAGCUUUGCUAC | 1836 | GUAGCAAAGCUGAUGACCU | 1837 |
| GGUCAUCAGCUUUGCUACU | 1838 | AGUAGCAAAGCUGAUGACC | 1839 |
| GCUUUGCUACUGUCACAGA | 1840 | UCUGUGACAGUAGCAAAGC | 1841 |
| CUUUGCUACUGUCACAGAC | 1842 | GUCUGUGACAGUAGCAAAG | 1843 |
| UUUGCUACUGUCACAGACU | 1844 | AGUCUGUGACAGUAGCAAA | 1845 |
| UUGCUACUGUCACAGACUC | 1846 | GAGUCUGUGACAGUAGCAA | 1847 |
| UGCUACUGUCACAGACUCC | 1848 | GGAGUCUGUGACAGUAGCA | 1849 |
| ACUGUCACAGACUCCACUU | 1850 | AAGUGGAGUCUGUGACAGU | 1851 |
| CUGUCACAGACUCCACUUC | 1852 | GAAGUGGAGUCUGUGACAG | 1853 |
| UGUCACAGACUCCACUUCA | 1854 | UGAAGUGGAGUCUGUGACA | 1855 |
| GUCACAGACUCCACUUCAG | 1856 | CUGAAGUGGAGUCUGUGAC | 1857 |

TABLE 3-continued

| Sense Sequence | SEQ ID NO: | Antisense Sequence | SEQ ID NO: |
|---|---|---|---|
| UCACAGACUCCACUUCAGC | 1858 | GCUGAAGUGGAGUCUGUGA | 1859 |
| CACAGACUCCACUUCAGCC | 1860 | GGCUGAAGUGGAGUCUGUG | 1861 |
| UCCACUUCAGCCUACAGCU | 1862 | AGCUGUAGGCUGAAGUGGA | 1863 |
| CCACUUCAGCCUACAGCUC | 1864 | GAGCUGUAGGCUGAAGUGG | 1865 |
| CACUUCAGCCUACAGCUCC | 1866 | GGAGCUGUAGGCUGAAGUG | 1867 |
| ACUUCAGCCUACAGCUCCC | 1868 | GGGAGCUGUAGGCUGAAGU | 1869 |
| CCUACAGCUCCCUGCUCAC | 1870 | GUGAGCAGGGAGCUGUAGG | 1871 |
| CUACAGCUCCCUGCUCACU | 1872 | AGUGAGCAGGGAGCUGUAG | 1873 |
| UACAGCUCCCUGCUCACUU | 1874 | AAGUGAGCAGGGAGCUGUA | 1875 |
| GCUCCCUGCUCACUUUUCA | 1876 | UGAAAAGUGAGCAGGGAG | 1877 |
| CUCCCUGCUCACUUUUCAC | 1878 | GUGAAAAGUGAGCAGGGAG | 1879 |
| GCUCACUUUUCACCUGUCC | 1880 | GGACAGGUGAAAAGUGAGC | 1881 |
| CUCACUUUUCACCUGUCCA | 1882 | UGGACAGGUGAAAAGUGAG | 1883 |
| UGUCCACUCCUCGGUCCCA | 1884 | UGGGACCGAGGAGUGGACA | 1885 |
| UCGGUCCCACCACCUGUAC | 1886 | GUACAGGUGGUGGGACCGA | 1887 |
| CCACCACCUGUACCAUGCC | 1888 | GGCAUGGUACAGGUGGUGG | 1889 |
| CACCACCUGUACCAUGCCC | 1890 | GGGCAUGGUACAGGUGGUG | 1891 |
| ACCACCUGUACCAUGCCCG | 1892 | CGGGCAUGGUACAGGUGGU | 1893 |
| CACCCUUCCUGGCACUCUU | 1894 | AAGAGUGCCAGGAAGGGUG | 1895 |
| ACCCUUCCUGGCACUCUUU | 1896 | AAAGAGUGCCAGGAAGGGU | 1897 |
| CCCUUCCUGGCACUCUUUG | 1898 | CAAAGAGUGCCAGGAAGGG | 1899 |
| CCUUCCUGGCACUCUUUGC | 1900 | GCAAAGAGUGCCAGGAAGG | 1901 |
| UUCCUGGCACUCUUUGCUU | 1902 | AAGCAAAGAGUGCCAGGAA | 1903 |
| UCCUGGCACUCUUUGCUUG | 1904 | CAAGCAAAGAGUGCCAGGA | 1905 |
| CCUGGCACUCUUUGCUUGA | 1906 | UCAAGCAAAGAGUGCCAGG | 1907 |
| CUGGCACUCUUUGCUUGAG | 1908 | CUCAAGCAAAGAGUGCCAG | 1909 |
| UGGCACUCUUUGCUUGAGG | 1910 | CCUCAAGCAAAGAGUGCCA | 1911 |
| GGCACUCUUUGCUUGAGGA | 1912 | UCCUCAAGCAAAGAGUGCC | 1913 |
| GCACUCUUUGCUUGAGGAU | 1914 | AUCCUCAAGCAAAGAGUGC | 1915 |
| CACUCUUUGCUUGAGGAUC | 1916 | GAUCCUCAAGCAAAGAGUG | 1917 |
| ACUCUUUGCUUGAGGAUCU | 1918 | AGAUCCUCAAGCAAAGAGU | 1919 |
| CUCUUUGCUUGAGGAUCUU | 1920 | AAGAUCCUCAAGCAAAGAG | 1921 |
| UCUUUGCUUGAGGAUCUUC | 1922 | GAAGAUCCUCAAGCAAAGA | 1923 |
| UGCUUGAGGAUCUUCCGAU | 1924 | AUCGGAAGAUCCUCAAGCA | 1925 |
| GCUUGAGGAUCUUCCGAUG | 1926 | CAUCGGAAGAUCCUCAAGC | 1927 |
| GCACUCUCCUGGCUGAGCA | 1928 | UGCUCAGCCAGGAGAGUGC | 1929 |
| CUCCUGGCUGAGCACCACA | 1930 | UGUGGUGCUCAGCCAGGAG | 1931 |
| UGGCUGAGCACCACAUCAC | 1932 | GUGAUGUGGUGCUCAGCCA | 1933 |
| GGCUGAGCACCACAUCACC | 1934 | GGUGAUGUGGUGCUCAGCC | 1935 |
| GCUGAGCACCACAUCACCA | 1936 | UGGUGAUGUGGUGCUCAGC | 1937 |
| CUGAGCACCACAUCACCAA | 1938 | UUGGUGAUGUGGUGCUCAG | 1939 |
| CCAACCUGGGCUGGCAUAC | 1940 | GUAUGCCAGCCCAGGUUGG | 1941 |
| CAACCUGGGCUGGCAUACC | 1942 | GGUAUGCCAGCCCAGGUUG | 1943 |
| AACCUGGGCUGGCAUACCU | 1944 | AGGUAUGCCAGCCCAGGUU | 1945 |
| ACCUGGGCUGGCAUACCUU | 1946 | AAGGUAUGCCAGCCCAGGU | 1947 |
| CCUGGGCUGGCAUACCUUA | 1948 | UAAGGUAUGCCAGCCCAGG | 1949 |
| CUGGGCUGGCAUACCUUAA | 1950 | UUAAGGUAUGCCAGCCCAG | 1951 |
| UGGGCUGGCAUACCUUAAC | 1952 | GUUAAGGUAUGCCAGCCCA | 1953 |
| GGGCUGGCAUACCUUAACU | 1954 | AGUUAAGGUAUGCCAGCCC | 1955 |
| GGCUGGCAUACCUUAACUC | 1956 | GAGUUAAGGUAUGCCAGCC | 1957 |
| GCUGGCAUACCUUAACUCU | 1958 | AGAGUUAAGGUAUGCCAGC | 1959 |
| CAUACCUUAACUCUGCCCU | 1960 | AGGGCAGAGUUAAGGUAUG | 1961 |
| AUACCUUAACUCUGCCCUC | 1962 | GAGGGCAGAGUUAAGGUAU | 1963 |
| UACCUUAACUCUGCCCUCU | 1964 | AGAGGGCAGAGUUAAGGUA | 1965 |
| UCUGCCCUCUAGUGGCUUG | 1966 | CAAGCCACUAGAGGGCAGA | 1967 |
| CUGCCCUCUAGUGGCUUGA | 1968 | UCAAGCCACUAGAGGGCAG | 1969 |
| UGCCCUCUAGUGGCUUGAG | 1970 | CUCAAGCCACUAGAGGGCA | 1971 |
| AGAAGUCUGGUGUCCUGAA | 1972 | UUCAGGACACCAGACUUCU | 1973 |
| CAGGACACCAGCAGCCCUU | 1974 | AAGGGCUGCUGGUGUCCUG | 1975 |
| AGGACACCAGCAGCCCUUC | 1976 | GAAGGGCUGCUGGUGUCCU | 1977 |
| ACACCAGCAGCCCUUCCUA | 1978 | UAGGAAGGGCUGCUGGUGU | 1979 |
| CACCAGCAGCCCUUCCUAG | 1980 | CUAGGAAGGGCUGCUGGUG | 1981 |
| ACCAGCAGCCCUUCCUAGA | 1982 | UCUAGGAAGGGCUGCUGGU | 1983 |
| CCAGCAGCCCUUCCUAGAG | 1984 | CUCUAGGAAGGGCUGCUGG | 1985 |
| CAGCAGCCCUUCCUAGAGC | 1986 | GCUCUAGGAAGGGCUGCUG | 1987 |
| AGCAGCCCUUCCUAGAGCU | 1988 | AGCUCUAGGAAGGGCUGCU | 1989 |
| GCCCUUCCUAGAGCUUAAG | 1990 | CUUAAGCUCUAGGAAGGGC | 1991 |
| CCCUUCCUAGAGCUUAAGA | 1992 | UCUUAAGCUCUAGGAAGGG | 1993 |
| AGCUUAAGAUCCGAGCCAA | 1994 | UUGGCUCGGAUCUUAAGCU | 1995 |
| GCUUAAGAUCCGAGCCAAU | 1996 | AUUGGCUCGGAUCUUAAGC | 1997 |
| CUUAAGAUCCGAGCCAAUG | 1998 | CAUUGGCUCGGAUCUUAAG | 1999 |
| UUAAGAUCCGAGCCAAUGA | 2000 | UCAUUGGCUCGGAUCUUAA | 2001 |
| UAAGAUCCGAGCCAAUGAG | 2002 | CUCAUUGGCUCGGAUCUUA | 2003 |
| CGAGCCAAUGAGCCUGGAG | 2004 | CUCCAGGCUCAUUGGCUCG | 2005 |
| CCCUUAUGUUCAGGCGAG | 2006 | CUCGCCUGCAACAUAAGGG | 2007 |
| CAUUACGUAGACUUCCAGG | 2008 | CCUGGAAGUCUACGUAAUG | 2009 |

TABLE 3-continued

| Sense Sequence | SEQ ID NO: | Antisense Sequence | SEQ ID NO: |
|---|---|---|---|
| AUUACGUAGACUUCCAGGA | 2010 | UCCUGGAAGUCUACGUAAU | 2011 |
| UUACGUAGACUUCCAGGAA | 2012 | UUCCUGGAAGUCUACGUAA | 2013 |
| ACUGGAUACUGCAGCCCGA | 2014 | UCGGGCUGCAGUAUCCAGU | 2015 |
| CUGGAUACUGCAGCCCGAG | 2016 | CUCGGGCUGCAGUAUCCAG | 2017 |
| UGGAUACUGCAGCCCGAGG | 2018 | CCUCGGGCUGCAGUAUCCA | 2019 |
| GGGUACCAGCUGAAUUACU | 2020 | AGUAAUUCAGCUGGUACCC | 2021 |
| CUGAAUUACUGCAGUGGGC | 2022 | GCCCACUGCAGUAAUUCAG | 2023 |
| UGAAUUACUGCAGUGGGCA | 2024 | UGCCCACUGCAGUAAUUCA | 2025 |
| UGGCAGCCCAGGCAUUGCU | 2026 | AGCAAUGCCUGGGCUGCCA | 2027 |
| GCAUUGCUGCCUCUUUCCA | 2028 | UGGAAAGAGGCAGCAAUGC | 2029 |
| CAUUGCUGCCUCUUUCCAU | 2030 | AUGGAAAGAGGCAGCAAUG | 2031 |
| AUUGCUGCCUCUUUCCAUU | 2032 | AAUGGAAAGAGGCAGCAAU | 2033 |
| UGCUGCCUCUUUCCAUUCU | 2034 | AGAAUGGAAAGAGGCAGCA | 2035 |
| GCUGCCUCUUUCCAUUCUG | 2036 | CAGAAUGGAAAGAGGCAGC | 2037 |
| CUGCCUCUUUCCAUUCUGC | 2038 | GCAGAAUGGAAAGAGGCAG | 2039 |
| UGCCUCUUUCCAUUCUGCC | 2040 | GGCAGAAUGGAAAGAGGCA | 2041 |
| GCCUCUUUCCAUUCUGCCG | 2042 | CGGCAGAAUGGAAAGAGGC | 2043 |
| CCUCUUUCCAUUCUGCCGU | 2044 | ACGGCAGAAUGGAAAGAGG | 2045 |
| CUCUUUCCAUUCUGCCGUC | 2046 | GACGGCAGAAUGGAAAGAG | 2047 |
| CAUUCUGCCGUCUUCAGCC | 2048 | GGCUGAAGACGGCAGAAUG | 2049 |
| CUUCAGCCUCCUCAAAGCC | 2050 | GGCUUUGAGGAGGCUGAAG | 2051 |
| UUCAGCCUCCUCAAAGCCA | 2052 | UGGCUUUGAGGAGGCUGAA | 2053 |
| UCAGCCUCCUCAAAGCCAA | 2054 | UUGGCUUUGAGGAGGCUGA | 2055 |
| CAGCCUCCUCAAAGCCAAC | 2056 | GUUGGCUUUGAGGAGGCUG | 2057 |
| UCCUUGGCCUGCCAGUACC | 2058 | GGUACUGGCAGGCCAAGGA | 2059 |
| CCUGCCAGUACCUCCUGUU | 2060 | AACAGGAGGUACUGGCAGG | 2061 |
| CUGCCAGUACCUCCUGUUG | 2062 | CAACAGGAGGUACUGGCAG | 2063 |
| UGCCAGUACCUCCUGUUGU | 2064 | ACAACAGGAGGUACUGGCA | 2065 |
| GCCAGUACCUCCUGUUGUG | 2066 | CACAACAGGAGGUACUGGC | 2067 |
| CCAGUACCUCCUGUUGUGU | 2068 | ACACAACAGGAGGUACUGG | 2069 |
| CAGUACCUCCUGUUGUGUC | 2070 | GACACAACAGGAGGUACUG | 2071 |
| GUACCUCCUGUUGUGUCCC | 2072 | GGGACACAACAGGAGGUAC | 2073 |
| UACCUCCUGUUGUGUCCCU | 2074 | AGGGACACAACAGGAGGUA | 2075 |
| ACCUCCUGUUGUGUCCCUA | 2076 | UAGGGACACAACAGGAGGU | 2077 |
| CCUCCUGUUGUGUCCCUAC | 2078 | GUAGGGACACAACAGGAGG | 2079 |
| CUCCUGUUGUGUCCCUACU | 2080 | AGUAGGGACACAACAGGAG | 2081 |
| UUGUGUCCCUACUGCCCGA | 2082 | UCGGGCAGUAGGGACACAA | 2083 |
| UGUGUCCCUACUGCCCGAA | 2084 | UUCGGGCAGUAGGGACACA | 2085 |
| GUGUCCCUACUGCCCGAAG | 2086 | CUUCGGGCAGUAGGGACAC | 2087 |
| UGUCCCUACUGCCCGAAGG | 2088 | CCUUCGGGCAGUAGGGACA | 2089 |
| UCUCUCUCCUCUACCUGGA | 2090 | UCCAGGUAGAGGAGAGAGA | 2091 |
| UCUCCUCUACCUGGAUCAU | 2092 | AUGAUCCAGGUAGAGGAGA | 2093 |
| CUCCUCUACCUGGAUCAUA | 2094 | UAUGAUCCAGGUAGAGGAG | 2095 |
| UCCUCUACCUGGAUCAUAA | 2096 | UUAUGAUCCAGGUAGAGGA | 2097 |
| CCUCUACCUGGAUCAUAAU | 2098 | AUUAUGAUCCAGGUAGAGG | 2099 |
| CUCUACCUGGAUCAUAAUG | 2100 | CAUUAUGAUCCAGGUAGAG | 2101 |
| UCUACCUGGAUCAUAAUGG | 2102 | CCAUUAUGAUCCAGGUAGA | 2103 |
| CUACCUGGAUCAUAAUGGC | 2104 | GCCAUUAUGAUCCAGGUAG | 2105 |
| UACCUGGAUCAUAAUGGCA | 2106 | UGCCAUUAUGAUCCAGGUA | 2107 |
| ACCUGGAUCAUAAUGGCAA | 2108 | UUGCCAUUAUGAUCCAGGU | 2109 |
| CCUGGAUCAUAAUGGCAAU | 2110 | AUUGCCAUUAUGAUCCAGG | 2111 |
| CUGGAUCAUAAUGGCAAUG | 2112 | CAUUGCCAUUAUGAUCCAG | 2113 |
| UGGAUCAUAAUGGCAAUGU | 2114 | ACAUUGCCAUUAUGAUCCA | 2115 |
| GGAUCAUAAUGGCAAUGUG | 2116 | CACAUUGCCAUUAUGAUCC | 2117 |
| GAUCAUAAUGGCAAUGUGG | 2118 | CCACAUUGCCAUUAUGAUC | 2119 |
| AUAAUGGCAAUGUGGUCAA | 2120 | UUGACCACAUUGCCAUUAU | 2121 |
| UAAUGGCAAUGUGGUCAAG | 2122 | CUUGACCACAUUGCCAUUA | 2123 |
| AAUGGCAAUGUGGUCAAGA | 2124 | UCUUGACCACAUUGCCAUU | 2125 |
| AAUGUGGUCAAGACGGAUG | 2126 | CAUCCGUCUUGACCACAUU | 2127 |
| AUGUGGUCAAGACGGAUGU | 2128 | ACAUCCGUCUUGACCACAU | 2129 |
| UGUGGUCAAGACGGAUGUG | 2130 | CACAUCCGUCUUGACCACA | 2131 |
| GUGGUCAAGACGGAUGUGC | 2132 | GCACAUCCGUCUUGACCAC | 2133 |
| UGGUCAAGACGGAUGUGCC | 2134 | GGCACAUCCGUCUUGACCA | 2135 |
| GGUCAAGACGGAUGUGCCA | 2136 | UGGCACAUCCGUCUUGACC | 2137 |
| GUCAAGACGGAUGUGCCAG | 2138 | CUGGCACAUCCGUCUUGAC | 2139 |
| UCAAGACGGAUGUGCCAGA | 2140 | UCUGGCACAUCCGUCUUGA | 2141 |
| CAAGACGGAUGUGCCAGAU | 2142 | AUCUGGCACAUCCGUCUUG | 2143 |
| AAGACGGAUGUGCCAGAUA | 2144 | UAUCUGGCACAUCCGUCUU | 2145 |
| AGACGGAUGUGCCAGAUAU | 2146 | AUAUCUGGCACAUCCGUCU | 2147 |
| GACGGAUGUGCCAGAUAUG | 2148 | CAUAUCUGGCACAUCCGUC | 2149 |
| ACGGAUGUGCCAGAUAUGG | 2150 | CCAUAUCUGGCACAUCCGU | 2151 |
| CGGAUGUGCCAGAUAUGGU | 2152 | ACCAUAUCUGGCACAUCCG | 2153 |
| GGAUGUGCCAGAUAUGGUG | 2154 | CACCAUAUCUGGCACAUCC | 2155 |
| GAUGUGCCAGAUAUGGUGG | 2156 | CCACCAUAUCUGGCACAUC | 2157 |
| GCCAGAUAUGGUGGUGGAG | 2158 | CUCCACCACCAUAUCUGGC | 2159 |
| CCAGAUAUGGUGGUGGAGG | 2160 | CCUCCACCACCAUAUCUGG | 2161 |

TABLE 3-continued

| Sense Sequence | SEQ ID NO: | Antisense Sequence | SEQ ID NO: |
|---|---|---|---|
| CAGAUAUGGUGGUGGAGGC | 2162 | GCCUCCACCACCAUAUCUG | 2163 |
| AGAUAUGGUGGUGGAGGCC | 2164 | GGCCUCCACCACCAUAUCU | 2165 |
| GAUAUGGUGGUGGAGGCCU | 2166 | AGGCCUCCACCACCAUAUC | 2167 |
| AUAUGGUGGUGGAGGCCUG | 2168 | CAGGCCUCCACCACCAUAU | 2169 |
| CCUGUGGCUGCAGCUAGCA | 2170 | UGCUAGCUGCAGCCACAGG | 2171 |
| UGUGGCUGCAGCUAGCAAG | 2172 | CUUGCUAGCUGCAGCCACA | 2173 |
| GUGGCUGCAGCUAGCAAGA | 2174 | UCUUGCUAGCUGCAGCCAC | 2175 |
| UGGCUGCAGCUAGCAAGAG | 2176 | CUCUUGCUAGCUGCAGCCA | 2177 |
| GGCUGCAGCUAGCAAGAGG | 2178 | CCUCUUGCUAGCUGCAGCC | 2179 |
| CUGCAGCUAGCAAGAGGAC | 2180 | GUCCUCUUGCUAGCUGCAG | 2181 |
| CAGCUAGCAAGAGGACCUG | 2182 | CAGGUCCUCUUGCUAGCUG | 2183 |
| GCUAGCAAGAGGACCUGGG | 2184 | CCCAGGUCCUCUUGCUAGC | 2185 |
| AGACCAAGAUGAAGUUUCC | 2186 | GGAAACUUCAUCUUGGUCU | 2187 |
| UGAAGUUUCCCAGGCACAG | 2188 | CUGUGCCUGGGAAACUUCA | 2189 |
| GAAGUUUCCCAGGCACAGG | 2190 | CCUGUGCCUGGGAAACUUC | 2191 |
| UCCCAGGCACAGGGCAUCU | 2192 | AGAUGCCCUGUGCCUGGGA | 2193 |
| GGCAUCUGUGACUGGAGGC | 2194 | GCCUCCAGUCACAGAUGCC | 2195 |
| GCAUCUGUGACUGGAGGCA | 2196 | UGCCUCCAGUCACAGAUGC | 2197 |
| CAACCACCUGGCAAUAUGA | 2198 | UCAUAUUGCCAGGUGGUUG | 2199 |
| AACCACCUGGCAAUAUGAC | 2200 | GUCAUAUUGCCAGGUGGUU | 2201 |
| ACCACCUGGCAAUAUGACU | 2202 | AGUCAUAUUGCCAGGUGGU | 2203 |
| CCACCUGGCAAUAUGACUC | 2204 | GAGUCAUAUUGCCAGGUGG | 2205 |
| CACCUGGCAAUAUGACUCA | 2206 | UGAGUCAUAUUGCCAGGUG | 2207 |
| ACCUGGCAAUAUGACUCAC | 2208 | GUGAGUCAUAUUGCCAGGU | 2209 |
| CCUGGCAAUAUGACUCACU | 2210 | AGUGAGUCAUAUUGCCAGG | 2211 |
| CUGGCAAUAUGACUCACUU | 2212 | AAGUGAGUCAUAUUGCCAG | 2213 |
| UGGCAAUAUGACUCACUUG | 2214 | CAAGUGAGUCAUAUUGCCA | 2215 |
| AAUAUGACUCACUUGACCC | 2216 | GGGUCAAGUGAGUCAUAUU | 2217 |
| CCCUAUGGGACCCAAAUGG | 2218 | CCAUUUGGGUCCCAUAGGG | 2219 |
| CCUAUGGGACCCAAAUGGG | 2220 | CCCAUUUGGGUCCCAUAGG | 2221 |
| CUAUGGGACCCAAAUGGGC | 2222 | GCCCAUUUGGGUCCCAUAG | 2223 |
| UAUGGGACCCAAAUGGGCA | 2224 | UGCCCAUUUGGGUCCCAUA | 2225 |
| AUGGGACCCAAAUGGGCAC | 2226 | GUGCCCAUUUGGGUCCCAU | 2227 |
| CCCAAAUGGGCACUUUCUU | 2228 | AAGAAAGUGCCCAUUUGGG | 2229 |
| CCAAAUGGGCACUUUCUUG | 2230 | CAAGAAAGUGCCCAUUUGG | 2231 |
| CAAAUGGGCACUUUCUUGU | 2232 | ACAAGAAAGUGCCCAUUUG | 2233 |
| AAAUGGGCACUUUCUUGUC | 2234 | GACAAGAAAGUGCCCAUUU | 2235 |
| AAUGGGCACUUUCUUGUCU | 2236 | AGACAAGAAAGUGCCCAUU | 2237 |
| UGGGCACUUUCUUGUCUGA | 2238 | UCAGACAAGAAAGUGCCCA | 2239 |
| GGGCACUUUCUUGUCUGAG | 2240 | CUCAGACAAGAAAGUGCCC | 2241 |
| UGGCUUAUUCCAGGUUGGC | 2242 | GCCAACCUGGAAUAAGCCA | 2243 |
| GGCUUAUUCCAGGUUGGCU | 2244 | AGCCAACCUGGAAUAAGCC | 2245 |
| GCUUAUUCCAGGUUGGCUG | 2246 | CAGCCAACCUGGAAUAAGC | 2247 |
| CUUAUUCCAGGUUGGCUGA | 2248 | UCAGCCAACCUGGAAUAAG | 2249 |
| UUCCAGGUUGGCUGAUGUG | 2250 | CACAUCAGCCAACCUGGAA | 2251 |
| UCCAGGUUGGCUGAUGUGU | 2252 | ACACAUCAGCCAACCUGGA | 2253 |
| CCAGGUUGGCUGAUGUGUU | 2254 | AACACAUCAGCCAACCUGG | 2255 |
| CAGGUUGGCUGAUGUGUUG | 2256 | CAACACAUCAGCCAACCUG | 2257 |
| AGGUUGGCUGAUGUGUUGG | 2258 | CCAACACAUCAGCCAACCU | 2259 |
| GGUUGGCUGAUGUGUUGGG | 2260 | CCCAACACAUCAGCCAACC | 2261 |
| AGAUGGGUAAAGCGUUUCU | 2262 | AGAAACGCUUUACCCAUCU | 2263 |
| GAUGGGUAAAGCGUUUCUU | 2264 | AAGAAACGCUUUACCCAUC | 2265 |
| AUGGGUAAAGCGUUUCUUC | 2266 | GAAGAAACGCUUUACCCAU | 2267 |
| UGGGUAAAGCGUUUCUUCU | 2268 | AGAAGAAACGCUUUACCCA | 2269 |
| GGGUAAAGCGUUUCUUCUA | 2270 | UAGAAGAAACGCUUUACCC | 2271 |
| GGUAAAGCGUUUCUUCUAA | 2272 | UUAGAAGAAACGCUUUACC | 2273 |
| GUAAAGCGUUUCUUCUAAA | 2274 | UUUAGAAGAAACGCUUUAC | 2275 |
| UAAAGCGUUUCUUCUAAAG | 2276 | CUUUAGAAGAAACGCUUUA | 2277 |
| AAAGCGUUUCUUCUAAAGG | 2278 | CCUUUAGAAGAAACGCUUU | 2279 |
| AAGCGUUUCUUCUAAAGGG | 2280 | CCCUUUAGAAGAAACGCUU | 2281 |
| AAAGCAUGAUUUCCUGCCC | 2282 | GGGCAGGAAAUCAUGCUUU | 2283 |
| AAGCAUGAUUUCCUGCCCU | 2284 | AGGGCAGGAAAUCAUGCUU | 2285 |
| AGCAUGAUUUCCUGCCCUA | 2286 | UAGGGCAGGAAAUCAUGCU | 2287 |
| GCAUGAUUUCCUGCCCUAA | 2288 | UUAGGGCAGGAAAUCAUGC | 2289 |
| CAUGAUUUCCUGCCCUAAG | 2290 | CUUAGGGCAGGAAAUCAUG | 2291 |
| AUGAUUUCCUGCCCUAAGU | 2292 | ACUUAGGGCAGGAAAUCAU | 2293 |
| UGAUUUCCUGCCCUAAGUC | 2294 | GACUUAGGGCAGGAAAUCA | 2295 |
| GAUUUCCUGCCCUAAGUCC | 2296 | GGACUUAGGGCAGGAAAUC | 2297 |
| AUUUCCUGCCCUAAGUCCU | 2298 | AGGACUUAGGGCAGGAAAU | 2299 |
| UUUCCUGCCCUAAGUCCUG | 2300 | CAGGACUUAGGGCAGGAAA | 2301 |
| UUCCUGCCCUAAGUCCUGU | 2302 | ACAGGACUUAGGGCAGGAA | 2303 |
| UCCUGCCCUAAGUCCUGUG | 2304 | CACAGGACUUAGGGCAGGA | 2305 |
| AGAAGAUGUCAGGGACUAG | 2306 | CUAGUCCCUGACAUCUUCU | 2307 |
| GAAGAUGUCAGGGACUAGG | 2308 | CCUAGUCCCUGACAUCUUC | 2309 |
| AAGAUGUCAGGGACUAGGG | 2310 | CCCUAGUCCCUGACAUCUU | 2311 |
| AGAUGUCAGGGACUAGGGA | 2312 | UCCCUAGUCCCUGACAUCU | 2313 |

TABLE 3-continued

| Sense Sequence | SEQ ID NO: | Antisense Sequence | SEQ ID NO: |
|---|---|---|---|
| GUCAGGGACUAGGGAGGGA | 2314 | UCCCUCCCUAGUCCCUGAC | 2315 |
| UACUUAGCCUCUCCCAAGA | 2316 | UCUUGGGAGAGGCUAAGUA | 2317 |
| AGGAGGAAGCAGAUAGAUG | 2318 | CAUCUAUCUGCUUCCUCCU | 2319 |
| GGAGGAAGCAGAUAGAUGG | 2320 | CCAUCUAUCUGCUUCCUCC | 2321 |
| GAGGAAGCAGAUAGAUGGU | 2322 | ACCAUCUAUCUGCUUCCUC | 2323 |
| AGGAAGCAGAUAGAUGGUC | 2324 | GACCAUCUAUCUGCUUCCU | 2325 |
| GGAAGCAGAUAGAUGGUCC | 2326 | GGACCAUCUAUCUGCUUCC | 2327 |
| GAAGCAGAUAGAUGGUCCA | 2328 | UGGACCAUCUAUCUGCUUC | 2329 |
| UAGAUGGUCCAGCAGGCUU | 2330 | AAGCCUGCUGGACCAUCUA | 2331 |
| AGAUGGUCCAGCAGGCUUG | 2332 | CAAGCCUGCUGGACCAUCU | 2333 |
| GAUGGUCCAGCAGGCUUGA | 2334 | UCAAGCCUGCUGGACCAUC | 2335 |
| AUGGUCCAGCAGGCUUGAA | 2336 | UUCAAGCCUGCUGGACCAU | 2337 |
| UGGUCCAGCAGGCUUGAAG | 2338 | CUUCAAGCCUGCUGGACCA | 2339 |
| GGUCCAGCAGGCUUGAAGC | 2340 | GCUUCAAGCCUGCUGGACC | 2341 |
| GUCCAGCAGGCUUGAAGCA | 2342 | UGCUUCAAGCCUGCUGGAC | 2343 |
| UCCAGCAGGCUUGAAGCAG | 2344 | CUGCUUCAAGCCUGCUGGA | 2345 |
| CCCAGGGUAAGGGCUGUUG | 2346 | CAACAGCCCUUACCCUGGG | 2347 |
| GGGUAAGGGCUGUUGAGGU | 2348 | ACCUCAACAGCCCUUACCC | 2349 |
| GGUAAGGGCUGUUGAGGUA | 2350 | UACCUCAACAGCCCUUACC | 2351 |
| GUAAGGGCUGUUGAGGUAC | 2352 | GUACCUCAACAGCCCUUAC | 2353 |
| UAAGGGCUGUUGAGGUACC | 2354 | GGUACCUCAACAGCCCUUA | 2355 |
| AAGGGCUGUUGAGGUACCU | 2356 | AGGUACCUCAACAGCCCUU | 2357 |
| AGGGCUGUUGAGGUACCUU | 2358 | AAGGUACCUCAACAGCCCU | 2359 |
| GGGCUGUUGAGGUACCUUA | 2360 | UAAGGUACCUCAACAGCCC | 2361 |
| GGCUGUUGAGGUACCUUAA | 2362 | UUAAGGUACCUCAACAGCC | 2363 |
| GCUGUUGAGGUACCUUAAG | 2364 | CUUAAGGUACCUCAACAGC | 2365 |
| CUGUUGAGGUACCUUAAGG | 2366 | CCUUAAGGUACCUCAACAG | 2367 |
| UGUUGAGGUACCUUAAGGG | 2368 | CCCUUAAGGUACCUCAACA | 2369 |
| UAAGGGAAGGUCAAGAGGG | 2370 | CCCUCUUGACCUUCCCUUA | 2371 |
| AAGGGAAGGUCAAGAGGGA | 2372 | UCCCUCUUGACCUUCCCUU | 2373 |
| CGCUGAGGGAGGAUGCUUA | 2374 | UAAGCAUCCUCCCUCAGCG | 2375 |
| UGAGGGAGGAUGCUUAGGG | 2376 | CCCUAAGCAUCCUCCCUCA | 2377 |
| GGCACUAAGCCUAAGAAGU | 2378 | ACUUCUUAGGCUUAGUGCC | 2379 |
| GCACUAAGCCUAAGAAGUU | 2380 | AACUUCUUAGGCUUAGUGC | 2381 |
| CACUAAGCCUAAGAAGUUC | 2382 | GAACUUCUUAGGCUUAGUG | 2383 |
| ACUAAGCCUAAGAAGUUCC | 2384 | GGAACUUCUUAGGCUUAGU | 2385 |
| AGAUCGAGUCUCGCUCUGU | 2386 | ACAGAGCGAGACUCGAUCU | 2387 |
| GAUCGAGUCUCGCUCUGUC | 2388 | GACAGAGCGAGACUCGAUC | 2389 |
| AUCGAGUCUCGCUCUGUCA | 2390 | UGACAGAGCGAGACUCGAU | 2391 |
| AGUCUCGCUCUGUCACCAG | 2392 | CUGGUGACAGAGCGAGACU | 2393 |
| GUCUCGCUCUGUCACCAGG | 2394 | CCUGGUGACAGAGCGAGAC | 2395 |
| UCUCGCUCUGUCACCAGGC | 2396 | GCCUGGUGACAGAGCGAGA | 2397 |
| CUCGCUCUGUCACCAGGCU | 2398 | AGCCUGGUGACAGAGCGAG | 2399 |
| GUCACCAGGCUGGAGUGCA | 2400 | UGCACUCCAGCCUGGUGAC | 2401 |
| GGCUCACUGCAACCUCCGU | 2402 | ACGGAGGUUGCAGUGAGCC | 2403 |
| GCUCACUGCAACCUCCGUC | 2404 | GACGGAGGUUGCAGUGAGC | 2405 |
| UCCGUCUCCUGGGUUCAAG | 2406 | CUUGAACCCAGGAGACGGA | 2407 |
| CCGUCUCCUGGGUUCAAGU | 2408 | ACUUGAACCCAGGAGACGG | 2409 |
| CGUCUCCUGGGUUCAAGUG | 2410 | CACUUGAACCCAGGAGACG | 2411 |
| GUCUCCUGGGUUCAAGUGA | 2412 | UCACUUGAACCCAGGAGAC | 2413 |
| UGGGUUCAAGUGAUUCUUC | 2414 | GAAGAAUCACUUGAACCCA | 2415 |
| GGGUUCAAGUGAUUCUUCU | 2416 | AGAAGAAUCACUUGAACCC | 2417 |
| GGUUCAAGUGAUUCUUCUG | 2418 | CAGAAGAAUCACUUGAACC | 2419 |
| GUUCAAGUGAUUCUUCUGC | 2420 | GCAGAAGAAUCACUUGAAC | 2421 |
| UUCAAGUGAUUCUUCUGCC | 2422 | GGCAGAAGAAUCACUUGAA | 2423 |
| UCAAGUGAUUCUUCUGCCU | 2424 | AGGCAGAAGAAUCACUUGA | 2425 |
| CGAGCAGCUGGGAUUACAG | 2426 | CUGUAAUCCCAGCUGCUCG | 2427 |
| CAGCUGGGAUUACAGGCGC | 2428 | GCGCCUGUAAUCCCAGCUG | 2429 |
| ACAUGUUGGCCAGGAUGGU | 2430 | ACCAUCCUGGCCAACAUGU | 2431 |
| CAUGUUGGCCAGGAUGGUC | 2432 | GACCAUCCUGGCCAACAUG | 2433 |
| AUGUUGGCCAGGAUGGUCU | 2434 | AGACCAUCCUGGCCAACAU | 2435 |
| UGUUGGCCAGGAUGGUCUC | 2436 | GAGACCAUCCUGGCCAACA | 2437 |
| GUUGGCCAGGAUGGUCUCA | 2438 | UGAGACCAUCCUGGCCAAC | 2439 |
| UUGGCCAGGAUGGUCUCAA | 2440 | UUGAGACCAUCCUGGCCAA | 2441 |
| UGGCCAGGAUGGUCUCAAU | 2442 | AUUGAGACCAUCCUGGCCA | 2443 |
| GGCCAGGAUGGUCUCAAUC | 2444 | GAUUGAGACCAUCCUGGCC | 2445 |
| GCCAGGAUGGUCUCAAUCU | 2446 | AGAUUGAGACCAUCCUGGC | 2447 |
| CCAGGAUGGUCUCAAUCUC | 2448 | GAGAUUGAGACCAUCCUGG | 2449 |
| CAGGAUGGUCUCAAUCUCU | 2450 | AGAGAUUGAGACCAUCCUG | 2451 |
| AGGAUGGUCUCAAUCUCUU | 2452 | AAGAGAUUGAGACCAUCCU | 2453 |
| AUUAUAGGCGUGAGCCACC | 2454 | GGUGGCUCACGCCUAUAAU | 2455 |
| UUAUAGGCGUGAGCCACCG | 2456 | CGGUGGCUCACGCCUAUAA | 2457 |
| UAUAGGCGUGAGCCACCGC | 2458 | GCGGUGGCUCACGCCUAUA | 2459 |
| GCGCCUGGCUUAUACUUUC | 2460 | GAAAGUAUAAGCCAGGCGC | 2461 |
| CGCCUGGCUUAUACUUUCU | 2462 | AGAAAGUAUAAGCCAGGCG | 2463 |
| CCUGGCUUAUACUUUCUUA | 2464 | UAAGAAAGUAUAAGCCAGG | 2465 |

TABLE 3-continued

| Sense Sequence | SEQ ID NO: | Antisense Sequence | SEQ ID NO: |
|---|---|---|---|
| CUGGCUAUACUUUCUUAA | 2466 | UUAAGAAAGUAUAAGCCAG | 2467 |
| CAAAUGUGAGUCAUAAAGA | 2468 | UCUUUAUGACUCACAUUUG | 2469 |
| AAUGUGAGUCAUAAAGAAG | 2470 | CUUCUUUAUGACUCACAUU | 2471 |
| UGAGUCAUAAAGAAGGGUU | 2472 | AACCCUUCUUUAUGACUCA | 2473 |
| AGUCAUAAAGAAGGGUUAG | 2474 | CUAACCCUUCUUUAUGACU | 2475 |
| GUCAUAAAGAAGGGUUAGG | 2476 | CCUAACCCUUCUUUAUGAC | 2477 |
| UCAUAAAGAAGGGUUAGGG | 2478 | CCCUAACCCUUCUUUAUGA | 2479 |
| CAUAAAGAAGGGUUAGGGU | 2480 | ACCCUAACCCUUCUUUAUG | 2481 |
| AAGAAGGGUUAGGGUGAUG | 2482 | CAUCACCCUAACCCUUCUU | 2483 |
| AGAAGGGUUAGGGUGAUGG | 2484 | CCAUCACCCUAACCCUUCU | 2485 |
| GAAGGGUUAGGGUGAUGGU | 2486 | ACCAUCACCCUAACCCUUC | 2487 |
| AAGGGUUAGGGUGAUGGUC | 2488 | GACCAUCACCCUAACCCUU | 2489 |
| AGGGUUAGGGUGAUGGUCC | 2490 | GGACCAUCACCCUAACCCU | 2491 |
| GGGUUAGGGUGAUGGUCCA | 2492 | UGGACCAUCACCCUAACCC | 2493 |
| GGGUGAUGGUCCAGAGCAA | 2494 | UUGCUCUGGACCAUCACCC | 2495 |
| GGUGAUGGUCCAGAGCAAC | 2496 | GUUGCUCUGGACCAUCACC | 2497 |
| ACAGUUCUUCAAGUGUACU | 2498 | AGUACACUUGAAGAACUGU | 2499 |
| CAGUUCUUCAAGUGUACUC | 2500 | GAGUACACUUGAAGAACUG | 2501 |
| AGUUCUUCAAGUGUACUCU | 2502 | AGAGUACACUUGAAGAACU | 2503 |
| CAAGUGUACUCUGUAGGCU | 2504 | AGCCUACAGAGUACACUUG | 2505 |
| AAGUGUACUCUGUAGGCUU | 2506 | AAGCCUACAGAGUACACUU | 2507 |
| GUGUACUCUGUAGGCUUCU | 2508 | AGAAGCCUACAGAGUACAC | 2509 |
| UGUACUCUGUAGGCUUCUG | 2510 | CAGAAGCCUACAGAGUACA | 2511 |
| GUACUCUGUAGGCUUCUGG | 2512 | CCAGAAGCCUACAGAGUAC | 2513 |
| UACUCUGUAGGCUUCUGGG | 2514 | CCCAGAAGCCUACAGAGUA | 2515 |
| GUAGGCUUCUGGGAGGUCC | 2516 | GGACCUCCCAGAAGCCUAC | 2517 |
| UAGGCUUCUGGGAGGUCCC | 2518 | GGGACCUCCCAGAAGCCUA | 2519 |
| AGGCUUCUGGGAGGUCCCU | 2520 | AGGGACCUCCCAGAAGCCU | 2521 |
| GGCUUCUGGGAGGUCCCUU | 2522 | AAGGGACCUCCCAGAAGCC | 2523 |
| GCUUCUGGGAGGUCCCUUU | 2524 | AAAGGGACCUCCCAGAAGC | 2525 |
| CUUCUGGGAGGUCCCUUUU | 2526 | AAAAGGGACCUCCCAGAAG | 2527 |
| UUCUGGGAGGUCCCUUUUC | 2528 | GAAAAGGGACCUCCCAGAA | 2529 |
| UCUGGGAGGUCCCUUUUCA | 2530 | UGAAAAGGGACCUCCCAGA | 2531 |
| CAUGUUAUUGCCUUUUGA | 2532 | UCAAAAGGCAAUAACAUG | 2533 |
| AUUUGCCUUUUGAAUUCUC | 2534 | GAGAAUUCAAAAGGCAAAU | 2535 |
| UUUGCCUUUUGAAUUCUCA | 2536 | UGAGAAUUCAAAAGGCAAA | 2537 |
| UUGCCUUUUGAAUUCUCAU | 2538 | AUGAGAAUUCAAAAGGCAA | 2539 |
| UGCCUUUUGAAUUCUCAUU | 2540 | AAUGAGAAUUCAAAAGGCA | 2541 |
| GCCUUUUGAAUUCUCAUUA | 2542 | UAAUGAGAAUUCAAAAGGC | 2543 |
| AUUGUAUUGUGGAGUUUUC | 2544 | GAAAACUCCACAAUACAAU | 2545 |
| UUGUAUUGUGGAGUUUUCC | 2546 | GGAAAACUCCACAAUACAA | 2547 |
| AGUUUUCCAGAGGCCGUGU | 2548 | ACACGGCCUCUGGAAAACU | 2549 |
| GUUUUCCAGAGGCCGUGUG | 2550 | CACACGGCCUCUGGAAAAC | 2551 |
| UUUUCCAGAGGCCGUGUGA | 2552 | UCACACGGCCUCUGGAAAA | 2553 |
| UUUCCAGAGGCCGUGUGAC | 2554 | GUCACACGGCCUCUGGAAA | 2555 |
| UUCCAGAGGCCGUGUGACA | 2556 | UGUCACACGGCCUCUGGAA | 2557 |
| UCCAGAGGCCGUGUGACAU | 2558 | AUGUCACACGGCCUCUGGA | 2559 |
| CCAGAGGCCGUGUGACAUG | 2560 | CAUGUCACACGGCCUCUGG | 2561 |
| CAGAGGCCGUGUGACAUGU | 2562 | ACAUGUCACACGGCCUCUG | 2563 |
| AGAGGCCGUGUGACAUGUG | 2564 | CACAUGUCACACGGCCUCU | 2565 |
| GCCGUGUGACAUGUGAUUA | 2566 | UAAUCACAUGUCACACGGC | 2567 |
| CCGUGUGACAUGUGAUUAC | 2568 | GUAAUCACAUGUCACACGG | 2569 |
| CGUGUGACAUGUGAUUACA | 2570 | UGUAAUCACAUGUCACACG | 2571 |
| GAUUACAUCAUCUUUCUGA | 2572 | UCAGAAAGAUGAUGUAAUC | 2573 |
| AUUACAUCAUCUUUCUGAC | 2574 | GUCAGAAAGAUGAUGUAAU | 2575 |
| UUACAUCAUCUUUCUGACA | 2576 | UGUCAGAAAGAUGAUGUAA | 2577 |
| UACAUCAUCUUUCUGACAU | 2578 | AUGUCAGAAAGAUGAUGUA | 2579 |
| AUCUUUCUGACAUCAUUGU | 2580 | ACAAUGAUGUCAGAAAGAU | 2581 |
| AUUGUUAAUGGAAUGUGUG | 2582 | CACACAUUCCAUUAACAAU | 2583 |

In some embodiments, the siRNA molecules comprise or consist of the nucleotide sequences (sense and antisense strands) shown in Table 4.

TABLE 4

| Sense Sequence | SEQ ID NO: | Antisense Sequence | SEQ ID NO: |
|---|---|---|---|
| AAAGUGACUAAGAUGCUAA | 2584 | UUAGCAUCUUAGUCACUUU | 2585 |
| AAGUGACUAAGAUGCUAAG | 2586 | CUUAGCAUCUUAGUCACUU | 2587 |
| AGUGACUAAGAUGCUAAGA | 2588 | UCUUAGCAUCUUAGUCACU | 2589 |
| GUGACUAAGAUGCUAAGAG | 2590 | CUCUUAGCAUCUUAGUCAC | 2591 |
| UGACUAAGAUGCUAAGAGC | 2592 | GCUCUUAGCAUCUUAGUCA | 2593 |
| GACUAAGAUGCUAAGAGCG | 2594 | CGCUCUUAGCAUCUUAGUC | 2595 |
| ACUAAGAUGCUAAGAGCGU | 2596 | ACGCUCUUAGCAUCUUAGU | 2597 |
| CUAAGAUGCUAAGAGCGUA | 2598 | UACGCUCUUAGCAUCUUAG | 2599 |
| UAAGAUGCUAAGAGCGUAU | 2600 | AUACGCUCUUAGCAUCUUA | 2601 |
| AAGAUGCUAAGAGCGUAUU | 2602 | AAUACGCUCUUAGCAUCUU | 2603 |
| AGAUGCUAAGAGCGUAUUU | 2604 | AAAUACGCUCUUAGCAUCU | 2605 |

TABLE 4-continued

| Sense Sequence | SEQ ID NO: | Antisense Sequence | SEQ ID NO: |
| --- | --- | --- | --- |
| GAUGCUAAGAGCGUAUUUA | 2606 | UAAAUACGCUCUUAGCAUC | 2607 |
| AUGCUAAGAGCGUAUUUAU | 2608 | AUAAAUACGCUCUUAGCAU | 2609 |
| UAAGAGCGUAUUUAUAGCU | 2610 | AGCUAUAAAUACGCUCUUA | 2611 |
| AGAGCGUAUUUAUAGCUGA | 2612 | UCAGCUAUAAAUACGCUCU | 2613 |
| GAGCGUAUUUAUAGCUGAG | 2614 | CUCAGCUAUAAAUACGCUC | 2615 |
| AGCGUAUUUAUAGCUGAGC | 2616 | GCUCAGCUAUAAAUACGCU | 2617 |
| GCGUAUUUAUAGCUGAGCU | 2618 | AGCUCAGCUAUAAAUACGC | 2619 |
| CGUAUUUAUAGCUGAGCUC | 2620 | GAGCUCAGCUAUAAAUACG | 2621 |
| GUAUUUAUAGCUGAGCUCU | 2622 | AGAGCUCAGCUAUAAAUAC | 2623 |
| UAUUUAUAGCUGAGCUCUG | 2624 | CAGAGCUCAGCUAUAAAUA | 2625 |
| AUUUAUAGCUGAGCUCUGA | 2626 | UCAGAGCUCAGCUAUAAAU | 2627 |
| UUUAUAGCUGAGCUCUGAC | 2628 | GUCAGAGCUCAGCUAUAAA | 2629 |
| UUAUAGCUGAGCUCUGACG | 2630 | CGUCAGAGCUCAGCUAUAA | 2631 |
| AGCUGAGCUCUGACGUAAG | 2632 | CUUACGUCAGAGCUCAGCU | 2633 |
| GCUGAGCUCUGACGUAAGU | 2634 | ACUUACGUCAGAGCUCAGC | 2635 |
| CUGAGCUCUGACGUAAGUG | 2636 | CACUUACGUCAGAGCUCAG | 2637 |
| UGAGCUCUGACGUAAGUGU | 2638 | ACACUUACGUCAGAGCUCA | 2639 |
| GAGCUCUGACGUAAGUGUC | 2640 | GACACUUACGUCAGAGCUC | 2641 |
| AGGCCAGGCACAGCAGCAA | 2642 | UUGCUGCUGUGCCUGGCCU | 2643 |
| CAGCAAGCGGGUGGAAGA | 2644 | UCUUCCCACCCGCUUGCUG | 2645 |
| AGCAAGCGGGUGGGAAGAG | 2646 | CUCUUCCCACCCGCUUGCU | 2647 |
| CAAGCGGGUGGGAAGAGCU | 2648 | AGCUCUUCCCACCCGCUUG | 2649 |
| GGGCAUCUGACAGUGAGGG | 2650 | CCCUCACUGUCAGAUGCCC | 2651 |
| GGCAUCUGACAGUGAGGGU | 2652 | ACCCUCACUGUCAGAUGCC | 2653 |
| GUGACUCCUGCAGCCACUU | 2654 | AAGUGGCUGCAGGAGUCAC | 2655 |
| UGACUCCUGCAGCCACUUC | 2656 | GAAGUGGCUGCAGGAGUCA | 2657 |
| ACUCCUGCAGCCACUUCUU | 2658 | AAGAAGUGGCUGCAGGAGU | 2659 |
| CUCCUGCAGCCACUUCUUG | 2660 | CAAGAAGUGGCUGCAGGAG | 2661 |
| UCCUGCAGCCACUUCUUGU | 2662 | ACAAGAAGUGGCUGCAGGA | 2663 |
| CCUGCAGCCACUUCUUGUC | 2664 | GACAAGAAGUGGCUGCAGG | 2665 |
| CUGCAGCCACUUCUUGUCA | 2666 | UGACAAGAAGUGGCUGCAG | 2667 |
| UGACUGCCUACUGAUACCA | 2668 | UGGUAUCAGUAGGCAGUCA | 2669 |
| GACUGCCUACUGAUACCAA | 2670 | UUGGUAUCAGUAGGCAGUC | 2671 |
| ACAGGUAAGCCGUCUGAGG | 2672 | CCUCAGACGGCUUACCUGU | 2673 |
| CAGGUAAGCCGUCUGAGGC | 2674 | GCCUCAGACGGCUUACCUG | 2675 |
| AGGUAAGCCGUCUGAGGCA | 2676 | UGCCUCAGACGGCUUACCU | 2677 |
| GGUAAGCCGUCUGAGGCAC | 2678 | GUGCCUCAGACGGCUUACC | 2679 |
| GUAAGCCGUCUGAGGCACC | 2680 | GGUGCCUCAGACGGCUUAC | 2681 |
| UAAGCCGUCUGAGGCACCA | 2682 | UGGUGCCUCAGACGGCUUA | 2683 |
| AAGCCGUCUGAGGCACCAC | 2684 | GUGGUGCCUCAGACGGCUU | 2685 |
| UAGAUACCUCCACUUUGCU | 2686 | AGCAAAGUGGAGGUAUCUA | 2687 |
| GAUACCUCCACUUUGCUGA | 2688 | UCAGCAAAGUGGAGGUAUC | 2689 |
| AUACCUCCACUUUGCUGAC | 2690 | GUCAGCAAAGUGGAGGUAU | 2691 |
| CCACUUUGCUGACCAAUGU | 2692 | ACAUUGGUCAGCAAAGUGG | 2693 |
| UUUGCUGACCAAUGUUCCA | 2694 | UGGAACAUUGGUCAGCAAA | 2695 |
| UUGCUGACCAAUGUUCCAG | 2696 | CUGGAACAUUGGUCAGCAA | 2697 |
| UGCUGACCAAUGUUCCAGA | 2698 | UCUGGAACAUUGGUCAGCA | 2699 |
| GCUGACCAAUGUUCCAGAC | 2700 | GUCUGGAACAUUGGUCAGC | 2701 |
| CUGACCAAUGUUCCAGACC | 2702 | GGUCUGGAACAUUGGUCAG | 2703 |
| CCAAUGUUCCAGACCCGAG | 2704 | CUCGGGUCUGGAACAUUGG | 2705 |
| GGUAGAGGGCUGUCAUUUC | 2706 | GAAAUGACAGCCCUCUACC | 2707 |
| GUAGAGGGCUGUCAUUUCC | 2708 | GGAAAUGACAGCCCUCUAC | 2709 |
| UGUCAUUUCCCAGCCCAAC | 2710 | GUUGGGCUGGGAAAUGACA | 2711 |
| GAAUGGUUGCUGGGAGCUG | 2712 | CAGCUCCCAGCAACCAUUC | 2713 |
| CUGGACAGAGCUCUUGAAU | 2714 | AUUCAAGAGCUCUGUCCAG | 2715 |
| UGGACAGAGCUCUUGAAUG | 2716 | CAUUCAAGAGCUCUGUCCA | 2717 |
| CAGAGCUCUUGAAUGUGUU | 2718 | AACACAUUCAAGAGCUCUG | 2719 |
| AGAGCUCUUGAAUGUGUUU | 2720 | AAACACAUUCAAGAGCUCU | 2721 |
| AUGUGUUUCAGAGCUUGGG | 2722 | CCCAAGCUCUGAAACACAU | 2723 |
| AAAUGCAGGGUGGACAGGA | 2724 | UCCUGUCCACCCUGCAUUU | 2725 |
| AAUGCAGGGUGGACAGGAG | 2726 | CUCCUGUCCACCCUGCAUU | 2727 |
| AUGCAGGGUGGACAGGAGG | 2728 | CCUCCUGUCCACCCUGCAU | 2729 |
| GGUGGACAGGAGGGUCUAA | 2730 | UUAGACCCUCCUGUCCACC | 2731 |
| GUGGACAGGAGGGUCUAAU | 2732 | AUUAGACCCUCCUGUCCAC | 2733 |
| UGGACAGGAGGGUCUAAUC | 2734 | GAUUAGACCCUCCUGUCCA | 2735 |
| GGACAGGAGGGUCUAAUCG | 2736 | CGAUUAGACCCUCCUGUCC | 2737 |
| GACAGGAGGGUCUAAUCGU | 2738 | ACGAUUAGACCCUCCUGUC | 2739 |
| ACAGGAGGGUCUAAUCGUC | 2740 | GACGAUUAGACCCUCCUGU | 2741 |
| CAGGAGGGUCUAAUCGUCU | 2742 | AGACGAUUAGACCCUCCUG | 2743 |
| AGGAGGGUCUAAUCGUCUC | 2744 | GAGACGAUUAGACCCUCCU | 2745 |
| GGAGGGUCUAAUCGUCUCA | 2746 | UGAGACGAUUAGACCCUCC | 2747 |
| GAGGGUCUAAUCGUCUCAG | 2748 | CUGAGACGAUUAGACCCUC | 2749 |
| AGGGUCUAAUCGUCUCAGU | 2750 | ACUGAGACGAUUAGACCCU | 2751 |
| GGGUCUAAUCGUCUCAGUG | 2752 | CACUGAGACGAUUAGACCC | 2743 |
| GGUCUAAUCGUCUCAGUGC | 2754 | GCACUGAGACGAUUAGACC | 2755 |
| CCCACCAAAGAGUGCCCUG | 2756 | CAGGGCACUCUUUGGUGGG | 2757 |

TABLE 4-continued

| Sense Sequence | SEQ ID NO: | Antisense Sequence | SEQ ID NO: |
|---|---|---|---|
| CCACCAAAGAGUGCCCUGA | 2758 | UCAGGGCACUCUUUGGUGG | 2759 |
| CCAAAGAGUGCCCUGAGGU | 2760 | ACCUCAGGGCACUCUUUGG | 2761 |
| CAAAGAGUGCCCUGAGGUU | 2762 | AACCUCAGGGCACUCUUUG | 2763 |
| AAAGAGUGCCCUGAGGUUC | 2764 | GAACCUCAGGGCACUCUUU | 2765 |
| AAGAGUGCCCUGAGGUUCU | 2766 | AGAACCUCAGGGCACUCUU | 2767 |
| AGAGUGCCCUGAGGUUCUA | 2768 | UAGAACCUCAGGGCACUCU | 2769 |
| GAGUGCCCUGAGGUUCUAG | 2770 | CUAGAACCUCAGGGCACUC | 2771 |
| AGUGCCCUGAGGUUCUAGG | 2772 | CCUAGAACCUCAGGGCACU | 2773 |
| GUGCCCUGAGGUUCUAGGA | 2774 | UCCUAGAACCUCAGGGCAC | 2775 |
| CCUGAGGUUCUAGGAAGAG | 2776 | CUCUUCCUAGAACCUCAGG | 2777 |
| CUGAGGUUCUAGGAAGAGC | 2778 | GCUCUUCCUAGAACCUCAG | 2779 |
| UUCUAGGAAGAGCCUGGUA | 2780 | UACCAGGCUCUUCCUAGAA | 2781 |
| UCUAGGAAGAGCCUGGUAC | 2782 | GUACCAGGCUCUUCCUAGA | 2783 |
| CUAGGAAGAGCCUGGUACA | 2784 | UGUACCAGGCUCUUCCUAG | 2785 |
| UAGGAAGAGCCUGGUACAU | 2786 | AUGUACCAGGCUCUUCCUA | 2787 |
| AGGAAGAGCCUGGUACAUC | 2788 | GAUGUACCAGGCUCUUCCU | 2789 |
| GGAAGAGCCUGGUACAUCA | 2790 | UGAUGUACCAGGCUCUUCC | 2791 |
| GAAGAGCCUGGUACAUCAC | 2792 | GUGAUGUACCAGGCUCUUC | 2793 |
| AAGAGCCUGGUACAUCACC | 2794 | GGUGAUGUACCAGGCUCUU | 2795 |
| UCACCAAGCUCCAUUGCCA | 2796 | UGGCAAUGGAGCUUGGUGA | 2797 |
| CACCAAGCUCCAUUGCCAC | 2798 | GUGGCAAUGGAGCUUGGUG | 2799 |
| ACCAAGCUCCAUUGCCACG | 2800 | CGUGGCAAUGGAGCUUGGU | 2801 |
| CCAAGCUCCAUUGCCACGU | 2802 | ACGUGGCAAUGGAGCUUGG | 2803 |
| CAAGCUCCAUUGCCACGUG | 2804 | CACGUGGCAAUGGAGCUUG | 2805 |
| AAGCUCCAUUGCCACGUGU | 2806 | ACACGUGGCAAUGGAGCUU | 2807 |
| AGCUCCAUUGCCACGUGUU | 2808 | AACACGUGGCAAUGGAGCU | 2809 |
| CUCCAUUGCCACGUGUUUG | 2810 | CAAACACGUGGCAAUGGAG | 2811 |
| UCCAUUGCCACGUGUUUGU | 2812 | ACAAACACGUGGCAAUGGA | 2813 |
| CCAUUGCCACGUGUUUGUG | 2814 | CACAAACACGUGGCAAUGG | 2815 |
| CAUUGCCACGUGUUUGUGU | 2816 | ACACAAACACGUGGCAAUG | 2817 |
| AAAGGUAGCAGUGAUGUGG | 2818 | CCACAUCACUGCUACCUUU | 2819 |
| AAGGUAGCAGUGAUGUGGA | 2820 | UCCACAUCACUGCUACCUU | 2821 |
| AGGUAGCAGUGAUGUGGAU | 2822 | AUCCACAUCACUGCUACCU | 2823 |
| GGUAGCAGUGAUGUGGAUC | 2824 | GAUCCACAUCACUGCUACC | 2825 |
| GUAGCAGUGAUGUGGAUCC | 2826 | GGAUCCACAUCACUGCUAC | 2827 |
| UAGCAGUGAUGUGGAUCCU | 2828 | AGGAUCCACAUCACUGCUA | 2829 |
| AGCAGUGAUGUGGAUCCUG | 2830 | CAGGAUCCACAUCACUGCU | 2831 |
| GCAGUGAUGUGGAUCCUGA | 2832 | UCAGGAUCCACAUCACUGC | 2833 |
| CAGUGAUGUGGAUCCUGAA | 2834 | UUCAGGAUCCACAUCACUG | 2835 |
| AGUGAUGUGGAUCCUGAAG | 2836 | CUUCAGGAUCCACAUCACU | 2837 |
| GUGAUGUGGAUCCUGAAGA | 2838 | UCUUCAGGAUCCACAUCAC | 2839 |
| GAUGUGGAUCCUGAAGACA | 2840 | UGUCUUCAGGAUCCACAUC | 2841 |
| AUGUGGAUCCUGAAGACAG | 2842 | CUGUCUUCAGGAUCCACAU | 2843 |
| UGUGGAUCCUGAAGACAGU | 2844 | ACUGUCUUCAGGAUCCACA | 2845 |
| GUGGAUCCUGAAGACAGUC | 2846 | GACUGUCUUCAGGAUCCAC | 2847 |
| AUCCUGAAGACAGUCUCUC | 2848 | GAGAGACUGUCUUCAGGAU | 2849 |
| UCCUGAAGACAGUCUCUCU | 2850 | AGAGAGACUGUCUUCAGGA | 2851 |
| AGACAGUCUCUCUUCUCUG | 2852 | CAGAGAAGAGAGACUGUCU | 2853 |
| AGUCUCUCUUCUCUGGCAG | 2854 | CUGCCAGAGAAGAGAGACU | 2855 |
| CUCUUCUCUGGCAGUGUGA | 2856 | UCACACUGCAGAGAAGAG | 2857 |
| AACCAGCUUGUCCCUGUCU | 2858 | AGACAGGGACAAGCUGGUU | 2859 |
| CAGCUUGUCCCUGUCUCUU | 2860 | AAGAGACAGGGACAAGCUG | 2861 |
| CAGCUGCUGUCCAGAGGCA | 2862 | UGCCUCUGGACAGCAGCUG | 2863 |
| CACGGCACUGCCACAUGGU | 2864 | ACCAUGUGGCAGUGCCGUG | 2865 |
| ACGGCACUGCCACAUGGUG | 2866 | CACCAUGUGGCAGUGCCGU | 2867 |
| AUGGUGGACACUGGUGGUA | 2868 | UACCACCAGUGUCCACCAU | 2869 |
| UGGUGGACACUGGUGGUAC | 2870 | GUACCACCAGUGUCCACCA | 2871 |
| GGUGGACACUGGUGGUACU | 2872 | AGUACCACCAGUGUCCACC | 2873 |
| GUGGACACUGGUGGUACUG | 2874 | CAGUACCACCAGUGUCCAC | 2875 |
| UGGACACUGGUGGUACUGA | 2876 | UCAGUACCACCAGUGUCCA | 2877 |
| GGACACUGGUGGUACUGAG | 2878 | CUCAGUACCACCAGUGUCC | 2879 |
| GACACUGGUGGUACUGAGG | 2880 | CCUCAGUACCACCAGUGUC | 2881 |
| ACACUGGUGGUACUGAGGU | 2882 | ACCUCAGUACCACCAGUGU | 2883 |
| CACUGGUGGUACUGAGGUC | 2884 | GACCUCAGUACCACCAGUG | 2885 |
| ACUGGUGGUACUGAGGUCC | 2886 | GGACCUCAGUACCACCAGU | 2887 |
| CUGGUGGUACUGAGGUCCA | 2888 | UGGACCUCAGUACCACCAG | 2889 |
| UACUGAGGUCCAGCCUUCC | 2890 | GGAAGGCUGGACCUCAGUA | 2891 |
| CUGAGGUCCAGCCUUCCAA | 2892 | UUGGAAGGCUGGACCUCAG | 2893 |
| UGAGGUCCAGCCUUCCAAU | 2894 | AUUGGAAGGCUGGACCUCA | 2895 |
| GAGGUCCAGCCUUCCAAUU | 2896 | AAUUGGAAGGCUGGACCUC | 2897 |
| AGGUCCAGCCUUCCAAUUA | 2898 | UAAUUGGAAGGCUGGACCU | 2899 |
| GGUCCAGCCUUCCAAUUAG | 2900 | CUAAUUGGAAGGCUGGACC | 2901 |
| GUCCAGCCUUCCAAUUAGG | 2902 | CCUAAUUGGAAGGCUGGAC | 2903 |
| UCCAGCCUUCCAAUUAGGA | 2904 | UCCUAAUUGGAAGGCUGGA | 2905 |
| GCCUAGAUCUAAUAGUCUC | 2906 | GAGACUAUUAGAUCUAGGC | 2907 |
| CCUAGAUCUAAUAGUCUCU | 2908 | AGAGACUAUUAGAUCUAGG | 2909 |

TABLE 4-continued

| Sense Sequence | SEQ ID NO: | Antisense Sequence | SEQ ID NO: |
|---|---|---|---|
| CUAGAUCUAAUAGUCUCUC | 2910 | GAGAGACUAUUAGAUCUAG | 2911 |
| UAGAUCUAAUAGUCUCUCU | 2912 | AGAGAGACUAUUAGAUCUA | 2913 |
| CUAAUAGUCUCUCUUGACA | 2914 | UGUCAAGAGAGACUAUUAG | 2915 |
| UAAUAGUCUCUCUUGACAG | 2916 | CUGUCAAGAGAGACUAUUA | 2917 |
| AAUAGUCUCUCUUGACAGC | 2918 | GCUGUCAAGAGAGACUAUU | 2919 |
| AUGAGCAAAGUGGAGUAAA | 2920 | UUUACUCCACUUUGCUCAU | 2921 |
| UGAGCAAAGUGGAGUAAAG | 2922 | CUUUACUCCACUUUGCUCA | 2923 |
| GAGCAAAGUGGAGUAAAGA | 2924 | UCUUUACUCCACUUUGCUC | 2925 |
| GCAAAGUGGAGUAAAGACA | 2926 | UGUCUUUACUCCACUUUGC | 2927 |
| CAAAGUGGAGUAAAGACAC | 2928 | GUGUCUUUACUCCACUUUG | 2929 |
| AUUUCCAAAUCACACCCAC | 2930 | GUGGGUGUGAUUUGGAAAU | 2931 |
| UCCAAAUCACACCCACUUC | 2932 | GAAGUGGGUGUGAUUUGGA | 2933 |
| CCAAAUCACACCCACUUCC | 2934 | GGAAGUGGGUGUGAUUUGG | 2935 |
| AAAAGCUAGCAUGAGGCCC | 2936 | GGGCCUCAUGCUAGCUUUU | 2937 |
| AAAGCUAGCAUGAGGCCCA | 2938 | UGGGCCUCAUGCUAGCUUU | 2939 |
| AAGCUAGCAUGAGGCCCAC | 2940 | GUGGGCCUCAUGCUAGCUU | 2941 |
| CCCACCUUCAUGAAUUCAA | 2942 | UUGAAUUCAUGAAGGUGGG | 2943 |
| ACCUUCAUGAAUUCAAUGU | 2944 | ACAUUGAAUUCAUGAAGGU | 2945 |
| CCUUCAUGAAUUCAAUGUG | 2946 | CACAUUGAAUUCAUGAAGG | 2947 |
| CUUCAUGAAUUCAAUGUGG | 2948 | CCACAUUGAAUUCAUGAAG | 2949 |
| UCAUGAAUUCAAUGUGGAG | 2950 | CUCCACAUUGAAUUCAUGA | 2951 |
| CAUGAAUUCAAUGUGGAGG | 2952 | CCUCCACAUUGAAUUCAUG | 2953 |
| CAUUUAAAGCCAGUGAGGA | 2954 | UCCUCACUGGCUUUAAAUG | 2955 |
| UUUAAAGCCAGUGAGGACU | 2956 | AGUCCUCACUGGCUUUAAA | 2957 |
| AGGACUGGGUGUGGUGGCU | 2958 | AGCCACCACACCCAGUCCU | 2959 |
| GACUGGGUGUGGUGGCUCA | 2960 | UGAGCCACCACACCCAGUC | 2961 |
| ACUGGGUGUGGUGGCUCAU | 2962 | AUGAGCCACCACACCCAGU | 2963 |
| CUGGGUGUGGUGGCUCAUG | 2964 | CAUGAGCCACCACACCCAG | 2965 |
| UGGGUGUGGUGGCUCAUGU | 2966 | ACAUGAGCCACCACACCCA | 2967 |
| GGGUGUGGUGGCUCAUGUC | 2968 | GACAUGAGCCACCACACCC | 2969 |
| GGUGUGGUGGCUCAUGUCU | 2970 | AGACAUGAGCCACCACACC | 2971 |
| GUGUGGUGGCUCAUGUCUA | 2972 | UAGACAUGAGCCACCACAC | 2973 |
| UGUGGUGGCUCAUGUCUAU | 2974 | AUAGACAUGAGCCACCACA | 2975 |
| GAGGAUCGCUUGAGCCCAG | 2976 | CUGGGCUCAAGCGAUCCUC | 2977 |
| AAAUAAAUUAGCCUGUGUG | 2978 | CACACAGGCUAAUUUAUUU | 2979 |
| AAUUAGCCUGUGUGGUGUG | 2980 | CACACCACACAGGCUAAUU | 2981 |
| AUUAGCCUGUGUGGUGUGG | 2982 | CCACACCACACAGGCUAAU | 2983 |
| GCCUGUGUGGUGUGGUGUG | 2984 | CACACCACACCACACAGGC | 2985 |
| UGUGGUGUGGUGUGGUUGG | 2986 | CCAACCACACCACACCACA | 2987 |
| GGUGUGGUGUGGUUGGUGU | 2988 | ACACCAACCACACCACACC | 2989 |
| UGUGGUUGGUGUGGUGGCA | 2990 | UGCCACCACACCAACCACA | 2991 |
| GUGGUUGGUGUGGUGGCAC | 2992 | GUGCCACCACACCAACCAC | 2993 |
| UGGUUGGUGUGGUGGCACG | 2994 | CGUGCCACCACACCAACCA | 2995 |
| CACGCACCUGUAGACUUAG | 2996 | CUAAGUCUACAGGUGCUG | 2997 |
| ACGCACCUGUAGACUUAGC | 2998 | GCUAAGUCUACAGGUGCGU | 2999 |
| AGACUUAGCUACUCUGGAA | 3000 | UUCCAGAGUAGCUAAGUCU | 3001 |
| GACUUAGCUACUCUGGAAG | 3002 | CUUCCAGAGUAGCUAAGUC | 3003 |
| ACUUAGCUACUCUGGAAGC | 3004 | GCUUCCAGAGUAGCUAAGU | 3005 |
| GGAAGAAUCACUUAACCCA | 3006 | UGGGUUAAGUGAUUCUUCC | 3007 |
| UCACUUAACCCAGGAGGUC | 3008 | GACCUCCUGGGUUAAGUGA | 3009 |
| UUAACCCAGGAGGUCAAGG | 3010 | CCUUGACCUCCUGGGUUAA | 3011 |
| UAACCCAGGAGGUCAAGGC | 3012 | GCCUUGACCUCCUGGGUUA | 3013 |
| GUCAAGGCUGCAGUGAGCU | 3014 | AGCUCACUGCAGCCUUGAC | 3015 |
| UCAAGGCUGCAGUGAGCUG | 3016 | CAGCUCACUGCAGCCUUGA | 3017 |
| CAAGGCUGCAGUGAGCUGU | 3018 | ACAGCUCACUGCAGCCUUG | 3019 |
| AAGGCUGCAGUGAGCUGUG | 3020 | CACAGCUCACUGCAGCCUU | 3021 |
| CUGCAGUGAGCUGUGAUCA | 3022 | UGAUCACAGCUCACUGCAG | 3023 |
| GUCAGGUGCGGUGGCUCAU | 3024 | AUGAGCCACCGCACCUGAC | 3025 |
| UCAGGUGCGGUGGCUCAUG | 3026 | CAUGAGCCACCGCACCUGA | 3027 |
| UGCGGUGGCUCAUGCCUGU | 3028 | ACAGGCAUGAGCCACCGCA | 3029 |
| GCGGUGGCUCAUGCCUGUA | 3030 | UACAGGCAUGAGCCACCGC | 3031 |
| CGGUGGCUCAUGCCUGUAA | 3032 | UUACAGGCAUGAGCCACCG | 3033 |
| GGUGGCUCAUGCCUGUAAU | 3034 | AUUACAGGCAUGAGCCACC | 3035 |
| GUGGCUCAUGCCUGUAAUC | 3036 | GAUUACAGGCAUGAGCCAC | 3037 |
| UGGCUCAUGCCUGUAAUCC | 3038 | GGAUUACAGGCAUGAGCCA | 3039 |
| GGCUCAUGCCUGUAAUCCC | 3040 | GGGAUUACAGGCAUGAGCC | 3041 |
| AUGCCUGUAAUCCCAGCAC | 3042 | GUGCUGGGAUUACAGGCAU | 3043 |
| CAGCACUUUGGGAGGCCGA | 3044 | UCGGCCUCCCAAAGUGCUG | 3045 |
| AGCACUUUGGGAGGCCGAG | 3046 | CUCGGCCUCCCAAAGUGCU | 3047 |
| GCACCUGUAGUCCCAGCGA | 3048 | UCGCUGGGACUACAGGUGC | 3049 |
| CACCUGUAGUCCCAGCGAC | 3050 | GUCGCUGGGACUACAGGUG | 3051 |
| GGAGGCUGAGGCAGAAGAA | 3052 | UUCUUCUGCCUCAGCCUCC | 3053 |
| GAGGCUGAGGCAGAAGAAU | 3054 | AUUCUUCUGCCUCAGCCUC | 3055 |
| AGGCUGAGGCAGAAGAAUG | 3056 | CAUUCUUCUGCCUCAGCCU | 3057 |
| GGCUGAGGCAGAAGAAUGG | 3058 | CCAUUCUUCUGCCUCAGCC | 3059 |
| GCUGAGGCAGAAGAAUGGU | 3060 | ACCAUUCUUCUGCCUCAGC | 3061 |

TABLE 4-continued

| Sense Sequence | SEQ ID NO: | Antisense Sequence | SEQ ID NO: |
|---|---|---|---|
| CUGAGGCAGAAGAAUGGUG | 3062 | CACCAUUCUUCUGCCUCAG | 3063 |
| UGAGGCAGAAGAAUGGUGU | 3064 | ACACCAUUCUUCUGCCUCA | 3065 |
| GAGCUUGCAGUGAGCCGAG | 3066 | CUCGGCUCACUGCAAGCUC | 3067 |
| AAAAUGUGGUCAGGAGGGC | 3068 | GCCCUCCUGACCACAUUUU | 3069 |
| AACCAAGACUGCUGUAUUU | 3070 | AAAUACAGCAGUCUUGGUU | 3071 |
| ACCAAGACUGCUGUAUUUG | 3072 | CAAAUACAGCAGUCUUGGU | 3073 |
| CCAAGACUGCUGUAUUUGC | 3074 | GCAAAUACAGCAGUCUUGG | 3075 |
| CAAGACUGCUGUAUUUGCC | 3076 | GGCAAAUACAGCAGUCUUG | 3077 |
| AAGACUGCUGUAUUUGCCU | 3078 | AGGCAAAUACAGCAGUCUU | 3079 |
| GCUGUAUUUGCCUUGCUUU | 3080 | AAAGCAAGGCAAAUACAGC | 3081 |
| UUGCCUUGCUUUGUUGUCA | 3082 | UGACAACAAAGCAAGGCAA | 3083 |
| UGCCUUGCUUUGUUGUCAA | 3084 | UUGACAACAAAGCAAGGCA | 3085 |
| UUGUUGUCAAAAGCUCUUA | 3086 | UAAGAGCUUUUGACAACAA | 3087 |
| UGUUGUCAAAAGCUCUUAG | 3088 | CUAAGAGCUUUUGACAACA | 3089 |
| GUUGUCAAAAGCUCUUAGA | 3090 | UCUAAGAGCUUUUGACAAC | 3091 |
| UUGUCAAAAGCUCUUAGAG | 3092 | CUCUAAGAGCUUUUGACAA | 3093 |
| UCUUAGAGCUCCCAUUUUC | 3094 | GAAAAUGGGAGCUCUAAGA | 3095 |
| ACUUAGGAGGCUGAGGCA | 3096 | UGCCUCAGCCUCCUAAAGU | 3097 |
| CUUUAGGAGGCUGAGGCAA | 3098 | UUGCCUCAGCCUCCUAAAG | 3099 |
| UUUAGGAGGCUGAGGCAAG | 3100 | CUUGCCUCAGCCUCCUAAA | 3101 |
| UUAGGAGGCUGAGGCAAGU | 3102 | ACUUGCCUCAGCCUCCUAA | 3103 |
| UAGGAGGCUGAGGCAAGUG | 3104 | CACUUGCCUCAGCCUCCUA | 3105 |
| AGGAGGCUGAGGCAAGUGG | 3106 | CCACUUGCCUCAGCCUCCU | 3107 |
| GGAGGCUGAGGCAAGUGGA | 3108 | UCCACUUGCCUCAGCCUCC | 3109 |
| GAGGCUGAGGCAAGUGGAU | 3110 | AUCCACUUGCCUCAGCCUC | 3111 |
| GUGGAUUGCUUGAGCCCAG | 3112 | CUGGGCUCAAGCAAUCCAC | 3113 |
| UGGAUUGCUUGAGCCCAGG | 3114 | CCUGGGCUCAAGCAAUCCA | 3115 |
| GGAUUGCUUGAGCCCAGGA | 3116 | UCCUGGGCUCAAGCAAUCC | 3117 |
| GAUUGCUUGAGCCCAGGAG | 3118 | CUCCUGGGCUCAAGCAAUC | 3119 |
| AUUGCUUGAGCCCAGGAGU | 3120 | ACUCCUGGGCUCAAGCAAU | 3121 |
| UUGCUUGAGCCCAGGAGUU | 3122 | AACUCCUGGGCUCAAGCAA | 3123 |
| UGCUUGAGCCCAGGAGUUC | 3124 | GAACUCCUGGGCUCAAGCA | 3125 |
| UGAGCCCAGGAGUUCAAGA | 3126 | UCUUGAACUCCUGGGCUCA | 3127 |
| AUUAGCCAGGUGUGGUGGU | 3128 | ACCACCACACCUGGCUAAU | 3129 |
| UUAGCCAGGUGUGGUGGUG | 3130 | CACCACCACACCUGGCUAA | 3131 |
| GUGCGCACCUGUAGUCCCA | 3132 | UGGGACUACAGGUGCGCAC | 3133 |
| UGCGCACCUGUAGUCCCAA | 3134 | UUGGGACUACAGGUGCGCA | 3135 |
| GCGCACCUGUAGUCCCAAC | 3136 | GUUGGGACUACAGGUGCGC | 3137 |
| CGCACCUGUAGUCCCAACU | 3138 | AGUUGGGACUACAGGUGCG | 3139 |
| UACUAAGGAGGCUGAGGCA | 3140 | UGCCUCAGCCUCCUUAGUA | 3141 |
| ACUAAGGAGGCUGAGGCAG | 3142 | CUGCCUCAGCCUCCUUAGU | 3143 |
| UUCAAGGCUGCAGUGAGCU | 3144 | AGCUCACUGCAGCCUUGAA | 3145 |
| UCAAGGCUGCAGUGAGCUA | 3146 | UAGCUCACUGCAGCCUUGA | 3147 |
| CAAGGCUGCAGUGAGCUAU | 3148 | AUAGCUCACUGCAGCCUUG | 3149 |
| AAGGCUGCAGUGAGCUAUG | 3150 | CAUAGCUCACUGCAGCCUU | 3151 |
| UGCAGUGAGCUAUGAUUGU | 3152 | ACAAUCAUAGCUCACUGCA | 3153 |
| GCAGUGAGCUAUGAUUGUG | 3154 | CACAAUCAUAGCUCACUGC | 3155 |
| CAGUGAGCUAUGAUUGUGC | 3156 | GCACAAUCAUAGCUCACUG | 3157 |
| GGAGGCCUGGCACUACUUC | 3158 | GAAGUAGUGCCAGGCCUCC | 3159 |
| GAGGCCUGGCACUACUUCU | 3160 | AGAAGUAGUGCCAGGCCUC | 3161 |
| AGGCCUGGCACUACUUCUA | 3162 | UAGAAGUAGUGCCAGGCCU | 3163 |
| GGCCUGGCACUACUUCUAG | 3164 | CUAGAAGUAGUGCCAGGCC | 3165 |
| GCCUGGCACUACUUCUAGG | 3166 | CCUAGAAGUAGUGCCAGGC | 3167 |
| CCUGGCACUACUUCUAGGA | 3168 | UCCUAGAAGUAGUGCCAGG | 3169 |
| CUGGCACUACUUCUAGGAU | 3170 | AUCCUAGAAGUAGUGCCAG | 3171 |
| UGGCACUACUUCUAGGAUG | 3172 | CAUCCUAGAAGUAGUGCCA | 3173 |
| AAUUUAGGCAACUCUCACA | 3174 | UGUGAGAGUUGCCUAAAUU | 3175 |
| AUUUAGGCAACUCUCACAG | 3176 | CUGUGAGAGUUGCCUAAAU | 3177 |
| UUUAGGCAACUCUCACAGU | 3178 | ACUGUGAGAGUUGCCUAAA | 3179 |
| UUAGGCAACUCUCACAGUC | 3180 | GACUGUGAGAGUUGCCUAA | 3181 |
| UAGGCAACUCUCACAGUCC | 3182 | GGACUGUGAGAGUUGCCUA | 3183 |
| AGGCAACUCUCACAGUCCC | 3184 | GGGACUGUGAGAGUUGCCU | 3185 |
| GGCAACUCUCACAGUCCCU | 3186 | AGGGACUGUGAGAGUUGCC | 3187 |
| GCAACUCUCACAGUCCCUU | 3188 | AAGGGACUGUGAGAGUUGC | 3189 |
| CAACUCUCACAGUCCCUUG | 3190 | CAAGGGACUGUGAGAGUUG | 3191 |
| AACUCUCACAGUCCCUUGA | 3192 | UCAAGGGACUGUGAGAGUU | 3193 |
| ACUCUCACAGUCCCUUGAA | 3194 | UUCAAGGGACUGUGAGAGU | 3195 |
| AGAAGUGGCAGCUGGGUAU | 3196 | AUACCCAGCUGCCACUUCU | 3197 |
| GAAGUGGCAGCUGGGUAUA | 3198 | UAUACCCAGCUGCCACUUC | 3199 |
| AAGUGGCAGCUGGGUAUAG | 3200 | CUAUACCCAGCUGCCACUU | 3201 |
| AGUGGCAGCUGGGUAUAGG | 3202 | CCUAUACCCAGCUGCCACU | 3203 |
| GUGGCAGCUGGGUAUAGGC | 3204 | GCCUAUACCCAGCUGCCAC | 3205 |
| UGGCAGCUGGGUAUAGGCC | 3206 | GGCCUAUACCCAGCUGCCA | 3207 |
| GCAGCUGGGUAUAGGCCCU | 3208 | AGGGCCUAUACCCAGCUGC | 3209 |
| CAGCUGGGUAUAGGCCCUC | 3210 | GAGGGCCUAUACCCAGCUG | 3211 |
| AGCUGGGUAUAGGCCCUCC | 3212 | GGAGGGCCUAUACCCAGCU | 3213 |

TABLE 4-continued

| Sense Sequence | SEQ ID NO: | Antisense Sequence | SEQ ID NO: |
|---|---|---|---|
| GGUAUAGGCCCUCCCAAGU | 3214 | ACUUGGGAGGGCCUAUACC | 3215 |
| GUAUAGGCCCUCCCAAGUG | 3216 | CACUUGGGAGGGCCUAUAC | 3217 |
| UAUAGGCCCUCCCAAGUGU | 3218 | ACACUUGGGAGGGCCUAUA | 3219 |
| AUAGGCCCUCCCAAGUGUC | 3220 | GACACUUGGGAGGGCCUAU | 3221 |
| UAGGCCCUCCCAAGUGUCA | 3222 | UGACACUUGGGAGGGCCUA | 3223 |
| CCCUCCCAAGUGUCAUGCC | 3224 | GGCAUGACACUUGGGAGGG | 3225 |
| CCUCCCAAGUGUCAUGCCC | 3226 | GGGCAUGACACUUGGGAGG | 3227 |
| CCCUGACAGUCCUGAUGGA | 3228 | UCCAUCAGGACUGUCAGGG | 3229 |
| CUGAUGGACUCUGCCCUGU | 3230 | ACAGGGCAGAGUCCAUCAG | 3231 |
| UGAUGGACUCUGCCCUGUG | 3232 | CACAGGGCAGAGUCCAUCA | 3233 |
| UGGACUCUGCCCUGUGUAA | 3234 | UUACACAGGGCAGAGUCCA | 3235 |
| GGACUCUGCCCUGUGUAAG | 3236 | CUUACACAGGGCAGAGUCC | 3237 |
| GACUCUGCCCUGUGUAAGA | 3238 | UCUUACACAGGGCAGAGUC | 3239 |
| CUGCCCUGUGUAAGAUUGC | 3240 | GCAAUCUUACACAGGGCAG | 3241 |
| UGCCCUGUGUAAGAUUGCA | 3242 | UGCAAUCUUACACAGGGCA | 3243 |
| GCCCUGUGUAAGAUUGCAU | 3244 | AUGCAAUCUUACACAGGGC | 3245 |
| CCCUGUGUAAGAUUGCAUC | 3246 | GAUGCAAUCUUACACAGGG | 3247 |
| CUGUGUAAGAUUGCAUCAC | 3248 | GUGAUGCAAUCUUACACAG | 3249 |
| UGUGUAAGAUUGCAUCACC | 3250 | GGUGAUGCAAUCUUACACA | 3251 |
| GUGUAAGAUUGCAUCACCA | 3252 | UGGUGAUGCAAUCUUACAC | 3253 |
| UGUAAGAUUGCAUCACCAC | 3254 | GUGGUGAUGCAAUCUUACA | 3255 |
| CACCACCACCACCACCUCU | 3256 | AGAGGUGGUGGUGGUGGUG | 3257 |
| ACCACCACCACCACCUCUC | 3258 | GAGAGGUGGUGGUGGUGGU | 3259 |
| CCACCACCACCACCUCUCU | 3260 | AGAGAGGUGGUGGUGGUGG | 3261 |
| CACCACCACCACCUCUCUG | 3262 | CAGAGAGGUGGUGGUGGUG | 3263 |
| ACCACCACCACCUCUCUGG | 3264 | CCAGAGAGGUGGUGGUGGU | 3265 |
| UGGCCCUCCUCCACAUCAU | 3266 | AUGAUGUGGAGGAGGGCCA | 3267 |
| GGCCCUCCUCCACAUCAUG | 3268 | CAUGAUGUGGAGGAGGGCC | 3269 |
| GCCCUCCUCCACAUCAUGC | 3270 | GCAUGAUGUGGAGGAGGGC | 3271 |
| CCCUCCUCCACAUCAUGCU | 3272 | AGCAUGAUGUGGAGGAGGG | 3273 |
| CCUCCUCCACAUCAUGCUC | 3274 | GAGCAUGAUGUGGAGGAGG | 3275 |
| CUCCUCCACAUCAUGCUCC | 3276 | GGAGCAUGAUGUGGAGGAG | 3277 |
| UCCUCCACAUCAUGCUCCA | 3278 | UGGAGCAUGAUGUGGAGGA | 3279 |
| CCUCCACAUCAUGCUCCAC | 3280 | GUGGAGCAUGAUGUGGAGG | 3281 |
| CUCCACAUCAUGCUCCACA | 3282 | UGUGGAGCAUGAUGUGGAG | 3283 |
| ACAUCAUGCUCCACAUCAU | 3284 | AUGAUGUGGAGCAUGAUGU | 3285 |
| AUGCUCCACAUCAUGCUCC | 3286 | GGAGCAUGAUGUGGAGCAU | 3287 |
| GCUCCACAUCAUGCUCCAG | 3288 | CUGGAGCAUGAUGUGGAGC | 3289 |
| CUCCACAUCAUGCUCCAGG | 3290 | CCUGGAGCAUGAUGUGGAG | 3291 |
| UCCACAUCAUGCUCCAGGC | 3292 | GCCUGGAGCAUGAUGUGGA | 3293 |
| CCACAUCAUGCUCCAGGCC | 3294 | GGCCUGGAGCAUGAUGUGG | 3295 |
| CACAUCAUGCUCCAGGCCA | 3296 | UGGCCUGGAGCAUGAUGUG | 3297 |
| ACAUCAUGCUCCAGGCCAA | 3298 | UUGGCCUGGAGCAUGAUGU | 3299 |
| CAUCAUGCUCCAGGCCAAC | 3300 | GUUGGCCUGGAGCAUGAUG | 3301 |
| AUCAUGCUCCAGGCCAACU | 3302 | AGUUGGCCUGGAGCAUGAU | 3303 |
| UCAUGCUCCAGGCCAACUG | 3304 | CAGUUGGCCUGGAGCAUGA | 3305 |
| GUGACUUCUGUGCCUCGUG | 3306 | CACGAGGCACAGAAGUCAC | 3307 |
| UGACUUCUGUGCCUCGUGG | 3308 | CCACGAGGCACAGAAGUCA | 3309 |
| GACUUCUGUGCCUCGUGGC | 3310 | GCCACGAGGCACAGAAGUC | 3311 |
| CACCUGGGCCUGAGCAAGA | 3312 | UCUUGCUCAGGCCCAGGUG | 3313 |
| ACCUGGGCCUGAGCAAGAG | 3314 | CUCUUGCUCAGGCCCAGGU | 3315 |
| AGCAAGAGGGCUCCAUUCU | 3316 | AGAAUGGAGCCCUCUUGCU | 3317 |
| GCAAGAGGGCUCCAUUCUC | 3318 | GAGAAUGGAGCCCUCUUGC | 3319 |
| CAAGAGGGCUCCAUUCUCC | 3320 | GGAGAAUGGAGCCCUCUUG | 3321 |
| AGAGGGCUCCAUUCUCCUA | 3322 | UAGGAGAAUGGAGCCCUCU | 3323 |
| GAGGGCUCCAUUCUCCUAC | 3324 | GUAGGAGAAUGGAGCCCUC | 3325 |
| AGGGCUCCAUUCUCCUACC | 3326 | GGUAGGAGAAUGGAGCCCU | 3327 |
| GGGCUCCAUUCUCCUACCC | 3328 | GGGUAGGAGAAUGGAGCCC | 3329 |
| AACCCUCAUCCCUGUCCUA | 3330 | UAGGACAGGGAUGAGGGUU | 3331 |
| ACCCUCAUCCCUGUCCUAG | 3332 | CUAGGACAGGGAUGAGGGU | 3333 |
| CCCUCAUCCCUGUCCUAGC | 3334 | GCUAGGACAGGGAUGAGGG | 3335 |
| CCUCAUCCCUGUCCUAGCC | 3336 | GGCUAGGACAGGGAUGAGG | 3337 |
| GAAUUUCCUUCUGGCCUAA | 3338 | UAGGCCAGAAGGAAAAUUC | 3339 |
| AAUUUCCUUCUGGCCUAA | 3340 | UUAGGCCAGAAGGAAAAUU | 3341 |
| UGCUGCAGCAGUGGUGAAG | 3342 | CUUCACCACUGCUGCAGCA | 3343 |
| GCUGCAGCAGUGGUGAAGC | 3344 | GCUUCACCACUGCUGCAGC | 3345 |
| CUGCAGCAGUGGUGAAGCU | 3346 | AGCUUCACCACUGCUGCAG | 3347 |
| UGCAGCAGUGGUGAAGCUA | 3348 | UAGCUUCACCACUGCUGCA | 3349 |
| AAAGACUAGAGGUAUGAGG | 3350 | CCUCAUACCUCUAGUCUUU | 3351 |
| AAGACUAGAGGUAUGAGGG | 3352 | CCCUCAUACCUCUAGUCUU | 3353 |
| AGACUAGAGGUAUGAGGGA | 3354 | UCCCUCAUACCUCUAGUCU | 3355 |
| GACUAGAGGUAUGAGGGAA | 3356 | UUCCCUCAUACCUCUAGUC | 3357 |
| CCCACCUGGCUCAUAAGGC | 3358 | GCCUUAUGAGCCAGGUGGG | 3359 |
| CCACCUGGCUCAUAAGGCG | 3360 | CGCCUUAUGAGCCAGGUGG | 3361 |
| CACCUGGCUCAUAAGGCGU | 3362 | ACGCCUUAUGAGCCAGGUG | 3363 |
| ACCUGGCUCAUAAGGCGUU | 3364 | AACGCCUUAUGAGCCAGGU | 3365 |

TABLE 4-continued

| Sense Sequence | SEQ ID NO: | Antisense Sequence | SEQ ID NO: |
|---|---|---|---|
| CUGGCUCAUAAGGCGUUCC | 3366 | GGAACGCCUUAUGAGCCAG | 3367 |
| CUCAUAAGGCGUUCCCUCC | 3368 | GGAGGGAACGCCUUAUGAG | 3369 |
| UCAUAAGGCGUUCCCUCCC | 3370 | GGGAGGGAACGCCUUAUGA | 3371 |
| AAAUCAUCCUCUUUCUUGC | 3372 | GCAAGAAAGAGGAUGAUUU | 3373 |
| AAUCAUCCUCUUUCUUGCA | 3374 | UGCAAGAAAGAGGAUGAUU | 3375 |
| UCAUCCUCUUUCUUGCAUC | 3376 | GAUGCAAGAAAGAGGAUGA | 3377 |
| CAUCCUCUUUCUUGCAUCA | 3378 | UGAUGCAAGAAAGAGGAUG | 3379 |
| AUCCUCUUUCUUGCAUCAU | 3380 | AUGAUGCAAGAAAGAGGAU | 3381 |
| UCCUCUUUCUUGCAUCAUG | 3382 | CAUGAUGCAAGAAAGAGGA | 3383 |
| CUCUUUCUUGCAUCAUGCG | 3384 | CGCAUGAUGCAAGAAAGAG | 3385 |
| UCUUUCUUGCAUCAUGCGU | 3386 | ACGCAUGAUGCAAGAAAGA | 3387 |
| CUUUCUUGCAUCAUGCGUG | 3388 | CACGCAUGAUGCAAGAAAG | 3389 |
| UUUCUUGCAUCAUGCGUGU | 3390 | ACACGCAUGAUGCAAGAAA | 3391 |
| UUCUUGCAUCAUGCGUGUC | 3392 | GACACGCAUGAUGCAAGAA | 3393 |
| UCUUGCAUCAUGCGUGUCC | 3394 | GGACACGCAUGAUGCAAGA | 3395 |
| CUUGCAUCAUGCGUGUCCA | 3396 | UGGACACGCAUGAUGCAAG | 3397 |
| UCAUGCGUGUCCACAUUGC | 3398 | GCAAUGUGGACACGCAUGA | 3399 |
| CAUGCGUGUCCACAUUGCA | 3400 | UGCAAUGUGGACACGCAUG | 3401 |
| CCCUACUUCAGGCCCAGUC | 3402 | GACUGGGCCUGAAGUAGGG | 3403 |
| CCUACUUCAGGCCCAGUCA | 3404 | UGACUGGGCCUGAAGUAGG | 3405 |
| UUCAGGCCCAGUCACCAUG | 3406 | CAUGGUGACUGGGCCUGAA | 3407 |
| UCAGGCCCAGUCACCAUGG | 3408 | CCAUGGUGACUGGGCCUGA | 3409 |
| CCAGUCACCAUGGCCAGAU | 3410 | AUCUGGCCAUGGUGACUGG | 3411 |
| CAGUCACCAUGGCCAGAUG | 3412 | CAUCUGGCCAUGGUGACUG | 3413 |
| AGCACAGCUGGCCAAUCCU | 3414 | AGGAUUGGCCAGCUGUGCU | 3415 |
| GCACAGCUGGCCAAUCCUG | 3416 | CAGGAUUGGCCAGCUGUGC | 3417 |
| AGCUGGCCAAUCCUGGGAC | 3418 | GUCCCAGGAUUGGCCAGCU | 3419 |
| GCUGGCCAAUCCUGGGACU | 3420 | AGUCCCAGGAUUGGCCAGC | 3421 |
| CUGGCCAAUCCUGGGACUC | 3422 | GAGUCCCAGGAUUGGCCAG | 3423 |
| UGGCCAAUCCUGGGACUCA | 3424 | UGAGUCCCAGGAUUGGCCA | 3425 |
| AUCCUGGGACUCAGAGGGU | 3426 | ACCCUCUGAGUCCCAGGAU | 3427 |
| UCCUGGGACUCAGAGGGUA | 3428 | UACCCUCUGAGUCCCAGGA | 3429 |
| CCUGGGACUCAGAGGGUAG | 3430 | CUACCCUCUGAGUCCCAGG | 3431 |
| CUGGGACUCAGAGGGUAGG | 3432 | CCUACCCUCUGAGUCCCAG | 3433 |
| GGACUCAGAGGGUAGGUCG | 3434 | CGACCUACCCUCUGAGUCC | 3435 |
| GACUCAGAGGGUAGGUCGG | 3436 | CCGACCUACCCUCUGAGUC | 3437 |
| ACUCAGAGGGUAGGUCGGC | 3438 | GCCGACCUACCCUCUGAGU | 3439 |
| CUCAGAGGGUAGGUCGGCU | 3440 | AGCCGACCUACCCUCUGAG | 3441 |
| UCAGAGGGUAGGUCGGCUG | 3442 | CAGCCGACCUACCCUCUGA | 3443 |
| GGCUGGCUGACCACUAGGU | 3444 | ACCUAGUGGUCAGCCAGCC | 3445 |
| GCUGGCUGACCACUAGGUU | 3446 | AACCUAGUGGUCAGCCAGC | 3447 |
| CUGGCUGACCACUAGGUUU | 3448 | AAACCUAGUGGUCAGCCAG | 3449 |
| CUGACCACUAGGUUUGGAA | 3450 | UUCCAAACCUAGUGGUCAG | 3451 |
| UGACCACUAGGUUUGGAAG | 3452 | CUUCCAAACCUAGUGGUCA | 3453 |
| GACCACUAGGUUUGGAAGA | 3454 | UCUUCCAAACCUAGUGGUC | 3455 |
| ACCACUAGGUUUGGAAGAC | 3456 | GUCUUCCAAACCUAGUGGU | 3457 |
| CCACUAGGUUUGGAAGACC | 3458 | GGUCUUCCAAACCUAGUGG | 3459 |
| UAGGUUUGGAAGACCCAGG | 3460 | CCUGGGUCUUCCAAACCUA | 3461 |
| AGGUUUGGAAGACCCAGGC | 3462 | GCCUGGGUCUUCCAAACCU | 3463 |
| CAGGCAGCUGGCUCUAAAG | 3464 | CUUUAGAGCCAGCUGCCUG | 3465 |
| AGGCAGCUGGCUCUAAAGA | 3466 | UCUUUAGAGCCAGCUGCCU | 3467 |
| AGCUGGCUCUAAAGAGGCC | 3468 | GGCCUCUUUAGAGCCAGCU | 3469 |
| GCUGGCUCUAAAGAGGCCC | 3470 | GGGCCUCUUUAGAGCCAGC | 3471 |
| CCAGGUCAGUAGCCAGACA | 3472 | UGUCUGGCUACUGACCUGG | 3473 |
| GUCAGUAGCCAGACAUGAG | 3474 | CUCAUGUCUGGCUACUGAC | 3475 |
| GUAGCCAGACAUGAGCUGU | 3476 | ACAGCUCAUGUCUGGCUAC | 3477 |
| AGACAUGAGCUGUGAGGGU | 3478 | ACCCUCACAGCUCAUGUCU | 3479 |
| AUGAGCUGUGAGGGUCAAG | 3480 | CUUGACCCUCACAGCUCAU | 3481 |
| UGAGCUGUGAGGGUCAAGC | 3482 | GCUUGACCCUCACAGCUCA | 3483 |
| GAGCUGUGAGGGUCAAGCA | 3484 | UGCUUGACCCUCACAGCUC | 3485 |
| AGCUGUGAGGGUCAAGCAC | 3486 | GUGCUUGACCCUCACAGCU | 3487 |
| GUGAGGGUCAAGCACAGCU | 3488 | AGCUGUGCUUGACCCUCAC | 3489 |
| UGAGGGUCAAGCACAGCUA | 3490 | UAGCUGUGCUUGACCCUCA | 3491 |
| GAGGGUCAAGCACAGCUAU | 3492 | AUAGCUGUGCUUGACCCUC | 3493 |
| AGGGUCAAGCACAGCUAUC | 3494 | GAUAGCUGUGCUUGACCCU | 3495 |
| GGGUCAAGCACAGCUAUCC | 3496 | GGAUAGCUGUGCUUGACCC | 3497 |
| CAAGCACAGCUAUCCAUCA | 3498 | UGAUGGAUAGCUGUGCUUG | 3499 |
| CACAGCUAUCCAUCAGAUG | 3500 | CAUCUGAUGGAUAGCUGUG | 3501 |
| ACAGCUAUCCAUCAGAUGA | 3502 | UCAUCUGAUGGAUAGCUGU | 3503 |
| CAGCUAUCCAUCAGAUGAU | 3504 | AUCAUCUGAUGGAUAGCUG | 3505 |
| AGCUAUCCAUCAGAUGAUC | 3506 | GAUCAUCUGAUGGAUAGCU | 3507 |
| GCUAUCCAUCAGAUGAUCU | 3508 | AGAUCAUCUGAUGGAUAGC | 3509 |
| CUAUCCAUCAGAUGAUCUA | 3510 | UAGAUCAUCUGAUGGAUAG | 3511 |
| CAUCAGAUGAUCUACUUUC | 3512 | GAAAGUAGAUCAUCUGAUG | 3513 |
| AGAUGAUCUACUUUCAGCC | 3514 | GGCUGAAAGUAGAUCAUCU | 3515 |
| GAUCUACUUUCAGCCUUCC | 3516 | GGAAGGCUGAAAGUAGAUC | 3517 |

TABLE 4-continued

| Sense Sequence | SEQ ID NO: | Antisense Sequence | SEQ ID NO: |
|---|---|---|---|
| AUCUACUUUCAGCCUUCCU | 3518 | AGGAAGGCUGAAAGUAGAU | 3519 |
| CAAUAGAAGACAGGUGGCU | 3520 | AGCCACCUGUCUUCUAUUG | 3521 |
| AAUAGAAGACAGGUGGCUG | 3522 | CAGCCACCUGUCUUCUAUU | 3523 |
| CAGGUGGCUGUACCCUUGG | 3524 | CCAAGGGUACAGCCACCUG | 3525 |
| AGGUGGCUGUACCCUUGGC | 3526 | GCCAAGGGUACAGCCACCU | 3527 |
| GGCUGUACCCUUGGCCAAG | 3528 | CUUGGCCAAGGGUACAGCC | 3529 |
| UGGUGUCUGCUGUCACUGU | 3530 | ACAGUGACAGCAGACACCA | 3531 |
| GUCUGCUGUCACUGUGCCC | 3532 | GGGCACAGUGACAGCAGAC | 3533 |
| CUGCUGUCACUGUGCCCUC | 3534 | GAGGGCACAGUGACAGCAG | 3535 |
| UGCUGUCACUGUGCCCUCA | 3536 | UGAGGGCACAGUGACAGCA | 3537 |
| GCUGUCACUGUGCCCUCAU | 3538 | AUGAGGGCACAGUGACAGC | 3539 |
| CUGUCACUGUGCCCUCAUU | 3540 | AAUGAGGGCACAGUGACAG | 3541 |
| UGUCACUGUGCCCUCAUUG | 3542 | CAAUGAGGGCACAGUGACA | 3543 |
| GUCACUGUGCCCUCAUUGG | 3544 | CCAAUGAGGGCACAGUGAC | 3545 |
| ACUGUGCCCUCAUUGGCCC | 3546 | GGGCCAAUGAGGGCACAGU | 3547 |
| CCCAGCAAUCAGACUCAAC | 3548 | GUUGAGUCUGAUUGCUGGG | 3549 |
| GGAGCAACUGCCAUCCGAG | 3550 | CUCGGAUGGCAGUUGCUCC | 3551 |
| GAGCAACUGCCAUCCGAGG | 3552 | CCUCGGAUGGCAGUUGCUC | 3553 |
| AGCAACUGCCAUCCGAGGC | 3554 | GCCUCGGAUGGCAGUUGCU | 3555 |
| GCAACUGCCAUCCGAGGCU | 3556 | AGCCUCGGAUGGCAGUUGC | 3557 |
| CAACUGCCAUCCGAGGCUC | 3558 | GAGCCUCGGAUGGCAGUUG | 3559 |
| GCCAUCCGAGGCUCCUGAA | 3560 | UUCAGGAGCCUCGGAUGGC | 3561 |
| AACCAGGGCCAUUCACCAG | 3562 | CUGGUGAAUGGCCCUGGUU | 3563 |
| ACCAGGGCCAUUCACCAGG | 3564 | CCUGGUGAAUGGCCCUGGU | 3565 |
| CCAGGGCCAUUCACCAGGA | 3566 | UCCUGGUGAAUGGCCCUGG | 3567 |
| CAGGGCCAUUCACCAGGAG | 3568 | CUCCUGGUGAAUGGCCCUG | 3569 |
| GGCCAUUCACCAGGAGCAU | 3570 | AUGCUCCUGGUGAAUGGCC | 3571 |
| GCCAUUCACCAGGAGCAUG | 3572 | CAUGCUCCUGGUGAAUGGC | 3573 |
| CCAUUCACCAGGAGCAUGC | 3574 | GCAUGCUCCUGGUGAAUGG | 3575 |
| CAUUCACCAGGAGCAUGCG | 3576 | CGCAUGCUCCUGGUGAAUG | 3577 |
| AUUCACCAGGAGCAUGCGG | 3578 | CCGCAUGCUCCUGGUGAAU | 3579 |
| UUCACCAGGAGCAUGCGGC | 3580 | GCCGCAUGCUCCUGGUGAA | 3581 |
| UCACCAGGAGCAUGCGGCU | 3582 | AGCCGCAUGCUCCUGGUGA | 3583 |
| AGCAUGCGGCUCCCUGAUG | 3584 | CAUCAGGGAGCCGCAUGCU | 3585 |
| GCAUGCGGCUCCCUGAUGU | 3586 | ACAUCAGGGAGCCGCAUGC | 3587 |
| CAUGCGGCUCCCUGAUGUC | 3588 | GACAUCAGGGAGCCGCAUG | 3589 |
| AUGCGGCUCCCUGAUGUCC | 3590 | GGACAUCAGGGAGCCGCAU | 3591 |
| UGCGGCUCCCUGAUGUCCA | 3592 | UGGACAUCAGGGAGCCGCA | 3593 |
| GCUCCCUGAUGUCCAGCUC | 3594 | GAGCUGGACAUCAGGGAGC | 3595 |
| CUCCCUGAUGUCCAGCUCU | 3596 | AGAGCUGGACAUCAGGGAG | 3597 |
| UCCCUGAUGUCCAGCUCUG | 3598 | CAGAGCUGGACAUCAGGGA | 3599 |
| CCCUGAUGUCCAGCUCUGG | 3600 | CCAGAGCUGGACAUCAGGG | 3601 |
| CCUGAUGUCCAGCUCUGGC | 3602 | GCCAGAGCUGGACAUCAGG | 3603 |
| CUGAUGUCCAGCUCUGGCU | 3604 | AGCCAGAGCUGGACAUCAG | 3605 |
| UCUGGUGCUGGAGCUAGCC | 3606 | GGCUAGCUCCAGCACCAGA | 3607 |
| UGGUGCUGGAGCUAGCCAA | 3608 | UUGGCUAGCUCCAGCACCA | 3609 |
| GGUGCUGGAGCUAGCCAAG | 3610 | CUUGGCUAGCUCCAGCACC | 3611 |
| GUGCUGGAGCUAGCCAAGC | 3612 | GCUUGGCUAGCUCCAGCAC | 3613 |
| GCUGGAGCUAGCCAAGCAG | 3614 | CUGCUUGGCUAGCUCCAGC | 3615 |
| CUGGAGCUAGCCAAGCAGC | 3616 | GCUGCUUGGCUAGCUCCAG | 3617 |
| UGGAGCUAGCCAAGCAGCA | 3618 | UGCUGCUUGGCUAGCUCCA | 3619 |
| GGAGCUAGCCAAGCAGCAA | 3620 | UUGCUGCUUGGCUAGCUCC | 3621 |
| GAGCUAGCCAAGCAGCAAA | 3622 | UUUGCUGCUUGGCUAGCUC | 3623 |
| AGCUAGCCAAGCAGCAAAU | 3624 | AUUUGCUGCUUGGCUAGCU | 3625 |
| GCUAGCCAAGCAGCAAAUC | 3626 | GAUUUGCUGCUUGGCUAGC | 3627 |
| CAGCAAAUCCUGGAUGGGU | 3628 | ACCCAUCCAGGAUUUGCUG | 3629 |
| AGCAAAUCCUGGAUGGGUU | 3630 | AACCCAUCCAGGAUUUGCU | 3631 |
| GCAAAUCCUGGAUGGGUUG | 3632 | CAACCCAUCCAGGAUUUGC | 3633 |
| CAAAUCCUGGAUGGGUUGC | 3634 | GCAACCCAUCCAGGAUUUG | 3635 |
| AAAUCCUGGAUGGGUUGCA | 3636 | UGCAACCCAUCCAGGAUUU | 3637 |
| GGUUGCACCUGACCAGUCG | 3638 | CGACUGGUCAGGUGCAACC | 3639 |
| GUUGCACCUGACCAGUCGU | 3640 | ACGACUGGUCAGGUGCAAC | 3641 |
| UUGCACCUGACCAGUCGUC | 3642 | GACGACUGGUCAGGUGCAA | 3643 |
| UGCACCUGACCAGUCGUCC | 3644 | GGACGACUGGUCAGGUGCA | 3645 |
| UGACCAGUCGUCCCAGAAU | 3646 | AUUCUGGGACGACUGGUCA | 3647 |
| GACCAGUCGUCCCAGAAUA | 3648 | UAUUCUGGGACGACUGGUC | 3649 |
| ACCAGUCGUCCCAGAAUAA | 3650 | UUAUUCUGGGACGACUGGU | 3651 |
| CCAGUCGUCCCAGAAUAAC | 3652 | GUUAUUCUGGGACGACUGG | 3653 |
| CAGUCGUCCCAGAAUAACU | 3654 | AGUUAUUCUGGGACGACUG | 3655 |
| AGUCGUCCCAGAAUAACUC | 3656 | GAGUUAUUCUGGGACGACU | 3657 |
| GUCGUCCCAGAAUAACUCA | 3658 | UGAGUUAUUCUGGGACGAC | 3659 |
| UCGUCCCAGAAUAACUCAU | 3660 | AUGAGUUAUUCUGGGACGA | 3661 |
| CGUCCCAGAAUAACUCAUC | 3662 | GAUGAGUUAUUCUGGGACG | 3663 |
| GUCCCAGAAUAACUCAUCC | 3664 | GGAUGAGUUAUUCUGGGAC | 3665 |
| UCCCAGAAUAACUCAUCCU | 3666 | AGGAUGAGUUAUUCUGGGA | 3667 |
| CCCAGAAUAACUCAUCCUC | 3668 | GAGGAUGAGUUAUUCUGGG | 3669 |

TABLE 4-continued

| Sense Sequence | SEQ ID NO: | Antisense Sequence | SEQ ID NO: |
|---|---|---|---|
| GACUACAGCCAGGGAGUGU | 3670 | ACACUCCCUGGCUGUAGUC | 3671 |
| ACUACAGCCAGGGAGUGUG | 3672 | CACACUCCCUGGCUGUAGU | 3673 |
| CUACAGCCAGGGAGUGUGG | 3674 | CCACACUCCCUGGCUGUAG | 3675 |
| GAGUGUGGCUCCAGGGAAU | 3676 | AUUCCCUGGAGCCACACUC | 3677 |
| GGGAGGAGGUCAUCAGCUU | 3678 | AAGCUGAUGACCUCCUCCC | 3679 |
| GAGGUCAUCAGCUUUGCUA | 3680 | UAGCAAAGCUGAUGACCUC | 3681 |
| AGGUCAUCAGCUUUGCUAC | 3682 | GUAGCAAAGCUGAUGACCU | 3683 |
| GGUCAUCAGCUUUGCUACU | 3684 | AGUAGCAAAGCUGAUGACC | 3685 |
| GCUUUGCUACUGUCACAGG | 3686 | CCUGUGACAGUAGCAAAGC | 3687 |
| CUUUGCUACUGUCACAGGU | 3688 | ACCUGUGACAGUAGCAAAG | 3689 |
| UUUGCUACUGUCACAGGUG | 3690 | CACCUGUGACAGUAGCAAA | 3691 |
| UUGCUACUGUCACAGGUGG | 3692 | CCACCUGUGACAGUAGCAA | 3693 |
| UGCUACUGUCACAGGUGGG | 3694 | CCCACCUGUGACAGUAGCA | 3695 |
| GCUACUGUCACAGGUGGGU | 3696 | ACCCACCUGUGACAGUAGC | 3697 |
| CUACUGUCACAGGUGGGUG | 3698 | CACCCACCUGUGACAGUAG | 3699 |
| CAGGCAAAGAGCAGACAGG | 3700 | CCUGUCUGCUCUUUGCCUG | 3701 |
| GGCAGGGACUGGUUGCAGA | 3702 | UCUGCAACCAGUCCCUGCC | 3703 |
| GCAGGGACUGGUUGCAGAG | 3704 | CUCUGCAACCAGUCCCUGC | 3705 |
| AGGGACUGGUUGCAGAGGA | 3706 | UCCUCUGCAACCAGUCCCU | 3707 |
| GGGACUGGUUGCAGAGGAC | 3708 | GUCCUCUGCAACCAGUCCC | 3709 |
| GGACUGGUUGCAGAGGACA | 3710 | UGUCCUCUGCAACCAGUCC | 3711 |
| GACUGGUUGCAGAGGACAC | 3712 | GUGUCCUCUGCAACCAGUC | 3713 |
| UUUUCUAGAGGUAGGUUCG | 3714 | CGAACCUACCUCUAGAAAA | 3715 |
| UUUCUAGAGGUAGGUUCGA | 3716 | UCGAACCUACCUCUAGAAA | 3717 |
| UUCUAGAGGUAGGUUCGAG | 3718 | CUCGAACCUACCUCUAGAA | 3719 |
| UCUAGAGGUAGGUUCGAGG | 3720 | CCUCGAACCUACCUCUAGA | 3721 |
| CUAGAGGUAGGUUCGAGGG | 3722 | CCCUCGAACCUACCUCUAG | 3723 |
| UAGAGGUAGGUUCGAGGGA | 3724 | UCCCUCGAACCUACCUCUA | 3725 |
| GAGCUUCAUCUCUACUCAC | 3726 | GUGAGUAGAGAUGAAGCUC | 3727 |
| AGCUUCAUCUCUACUCACA | 3728 | UGUGAGUAGAGAUGAAGCU | 3729 |
| GCUUCAUCUCUACUCACAU | 3730 | AUGUGAGUAGAGAUGAAGC | 3731 |
| CUUCAUCUCUACUCACAUU | 3732 | AAUGUGAGUAGAGAUGAAG | 3733 |
| AUCUCUACUCACAUUUUCU | 3734 | AGAAAAUGUGAGUAGAGAU | 3735 |
| UCUCUACUCACAUUUUCUU | 3736 | AAGAAAAUGUGAGUAGAGA | 3737 |
| UCACAUUUCUUUCCCUUU | 3738 | AAAGGGAAAGAAAAUGUGA | 3739 |
| CCCUUUUCUGUCUUUCGGG | 3740 | CCCGAAAGACAGAAAAGGG | 3741 |
| CCUUUUCUGUCUUUCGGGC | 3742 | GCCCGAAAGACAGAAAAGG | 3743 |
| CUUUUCUGUCUUUCGGGCA | 3744 | UGCCCGAAAGACAGAAAAG | 3745 |
| UUUCGGGCAGACUCCACUU | 3746 | AAGUGGAGUCUGCCCGAAA | 3747 |
| UUCGGGCAGACUCCACUU | 3748 | GAAGUGGAGUCUGCCCGAA | 3749 |
| UCGGGCAGACUCCACUUCA | 3750 | UGAAGUGGAGUCUGCCCGA | 3751 |
| CGGGCAGACUCCACUUCAG | 3752 | CUGAAGUGGAGUCUGCCCG | 3753 |
| GGGCAGACUCCACUUCAGC | 3754 | GCUGAAGUGGAGUCUGCCC | 3755 |
| GGCAGACUCCACUUCAGCC | 3756 | GGCUGAAGUGGAGUCUGCC | 3757 |
| UCCACUUCAGCCUACAGCU | 3758 | AGCUGUAGGCUGAAGUGGA | 3759 |
| CCACUUCAGCCUACAGCUC | 3760 | GAGCUGUAGGCUGAAGUGG | 3761 |
| CACUUCAGCCUACAGCUCC | 3762 | GGAGCUGUAGGCUGAAGUG | 3763 |
| ACUUCAGCCUACAGCUCCC | 3764 | GGGAGCUGUAGGCUGAAGU | 3765 |
| CCUACAGCUCCCUGCUCAC | 3766 | GUGAGCAGGGAGCUGUAGG | 3767 |
| CUACAGCUCCCUGCUCACU | 3768 | AGUGAGCAGGGAGCUGUAG | 3769 |
| UACAGCUCCCUGCUCACUU | 3770 | AAGUGAGCAGGGAGCUGUA | 3771 |
| GCUCCCUGCUCACUUUUCA | 3772 | UGAAAAGUGAGCAGGGAGC | 3773 |
| CUCCCUGCUCACUUUUCAC | 3774 | GUGAAAAGUGAGCAGGGAG | 3775 |
| GCUCACUUUUCACCUGUCC | 3776 | GGACAGGUGAAAAGUGAGC | 3777 |
| CUCACUUUUCACCUGUCCA | 3778 | UGGACAGGUGAAAAGUGAG | 3779 |
| UGUCCACUCCUCGGUCCCA | 3780 | UGGGACCGAGGAGUGGACA | 3781 |
| UCGGUCCCACCACCUGUAC | 3782 | GUACAGGUGGUGGGACCGA | 3783 |
| CCACCACCUGUACCAUGCC | 3784 | GGCAUGGUACAGGUGGUGG | 3785 |
| CACCACCUGUACCAUGCCC | 3786 | GGGCAUGGUACAGGUGGUG | 3787 |
| ACCACCUGUACCAUGCCCG | 3788 | CGGGCAUGGUACAGGUGGU | 3789 |
| CACCCUUCCUGGCACUCUU | 3790 | AAGAGUGCCAGGAAGGGUG | 3791 |
| ACCCUUCCUGGCACUCUUU | 3792 | AAAGAGUGCCAGGAAGGGU | 3793 |
| CCCUUCCUGGCACUCUUUG | 3794 | CAAAGAGUGCCAGGAAGGG | 3795 |
| CCUUCCUGGCACUCUUUGC | 3796 | GCAAAGAGUGCCAGGAAGG | 3797 |
| UUCCUGGCACUCUUUGCUU | 3798 | AAGCAAAGAGUGCCAGGAA | 3799 |
| UCCUGGCACUCUUUGCUUG | 3800 | CAAGCAAAGAGUGCCAGGA | 3801 |
| CCUGGCACUCUUUGCUUGA | 3802 | UCAAGCAAAGAGUGCCAGG | 3803 |
| CUGGCACUCUUUGCUUGAG | 3804 | CUCAAGCAAAGAGUGCCAG | 3805 |
| UGGCACUCUUUGCUUGAGG | 3806 | CCUCAAGCAAAGAGUGCCA | 3807 |
| GGCACUCUUUGCUUGAGGA | 3808 | UCCUCAAGCAAAGAGUGCC | 3809 |
| GCACUCUUUGCUUGAGGAU | 3810 | AUCCUCAAGCAAAGAGUGC | 3811 |
| CACUCUUUGCUUGAGGAUC | 3812 | GAUCCUCAAGCAAAGAGUG | 3813 |
| ACUCUUUGCUUGAGGAUCU | 3814 | AGAUCCUCAAGCAAAGAGU | 3815 |
| CUCUUUGCUUGAGGAUCUU | 3816 | AAGAUCCUCAAGCAAAGAG | 3817 |
| UCUUUGCUUGAGGAUCUUC | 3818 | GAAGAUCCUCAAGCAAAGA | 3819 |
| UGCUUGAGGAUCUUCCGAU | 3820 | AUCGGAAGAUCCUCAAGCA | 3821 |

TABLE 4-continued

| Sense Sequence | SEQ ID NO: | Antisense Sequence | SEQ ID NO: |
|---|---|---|---|
| GCUUGAGGAUCUUCCGAUG | 3822 | CAUCGGAAGAUCCUCAAGC | 3823 |
| GCACUCUCCUGGCUGAGCA | 3824 | UGCUCAGCCAGGAGAGUGC | 3825 |
| CUCCUGGCUGAGCACCACA | 3826 | UGUGGUGCUCAGCCAGGAG | 3827 |
| UGGCUGAGCACCACAUCAC | 3828 | GUGAUGUGGUGCUCAGCCA | 3829 |
| GGCUGAGCACCACAUCACC | 3830 | GGUGAUGUGGUGCUCAGCC | 3831 |
| GCUGAGCACCACAUCACCA | 3832 | UGGUGAUGUGGUGCUCAGC | 3833 |
| CUGAGCACCACAUCACCAA | 3834 | UUGGUGAUGUGGUGCUCAG | 3835 |
| CCAACCUGGGCUGGCAUAC | 3836 | GUAUGCCAGCCCAGGUUGG | 3837 |
| CAACCUGGGCUGGCAUACC | 3838 | GGUAUGCCAGCCCAGGUUG | 3839 |
| AACCUGGGCUGGCAUACCU | 3840 | AGGUAUGCCAGCCCAGGUU | 3841 |
| ACCUGGGCUGGCAUACCUU | 3842 | AAGGUAUGCCAGCCCAGGU | 3843 |
| CCUGGGCUGGCAUACCUUA | 3844 | UAAGGUAUGCCAGCCCAGG | 3845 |
| CUGGGCUGGCAUACCUUAA | 3846 | UUAAGGUAUGCCAGCCCAG | 3847 |
| UGGGCUGGCAUACCUUAAC | 3848 | GUUAAGGUAUGCCAGCCCA | 3849 |
| GGGCUGGCAUACCUUAACU | 3850 | AGUUAAGGUAUGCCAGCCC | 3851 |
| GGCUGGCAUACCUUAACUC | 3852 | GAGUUAAGGUAUGCCAGCC | 3853 |
| GCUGGCAUACCUUAACUCU | 3854 | AGAGUUAAGGUAUGCCAGC | 3855 |
| CAUACCUUAACUCUGCCCU | 3856 | AGGGCAGAGUUAAGGUAUG | 3857 |
| AUACCUUAACUCUGCCCUC | 3858 | GAGGGCAGAGUUAAGGUAU | 3859 |
| UACCUUAACUCUGCCCUCU | 3860 | AGAGGGCAGAGUUAAGGUA | 3861 |
| UCUGCCCUCUAGUGGCUUG | 3862 | CAAGCCACUAGAGGGCAGA | 3863 |
| CUGCCCUCUAGUGGCUUGA | 3864 | UCAAGCCACUAGAGGGCAG | 3865 |
| UGCCCUCUAGUGGCUUGAG | 3866 | CUCAAGCCACUAGAGGGCA | 3867 |
| AGAAGUCUGGUGUCCUGAA | 3868 | UUCAGGCACCAGACUUCU | 3869 |
| CAGGACACCAGCAGCCCUU | 3870 | AAGGGCUGCUGGUGUCCUG | 3871 |
| AGGACACCAGCAGCCCUUC | 3872 | GAAGGGCUGCUGGUGUCCU | 3873 |
| ACACCAGCAGCCCUUCCUA | 3874 | UAGGAAGGGCUGCUGGUGU | 3875 |
| CACCAGCAGCCCUUCCUAG | 3876 | CUAGGAAGGGCUGCUGGUG | 3877 |
| ACCAGCAGCCCUUCCUAGA | 3878 | UCUAGGAAGGGCUGCUGGU | 3879 |
| CCAGCAGCCCUUCCUAGAG | 3880 | CUCUAGGAAGGGCUGCUGG | 3881 |
| CAGCAGCCCUUCCUAGAGC | 3882 | GCUCUAGGAAGGGCUGCUG | 3883 |
| AGCAGCCCUUCCUAGAGCU | 3884 | AGCUCUAGGAAGGGCUGCU | 3885 |
| GCCCUUCCUAGAGCUUAAG | 3886 | CUUAAGCUCUAGGAAGGGC | 3887 |
| CCCUUCCUAGAGCUUAAGA | 3888 | UCUUAAGCUCUAGGAAGGG | 3889 |
| AGCUUAAGAUCCGAGCCAA | 3890 | UUGGCUCGGAUCUUAAGCU | 3891 |
| GCUUAAGAUCCGAGCCAAU | 3892 | AUUGGCUCGGAUCUUAAGC | 3893 |
| CUUAAGAUCCGAGCCAAUG | 3894 | CAUUGGCUCGGAUCUUAAG | 3895 |
| UUAAGAUCCGAGCCAAUGA | 3896 | UCAUUGGCUCGGAUCUUAA | 3897 |
| UAAGAUCCGAGCCAAUGAG | 3898 | CUCAUUGGCUCGGAUCUUA | 3899 |
| CGAGCCAAUGAGCCUGGAG | 3900 | CUCCAGGCUCAUUGGCUCG | 3901 |
| CCCUUAUGUUGCAGGCGAG | 3902 | CUCGCCUGCAACAUAAGGG | 3903 |
| CAUUACGUAGACUUCCAGG | 3904 | CCUGGAAGUCUACGUAAUG | 3905 |
| AUUACGUAGACUUCCAGGA | 3906 | UCCUGGAAGUCUACGUAAU | 3907 |
| UUACGUAGACUUCCAGGAA | 3908 | UUCCUGGAAGUCUACGUAA | 3909 |
| ACUGGAUACUGCAGCCCGA | 3910 | UCGGGCUGCAGUAUCCAGU | 3911 |
| CUGGAUACUGCAGCCCGAG | 3912 | CUCGGGCUGCAGUAUCCAG | 3913 |
| UGGAUACUGCAGCCCGAGG | 3914 | CCUCGGGCUGCAGUAUCCA | 3915 |
| GGGUACCAGCUGAAUUACU | 3916 | AGUAAUUCAGCUGGUACCC | 3917 |
| CUGAAUUACUGCAGUGGGC | 3918 | GCCCACUGCAGUAAUUCAG | 3919 |
| UGAAUUACUGCAGUGGGCA | 3920 | UGCCCACUGCAGUAAUUCA | 3921 |
| UGGCAGCCCAGGCAUUGCU | 3922 | AGCAAUGCCUGGGCUGCCA | 3923 |
| GCAUUGCUGCCUCUUUCCA | 3924 | UGGAAAGAGGCAGCAAUGC | 3925 |
| CAUUGCUGCCUCUUUCCAU | 3926 | AUGGAAAGAGGCAGCAAUG | 3927 |
| AUUGCUGCCUCUUUCCAUU | 3928 | AAUGGAAAGAGGCAGCAAU | 3929 |
| UGCUGCCUCUUUCCAUUCU | 3930 | AGAAUGGAAAGAGGCAGCA | 3931 |
| GCUGCCUCUUUCCAUUCUG | 3932 | CAGAAUGGAAAGAGGCAGC | 3933 |
| CUGCCUCUUUCCAUUCUGC | 3934 | GCAGAAUGGAAAGAGGCAG | 3935 |
| UGCCUCUUUCCAUUCUGCC | 3936 | GGCAGAAUGGAAAGAGGCA | 3937 |
| GCCUCUUUCCAUUCUGCCG | 3938 | CGGCAGAAUGGAAAGAGGC | 3939 |
| CCUCUUUCCAUUCUGCCGU | 3940 | ACGGCAGAAUGGAAAGAGG | 3941 |
| CUCUUUCCAUUCUGCCGUC | 3942 | GACGGCAGAAUGGAAAGAG | 3943 |
| CAUUCUGCCGUCUUCAGCC | 3944 | GGCUGAAGACGGCAGAAUG | 3945 |
| CUUCAGCCUCCUCAAAGCC | 3946 | GGCUUUGAGGAGGCUGAAG | 3947 |
| UUCAGCCUCCUCAAAGCCA | 3948 | UGGCUUUGAGGAGGCUGAA | 3949 |
| UCAGCCUCCUCAAAGCCAA | 3950 | UUGGCUUUGAGGAGGCUGA | 3951 |
| CAGCCUCCUCAAAGCCAAC | 3952 | GUUGGCUUUGAGGAGGCUG | 3953 |
| UCCUUGGCUGCCAGUACC | 3954 | GGUACUGGCAGGCCAAGGA | 3955 |
| CCUGCCAGUACCUCCUGUU | 3956 | AACAGGAGGUACUGGCAGG | 3957 |
| CUGCCAGUACCUCCUGUUG | 3958 | CAACAGGAGGUACUGGCAG | 3959 |
| UGCCAGUACCUCCUGUUGU | 3960 | ACAACAGGAGGUACUGGCA | 3961 |
| GCCAGUACCUCCUGUUGUG | 3962 | CACAACAGGAGGUACUGGC | 3963 |
| CCAGUACCUCCUGUUGUGU | 3964 | ACACAACAGGAGGUACUGG | 3965 |
| CAGUACCUCCUGUUGUGUC | 3966 | GACACAACAGGAGGUACUG | 3967 |
| GUACCUCCUGUUGUGUCCC | 3968 | GGGACACAACAGGAGGUAC | 3969 |
| UACCUCCUGUUGUGUCCCU | 3970 | AGGGACACAACAGGAGGUA | 3971 |
| ACCUCCUGUUGUGUCCCUA | 3972 | UAGGGACACAACAGGAGGU | 3973 |

TABLE 4-continued

| Sense Sequence | SEQ ID NO: | Antisense Sequence | SEQ ID NO: |
|---|---|---|---|
| CCUCCUGUUGUGUCCCUAC | 3974 | GUAGGGACACAACAGGAGG | 3975 |
| CUCCUGUUGUGUCCCUACU | 3976 | AGUAGGGACACAACAGGAG | 3977 |
| UUGUGUCCCUACUGCCCGA | 3978 | UCGGGCAGUAGGGACACAA | 3979 |
| UGUGUCCCUACUGCCCGAA | 3980 | UUCGGGCAGUAGGGACACA | 3981 |
| GUGUCCCUACUGCCCGAAG | 3982 | CUUCGGGCAGUAGGGACAC | 3983 |
| UGUCCCUACUGCCCGAAGG | 3984 | CCUUCGGGCAGUAGGGACA | 3985 |
| UCUCUCCUCUACCUGGA | 3986 | UCCAGGUAGAGGAGAGAGA | 3987 |
| UCUCCUCUACCUGGAUCAU | 3988 | AUGAUCCAGGUAGAGGAGA | 3989 |
| CUCCUCUACCUGGAUCAUA | 3990 | UAUGAUCCAGGUAGAGGAG | 3991 |
| UCCUCUACCUGGAUCAUAA | 3992 | UUAUGAUCCAGGUAGAGGA | 3993 |
| CCUCUACCUGGAUCAUAAU | 3994 | AUUAUGAUCCAGGUAGAGG | 3995 |
| CUCUACCUGGAUCAUAAUG | 3996 | CAUUAUGAUCCAGGUAGAG | 3997 |
| UCUACCUGGAUCAUAAUGG | 3998 | CCAUUAUGAUCCAGGUAGA | 3999 |
| CUACCUGGAUCAUAAUGGC | 4000 | GCCAUUAUGAUCCAGGUAG | 4001 |
| UACCUGGAUCAUAAUGGCA | 4002 | UGCCAUUAUGAUCCAGGUA | 4003 |
| ACCUGGAUCAUAAUGGCAA | 4004 | UUGCCAUUAUGAUCCAGGU | 4005 |
| CCUGGAUCAUAAUGGCAAU | 4006 | AUUGCCAUUAUGAUCCAGG | 4007 |
| CUGGAUCAUAAUGGCAAUG | 4008 | CAUUGCCAUUAUGAUCCAG | 4009 |
| UGGAUCAUAAUGGCAAUGU | 4010 | ACAUUGCCAUUAUGAUCCA | 4011 |
| GGAUCAUAAUGGCAAUGUG | 4012 | CACAUUGCCAUUAUGAUCC | 4013 |
| GAUCAUAAUGGCAAUGUGG | 4014 | CCACAUUGCCAUUAUGAUC | 4015 |
| AUAAUGGCAAUGUGGUCAA | 4016 | UUGACCACAUUGCCAUUAU | 4017 |
| UAAUGGCAAUGUGGUCAAG | 4018 | CUUGACCACAUUGCCAUUA | 4019 |
| AAUGGCAAUGUGGUCAAGA | 4020 | UCUUGACCACAUUGCCAUU | 4021 |
| AAUGUGGUCAAGACGGAUG | 4022 | CAUCCGUCUUGACCACAUU | 4023 |
| AUGUGGUCAAGACGGAUGU | 4024 | ACAUCCGUCUUGACCACAU | 4025 |
| UGUGGUCAAGACGGAUGUG | 4026 | CACAUCCGUCUUGACCACA | 4027 |
| GUGGUCAAGACGGAUGUGC | 4028 | GCACAUCCGUCUUGACCAC | 4029 |
| UGGUCAAGACGGAUGUGCC | 4030 | GGCACAUCCGUCUUGACCA | 4031 |
| GGUCAAGACGGAUGUGCCA | 4032 | UGGCACAUCCGUCUUGACC | 4033 |
| GUCAAGACGGAUGUGCCAG | 4034 | CUGGCACAUCCGUCUUGAC | 4035 |
| UCAAGACGGAUGUGCCAGA | 4036 | UCUGGCACAUCCGUCUUGA | 4037 |
| CAAGACGGAUGUGCCAGAU | 4038 | AUCUGGCACAUCCGUCUUG | 4039 |
| AAGACGGAUGUGCCAGAUA | 4040 | UAUCUGGCACAUCCGUCUU | 4041 |
| AGACGGAUGUGCCAGAUAU | 4042 | AUAUCUGGCACAUCCGUCU | 4043 |
| GACGGAUGUGCCAGAUAUG | 4044 | CAUAUCUGGCACAUCCGUC | 4045 |
| ACGGAUGUGCCAGAUAUGG | 4046 | CCAUAUCUGGCACAUCCGU | 4047 |
| CGGAUGUGCCAGAUAUGGU | 4048 | ACCAUAUCUGGCACAUCCG | 4049 |
| GGAUGUGCCAGAUAUGGUG | 4050 | CACCAUAUCUGGCACAUCC | 4051 |
| GAUGUGCCAGAUAUGGUGG | 4052 | CCACCAUAUCUGGCACAUC | 4053 |
| GCCAGAUAUGGUGGUGGAG | 4054 | CUCCACCACCAUAUCUGGC | 4055 |
| CCAGAUAUGGUGGUGGAGG | 4056 | CCUCCACCACCAUAUCUGG | 4057 |
| CAGAUAUGGUGGUGGAGGC | 4058 | GCCUCCACCACCAUAUCUG | 4059 |
| AGAUAUGGUGGUGGAGGCC | 4060 | GGCCUCCACCACCAUAUCU | 4061 |
| GAUAUGGUGGUGGAGGCCU | 4062 | AGGCCUCCACCACCAUAUC | 4063 |
| AUAUGGUGGUGGAGGCCUG | 4064 | CAGGCCUCCACCACCAUAU | 4065 |
| CCUGUGGCUGCAGCUAGCA | 4066 | UGCUAGCUGCAGCCACAGG | 4067 |
| UGUGGCUGCAGCUAGCAAG | 4068 | CUUGCUAGCUGCAGCCACA | 4069 |
| GUGGCUGCAGCUAGCAAGA | 4070 | UCUUGCUAGCUGCAGCCAC | 4071 |
| UGGCUGCAGCUAGCAAGAG | 4072 | CUCUUGCUAGCUGCAGCCA | 4073 |
| GGCUGCAGCUAGCAAGAGG | 4074 | CCUCUUGCUAGCUGCAGCC | 4075 |
| CUGCAGCUAGCAAGAGGAC | 4076 | GUCCUCUUGCUAGCUGCAG | 4077 |
| CAGCUAGCAAGAGGACCUG | 4078 | CAGGUCCUCUUGCUAGCUG | 4079 |
| GCUAGCAAGAGGACCUGGG | 4080 | CCCAGGUCCUCUUGCUAGC | 4081 |
| AGACCAAGAUGAAGUUUCC | 4082 | GGAAACUUCAUCUUGGUCU | 4083 |
| UGAAGUUUCCCAGGCACAG | 4084 | CUGUGCCUGGGAAACUUCA | 4085 |
| GAAGUUUCCCAGGCACAGG | 4086 | CCUGUGCCUGGGAAACUUC | 4087 |
| UCCCAGGCACAGGGCAUCU | 4088 | AGAUGCCCGUGCCUGGGA | 4089 |
| GGCAUCUGUGACUGGAGGC | 4090 | GCCUCCAGUCACAGAUGCC | 4091 |
| GCAUCUGUGACUGGAGGCA | 4092 | UGCCUCCAGUCACAGAUGC | 4093 |
| CAACCACCUGGCAAUAUGA | 4094 | UCAUAUUGCCAGGUGGUUG | 4095 |
| AACCACCUGGCAAUAUGAC | 4096 | GUCAUAUUGCCAGGUGGUU | 4097 |
| ACCACCUGGCAAUAUGACU | 4098 | AGUCAUAUUGCCAGGUGGU | 4099 |
| CCACCUGGCAAUAUGACUC | 4100 | GAGUCAUAUUGCCAGGUGG | 4101 |
| CACCUGGCAAUAUGACUCA | 4102 | UGAGUCAUAUUGCCAGGUG | 4103 |
| ACCUGGCAAUAUGACUCAC | 4104 | GUGAGUCAUAUUGCCAGGU | 4105 |
| CCUGGCAAUAUGACUCACU | 4106 | AGUGAGUCAUAUUGCCAGG | 4107 |
| CUGGCAAUAUGACUCACUU | 4108 | AAGUGAGUCAUAUUGCCAG | 4109 |
| UGGCAAUAUGACUCACUUG | 4110 | CAAGUGAGUCAUAUUGCCA | 4111 |
| AAUAUGACUCACUUGACCC | 4112 | GGGUCAAGUGAGUCAUAUU | 4113 |
| CCCUAUGGGACCCAAAUGG | 4114 | CCAUUUGGGUCCCAUAGGG | 4115 |
| CCUAUGGGACCCAAAUGGG | 4116 | CCCAUUUGGGUCCCAUAGG | 4117 |
| CUAUGGGACCCAAAUGGGC | 4118 | GCCCAUUUGGGUCCCAUAG | 4119 |
| UAUGGGACCCAAAUGGGCA | 4120 | UGCCCAUUUGGGUCCCAUA | 4121 |
| AUGGGACCCAAAUGGGCAC | 4122 | GUGCCCAUUUGGGUCCCAU | 4123 |
| CCCAAAUGGGCACUUUCUU | 4124 | AAGAAAGUGCCCAUUUGGG | 4125 |

TABLE 4-continued

| Sense Sequence | SEQ ID NO: | Antisense Sequence | SEQ ID NO: |
|---|---|---|---|
| CCAAAUGGGCACUUUCUUG | 4126 | CAAGAAAGUGCCCAUUUGG | 4127 |
| CAAAUGGGCACUUUCUUGU | 4128 | ACAAGAAAGUGCCCAUUUG | 4129 |
| AAAUGGGCACUUUCUUGUC | 4130 | GACAAGAAAGUGCCCAUUU | 4131 |
| AAUGGGCACUUUCUUGUCU | 4132 | AGACAAGAAAGUGCCCAUU | 4133 |
| UGGGCACUUUCUUGUCUGA | 4134 | UCAGACAAGAAAGUGCCCA | 4135 |
| GGGCACUUUCUUGUCUGAG | 4136 | CUCAGACAAGAAAGUGCCC | 4137 |
| UGGCUUAUUCCAGGUUGGC | 4138 | GCCAACCUGGAAUAAGCCA | 4139 |
| GGCUUAUUCCAGGUUGGCU | 4140 | AGCCAACCUGGAAUAAGCC | 4141 |
| GCUUAUUCCAGGUUGGCUG | 4142 | CAGCCAACCUGGAAUAAGC | 4143 |
| CUUAUUCCAGGUUGGCUGA | 4144 | UCAGCCAACCUGGAAUAAG | 4145 |
| UUCCAGGUUGGCUGAUGUG | 4146 | CACAUCAGCCAACCUGGAA | 4147 |
| UCCAGGUUGGCUGAUGUGU | 4148 | ACACAUCAGCCAACCUGGA | 4149 |
| CCAGGUUGGCUGAUGUGUU | 4150 | AACACAUCAGCCAACCUGG | 4151 |
| CAGGUUGGCUGAUGUGUUG | 4152 | CAACACAUCAGCCAACCUG | 4153 |
| AGGUUGGCUGAUGUGUUGG | 4154 | CCAACACAUCAGCCAACCU | 4155 |
| GGUUGGCUGAUGUGUUGGG | 4156 | CCCAACACAUCAGCCAACC | 4157 |
| AGAUGGGUAAAGCGUUUCU | 4158 | AGAAACGCUUUACCCAUCU | 4159 |
| GAUGGGUAAAGCGUUUCUU | 4160 | AAGAAACGCUUUACCCAUC | 4161 |
| AUGGGUAAAGCGUUUCUUC | 4162 | GAAGAAACGCUUUACCCAU | 4163 |
| UGGGUAAAGCGUUUCUUCU | 4164 | AGAAGAAACGCUUUACCCA | 4165 |
| GGGUAAAGCGUUUCUUCUA | 4166 | UAGAAGAAACGCUUUACCC | 4167 |
| GGUAAAGCGUUUCUUCUAA | 4168 | UUAGAAGAAACGCUUUACC | 4169 |
| GUAAAGCGUUUCUUCUAAA | 4170 | UUUAGAAGAAACGCUUUAC | 4171 |
| UAAAGCGUUUCUUCUAAAG | 4172 | CUUUAGAAGAAACGCUUUA | 4173 |
| AAAGCGUUUCUUCUAAAGG | 4174 | CCUUUAGAAGAAACGCUUU | 4175 |
| AAGCGUUUCUUCUAAAGGG | 4176 | CCCUUUAGAAGAAACGCUU | 4177 |
| AAAGCAUGAUUCCUGCCC | 4178 | GGGCAGGAAAUCAUGCUUU | 4179 |
| AAGCAUGAUUUCCUGCCCU | 4180 | AGGGCAGGAAAUCAUGCUU | 4181 |
| AGCAUGAUUUCCUGCCCUA | 4182 | UAGGGCAGGAAAUCAUGCU | 4183 |
| GCAUGAUUUCCUGCCCUAA | 4184 | UUAGGGCAGGAAAUCAUGC | 4185 |
| CAUGAUUUCCUGCCCUAAG | 4186 | CUUAGGGCAGGAAAUCAUG | 4187 |
| AUGAUUUCCUGCCCUAAGU | 4188 | ACUUAGGGCAGGAAAUCAU | 4189 |
| UGAUUUCCUGCCCUAAGUC | 4190 | GACUUAGGGCAGGAAAUCA | 4191 |
| GAUUUCCUGCCCUAAGUCC | 4192 | GGACUUAGGGCAGGAAAUC | 4193 |
| AUUUCCUGCCCUAAGUCCU | 4194 | AGGACUUAGGGCAGGAAAU | 4195 |
| UUUCCUGCCCUAAGUCCUG | 4196 | CAGGACUUAGGGCAGGAAA | 4197 |
| UUCCUGCCCUAAGUCCUGU | 4198 | ACAGGACUUAGGGCAGGAA | 4199 |
| UCCUGCCCUAAGUCCUGUG | 4200 | CACAGGACUUAGGGCAGGA | 4201 |
| AGAAGAUGUCAGGGACUAG | 4202 | CUAGUCCCUGACAUCUUCU | 4203 |
| GAAGAUGUCAGGGACUAGG | 4204 | CCUAGUCCCUGACAUCUUC | 4205 |
| AAGAUGUCAGGGACUAGGG | 4206 | CCCUAGUCCCUGACAUCUU | 4207 |
| AGAUGUCAGGGACUAGGGA | 4208 | UCCCUAGUCCCUGACAUCU | 4209 |
| GUCAGGGACUAGGGAGGGA | 4210 | UCCCUCCCUAGUCCCUGAC | 4211 |
| UACUUAGCCUCUCCCAAGA | 4212 | UCUUGGGAGAGGCUAAGUA | 4213 |
| AGGAGGAAGCAGAUAGAUG | 4214 | CAUCUAUCUGCUUCCUCCU | 4215 |
| GGAGGAAGCAGAUAGAUGG | 4216 | CCAUCUAUCUGCUUCCUCC | 4217 |
| GAGGAAGCAGAUAGAUGGU | 4218 | ACCAUCUAUCUGCUUCCUC | 4219 |
| AGGAAGCAGAUAGAUGGUC | 4220 | GACCAUCUAUCUGCUUCCU | 4221 |
| GGAAGCAGAUAGAUGGUCC | 4222 | GGACCAUCUAUCUGCUUCC | 4223 |
| GAAGCAGAUAGAUGGUCCA | 4224 | UGGACCAUCUAUCUGCUUC | 4225 |
| UAGAUGGUCCAGCAGGCUU | 4226 | AAGCCUGCUGGACCAUCUA | 4227 |
| AGAUGGUCCAGCAGGCUUG | 4228 | CAAGCCUGCUGGACCAUCU | 4229 |
| GAUGGUCCAGCAGGCUUGA | 4230 | UCAAGCCUGCUGGACCAUC | 4231 |
| AUGGUCCAGCAGGCUUGAA | 4232 | UUCAAGCCUGCUGGACCAU | 4233 |
| UGGUCCAGCAGGCUUGAAG | 4234 | CUUCAAGCCUGCUGGACCA | 4235 |
| GGUCCAGCAGGCUUGAAGC | 4236 | GCUUCAAGCCUGCUGGACC | 4237 |
| GUCCAGCAGGCUUGAAGCA | 4238 | UGCUUCAAGCCUGCUGGAC | 4239 |
| UCCAGCAGGCUUGAAGCAG | 4240 | CUGCUUCAAGCCUGCUGGA | 4241 |
| CCCAGGGUAAGGGCUGUUG | 4242 | CAACAGCCCUUACCCUGGG | 4243 |
| GGGUAAGGGCUGUUGAGGU | 4244 | ACCUCAACAGCCCUUACCC | 4245 |
| GGUAAGGGCUGUUGAGGUA | 4246 | UACCUCAACAGCCCUUACC | 4247 |
| GUAAGGGCUGUUGAGGUAC | 4248 | GUACCUCAACAGCCCUUAC | 4249 |
| UAAGGGCUGUUGAGGUACC | 4250 | GGUACCUCAACAGCCCUUA | 4251 |
| AAGGGCUGUUGAGGUACCU | 4252 | AGGUACCUCAACAGCCCUU | 4253 |
| AGGGCUGUUGAGGUACCUU | 4254 | AAGGUACCUCAACAGCCCU | 4255 |
| GGGCUGUUGAGGUACCUUA | 4256 | UAAGGUACCUCAACAGCCC | 4257 |
| GGCUGUUGAGGUACCUUAA | 4258 | UUAAGGUACCUCAACAGCC | 4259 |
| GCUGUUGAGGUACCUUAAG | 4260 | CUUAAGGUACCUCAACAGC | 4261 |
| CUGUUGAGGUACCUUAAGG | 4262 | CCUUAAGGUACCUCAACAG | 4263 |
| UGUUGAGGUACCUUAAGGG | 4264 | CCCUUAAGGUACCUCAACA | 4265 |
| UAAGGGAAGGUCAAGAGGG | 4266 | CCCUCUUGACCUUCCCUUA | 4267 |
| AAGGGAAGGUCAAGAGGGA | 4268 | UCCCUCUUGACCUUCCCUU | 4269 |
| CGCUGAGGGAGGAUGCUUA | 4270 | UAAGCAUCCUCCCUCAGCG | 4271 |
| UGAGGGAGGAUGCUUAGGG | 4272 | CCCUAAGCAUCCUCCCUCA | 4273 |
| GGCACUAAGCCUAAGAAGU | 4274 | ACUUCUUAGGCUUAGUGCC | 4275 |
| GCACUAAGCCUAAGAAGUU | 4276 | AACUUCUUAGGCUUAGUGC | 4277 |

TABLE 4-continued

| Sense Sequence | SEQ ID NO: | Antisense Sequence | SEQ ID NO: |
|---|---|---|---|
| CACUAAGCCUAAGAAGUUC | 4278 | GAACUUCUUAGGCUUAGUG | 4279 |
| ACUAAGCCUAAGAAGUUCC | 4280 | GGAACUUCUUAGGCUUAGU | 4281 |
| AGAUCGAGUCUCGCUCUGU | 4282 | ACAGAGCGAGACUCGAUCU | 4283 |
| GAUCGAGUCUCGCUCUGUC | 4284 | GACAGAGCGAGACUCGAUC | 4285 |
| AUCGAGUCUCGCUCUGUCA | 4286 | UGACAGAGCGAGACUCGAU | 4287 |
| AGUCUCGCUCUGUCACCAG | 4288 | CUGGUGACAGAGCGAGACU | 4289 |
| GUCUCGCUCUGUCACCAGG | 4290 | CCUGGUGACAGAGCGAGAC | 4291 |
| UCUCGCUCUGUCACCAGGC | 4292 | GCCUGGUGACAGAGCGAGA | 4293 |
| CUCGCUCUGUCACCAGGCU | 4294 | AGCCUGGUGACAGAGCGAG | 4295 |
| GUCACCAGGCUGGAGUGCA | 4296 | UGCACUCCAGCCUGGUGAC | 4297 |
| GGCUCACUGCAACCUCCGU | 4298 | ACGGAGGUUGCAGUGAGCC | 4299 |
| GCUCACUGCAACCUCCGUC | 4300 | GACGGAGGUUGCAGUGAGC | 4301 |
| UCCGUCUCCUGGGUUCAAG | 4302 | CUUGAACCCAGGAGACGGA | 4303 |
| CCGUCUCCUGGGUUCAAGU | 4304 | ACUUGAACCCAGGAGACGG | 4305 |
| CGUCUCCUGGGUUCAAGUG | 4306 | CACUUGAACCCAGGAGACG | 4307 |
| GUCUCCUGGGUUCAAGUGA | 4308 | UCACUUGAACCCAGGAGAC | 4309 |
| UGGGUUCAAGUGAUUCUUC | 4310 | GAAGAAUCACUUGAACCCA | 4311 |
| GGGUUCAAGUGAUUCUUCU | 4312 | AGAAGAAUCACUUGAACCC | 4313 |
| GGUUCAAGUGAUUCUUCUG | 4314 | CAGAAGAAUCACUUGAACC | 4315 |
| GUUCAAGUGAUUCUUCUGC | 4316 | GCAGAAGAAUCACUUGAAC | 4317 |
| UUCAAGUGAUUCUUCUGCC | 4318 | GGCAGAAGAAUCACUUGAA | 4319 |
| UCAAGUGAUUCUUCUGCCU | 4320 | AGGCAGAAGAAUCACUUGA | 4321 |
| CGAGCAGCUGGGAUUACAG | 4322 | CUGUAAUCCCAGCUGCUCG | 4323 |
| CAGCUGGGAUUACAGGCGC | 4324 | GCGCCUGUAAUCCCAGCUG | 4325 |
| ACAUGUUGGCCAGGAUGGU | 4326 | ACCAUCCUGGCCAACAUGU | 4327 |
| CAUGUUGGCCAGGAUGGUC | 4328 | GACCAUCCUGGCCAACAUG | 4329 |
| AUGUUGGCCAGGAUGGUCU | 4330 | AGACCAUCCUGGCCAACAU | 4331 |
| UGUUGGCCAGGAUGGUCUC | 4332 | GAGACCAUCCUGGCCAACA | 4333 |
| GUUGGCCAGGAUGGUCUCA | 4334 | UGAGACCAUCCUGGCCAAC | 4335 |
| UUGGCCAGGAUGGUCUCAA | 4336 | UUGAGACCAUCCUGGCCAA | 4337 |
| UGGCCAGGAUGGUCUCAAU | 4338 | AUUGAGACCAUCCUGGCCA | 4339 |
| GGCCAGGAUGGUCUCAAUC | 4340 | GAUUGAGACCAUCCUGGCC | 4341 |
| GCCAGGAUGGUCUCAAUCU | 4342 | AGAUUGAGACCAUCCUGGC | 4343 |
| CCAGGAUGGUCUCAAUCUC | 4344 | GAGAUUGAGACCAUCCUGG | 4345 |
| CAGGAUGGUCUCAAUCUCU | 4346 | AGAGAUUGAGACCAUCCUG | 4347 |
| AGGAUGGUCUCAAUCUCUU | 4348 | AAGAGAUUGAGACCAUCCU | 4349 |
| AUUAUAGGCGUGAGCCACC | 4350 | GGUGGCUCACGCCUAUAAU | 4351 |
| UUAUAGGCGUGAGCCACCG | 4352 | CGGUGGCUCACGCCUAUAA | 4353 |
| UAUAGGCGUGAGCCACCGC | 4354 | GCGGUGGCUCACGCCUAUA | 4355 |
| GCGCCUGGCUUAUACUUUC | 4356 | GAAAGUAUAAGCCAGGCGC | 4357 |
| CGCCUGGCUUAUACUUUCU | 4358 | AGAAAGUAUAAGCCAGGCG | 4359 |
| CCUGGCUUAUACUUUCUUA | 4360 | UAAGAAAGUAUAAGCCAGG | 4361 |
| CUGGCUUAUACUUUCUUAA | 4362 | UUAAGAAAGUAUAAGCCAG | 4363 |
| CAAAUGUGAGUCAUAAAGA | 4364 | UCUUUAUGACUCACAUUUG | 4365 |
| AAUGUGAGUCAUAAAGAAG | 4366 | CUUCUUUAUGACUCACAUU | 4367 |
| UGAGUCAUAAAGAAGGGUU | 4368 | AACCCUUCUUUAUGACUCA | 4369 |
| AGUCAUAAAGAAGGGUUAG | 4370 | CUAACCCUUCUUUAUGACU | 4371 |
| GUCAUAAAGAAGGGUUAGG | 4372 | CCUAACCCUUCUUUAUGAC | 4373 |
| UCAUAAAGAAGGGUUAGGG | 4374 | CCCUAACCCUUCUUUAUGA | 4375 |
| CAUAAAGAAGGGUUAGGGU | 4376 | ACCCUAACCCUUCUUUAUG | 4377 |
| AAGAAGGGUUAGGGUGAUG | 4378 | CAUCACCCUAACCCUUCUU | 4379 |
| AGAAGGGUUAGGGUGAUGG | 4380 | CCAUCACCCUAACCCUUCU | 4381 |
| GAAGGGUUAGGGUGAUGGU | 4382 | ACCAUCACCCUAACCCUUC | 4383 |
| AAGGGUUAGGGUGAUGGUC | 4384 | GACCAUCACCCUAACCCUU | 4385 |
| AGGGUUAGGGUGAUGGUCC | 4386 | GGACCAUCACCCUAACCCU | 4387 |
| GGGUUAGGGUGAUGGUCCA | 4388 | UGGACCAUCACCCUAACCC | 4389 |
| GGGUGAUGGUCCAGAGCAA | 4390 | UUGCUCUGGACCAUCACCC | 4391 |
| GGUGAUGGUCCAGAGCAAC | 4392 | GUUGCUCUGGACCAUCACC | 4393 |
| ACAGUUCUUCAAGUGUACU | 4394 | AGUACACUUGAAGAACUGU | 4395 |
| CAGUUCUUCAAGUGUACUC | 4396 | GAGUACACUUGAAGAACUG | 4397 |
| AGUUCUUCAAGUGUACUCU | 4398 | AGAGUACACUUGAAGAACU | 4399 |
| CAAGUGUACUCUGUAGGCU | 4400 | AGCCUACAGAGUACACUUG | 4401 |
| AAGUGUACUCUGUAGGCUU | 4402 | AAGCCUACAGAGUACACUU | 4403 |
| GUGUACUCUGUAGGCUUCU | 4404 | AGAAGCCUACAGAGUACAC | 4405 |
| UGUACUCUGUAGGCUUCUG | 4406 | CAGAAGCCUACAGAGUACA | 4407 |
| GUACUCUGUAGGCUUCUGG | 4408 | CCAGAAGCCUACAGAGUAC | 4409 |
| UACUCUGUAGGCUUCUGGG | 4410 | CCCAGAAGCCUACAGAGUA | 4411 |
| GUAGGCUUCUGGGAGGUCC | 4412 | GGACCUCCCAGAAGCCUAC | 4413 |
| UAGGCUUCUGGGAGGUCCC | 4414 | GGGACCUCCCAGAAGCCUA | 4415 |
| AGGCUUCUGGGAGGUCCCU | 4416 | AGGGACCUCCCAGAAGCCU | 4417 |
| GGCUUCUGGGAGGUCCCUU | 4418 | AAGGGACCUCCCAGAAGCC | 4419 |
| GCUUCUGGGAGGUCCCUUU | 4420 | AAAGGGACCUCCCAGAAGC | 4421 |
| CUUCUGGGAGGUCCCUUUU | 4422 | AAAAGGGACCUCCCAGAAG | 4423 |
| UUCUGGGAGGUCCCUUUUC | 4424 | GAAAAGGGACCUCCCAGAA | 4425 |
| UCUGGGAGGUCCCUUUUCA | 4426 | UGAAAAGGGACCUCCCAGA | 4427 |
| CAUGUUAUUGCCUUUUGA | 4428 | UCAAAAGGCAAUAACAUG | 4429 |

TABLE 4-continued

| Sense Sequence | SEQ ID NO: | Antisense Sequence | SEQ ID NO: |
|---|---|---|---|
| AUUUGCCUUUUGAAUUCUC | 4430 | GAGAAUUCAAAAGGCAAAU | 4431 |
| UUUGCCUUUUGAAUUCUCA | 4432 | UGAGAAUUCAAAAGGCAAA | 4433 |
| UUGCCUUUUGAAUUCUCAU | 4434 | AUGAGAAUUCAAAAGGCAA | 4435 |
| UGCCUUUUGAAUUCUCAUU | 4436 | AAUGAGAAUUCAAAAGGCA | 4437 |
| GCCUUUUGAAUUCUCAUUA | 4438 | UAAUGAGAAUUCAAAAGGC | 4439 |
| AUUGUAUUGUGGAGUUUUC | 4440 | GAAAACUCCACAAUACAAU | 4441 |
| UUGUAUUGUGGAGUUUUCC | 4442 | GGAAAACUCCACAAUACAA | 4443 |
| AGUUUUCCAGAGGCCGUGU | 4444 | ACACGGCCUCUGGAAAACU | 4445 |
| GUUUUCCAGAGGCCGUGUG | 4446 | CACACGGCCUCUGGAAAAC | 4447 |
| UUUUCCAGAGGCCGUGUGA | 4448 | UCACACGGCCUCUGGAAAA | 4449 |
| UUUCCAGAGGCCGUGUGAC | 4450 | GUCACACGGCCUCUGGAAA | 4451 |
| UUCCAGAGGCCGUGUGACA | 4452 | UGUCACACGGCCUCUGGAA | 4453 |
| UCCAGAGGCCGUGUGACAU | 4454 | AUGUCACACGGCCUCUGGA | 4455 |
| CCAGAGGCCGUGUGACAUG | 4456 | CAUGUCACACGGCCUCUGG | 4457 |
| CAGAGGCCGUGUGACAUGU | 4458 | ACAUGUCACACGGCCUCUG | 4459 |
| AGAGGCCGUGUGACAUGUG | 4460 | CACAUGUCACACGGCCUCU | 4461 |
| GCCGUGUGACAUGUGAUUA | 4462 | UAAUCACAUGUCACACGGC | 4463 |
| CCGUGUGACAUGUGAUUAC | 4464 | GUAAUCACAUGUCACACGG | 4465 |
| CGUGUGACAUGUGAUUACA | 4466 | UGUAAUCACAUGUCACACG | 4467 |
| GAUUACAUCAUCUUUCUGA | 4468 | UCAGAAAGAUGAUGUAAUC | 4469 |
| AUUACAUCAUCUUUCUGAC | 4470 | GUCAGAAAGAUGAUGUAAU | 4471 |
| UUACAUCAUCUUUCUGACA | 4472 | UGUCAGAAAGAUGAUGUAA | 4473 |
| UACAUCAUCUUUCUGACAU | 4474 | AUGUCAGAAAGAUGAUGUA | 4475 |
| AUCUUUCUGACAUCAUUGU | 4476 | ACAAUGAUGUCAGAAAGAU | 4477 |
| AUUGUUAAUGGAAUGUGUG | 4478 | CACACAUUCCAUUAACAAU | 4479 |
| GAAUGUGUGCUUGUAUGGU | 4480 | ACCAUACAAGCACACAUUC | 4481 |
| AAUGUGUGCUUGUAUGGUC | 4482 | GACCAUACAAGCACACAUU | 4483 |
| AUGUGUGCUUGUAUGGUCU | 4484 | AGACCAUACAAGCACACAU | 4485 |
| UGUGUGCUUGUAUGGUCUU | 4486 | AAGACCAUACAAGCACACA | 4487 |
| GUGUGCUUGUAUGGUCUUG | 4488 | CAAGACCAUACAAGCACAC | 4489 |
| UGUGCUUGUAUGGUCUUGU | 4490 | ACAAGACCAUACAAGCACA | 4491 |
| GUGCUUGUAUGGUCUUGUG | 4492 | CACAAGACCAUACAAGCAC | 4493 |
| UGCUUGUAUGGUCUUGUGU | 4494 | ACACAAGACCAUACAAGCA | 4495 |
| GCUUGUAUGGUCUUGUGUU | 4496 | AACACAAGACCAUACAAGC | 4497 |
| CUUGUAUGGUCUUGUGUUA | 4498 | UAACACAAGACCAUACAAG | 4499 |
| UAUGGUCUUGUGUUACAGU | 4500 | ACUGUAACACAAGACCAUA | 4501 |
| AUGGUCUUGUGUUACAGUC | 4502 | GACUGUAACACAAGACCAU | 4503 |
| AGUCUCGCUCUGUCGCCCA | 4504 | UGGGCGACAGAGCGAGACU | 4505 |
| CAAUCUCGGCUCACUGCAA | 4506 | UUGCAGUGAGCCGAGAUUG | 4507 |
| AAUCUCGGCUCACUGCAAC | 4508 | GUUGCAGUGAGCCGAGAUU | 4509 |
| AUCUCGGCUCACUGCAACC | 4510 | GGUUGCAGUGAGCCGAGAU | 4511 |
| UCUCGGCUCACUGCAACCU | 4512 | AGGUUGCAGUGAGCCGAGA | 4513 |
| CUCACUGCAACCUCCACCU | 4514 | AGGUGGAGGUUGCAGUGAG | 4515 |
| UCACUGCAACCUCCACCUC | 4516 | GAGGUGGAGGUUGCAGUGA | 4517 |
| CACUGCAACCUCCACCUCC | 4518 | GGAGGUGGAGGUUGCAGUG | 4519 |
| ACUGCAACCUCCACCUCCC | 4520 | GGGAGGUGGAGGUUGCAGU | 4521 |
| AGCCUCCUGAGUAGCUGGG | 4522 | CCCAGCUACUCAGGAGGCU | 4523 |
| GCCUCCUGAGUAGCUGGGA | 4524 | UCCCAGCUACUCAGGAGGC | 4525 |
| CCUCCUGAGUAGCUGGGAC | 4526 | GUCCCAGCUACUCAGGAGG | 4527 |
| CUCCUGAGUAGCUGGGACU | 4528 | AGUCCCAGCUACUCAGGAG | 4529 |
| UCCUGAGUAGCUGGGACUA | 4530 | UAGUCCCAGCUACUCAGGA | 4531 |
| UAGCUGGGACUACAGGCCU | 4532 | AGGCCUGUAGUCCCAGCUA | 4533 |
| AGCUGGGACUACAGGCCUG | 4534 | CAGGCCUGUAGUCCCAGCU | 4535 |
| GCCACCAUGCCCAGCUAUU | 4536 | AAUAGCUGGGCAUGGUGGC | 4537 |
| CCACCAUGCCCAGCUAUUU | 4538 | AAAUAGCUGGGCAUGGUGG | 4539 |
| CACCAUGCCCAGCUAUUUU | 4540 | AAAAUAGCUGGGCAUGGUG | 4541 |
| GGGUUUCACCAUGUUGGCC | 4542 | GGCCAACAUGGUGAAACCC | 4543 |
| GGUUUCACCAUGUUGGCCA | 4544 | UGGCCAACAUGGUGAAACC | 4545 |
| GUUUCACCAUGUUGGCCAG | 4546 | CUGGCCAACAUGGUGAAAC | 4547 |
| CACCAUGUUGGCCAGGCUG | 4548 | CAGCCUGGCCAACAUGGUG | 4549 |
| ACCAUGUUGGCCAGGCUGG | 4550 | CCAGCCUGGCCAACAUGGU | 4551 |
| CCAUGUUGGCCAGGCUGGU | 4552 | ACCAGCCUGGCCAACAUGG | 4553 |
| CAUGUUGGCCAGGCUGGUC | 4554 | GACCAGCCUGGCCAACAUG | 4555 |
| AUGUUGGCCAGGCUGGUCU | 4556 | AGACCAGCCUGGCCAACAU | 4557 |
| UGUUGGCCAGGCUGGUCUC | 4558 | GAGACCAGCCUGGCCAACA | 4559 |
| CUUGAGGUGAUCCGCCUGC | 4560 | GCAGGCGGAUCACCUCAAG | 4561 |
| UUGAGGUGAUCCGCCUGCC | 4562 | GGCAGGCGGAUCACCUCAA | 4563 |
| UGAGGUGAUCCGCCUGCCU | 4564 | AGGCAGGCGGAUCACCUCA | 4565 |
| CCAAAGUGCUGGGAUUACA | 4566 | UGUAAUCCCAGCACUUUGG | 4567 |
| CAAAGUGCUGGGAUUACAG | 4568 | CUGUAAUCCCAGCACUUUG | 4569 |
| GUGCUGGGAUUACAGGUCU | 4570 | AGACCUGUAAUCCCAGCAC | 4571 |
| UGCUGGGAUUACAGGUCUG | 4572 | CAGACCUGUAAUCCCAGCA | 4573 |
| GCUGGGAUUACAGGUCUGA | 4574 | UCAGACCUGUAAUCCCAGC | 4575 |
| CUGGGAUUACAGGUCUGAG | 4576 | CUCAGACCUGUAAUCCCAG | 4577 |
| GGCUGAGCCACUGUGCCU | 4578 | AGGCACAGUGGCUCAGCC | 4579 |
| GUCUGAGCCACUGUGCCUA | 4580 | UAGGCACAGUGGCUCAGAC | 4581 |

TABLE 4-continued

| Sense Sequence | SEQ ID NO: | Antisense Sequence | SEQ ID NO: |
|---|---|---|---|
| UCUGAGCCACUGUGCCUAA | 4582 | UUAGGCACAGUGGCUCAGA | 4583 |
| CUGAGCCACUGUGCCUAAC | 4584 | GUUAGGCACAGUGGCUCAG | 4585 |
| UGAGCCACUGUGCCUAACC | 4586 | GGUUAGGCACAGUGGCUCA | 4587 |
| CACUGUGCCUAACCUAAUG | 4588 | CAUUAGGUUAGGCACAGUG | 4589 |
| ACUGUGCCUAACCUAAUGA | 4590 | UCAUUAGGUUAGGCACAGU | 4591 |
| CUGUGCCUAACCUAAUGAC | 4592 | GUCAUUAGGUUAGGCACAG | 4593 |
| UGUGCCUAACCUAAUGACU | 4594 | AGUCAUUAGGUUAGGCACA | 4595 |
| GUGCCUAACCUAAUGACUU | 4596 | AAGUCAUUAGGUUAGGCAC | 4597 |
| UGCCUAACCUAAUGACUUU | 4598 | AAAGUCAUUAGGUUAGGCA | 4599 |
| GCCUAACCUAAUGACUUUU | 4600 | AAAAGUCAUUAGGUUAGGC | 4601 |
| CCUAACCUAAUGACUUUUA | 4602 | UAAAAGUCAUUAGGUUAGG | 4603 |
| ACCUAAUGACUUUUAAGAG | 4604 | CUCUUAAAAGUCAUUAGGU | 4605 |
| CUUUUAAGAGUAUAGAGGA | 4606 | UCCUCUAUACUCUUAAAAG | 4607 |
| GACUCACUGGUCUAUAGAA | 4608 | UUCUAUAGACCAGUGAGUC | 4609 |
| AAAGUAAGGUGUUCUAAGA | 4610 | UCUUAGAACACCUUACUUU | 4611 |
| GAGCUCUUCUUGCUGGGCA | 4612 | UGCCCAGCAAGAAGAGCUC | 4613 |
| AGCUCUUCUUGCUGGGCAC | 4614 | GUGCCCAGCAAGAAGAGCU | 4615 |
| GCUCUUCUUGCUGGGCACC | 4616 | GGUGCCCAGCAAGAAGAGC | 4617 |
| CUCUUCUUGCUGGGCACCG | 4618 | CGGUGCCCAGCAAGAAGAG | 4619 |
| UCUUCUUGCUGGGCACCGG | 4620 | CCGGUGCCCAGCAAGAAGA | 4621 |
| CUUCUUGCUGGGCACCGGU | 4622 | ACCGGUGCCCAGCAAGAAG | 4623 |
| UUCUUGCUGGGCACCGGUG | 4624 | CACCGGUGCCCAGCAAGAA | 4625 |
| CCCAGGAGUUCGAGGCUAU | 4626 | AUAGCCUCGAACUCCUGGG | 4627 |
| CCAGGAGUUCGAGGCUAUG | 4628 | CAUAGCCUCGAACUCCUGG | 4629 |
| AGUUCGAGGCUAUGAUCAC | 4630 | GUGAUCAUAGCCUCGAACU | 4631 |
| GUUCGAGGCUAUGAUCACA | 4632 | UGUGAUCAUAGCCUCGAAC | 4633 |
| UUCGAGGCUAUGAUCACAC | 4634 | GUGUGAUCAUAGCCUCGAA | 4635 |
| UCGAGGCUAUGAUCACACU | 4636 | AGUGUGAUCAUAGCCUCGA | 4637 |
| CGAGGCUAUGAUCACACUU | 4638 | AAGUGUGAUCAUAGCCUCG | 4639 |
| GAGGCUAUGAUCACACUUG | 4640 | CAAGUGUGAUCAUAGCCUC | 4641 |
| UGCACUCCAGCCUGGGCAA | 4642 | UUGCCCAGGCUGGAGUGCA | 4643 |
| GCACUCCAGCCUGGGCAAA | 4644 | UUUGCCCAGGCUGGAGUGC | 4645 |
| CACUCCAGCCUGGGCAAAU | 4646 | AUUUGCCCAGGCUGGAGUG | 4647 |
| ACUCCAGCCUGGGCAAAUA | 4648 | UAUUUGCCCAGGCUGGAGU | 4649 |
| UACAUAAUAGCUCCUCUG | 4650 | CAGAGGAGCUAUUUAUGUA | 4651 |
| ACAUAAUAGCUCCUCUGG | 4652 | CCAGAGGAGCUAUUUAUGU | 4653 |
| CAUAAUAGCUCCUCUGGA | 4654 | UCCAGAGGAGCUAUUUAUG | 4655 |
| AUAAAUAGCUCCUCUGGAA | 4656 | UUCCAGAGGAGCUAUUUAU | 4657 |
| AAAUAGCUCCUCUGGAAGA | 4658 | UCUUCCAGAGGAGCUAUUU | 4659 |
| AGGCUGGGACAGGAGCAUG | 4660 | CAUGCUCCUGUCCCAGCCU | 4661 |
| GGCUGGGACAGGAGCAUGU | 4662 | ACAUGCUCCUGUCCCAGCC | 4663 |
| GCUGGGACAGGAGCAUGUG | 4664 | CACAUGCUCCUGUCCCAGC | 4665 |
| UGGGACAGGAGCAUGUGUG | 4666 | CACACAUGCUCCUGUCCCA | 4667 |
| GGGACAGGAGCAUGUGUGG | 4668 | CCACACAUGCUCCUGUCCC | 4669 |
| GGACAGGAGCAUGUGUGGG | 4670 | CCCACACAUGCUCCUGUCC | 4671 |
| UUUUCAGUGCCCAUUAGUC | 4672 | GACUAAUGGGCACUGAAAA | 4673 |
| UUUCAGUGCCCAUUAGUCU | 4674 | AGACUAAUGGGCACUGAAA | 4675 |
| UUCAGUGCCCAUUAGUCUG | 4676 | CAGACUAAUGGGCACUGAA | 4677 |
| CAGUGCCCAUUAGUCUGGU | 4678 | ACCAGACUAAUGGGCACUG | 4679 |
| AGUGCCCAUUAGUCUGGUC | 4680 | GACCAGACUAAUGGGCACU | 4681 |
| GUGCCCAUUAGUCUGGUCU | 4682 | AGACCAGACUAAUGGGCAC | 4683 |
| UGCCCAUUAGUCUGGUCUG | 4684 | CAGACCAGACUAAUGGGCA | 4685 |
| GCCCAUUAGUCUGGUCUGA | 4686 | UCAGACCAGACUAAUGGGC | 4687 |
| GUCUGGUCUGACUGAGCUG | 4688 | CAGCUCAGUCAGACCAGAC | 4689 |
| UCUGGUCUGACUGAGCUGG | 4690 | CCAGCUCAGUCAGACCAGA | 4691 |
| CUGGUCUGACUGAGCUGGG | 4692 | CCCAGCUCAGUCAGACCAG | 4693 |
| UGGUCUGACUGAGCUGGGU | 4694 | ACCCAGCUCAGUCAGACCA | 4695 |
| GGUCUGACUGAGCUGGGUC | 4696 | GACCCAGCUCAGUCAGACC | 4697 |
| GUCUGACUGAGCUGGGUCU | 4698 | AGACCCAGCUCAGUCAGAC | 4699 |
| UCUGACUGAGCUGGGUCUC | 4700 | GAGACCCAGCUCAGUCAGA | 4701 |
| CUGACUGAGCUGGGUCUCU | 4702 | AGAGACCCAGCUCAGUCAG | 4703 |
| UGACUGAGCUGGGUCUCUG | 4704 | CAGAGACCCAGCUCAGUCA | 4705 |
| GACUGAGCUGGGUCUCUGA | 4706 | UCAGAGACCCAGCUCAGUC | 4707 |
| ACUGAGCUGGGUCUCUGAC | 4708 | GUCAGAGACCCAGCUCAGU | 4709 |
| GGGAUAACUAGCCUGGGUC | 4710 | GACCCAGGCUAGUUAUCCC | 4711 |
| GGAUAACUAGCCUGGGUCA | 4712 | UGACCCAGGCUAGUUAUCC | 4713 |
| GAUAACUAGCCUGGGUCAA | 4714 | UUGACCCAGGCUAGUUAUC | 4715 |
| AUAACUAGCCUGGGUCAAA | 4716 | UUUGACCCAGGCUAGUUAU | 4717 |
| UAACUAGCCUGGGUCAAAG | 4718 | CUUUGACCCAGGCUAGUUA | 4719 |
| AACUAGCCUGGGUCAAAGU | 4720 | ACUUUGACCCAGGCUAGUU | 4721 |
| ACUAGCCUGGGUCAAAGUC | 4722 | GACUUUGACCCAGGCUAGU | 4723 |
| CUAGCCUGGGUCAAAGUCC | 4724 | GGACUUUGACCCAGGCUAG | 4725 |
| UAGCCUGGGUCAAAGUCCC | 4726 | GGGACUUUGACCCAGGCUA | 4727 |
| GGUCAAAGUCCCAGAUCUC | 4728 | GAGAUCUGGGACUUUGACC | 4729 |
| GUCAAAGUCCCAGAUCUCC | 4730 | GGAGAUCUGGGACUUUGAC | 4731 |
| UCAAAGUCCCAGAUCUCCC | 4732 | GGGAGAUCUGGGACUUUGA | 4733 |

TABLE 4-continued

| Sense Sequence | SEQ ID NO: | Antisense Sequence | SEQ ID NO: |
|---|---|---|---|
| CCUACCUUCACCUUUUCUU | 4734 | AAGAAAAGGUGAAGGUAGG | 4735 |
| CCUUCACCUUUUCUUUUCC | 4736 | GGAAAAGAAAAGGUGAAGG | 4737 |
| AACCCACUGACCUUCCACA | 4738 | UGUGGAAGGUCAGUGGGUU | 4739 |
| ACCCACUGACCUUCCACAC | 4740 | GUGUGGAAGGUCAGUGGGU | 4741 |
| ACUGACCUUCCACACCCAA | 4742 | UUGGGUGUGGAAGGUCAGU | 4743 |
| CUGACCUUCCACACCCAAG | 4744 | CUUGGGUGUGGAAGGUCAG | 4745 |
| GGGUGGUUCUUGGAAGCAG | 4746 | CUGCUUCCAAGAACCACCC | 4747 |
| GGUGGUUCUUGGAAGCAGA | 4748 | UCUGCUUCCAAGAACCACC | 4749 |
| GUGGUUCUUGGAAGCAGAG | 4750 | CUCUGCUUCCAAGAACCAC | 4751 |
| UGGUUCUUGGAAGCAGAGC | 4752 | GCUCUGCUUCCAAGAACCA | 4753 |
| GGUUCUUGGAAGCAGAGCU | 4754 | AGCUCUGCUUCCAAGAACC | 4755 |
| GUUCUUGGAAGCAGAGCUA | 4756 | UAGCUCUGCUUCCAAGAAC | 4757 |
| UUCUUGGAAGCAGAGCUAG | 4758 | CUAGCUCUGCUUCCAAGAA | 4759 |
| CUUGGAAGCAGAGCUAGGA | 4760 | UCCUAGCUCUGCUUCCAAG | 4761 |
| UGGAAGCAGAGCUAGGAUG | 4762 | CAUCCUAGCUCUGCUUCCA | 4763 |
| GGAAGCAGAGCUAGGAUGU | 4764 | ACAUCCUAGCUCUGCUUCC | 4765 |
| AGCUAGGAUGUGGGAGGUC | 4766 | GACCUCCCACAUCCUAGCU | 4767 |
| GCUAGGAUGUGGGAGGUCU | 4768 | AGACCUCCCACAUCCUAGC | 4769 |
| CUAGGAUGUGGGAGGUCUG | 4770 | CAGACCUCCCACAUCCUAG | 4771 |
| UAGGAUGUGGGAGGUCUGC | 4772 | GCAGACCUCCCACAUCCUA | 4773 |
| AGGAUGUGGGAGGUCUGCC | 4774 | GGCAGACCUCCCACAUCCU | 4775 |
| GGAUGUGGGAGGUCUGCCU | 4776 | AGGCAGACCUCCCACAUCC | 4777 |
| GAUGUGGGAGGUCUGCCUG | 4778 | CAGGCAGACCUCCCACAUC | 4779 |
| AUGUGGGAGGUCUGCCUGU | 4780 | ACAGGCAGACCUCCCACAU | 4781 |
| UUUCCUUGUCAUGCUUCCU | 4782 | AGGAAGCAUGACAAGGAAA | 4783 |
| UUCCUUGUCAUGCUUCCUC | 4784 | GAGGAAGCAUGACAAGGAA | 4785 |
| UGUCAUGCUUCCUCCUCUU | 4786 | AAGAGGAGGAAGCAUGACA | 4787 |
| UCAUGCUUCCUCCUCUUUC | 4788 | GAAAGAGGAGGAAGCAUGA | 4789 |
| CUUCCUCCUCUUUCUCAUA | 4790 | UAUGAGAAAGAGGAGGAAG | 4791 |
| UCCUCCUCUUUCUCAUAAA | 4792 | UUUAUGAGAAAGAGGAGGA | 4793 |
| CCUCCUCUUUCUCAUAAAA | 4794 | UUUUAUGAGAAAGAGGAGG | 4795 |
| UCACGAUGGCAAUGCAAAU | 4796 | AUUUGCAUUGCCAUCGUGA | 4797 |
| CACGAUGGCAAUGCAAAUC | 4798 | GAUUUGCAUUGCCAUCGUG | 4799 |
| ACGAUGGCAAUGCAAAUCU | 4800 | AGAUUUGCAUUGCCAUCGU | 4801 |
| CGAUGGCAAUGCAAAUCUA | 4802 | UAGAUUUGCAUUGCCAUCG | 4803 |
| GAUGGCAAUGCAAAUCUAA | 4804 | UUAGAUUUGCAUUGCCAUC | 4805 |
| UGGCAAUGCAAAUCUAAAG | 4806 | CUUUAGAUUUGCAUUGCCA | 4807 |
| GGCAAUGCAAAUCUAAAGA | 4808 | UCUUUAGAUUUGCAUUGCC | 4809 |
| AUGCAAAUCUAAAGAGGCA | 4810 | UGCCUCUUUAGAUUUGCAU | 4811 |
| GCAAAUCUAAAGAGGCAGG | 4812 | CCUGCCUCUUUAGAUUUGC | 4813 |
| CAAAUCUAAAGAGGCAGGG | 4814 | CCCUGCCUCUUUAGAUUUG | 4815 |
| AAAUCUAAAGAGGCAGGGC | 4816 | GCCCUGCCUCUUUAGAUUU | 4817 |
| ACUUCCCUGUCAGGCAGUA | 4818 | UACUGCCUGACAGGGAAGU | 4819 |
| CUUCCCUGUCAGGCAGUAC | 4820 | GUACUGCCUGACAGGGAAG | 4821 |
| UUCCCUGUCAGGCAGUACC | 4822 | GGUACUGCCUGACAGGGAA | 4823 |
| UCCCUGUCAGGCAGUACCG | 4824 | CGGUACUGCCUGACAGGGA | 4825 |
| CCUGUCAGGCAGUACCGCU | 4826 | AGCGGUACUGCCUGACAGG | 4827 |
| CUGUCAGGCAGUACCGCUG | 4828 | CAGCGGUACUGCCUGACAG | 4829 |
| UGUCAGGCAGUACCGCUGG | 4830 | CCAGCGGUACUGCCUGACA | 4831 |
| AGGCAGUACCGCUGGGCAU | 4832 | AUGCCCAGCGGUACUGCCU | 4833 |
| GGCAGUACCGCUGGGCAUA | 4834 | UAUGCCCAGCGGUACUGCC | 4835 |
| GCAGUACCGCUGGGCAUAG | 4836 | CUAUGCCCAGCGGUACUGC | 4837 |
| UACCGCUGGGCAUAGCAAC | 4838 | GUUGCUAUGCCCAGCGGUA | 4839 |
| ACCGCUGGGCAUAGCAACC | 4840 | GGUUGCUAUGCCCAGCGGU | 4841 |
| CCGCUGGGCAUAGCAACCU | 4842 | AGGUUGCUAUGCCCAGCGG | 4843 |
| CCUCUGCCUCUCCGUUUCU | 4844 | AGAAACGGAGAGGCAGAGG | 4845 |
| UGCCUCUCCGUUUCUCAGA | 4846 | UCUGAGAAACGGAGAGGCA | 4847 |
| UCUCCGUUUCUCAGAGCUC | 4848 | GAGCUCUGAGAAACGGAGA | 4849 |
| CUCCGUUUCUCAGAGCUCA | 4850 | UGAGCUCUGAGAAACGGAG | 4851 |
| UCCGUUUCUCAGAGCUCAC | 4852 | GUGAGCUCUGAGAAACGGA | 4853 |
| CCGUUUCUCAGAGCUCACA | 4854 | UGUGAGCUCUGAGAAACGG | 4855 |
| CGUUUCUCAGAGCUCACAU | 4856 | AUGUGAGCUCUGAGAAACG | 4857 |
| UUUCUCAGAGCUCACAUAU | 4858 | AUAUGUGAGCUCUGAGAAA | 4859 |
| AGAGCUCACAUAUCCACCU | 4860 | AGGUGGAUAUGUGAGCUCU | 4861 |
| GAGCUCACAUAUCCACCUC | 4862 | GAGGUGGAUAUGUGAGCUC | 4863 |
| AGCUCACAUAUCCACCUCC | 4864 | GGAGGUGGAUAUGUGAGCU | 4865 |
| CAUAUCCACCUCCUGGGCU | 4866 | AGCCCAGGAGGUGGAUAUG | 4867 |
| AUAUCCACCUCCUGGGCUU | 4868 | AAGCCCAGGAGGUGGAUAU | 4869 |
| UAUCCACCUCCUGGGCUUU | 4870 | AAAGCCCAGGAGGUGGAUA | 4871 |
| AUCCACCUCCUGGGCUUUU | 4872 | AAAAGCCCAGGAGGUGGAU | 4873 |
| UCCACCUCCUGGGCUUUUA | 4874 | UAAAAGCCCAGGAGGUGGA | 4875 |
| CCACCUCCUGGGCUUUUAA | 4876 | UUAAAAGCCCAGGAGGUGG | 4877 |
| UCCUGGGCUUUUAAGUGGG | 4878 | CCCACUUAAAAGCCCAGGA | 4879 |
| CCUGGGCUUUUAAGUGGGC | 4880 | GCCCACUUAAAAGCCCAGG | 4881 |
| CUGGGCUUUUAAGUGGGCU | 4882 | AGCCCACUUAAAAGCCCAG | 4883 |
| UGGGCUUUUAAGUGGGCUU | 4884 | AAGCCCACUUAAAAGCCCA | 4885 |

TABLE 4-continued

| Sense Sequence | SEQ ID NO: | Antisense Sequence | SEQ ID NO: |
|---|---|---|---|
| GGGCUUUUAAGUGGGCUUU | 4886 | AAAGCCCACUUAAAAGCCC | 4887 |
| UUUUAAGUGGGCUUUAGUG | 4888 | CACUAAAGCCCACUUAAAA | 4889 |
| UUUAAGUGGGCUUUAGUGA | 4890 | UCACUAAAGCCCACUUAAA | 4891 |
| UUAAGUGGGCUUUAGUGAG | 4892 | CUCACUAAAGCCCACUUAA | 4893 |
| UAAGUGGGCUUUAGUGAGG | 4894 | CCUCACUAAAGCCCACUUA | 4895 |
| AAGUGGGCUUUAGUGAGGG | 4896 | CCCUCACUAAAGCCCACUU | 4897 |
| GGGCUCCUCCUUCAACUGG | 4898 | CCAGUUGAAGGAGGAGCCC | 4899 |
| GGCUCCUCCUUCAACUGGG | 4900 | CCCAGUUGAAGGAGGAGCC | 4901 |
| GCUCCUCCUUCAACUGGGC | 4902 | GCCCAGUUGAAGGAGGAGC | 4903 |
| CAACUGGGCUCCUCCUUCA | 4904 | UGAAGGAGGAGCCCAGUUG | 4905 |
| AACUGGGCUCCUCCUUCAG | 4906 | CUGAAGGAGGAGCCCAGUU | 4907 |
| UGGGCUCCUCCUUCAGUUC | 4908 | GAACUGAAGGAGGAGCCCA | 4909 |
| GGGCUCCUCCUUCAGUUCC | 4910 | GGAACUGAAGGAGGAGCCC | 4911 |
| CCCAGCUCUUCUGCUUCGA | 4912 | UCGAAGCAGAAGAGCUGGG | 4913 |
| CCAGCUCUUCUGCUUCGAC | 4914 | GUCGAAGCAGAAGAGCUGG | 4915 |
| CAGCUCUUCUGCUUCGACU | 4916 | AGUCGAAGCAGAAGAGCUG | 4917 |
| AGCUCUUCUGCUUCGACUC | 4918 | GAGUCGAAGCAGAAGAGCU | 4919 |
| GCUCUUCUGCUUCGACUCC | 4920 | GGAGUCGAAGCAGAAGAGC | 4921 |
| CUCUUCUGCUUCGACUCCG | 4922 | CGGAGUCGAAGCAGAAGAG | 4923 |
| UCUUCUGCUUCGACUCCGA | 4924 | UCGGAGUCGAAGCAGAAGA | 4925 |
| CUUCUGCUUCGACUCCGAG | 4926 | CUCGGAGUCGAAGCAGAAG | 4927 |
| UUCGACUCCGAGCGGGUGU | 4928 | ACACCCGCUCGGAGUCGAA | 4929 |
| UCCGAGCGGGUGUCAUGUG | 4930 | CACAUGACACCCGCUCGGA | 4931 |
| CCGAGCGGGUGUCAUGUGU | 4932 | ACACAUGACACCCGCUCGG | 4933 |
| CGAGCGGGUGUCAUGUGUG | 4934 | CACACAUGACACCCGCUCG | 4935 |
| GAGCGGGUGUCAUGUGUGA | 4936 | UCACACAUGACACCCGCUC | 4937 |

The inhibitory nucleic acid molecules disclosed herein can comprise RNA, DNA, or both RNA and DNA. The inhibitory nucleic acid molecules can also be linked or fused to a heterologous nucleic acid sequence, such as in a vector, or a heterologous label. For example, the inhibitory nucleic acid molecules disclosed herein can be within a vector or as an exogenous donor sequence comprising the inhibitory nucleic acid molecule and a heterologous nucleic acid sequence. The inhibitory nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed inhibitory nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The inhibitory nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, —O[(CH$_2$)$_n$O]$_m$CH$_3$, —O(CH$_2$)$_n$OCH$_3$, —O(CH$_2$)$_n$NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m, independently, are from 1 to about 10. Other modifications at the 2' position include, but are not limited to, $C_{1-10}$alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as CH$_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

In some embodiments, the antisense nucleic acid molecules are gapmers, whereby the first one to seven nucleotides at the 5' and 3' ends each have 2'-methoxyethyl (2'-MOE) modifications. In some embodiments, the first five nucleotides at the 5' and 3' ends each have 2'-MOE modifications. In some embodiments, the first one to seven nucleotides at the 5' and 3' ends are RNA nucleotides. In some embodiments, the first five nucleotides at the 5' and 3' ends are RNA nucleotides. In some embodiments, each of the backbone linkages between the nucleotides is a phosphorothioate linkage.

In some embodiments, the siRNA molecules have termini modifications. In some embodiments, the 5' end of the antisense strand is phosphorylated. In some embodiments, 5'-phosphate analogs that cannot be hydrolyzed, such as 5'-(E)-vinyl-phosphonate are used.

In some embodiments, the siRNA molecules have backbone modifications. In some embodiments, the modified phosphodiester groups that link consecutive ribose nucleosides have been shown to enhance the stability and in vivo bioavailability of siRNAs The non-ester groups (—OH, =O) of the phosphodiester linkage can be replaced with sulfur, boron, or acetate to give phosphorothioate, boranophosphate, and phosphonoacetate linkages. In addition, substituting the phosphodiester group with a phosphotriester can facilitate cellular uptake of siRNAs and retention on serum components by eliminating their negative charge. In some embodiments, the siRNA molecules have sugar modifications. In some embodiments, the sugars are deprotonated (reaction catalyzed by exo- and endonucleases) whereby the 2'-hydroxyl can act as a nucleophile and attack the adjacent phosphorous in the phosphodiester bond. Such alternatives include 2'-O-methyl, 2'-O-methoxyethyl, and 2'-fluoro modifications.

In some embodiments, the siRNA molecules have base modifications. In some embodiments, the bases can be substituted with modified bases such as pseudouridine, 5'-methylcytidine, N6-methyladenosine, inosine, and N7-methylguanosine.

In some embodiments, the siRNA molecules are conjugated to lipids. Lipids can be conjugated to the 5' or 3' termini of siRNA to improve their in vivo bioavailability by allowing them to associate with serum lipoproteins. Representative lipids include, but are not limited to, cholesterol and vitamin E, and fatty acids, such as palmitate and tocopherol.

In some embodiments, a representative siRNA has the following formula:
Sense: mN*mN*/i2FN/mN/i2FN/mN/i2FN/mN/i2FN/mN/i2FN/mN/i2FN/mN/i2FN/mN/i2FN/*mN*/32FN/
Antisense: /52FN/*/i2FN/*mN/i2FN/mN/i2FN/mN/i2FN/mN/i2FN/mN/i2FN/mN/i2FN/mN/i2FN/mN/i2FN/mN*N*N wherein: "N" is the base; "2F" is a 2'-F modification; "m" is a 2'-O-methyl modification, "I" is an internal base; and "*" is a phosphorothioate backbone linkage.

The present disclosure also provides vectors comprising any one or more of the inhibitory nucleic acid molecules disclosed herein. In some embodiments, the vectors comprise any one or more of the inhibitory nucleic acid molecules disclosed herein and a heterologous nucleic acid. The vectors can be viral or nonviral vectors capable of transporting a nucleic acid molecule. In some embodiments, the vector is a plasmid or cosmid (such as, for example, a circular double-stranded DNA into which additional DNA segments can be ligated). In some embodiments, the vector is a viral vector, wherein additional DNA segments can be ligated into the viral genome. Expression vectors include, but are not limited to, plasmids, cosmids, retroviruses, adenoviruses, adeno-associated viruses (AAV), plant viruses such as cauliflower mosaic virus and tobacco mosaic virus, yeast artificial chromosomes (YACs), Epstein-Barr (EBV)-derived episomes, and other expression vectors known in the art.

The present disclosure also provides compositions comprising any one or more of the inhibitory nucleic acid molecules disclosed herein. In some embodiments, the composition is a pharmaceutical composition. In some embodiments, the compositions comprise a carrier and/or excipient. Examples of carriers include, but are not limited to, poly (lactic acid) (PLA) microspheres, poly(D,L-lactic-coglycolic-acid) (PLGA) microspheres, liposomes, micelles, inverse micelles, lipid cochleates, and lipid microtubules. A carrier may comprise a buffered salt solution such as PBS, HBSS, etc.

In some embodiments, the INHBE inhibitor comprises a nuclease agent that induces one or more nicks or double-strand breaks at a recognition sequence(s) or a DNA-binding protein that binds to a recognition sequence within an INHBE genomic nucleic acid molecule. The recognition sequence can be located within a coding region of the INHBE gene, or within regulatory regions that influence the expression of the gene. A recognition sequence of the DNA-binding protein or nuclease agent can be located in an intron, an exon, a promoter, an enhancer, a regulatory region, or any non-protein coding region. The recognition sequence can include or be proximate to the start codon of the INHBE gene. For example, the recognition sequence can be located about 10, about 20, about 30, about 40, about 50, about 100, about 200, about 300, about 400, about 500, or about 1,000 nucleotides from the start codon. As another example, two or more nuclease agents can be used, each targeting a nuclease recognition sequence including or proximate to the start codon. As another example, two nuclease agents can be used, one targeting a nuclease recognition sequence including or proximate to the start codon, and one targeting a nuclease recognition sequence including or proximate to the stop codon, wherein cleavage by the nuclease agents can result in deletion of the coding region between the two nuclease recognition sequences. Any nuclease agent that induces a nick or double-strand break into a desired recognition sequence can be used in the methods and compositions disclosed herein. Any DNA-binding protein that binds to a desired recognition sequence can be used in the methods and compositions disclosed herein.

Suitable nuclease agents and DNA-binding proteins for use herein include, but are not limited to, zinc finger protein or zinc finger nuclease (ZFN) pair, Transcription Activator-Like Effector (TALE) protein or Transcription Activator-Like Effector Nuclease (TALEN), or Clustered Regularly Interspersed Short Palindromic Repeats (CRISPR)/CRISPR-associated (Cas) systems. The length of the recognition sequence can vary, and includes, for example, recognition sequences that are about 30-36 bp for a zinc finger protein or ZFN pair, about 15-18 bp for each ZFN, about 36 bp for a TALE protein or TALEN, and about 20 bp for a CRISPR/Cas guide RNA.

In some embodiments, CRISPR/Cas systems can be used to modify an INHBE genomic nucleic acid molecule within a cell. The methods and compositions disclosed herein can employ CRISPR-Cas systems by utilizing CRISPR complexes (comprising a guide RNA (gRNA) complexed with a Cas protein) for site-directed cleavage of INHBE nucleic acid molecules.

Cas proteins generally comprise at least one RNA recognition or binding domain that can interact with gRNAs. Cas proteins can also comprise nuclease domains (such as, for example, DNase or RNase domains), DNA binding domains, helicase domains, protein-protein interaction domains, dimerization domains, and other domains. Suitable Cas proteins include, for example, a wild type Cas9 protein and a wild type Cpf1 protein (such as, for example, FnCpf1). A Cas protein can have full cleavage activity to create a double-strand break in an INHBE genomic nucleic acid molecule or it can be a nickase that creates a single-strand break in an INHBE genomic nucleic acid molecule. Additional examples of Cas proteins include, but are not limited to, Cas1, Cas1B, Cast, Cas3, Cas4, Cas5, Cas5e (CasD), Cas6, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof. In some embodiments, a Cas system, such as Cas12a, can have multiple gRNAs encoded into a single crRNA. Cas proteins can also be operably linked to heterologous polypeptides as fusion proteins. For example, a Cas protein can be fused to a cleavage domain, an epigenetic modification domain, a transcriptional activation domain, or a transcriptional repressor domain. Cas proteins can be provided in any form. For example, a Cas protein can be provided in the form of a protein, such as a Cas protein complexed with a gRNA. Alternately, a Cas protein can be provided in the form of a nucleic acid molecule encoding the Cas protein, such as an RNA or DNA.

In some embodiments, targeted genetic modifications of INHBE genomic nucleic acid molecules can be generated by contacting a cell with a Cas protein and one or more gRNAs that hybridize to one or more gRNA recognition sequences within a target genomic locus in the INHBE genomic nucleic acid molecule. For example, a gRNA recognition sequence can be located within a region of SEQ ID NO:1. The gRNA recognition sequence can include or be proximate to the start codon of an INHBE genomic nucleic acid molecule or the stop codon of an INHBE genomic nucleic acid molecule. For example, the gRNA recognition sequence can be located from about 10, from about 20, from about 30, from about 40, from about 50, from about 100, from about 200, from about 300, from about 400, from about 500, or from about 1,000 nucleotides of the start codon or the stop codon.

The gRNA recognition sequences within a target genomic locus in an INHBE genomic nucleic acid molecule are located near a Protospacer Adjacent Motif (PAM) sequence, which is a 2-6 base pair DNA sequence immediately following the DNA sequence targeted by the Cas9 nuclease. The canonical PAM is the sequence 5'-NGG-3' where "N" is any nucleobase followed by two guanine ("G") nucleobases. gRNAs can transport Cas9 to anywhere in the genome for gene editing, but no editing can occur at any site other than one at which Cas9 recognizes PAM. In addition, 5'-NGA-3' can be a highly efficient non-canonical PAM for human cells. Generally, the PAM is about 2-6 nucleotides downstream of the DNA sequence targeted by the gRNA. The PAM can flank the gRNA recognition sequence. In some embodiments, the gRNA recognition sequence can be flanked on the 3' end by the PAM. In some embodiments, the gRNA recognition sequence can be flanked on the 5' end by the PAM. For example, the cleavage site of Cas proteins can be about 1 to about 10, about 2 to about 5 base pairs, or three base pairs upstream or downstream of the PAM sequence. In some embodiments (such as when Cas9 from *S. pyogenes* or a closely related Cas9 is used), the PAM sequence of the non-complementary strand can be 5'-NGG-3', where N is any DNA nucleotide and is immediately 3' of the gRNA recognition sequence of the non-complementary strand of the target DNA. As such, the PAM sequence of the complementary strand would be 5'-CCN-3', where N is any DNA nucleotide and is immediately 5' of the gRNA recognition sequence of the complementary strand of the target DNA.

A gRNA is an RNA molecule that binds to a Cas protein and targets the Cas protein to a specific location within an INHBE genomic nucleic acid molecule. An exemplary gRNA is a gRNA effective to direct a Cas enzyme to bind to or cleave an INHBE genomic nucleic acid molecule, wherein the gRNA comprises a DNA-targeting segment that hybridizes to a gRNA recognition sequence within the INHBE genomic nucleic acid molecule. Exemplary gRNAs comprise a DNA-targeting segment that hybridizes to a gRNA recognition sequence present within an INHBE genomic nucleic acid molecule that includes or is proximate to the start codon or the stop codon. For example, a gRNA can be selected such that it hybridizes to a gRNA recognition sequence that is located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the start codon or located from about 5, from about 10, from about 15, from about 20, from about 25, from about 30, from about 35, from about 40, from about 45, from about 50, from about 100, from about 200, from about 300, from about 400, from about 500, or from about 1,000 nucleotides of the stop codon. Suitable gRNAs can comprise from about 17 to about 25 nucleotides, from about 17 to about 23 nucleotides, from about 18 to about 22 nucleotides, or from about 19 to about 21 nucleotides. In some embodiments, the gRNAs can comprise 20 nucleotides.

Examples of suitable gRNA recognition sequences located within the human INHBE reference gene are set forth in Table 5 as SEQ ID NOs:9-27.

TABLE 5

Guide RNA Recognition Sequences Near INHBE Variation(s)

| Strand | gRNA Recognition Sequence | SEQ ID NO: |
|---|---|---|
| - | CGTCTGTTGAGTCTGATTGC | 9 |
| + | GACGGAGCAACTGCCATCCG | 10 |
| - | ATCAGGGAGCCGCATGCTCC | 11 |
| + | CTGAACCAGGGCCATTCACC | 12 |
| - | CCTGGTTCAGGAGCCTCGGA | 13 |
| + | CATCCGAGGCTCCTGAACCA | 14 |
| + | CCATCCGAGGCTCCTGAACC | 15 |
| - | GCCACCTGTCTTCTATTGTC | 16 |
| - | AGCCGCATGCTCCTGGTGAA | 17 |
| - | GTCTGTTGAGTCTGATTGCT | 18 |
| + | AAGACAGGTGGCTGTACCCT | 19 |
| - | CTGATTGCTGGGGCCAATG | 20 |
| - | TGATTGCTGGGGCCAATGA | 21 |
| - | CCACCTGTCTTCTATTGTCT | 22 |
| - | ATGCTCCTGGTGAATGGCCC | 23 |
| - | CTGTTGAGTCTGATTGCTGG | 24 |
| - | CTGGTGAATGGCCCTGGTTC | 25 |
| - | ACCACTGCCACACCTACCCT | 26 |
| - | TCTGTTGAGTCTGATTGCTG | 27 |

The Cas protein and the gRNA form a complex, and the Cas protein cleaves the target INHBE genomic nucleic acid molecule. The Cas protein can cleave the nucleic acid molecule at a site within or outside of the nucleic acid sequence present in the target INHBE genomic nucleic acid molecule to which the DNA-targeting segment of a gRNA will bind. For example, formation of a CRISPR complex (comprising a gRNA hybridized to a gRNA recognition sequence and complexed with a Cas protein) can result in cleavage of one or both strands in or near (such as, for example, within 1, 2, 3, 4, 5, 6, 7, 8, 9, 10, 20, 50, or more base pairs from) the nucleic acid sequence present in the INHBE genomic nucleic acid molecule to which a DNA-targeting segment of a gRNA will bind.

Such methods can result, for example, in an INHBE genomic nucleic acid molecule in which a region of SEQ ID NO:1 is disrupted, the start codon is disrupted, the stop codon is disrupted, or the coding sequence is disrupted or deleted. Optionally, the cell can be further contacted with one or more additional gRNAs that hybridize to additional gRNA recognition sequences within the target genomic locus in the INHBE genomic nucleic acid molecule. By contacting the cell with one or more additional gRNAs (such as, for example, a second gRNA that hybridizes to a second gRNA recognition sequence), cleavage by the Cas protein can create two or more double-strand breaks or two or more single-strand breaks.

The methods and compositions disclosed herein can utilize exogenous donor sequences (e.g., targeting vectors or repair templates) to modify an INHBE gene, either without cleavage of the INHBE gene or following cleavage of the INHBE gene with a nuclease agent. An exogenous donor sequence refers to any nucleic acid or vector that includes the elements that are required to enable site-specific recombination with a target sequence. Using exogenous donor sequences in combination with nuclease agents may result in more precise modifications within the INHBE gene by promoting homology-directed repair.

In such methods, the nuclease agent cleaves the INHBE gene to create a single-strand break (nick) or double-strand break, and the exogenous donor sequence recombines the INHBE gene via non-homologous end joining (NHEJ)-mediated ligation or through a homology-directed repair event. Optionally, repair with the exogenous donor sequence removes or disrupts the nuclease cleavage site so that alleles that have been targeted cannot be re-targeted by the nuclease agent.

Exogenous donor sequences can comprise deoxyribonucleic acid (DNA) or ribonucleic acid (RNA), they can be single-stranded or double-stranded, and they can be in linear or circular form. For example, an exogenous donor sequence can be a single-stranded oligodeoxynucleotide (ssODN). See, e.g., Yoshimi et al., Nat. Commun., 2016, 7, 10431. An exemplary exogenous donor sequence is from about 50 nucleotides to about 5 kb in length, from about 50 nucleotides to about 3 kb in length, or from about 50 to about 1,000 nucleotides in length. Other exemplary exogenous donor sequences are from about 40 to about 200 nucleotides in length. For example, an exogenous donor sequence can be from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150, from about 150 to about 160, from about 160 to about 170, from about 170 to about 180, from about 180 to about 190, or from about 190 to about 200 nucleotides in length. Alternately, an exogenous donor sequence can be from about 50 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1,000 nucleotides in length. Alternately, an exogenous donor sequence can be from about 1 kb to about 1.5 kb, from about 1.5 kb to about 2 kb, from about 2 kb to about 2.5 kb, from about 2.5 kb to about 3 kb, from about 3 kb to about 3.5 kb, from about 3.5 kb to about 4 kb, from about 4 kb to about 4.5 kb, or from about 4.5 kb to about 5 kb in length. Alternately, an exogenous donor sequence can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length.

In some examples, an exogenous donor sequence is an ssODN that is from about 80 nucleotides and about 200 nucleotides in length (e.g., about 120 nucleotides in length). In another example, an exogenous donor sequences is an ssODN that is from about 80 nucleotides and about 3 kb in length. Such an ssODN can have homology arms, for example, that are each from about 40 nucleotides and about 60 nucleotides in length. Such an ssODN can also have homology arms, for example, that are each from about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor sequences can include modifications or sequences that provide for additional desirable features (e.g., modified or regulated stability; tracking or detecting with a fluorescent label; a binding site for a protein or protein complex; and so forth). Exogenous donor sequences can comprise one or more fluorescent labels, purification tags, epitope tags, or a combination thereof. For example, an exogenous donor sequence can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and-6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor sequence that has been directly integrated into a cleaved INHBE gene having protruding ends compatible with the ends of the exogenous donor sequence. The label or tag can be at the 5' end, the 3' end, or internally within the exogenous donor sequence. For example, an exogenous donor sequence can be conjugated at 5' end with the IR700 fluorophore from Integrated DNA Technologies (5'IRDYE® 700). Exogenous donor sequences can also comprise nucleic acid inserts including segments of DNA to be integrated in the INHBE gene. Integration of a nucleic acid insert in the INHBE gene can result in addition of a nucleic acid sequence of interest in the INHBE gene, deletion of a nucleic acid sequence of interest in the INHBE gene, or replacement of a nucleic acid sequence of interest in the INHBE gene (i.e., deletion and insertion). Some exogenous donor sequences are designed for insertion of a nucleic acid insert in the INHBE gene without any corresponding deletion in the INHBE gene. Other exogenous donor sequences are designed to delete a nucleic acid sequence of interest in the INHBE gene without any corresponding insertion of a nucleic acid insert. Yet other exogenous donor sequences are designed to delete a nucleic acid sequence of interest in the INHBE gene and replace it with a nucleic acid insert.

The nucleic acid insert or the corresponding nucleic acid in the INHBE gene being deleted and/or replaced can be various lengths. An exemplary nucleic acid insert or corresponding nucleic acid in the INHBE gene being deleted and/or replaced is from about 1 nucleotide to about 5 kb in length or is from about 1 nucleotide to about 1,000 nucleotides in length. For example, a nucleic acid insert or a corresponding nucleic acid in the INHBE gene being deleted and/or replaced can be from about 1 to about 10, from about 10 to about 20, from about 20 to about 30, from about 30 to about 40, from about 40 to about 50, from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150, from about 150 to about 160, from about 160 to about 170, from about 170 to about 180, from about 180 to about 190, or from about 190 to about 200 nucleotides in length. Likewise, a nucleic acid insert or a corresponding nucleic acid in the INHBE gene being deleted and/or replaced can be from about 1 to about 100, from about 100 to about 200, from about 200 to about 300, from about 300 to about 400, from about 400 to about 500, from about 500 to about 600, from about 600 to about 700, from about 700 to about 800, from about 800 to about 900, or from about 900 to about 1,000 nucleotides in length. Likewise, a nucleic acid insert or a corresponding nucleic acid in the INHBE gene being deleted and/or replaced can be from about 1 kb to about 1.5 kb, from about 1.5 kb to about 2 kb, from about 2 kb to about 2.5 kb, from about 2.5 kb to about 3 kb, from about 3 kb to about 3.5 kb, from about 3.5 kb to about 4 kb, from about 4 kb to about 4.5 kb, or from about 4.5 kb to about 5 kb in length.

The nucleic acid insert can comprise genomic DNA or any other type of DNA. For example, the nucleic acid insert can comprise cDNA.

The nucleic acid insert can comprise a sequence that is homologous to all or part of the INHBE gene (e.g., a portion of the gene encoding a particular motif or region of an INHBE protein). For example, the nucleic acid insert can comprise a sequence that comprises one or more point mutations (e.g., 1, 2, 3, 4, 5, or more) or one or more nucleotide insertions or deletions compared with a sequence targeted for replacement in the INHBE gene. The nucleic acid insert or the corresponding nucleic acid in the INHBE gene being deleted and/or replaced can be a coding region such as an exon; a non-coding region such as an intron, an untranslated region, or a regulatory region (e.g., a promoter, an enhancer, or a transcriptional repressor-binding element); or any combination thereof.

The nucleic acid insert can also comprise a conditional allele. The conditional allele can be a multifunctional allele, as described in US 2011/0104799. For example, the conditional allele can comprise: a) an actuating sequence in sense orientation with respect to transcription of a target gene; b) a drug selection cassette (DSC) in sense or antisense orientation; c) a nucleotide sequence of interest (NSI) in antisense orientation; and d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that i) lacks the actuating sequence and the DSC; and ii) contains the NSI in sense orientation and the COIN in antisense orientation. See, e.g., US 2011/0104799.

Nucleic acid inserts can also comprise a polynucleotide encoding a selection marker. Alternately, the nucleic acid inserts can lack a polynucleotide encoding a selection marker. The selection marker can be contained in a selection cassette. Optionally, the selection cassette can be a self-deleting cassette. See, e.g., U.S. Pat. No. 8,697,851 and US 2013/0312129. As an example, the self-deleting cassette can comprise a Cre gene (comprises two exons encoding a Cre recombinase, which are separated by an intron) operably linked to a mouse Prm1 promoter and a neomycin resistance gene operably linked to a human ubiquitin promoter. Exemplary selection markers include neomycin phosphotransferase ($neo^r$), hygromycin B phosphotransferase ($hyg^r$), puromycin-N-acetyltransferase ($puro^r$), blasticidin S deaminase ($bsr^r$), xanthine/guanine phosphoribosyl transferase (gpt), or herpes simplex virus thymidine kinase (HSV-k), or a combination thereof. The polynucleotide encoding the selection marker can be operably linked to a promoter active in a cell being targeted. Examples of promoters are described elsewhere herein.

The nucleic acid insert can also comprise a reporter gene. Exemplary reporter genes include those encoding luciferase, β-galactosidase, green fluorescent protein (GFP), enhanced green fluorescent protein (eGFP), cyan fluorescent protein (CFP), yellow fluorescent protein (YFP), enhanced yellow fluorescent protein (eYFP), blue fluorescent protein (BFP), enhanced blue fluorescent protein (eBFP), DsRed, ZsGreen, MmGFP, mPlum, mCherry, tdTomato, mStrawberry, J-Red, mOrange, mKO, mCitrine, Venus, YPet, Emerald, CyPet, Cerulean, T-Sapphire, and alkaline phosphatase. Such reporter genes can be operably linked to a promoter active in a cell being targeted. Examples of promoters are described elsewhere herein.

The nucleic acid insert can also comprise one or more expression cassettes or deletion cassettes. A given cassette can comprise one or more of a nucleotide sequence of interest, a polynucleotide encoding a selection marker, and a reporter gene, along with various regulatory components that influence expression. Examples of selectable markers and reporter genes that can be included are discussed in detail elsewhere herein. The nucleic acid insert can comprise a nucleic acid flanked with site-specific recombination target sequences. Alternately, the nucleic acid insert can comprise one or more site-specific recombination target sequences. Although the entire nucleic acid insert can be flanked by such site-specific recombination target sequences, any region or individual polynucleotide of interest within the nucleic acid insert can also be flanked by such sites. Site-specific recombination target sequences, which can flank the nucleic acid insert or any polynucleotide of interest in the nucleic acid insert can include, for example, loxP, lox511, lox2272, lox66, lox71, loxM2, lox5171, FRT, FRT11, FRT71, attp, att, FRT, rox, or a combination thereof. In some examples, the site-specific recombination sites flank a polynucleotide encoding a selection marker and/or a reporter gene contained within the nucleic acid insert. Following integration of the nucleic acid insert in the INHBE gene, the sequences between the site-specific recombination sites can be removed. Optionally, two exogenous donor sequences can be used, each with a nucleic acid insert comprising a site-specific recombination site. The exogenous donor sequences can be targeted to 5' and 3' regions flanking a nucleic acid of interest. Following integration of the two nucleic acid inserts into the target genomic locus, the nucleic acid of interest between the two inserted site-specific recombination sites can be removed.

Nucleic acid inserts can also comprise one or more restriction sites for restriction endonucleases (i.e., restriction enzymes), which include Type I, Type II, Type III, and Type IV endonucleases. Type I and Type III restriction endonucleases recognize specific recognition sequences, but typically cleave at a variable position from the nuclease binding site, which can be hundreds of base pairs away from the cleavage site (recognition sequence). In Type II systems the restriction activity is independent of any methylase activity, and cleavage typically occurs at specific sites within or near to the binding site. Most Type II enzymes cut palindromic sequences, however Type IIa enzymes recognize non-palindromic recognition sequences and cleave outside of the recognition sequence, Type IIb enzymes cut sequences twice with both sites outside of the recognition sequence, and Type IIs enzymes recognize an asymmetric recognition sequence and cleave on one side and at a defined distance of about 1-20 nucleotides from the recognition sequence. Type IV restriction enzymes target methylated DNA. Restriction enzymes are further described and classified, for example in the REBASE database (webpage at rebase.neb.com; Roberts et al., Nucleic Acids Res., 2003, 31, 418-420; Roberts et al., Nucleic Acids Res., 2003, 31, 1805-1812; and Belfort et al., in Mobile DNA II, 2002, pp. 761-783, Eds. Craigie et al., (ASM Press, Washington, D.C.)).

Some exogenous donor sequences have short single-stranded regions at the 5' end and/or the 3' end that are complementary to one or more overhangs created by nuclease-mediated or Cas-protein-mediated cleavage at the target genomic locus (e.g., in the INHBE gene). These overhangs can also be referred to as 5' and 3' homology arms. For example, some exogenous donor sequences have short single-stranded regions at the 5' end and/or the 3' end that are complementary to one or more overhangs created by Cas-protein-mediated cleavage at 5' and/or 3' target sequences at the target genomic locus. Some such exogenous donor sequences have a complementary region only at the 5' end or only at the 3' end. For example, some such exogenous donor sequences have a complementary region only at the 5' end complementary to an overhang created at a 5' target sequence at the target genomic locus or only at the 3' end complementary to an overhang created at a 3' target sequence at the target genomic locus. Other such exogenous donor sequences have complementary regions at both the 5' and 3' ends. For example, other such exogenous donor sequences have complementary regions at both the 5' and 3' ends e.g., complementary to first and second overhangs, respectively, generated by Cas-mediated cleavage at the target genomic locus. For example, if the exogenous donor sequence is double-stranded, the single-stranded complementary regions can extend from the 5' end of the top strand of the donor sequence and the 5' end of the bottom strand of the donor sequence, creating 5' overhangs on each end. Alternately, the single-stranded complementary region can extend from the 3' end of the top strand of the donor sequence and from the 3' end of the bottom strand of the template, creating 3' overhangs.

The complementary regions can be of any length sufficient to promote ligation between the exogenous donor sequence and the INHBE gene. Exemplary complementary regions are from about 1 to about 5 nucleotides in length, from about 1 to about 25 nucleotides in length, or from about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternately, the complementary region can be from about 5 to about 10, from about 10 to about 20, from about 20 to about 30, from about 30 to about 40, from about 40 to about 50, from about 50 to about 60, from about 60 to about 70, from about 70 to about 80, from about 80 to about 90, from about 90 to about 100, from about 100 to about 110, from about 110 to about 120, from about 120 to about 130, from about 130 to about 140, from about 140 to about 150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA recognition sequences corresponding with first, second, third, and fourth guide RNAs. The first and second guide RNA recognition sequences can be positioned to create a first cleavage site such that the nicks created by the first and second nickases on the first and second strands of DNA create a double-strand break (i.e., the first cleavage site comprises the nicks within the first and second guide RNA recognition sequences). Likewise, the third and fourth guide RNA recognition sequences can be positioned to create a second cleavage site such that the nicks created by the third and fourth nickases on the first and second strands of DNA create a double-strand break (i.e., the second cleavage site comprises the nicks within the third and fourth guide RNA recognition sequences). Preferably, the nicks within the first and second guide RNA recognition sequences and/or the third and fourth guide RNA recognition sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See, Ran et al., Cell, 2013, 154, 1380-1389; Mali et al., Nat. Biotech., 2013, 31, 833-838; and Shen et al., Nat. Methods, 2014, 11, 399-404. In such cases, a double-stranded exogenous donor sequence can be designed with single-stranded complementary regions that are complementary to the overhangs created by the nicks within the first and second guide RNA recognition sequences and by the nicks within the third and fourth guide RNA recognition sequences. Such an exogenous donor sequence can then be inserted by non-homologous-end-joining-mediated ligation.

Some exogenous donor sequences (i.e., targeting vectors) comprise homology arms. If the exogenous donor sequence also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor sequence. The 5' and 3' homology arms correspond to regions within the INHBE gene, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor sequence can be any degree of sequence identity that allows for homologous recombination to occur. For example, the amount of sequence identity shared by the homology arm of the exogenous donor sequence (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are from about 25 nucleotides to about 2.5 kb in length, are from about 25 nucleotides to about 1.5 kb in length, or are from about 25 to about 500 nucleotides in length. For example, a given homology arm (or each of the homology arms) and/or corresponding target sequence can comprise corresponding regions of homology that are from about 25 to about 30, from about 30 to about 40, from about 40 to about 50, from about 50 to about 60, from about 60 to about 70, from about 70 to about 80, from about 80 to about 90, from about 90 to about 100, from about 100 to about 150, from about 150 to about 200, from about 200 to about 250, from about 250 to about 300, from about 300 to about 350, from about 350 to about 400, from about 400 to about 450, or from about 450 to about 500 nucleotides in length, such that the homology arms have sufficient homology to undergo homologous recombination with the corresponding target sequences within the INHBE gene. Alternately, a given homology arm (or each homology arm) and/or corresponding target sequence can comprise corresponding regions of homology that are from about 0.5 kb to about 1 kb, from about 1 kb to about 1.5 kb, from about 1.5 kb to about 2 kb, or from about 2 kb to about 2.5 kb in length. For example, the homology arms can each be about 750 nucleotides in length. The homology arms can be symmetrical (each about the same size in length), or they can be asymmetrical (one longer than the other).

The homology arms can correspond to a locus that is native to a cell (e.g., the targeted locus). Alternately, for example, they can correspond to a region of a heterologous or exogenous segment of DNA that was integrated into the genome of the cell, including, for example, transgenes, expression cassettes, or heterologous or exogenous regions of DNA. Alternately, the homology arms of the targeting vector can correspond to a region of a yeast artificial chromosome (YAC), a bacterial artificial chromosome (BAC), a human artificial chromosome, or any other engineered region contained in an appropriate host cell. Still further, the homology arms of the targeting vector can correspond to or be derived from a region of a BAC library, a cosmid library, or a P1 phage library, or can be derived from synthetic DNA.

When a nuclease agent is used in combination with an exogenous donor sequence, the 5' and 3' target sequences are preferably located in sufficient proximity to the nuclease cleavage site so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the INHBE gene that correspond to the 5' and 3' homology arms of the exogenous donor sequence are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor sequence can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor sequence and the nuclease cleavage site can vary. For example, target sequences can be located 5' to the nuclease cleavage site, target sequences can be located 3' to the nuclease cleavage site, or the target sequences can flank the nuclease cleavage site.

Also provided are therapeutic methods and methods of treatment or prophylaxis of a metabolic disorder in a subject having or at risk for the disease using the methods disclosed herein for modifying or altering expression of an endogenous INHBE gene. Also provided are therapeutic methods and methods of treatment or prophylaxis of a metabolic disorder in a subject having or at risk for the disease using methods for decreasing expression of INHBE mRNA transcripts or using methods for providing recombinant nucleic acids encoding INHBE proteins, providing mRNAs encoding INHBE proteins, or providing INHBE proteins to the subject. The methods can comprise introducing one or more nucleic acids or proteins into the subject, into the liver of the subject, or into a cell (e.g., liver cell) of the subject (e.g., in vivo or ex vivo).

Also provided are therapeutic methods and methods of treatment or prophylaxis of a cardiovascular disease in a subject having or at risk for cardiovascular disease using the methods disclosed herein for modifying or altering expression of an endogenous INHBE gene. Also provided are therapeutic methods and methods of treatment or prophylaxis of a cardiovascular disease in a subject having or at risk for cardiovascular disease using methods for decreasing expression of INHBE mRNA transcripts or using methods for providing recombinant nucleic acids encoding INHBE proteins, providing mRNAs encoding INHBE proteins, or providing INHBE proteins to the subject. The methods can comprise introducing one or more nucleic acids or proteins into the subject, into the liver of the subject, or into a cell (e.g., liver cell) of the subject (e.g., in vivo or ex vivo).

Such methods can comprise genome editing or gene therapy. For example, an endogenous INHBE gene that does not encode a loss-of-function variant can be modified to comprise any of the loss-of-function variants described herein. As another example, an endogenous INHBE gene that does not encode a loss-of-function variant can be knocked out or inactivated. Likewise, an endogenous INHBE gene that does not encode a loss-of-function variant can be knocked out or inactivated, and an INHBE gene comprising any one of or any combination of the INHBE loss-of-function variants described herein can be introduced and expressed. Similarly, an endogenous INHBE gene that does not encode a loss-of-function variant can be knocked out or inactivated, and a recombinant DNA encoding any one of or any combination of the INHBE loss-of-function variants described herein can be introduced and expressed, an mRNA encoding any one of or any combination of INHBE loss-of-function variants described herein (or fragments thereof) can be introduced and expressed (e.g., intracellular protein replacement therapy), or a cDNA encoding any one of or any combination of INHBE loss-of-function variants described herein (or fragments thereof) can be introduced (e.g., protein replacement therapy).

Other such methods can comprise introducing and expressing a recombinant INHBE gene comprising any one of or any combination of INHBE loss-of-function variants described herein (e.g., the full INHBE variant or a minigene comprising the modification), introducing and expressing recombinant nucleic acids (e.g., DNA) encoding any one of or any combination of INHBE loss-of-function variants described herein or fragments thereof, introducing and expressing one or more mRNAs encoding any one of or any combination of INHBE loss-of-function variants described herein fragments thereof (e.g., intracellular protein replacement therapy), or introducing any one of or any combination of INHBE loss-of-function variants described herein (e.g., protein replacement therapy) without knocking out or inactivating an endogenous INHBE gene that does not encode a loss-of-function variant.

An INHBE gene or minigene or a DNA encoding any one of or any combination of INHBE loss-of-function variants described herein or fragments thereof can be introduced and expressed in the form of an expression vector that does not modify the genome, it can be introduced in the form of a targeting vector such that it genomically integrates into an INHBE locus, or it can be introduced such that it genomically integrates into a locus other than the INHBE locus, such as a safe harbor locus. The genomically integrated INHBE gene can be operably linked to an INHBE promoter or to another promoter, such as an endogenous promoter at the site of integration. Safe harbor loci are chromosomal sites where transgenes can be stably and reliably expressed in all tissues of interest without adversely affecting gene structure or expression. Safe harbor loci can have, for example, one or more or all of the following characteristics: distance of greater than 50 kb from the 5' end of any gene; distance of greater than 300 kb from any cancer-related gene; distance of greater than 300 kb from any microRNA; outside a gene transcription unit, and outside of ultra-conserved regions. Examples of suitable safe harbor loci include adeno-associated virus site 1 (AAVS1), the chemokine (CC motif) receptor 5 (CCR5) gene locus, and the human orthologue of mouse ROSA26 locus.

Combinations of INHBE protein isoforms or nucleic acids encoding INHBE protein isoforms that can be introduced and expressed include, any one or any combination of protein or mRNA isoforms described herein. For example, INHBE a nucleic acid encoding Isoform 1 (SEQ ID NO:2) encoding any one or any combination of loss-of-function variants described herein (alone or in combination with other isoforms) is introduced or expressed. Exemplary sequences for each of these isoforms and transcripts are provided elsewhere herein. It is understood, however, that gene sequences and within a population, mRNA sequences transcribed from such genes, and proteins translated from such mRNAs can vary due to polymorphisms such as single-nucleotide polymorphisms. The sequences provided herein for each transcript and isoform are only exemplary sequences. Other sequences are also possible.

In some embodiments, the methods comprise treating a subject who is not a carrier of any of the INHBE variant nucleic acid molecules described herein (or is only a heterozygous carrier of any one or any combination of the variant nucleic acid molecules described herein) and has or is susceptible to developing a metabolic disorder and/or a cardiovascular disease, comprising introducing into the subject or introducing into a liver cell in the subject: a) a nuclease agent (or nucleic acid encoding) that binds to a nuclease recognition sequence within an INHBE gene, wherein the nuclease recognition sequence includes or is proximate to a position of one of the INHBE variant nucleic acid molecules described herein; and b) an exogenous donor sequence comprising a 5' homology arm that hybridizes to a target sequence 5' of the position of one of the INHBE variant nucleic acid molecules described herein, a 3' homology arm that hybridizes to a target sequence 3' of the same INHBE variant nucleic acid molecule, and a nucleic acid insert comprising one or more of the variant nucleotides flanked by the 5' homology arm and the 3' homology arm. The nuclease agent can cleave the INHBE gene in a liver cell in the subject, and the exogenous donor sequence can recombine with the INHBE gene in the liver cell, wherein upon recombination of the exogenous donor sequence with the INHBE gene the nucleic acid insert encoding the loss-of-function variant is introduced, substituting the wild type nucleotide. Examples of nuclease agents (e.g., a Cas9 protein and a guide RNA) that can be used in such methods are disclosed elsewhere herein. Examples of suitable guide RNAs and guide RNA recognition sequences are disclosed elsewhere herein. Examples of exogenous donor sequences that can be used in such methods are disclosed elsewhere herein.

As another example, the methods can comprise treating a subject who is not a carrier of any of the INHBE variant nucleic acid molecules described herein (or is only a heterozygous carrier of any one or any combination of the variant nucleic acid molecules described herein) and has or is susceptible to developing a metabolic disorder and/or a cardiovascular disease, comprising introducing into the subject or introducing into a liver cell in the subject an exogenous donor sequence comprising a 5' homology arm that hybridizes to a target sequence 5' of the position of one of the INHBE variant nucleic acid molecules described herein, a 3' homology arm that hybridizes to a target sequence 3' of the same INHBE variant nucleic acid molecule, and a nucleic acid insert comprising one or more of the variant nucleotides flanked by the 5' homology arm and the 3' homology arm. The exogenous donor sequence can recombine with the INHBE gene in the liver cell, wherein upon recombination of the exogenous donor sequence with the INHBE gene the nucleic acid insert encoding the loss-of-function variant is introduced, substituting the wild type nucleotide. Examples of exogenous donor sequences that can be used in such methods are disclosed elsewhere herein.

In some embodiments, the methods comprise treating a subject who is not a carrier of any of the INHBE variant nucleic acid molecules described herein (or is only a heterozygous carrier of any one or any combination of the variant nucleic acid molecules described herein) and has or is susceptible to developing a metabolic disorder and/or a cardiovascular disease, comprising introducing into the subject or introducing into a liver cell in the subject: a) a nuclease agent (or nucleic acid encoding) that binds to a nuclease recognition sequence within an INHBE gene, wherein the nuclease recognition sequence comprises the start codon for the INHBE gene or is within about 10, 20, 30, 40, 50, 100, 200, 300, 400, 500, or 1,000 nucleotides of the start codon. The nuclease agent can cleave and disrupt expression of the INHBE gene in a liver cell in the subject. In some embodiments, the methods comprise treating a subject who is not a carrier of any of the INHBE variant nucleic acid molecules described herein (or is only a heterozygous carrier of any one or any combination of the INHBE variant nucleic acid molecules described herein) and has or is susceptible to developing a metabolic disorder and/or a cardiovascular disease, comprising introducing into the subject or introducing into a liver cell in the subject: a) a nuclease agent (or nucleic acid encoding) that binds to a nuclease recognition sequence within an INHBE gene, wherein the nuclease recognition sequence comprises the start codon for the INHBE gene or is within about 10, 20, 30, 40, 50, 100, 200, 300, 400, 500, or 1,000 nucleotides of the start codon or is selected from SEQ ID NOs: 1-7; and b) an expression vector comprising a recombinant INHBE gene comprising any one or any combination of loss-of-function variants described herein. The expression vector can be one that does not genomically integrate. Alternately, a targeting vector (i.e., exogenous donor sequence) can be introduced comprising a recombinant INHBE gene comprising any one or any combination of loss-of-function variants described herein. The nuclease agent can cleave and disrupt expression of the INHBE gene in a liver cell in the subject, and the expression vector can express the recombinant INHBE gene in the liver cell in the subject. Alternately, the genomically integrated, recombinant INHBE gene can express in the liver cell in the subject. Examples of nuclease agents (e.g., a nuclease-active Cas9 protein and guide RNA) that can be used in such methods are disclosed elsewhere herein. Examples of suitable guide RNAs and guide RNA recognition sequences are disclosed elsewhere herein. Step b) can Alternately comprise introducing an expression vector or targeting vector comprising a nucleic acid (e.g., DNA) encoding an INHBE protein that is at least 90%, at least 95%, at least 96%, at least 97%, at least 98%, at least 99%, or 100% identical to any INHBE isoform described herein or a fragment thereof and comprising any one or any combination of the INHBE variant nucleic acid molecules described herein. Likewise, step b) can alternately comprise introducing an mRNA encoding an INHBE protein that is at least 90%, at least 95%, at least 96%, at least 97%, at least 98%, at least 99%, or 100% identical to any INHBE mRNA isoform described herein or a fragment thereof and comprising any one or any combination of the INHBE variant nucleic acid molecules described herein. Likewise, step b) can alternately comprise introducing a protein comprising a sequence that is at least 90%, at least 95%, at least 96%, at least 97%, at least 98%, at least 99%, or 100% identical to any INHBE protein isoform described herein or a fragment thereof and comprising any one or any combination of loss-of-function variant polypeptides described herein.

In some embodiments, a second nuclease agent is also introduced into the subject or into the liver cell in the subject, wherein the second nuclease agent binds to a second nuclease recognition sequence within the INHBE gene, wherein the second nuclease recognition sequence comprises the stop codon for the INHBE gene or is within about 10, 20, 30, 40, 50, 100, 200, 300, 400, 500, or 1,000 nucleotides of the stop codon, wherein the nuclease agent cleaves the INHBE gene in the liver cell within both the first nuclease recognition sequence and the second nuclease recognition sequence, wherein the liver cell is modified to comprise a deletion between the first nuclease recognition sequence and the second nuclease recognition sequence. For example, the second nuclease agent can be a Cas9 protein and a guide RNA. Suitable guide RNAs and guide RNA recognition sequences in proximity to the stop codon are disclosed elsewhere herein.

Such methods can also comprise a method of treating a subject who is not a carrier of any of the INHBE variant nucleic acid molecules described herein (or is only a heterozygous carrier of any one or any combination of the INHBE variant nucleic acid molecules described herein) and has or is susceptible to developing a metabolic disorder and/or a cardiovascular disease, comprising introducing into the subject or introducing into a liver cell in the subject: a) a DNA-binding protein (or nucleic acid encoding) that binds to a DNA-binding protein recognition sequence within an INHBE gene, wherein the DNA-binding protein recognition sequence comprises the start codon for the INHBE gene or is within about 10, 20, 30, 40, 50, 100, 200, 300, 400, 500, or 1,000 nucleotides of the start codon. The DNA-binding protein can alter (e.g., reduce) expression of the INHBE gene in a liver cell in the subject. Such methods can also comprise a method of treating a subject who is not a carrier of any of the INHBE variant nucleic acid molecules described herein (or is only a heterozygous carrier of any one or any combination of the INHBE variant nucleic acid molecules described herein) and has or is susceptible to developing a metabolic disorder and/or a cardiovascular disease, comprising introducing into the subject or introducing into a liver cell in the subject: a) a DNA-binding protein (or nucleic acid encoding) that binds to a DNA-binding protein recognition sequence within an INHBE gene, wherein the DNA-binding protein recognition sequence comprises the start codon for the INHBE gene or is within about 10, 20, 30, 40, 50, 100, 200, 300, 400, 500, or 1,000 nucleotides of the start codon; and b) an expression vector comprising a recombinant INHBE gene comprising any one or any combination of loss-of-function variants described herein. The expression vector can be one that does not genomically integrate. Alternately, a targeting vector (i.e., exogenous donor sequence) can be introduced comprising a recombinant INHBE gene comprising any one or any combination of the INHBE variant nucleic acid molecules described herein. The DNA-binding protein can alter (e.g., reduce) expression of the INHBE gene in a liver cell in the subject, and the expression vector can express the recombinant INHBE gene in the liver cell in the subject. Alternately, the genomically integrated, recombinant INHBE gene can express in the liver cell in the subject. Examples of DNA-binding proteins suitable for use in such methods are disclosed elsewhere herein. Such DNA-binding proteins (e.g., Cas9 protein and guide RNA) can be fused or operably linked to a transcriptional repressor domain. For example, the DNA-binding protein can be a catalytically inactive Cas9 protein fused to a transcriptional repressor domain. Examples of suitable guide RNAs and guide RNA recognition sequences are disclosed elsewhere herein. Step b) can alternately comprise introducing an expression vector or targeting vector comprising a nucleic acid (e.g., DNA) encoding an INHBE protein that is at least 90%, at least 95%, at least 96%, at least 97%, at least 98%, at least 99%, or 100% identical to any INHBE isoform described herein or a fragment thereof and comprising any one or any combination of the INHBE variant nucleic acid molecules described herein. Likewise, step b) can alternately comprise introducing an mRNA encoding an INHBE protein that is at least 90%, at least 95%, at least 96%, at least 97%, at least 98%, at least 99%, or 100% identical any INHBE mRNA isoform described herein or a fragment thereof and comprising any one or any combination of the INHBE variant nucleic acid molecules described herein. Likewise, step b) can alternately comprise introducing a protein comprising a sequence that is at least 90%, at least 95%, at least 96%, at least 97%, at least 98%, at least 99%, or 100% identical to any INHBE protein isoform described herein or a fragment thereof and comprising any one or any combination of loss-of-function variant polypeptides described herein.

Other such methods can comprise method of treating a subject who is not a carrier of any of the INHBE variant nucleic acid molecules described herein (or is only a heterozygous carrier of any one or any combination of the INHBE variant nucleic acid molecules described herein) and has or is susceptible to developing a metabolic disorder and/or a cardiovascular disease, comprising introducing into the subject or introducing into a liver cell in the subject an expression vector, wherein the expression vector comprises a recombinant INHBE gene comprising any one or any combination of loss-of-function variants described herein, wherein the expression vector expresses the recombinant INHBE gene in a liver cell in the subject. The expression vector can be one that does not genomically integrate. Alternately, a targeting vector (i.e., exogenous donor sequence) can be introduced comprising a recombinant INHBE gene comprising any one or any combination of the INHBE variant nucleic acid molecules described herein. In methods in which an expression vector is used, the expression vector can express the recombinant INHBE gene in the liver cell in the subject. Alternately, in methods in which a recombinant INHBE gene is genomically integrated, the recombinant INHBE gene can express in the liver cell in the subject. Such methods can alternately comprise introducing an expression vector or targeting vector comprising a nucleic acid (e.g., DNA) encoding an INHBE protein that is at least 90%, at least 95%, at least 96%, at least 97%, at least 98%, at least 99%, or 100% identical to any INHBE isoform described herein or a fragment thereof and comprising any one or any combination of loss-of-function variants described herein. Likewise, such methods can alternately comprise introducing an mRNA encoding an INHBE protein that is at least 90%, at least 95%, at least 96%, at least 97%, at least 98%, at least 99%, or 100% identical to any INHBE mRNA isoform described herein or a fragment thereof and comprising any one or any combination of the INHBE variant nucleic acid molecules described herein. Likewise, such methods can alternately comprise introducing a protein comprising a sequence that is at least 90%, at least 95%, at least 96%, at least 97%, at least 98%, at least 99%, or 100% identical to any INHBE protein isoform described herein or a fragment thereof and comprising any one or any combination of loss-of-function variant polypeptides described herein.

Suitable expression vectors and recombinant INHBE genes for use in any of the above methods are disclosed elsewhere herein. For example, the recombinant INHBE gene can be the full length variant gene or can be an INHBE minigene in which one or more nonessential segments of the gene have been deleted with respect to a corresponding wild type INHBE gene. As an example, the deleted segments can comprise one or more intronic sequences. An example of a full INHBE gene is one that is at least 90%, at least 95%, at least 96%, at least 97%, at least 98%, or at least 99% identical to SEQ ID NO:1 when optimally aligned with SEQ ID NO:1.

In some embodiments, the methods comprise modifying a cell (e.g., a liver cell) in a subject having or susceptible to developing a chronic liver disease. In some embodiments, the methods comprise modifying a cell (e.g., a cardiac cell) in a subject having or susceptible to developing a cardiovascular disease. In such methods, the nuclease agents and/or exogenous donor sequences and/or recombinant expression vectors can be introduced into the cell via administration in an effective regime meaning a dosage, route of administration and frequency of administration that delays the onset, reduces the severity, inhibits further deterioration, and/or ameliorates at least one sign or symptom of the disease being treated. The term "symptom" refers to a subjective evidence of a disease as perceived by the subject, and a "sign" refers to objective evidence of a disease as observed by a physician. If a subject is already suffering from a disease, the regime can be referred to as a therapeutically effective regime. If the subject is at elevated risk of the disease relative to the general population but is not yet experiencing symptoms, the regime can be referred to as a prophylactically effective regime. In some instances, therapeutic or prophylactic efficacy can be observed in an individual patient relative to historical controls or past experience in the same subject. In other instances, therapeutic or prophylactic efficacy can be demonstrated in a preclinical or clinical trial in a population of treated subjects relative to a control population of untreated subjects.

Delivery can be any suitable method, as disclosed elsewhere herein. For example, the nuclease agents or exogenous donor sequences or recombinant expression vectors can be delivered by vector delivery, viral delivery, particle-mediated delivery, nanoparticle-mediated delivery, liposome-mediated delivery, exosome-mediated delivery, lipid-mediated delivery, lipid-nanoparticle-mediated delivery, cell-penetrating-peptide-mediated delivery, or implantable-device-mediated delivery. Some specific examples include hydrodynamic delivery, virus-mediated delivery, and lipid-nanoparticle-mediated delivery. Administration can be by any suitable route including, for example, parenteral, intravenous, oral, subcutaneous, intra-arterial, intracranial, intrathecal, intraperitoneal, topical, intranasal, or intramuscular. A specific example which is often used, for example, for protein replacement therapies is intravenous infusion. The frequency of administration and the number of dosages can depend on the half-life of the nuclease agents or exogenous donor sequences or recombinant expression vectors, the condition of the subject, and the route of administration among other factors. Pharmaceutical compositions for administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

Other such methods comprise an ex vivo method in a cell from a subject having or susceptible to developing a chronic liver disease and/or a cardiovascular disease. The cell with the targeted genetic modification can then be transplanted back into the subject.

In some embodiments, the INHBE inhibitor comprises a small molecule. In some embodiments, the INHBE inhibitor is any of the inhibitory nucleic acid molecules described herein. In some embodiments, the INHBE inhibitor comprises an antibody.

In some embodiments, the methods of treatment further comprise detecting the presence or absence of an INHBE variant nucleic acid molecule encoding an INHBE predicted loss-of-function polypeptide, or the presence of the corresponding INHBE polypeptide, or the quantification of the INHBE polypeptide or nucleic acid (such as RNA) in a biological sample from the subject. As used throughout the present disclosure, an "an INHBE variant nucleic acid molecule" is any INHBE nucleic acid molecule (such as, for example, genomic nucleic acid molecule, mRNA molecule, or cDNA molecule) encoding an INHBE polypeptide having a partial loss-of-function, a complete loss-of-function, a predicted partial loss-of-function, or a predicted complete loss-of-function.

The present disclosure also provides methods of treating a subject with a therapeutic agent that treats or inhibits a metabolic disorder, wherein the subject is suffering from the metabolic disorder. In some embodiments, the methods comprise determining whether the subject has an INHBE variant nucleic acid molecule encoding an INHBE predicted loss-of-function polypeptide by obtaining or having obtained a biological sample from the subject, and performing or having performed a genotyping assay on the biological sample to determine if the subject has a genotype comprising the INHBE variant nucleic acid molecule. When the subject is INHBE reference, the therapeutic agent that treats or inhibits the metabolic disorder is administered or continued to be administered to the subject in a standard dosage amount, and an INHBE inhibitor is administered to the subject. When the subject is heterozygous for an INHBE variant nucleic acid molecule, the therapeutic agent that treats or inhibits the metabolic disorder is administered or continued to be administered to the subject in an amount that is the same as or lower than a standard dosage amount, and an INHBE inhibitor is administered to the subject. When the subject is homozygous for an INHBE variant nucleic acid molecule, the therapeutic agent that treats or inhibits the metabolic disorder is administered or continued to be administered to the subject in an amount that is the same as or lower than a standard dosage amount. The presence of a genotype having an INHBE variant nucleic acid molecule encoding an INHBE predicted loss-of-function polypeptide indicates the subject has a decreased risk of developing a metabolic disorder. In some embodiments, the subject is INHBE reference. In some embodiments, the subject is heterozygous for an INHBE variant nucleic acid molecule encoding an INHBE predicted loss-of-function polypeptide.

For subjects that are genotyped or determined to be either INHBE reference or heterozygous for an INHBE variant nucleic acid molecule encoding an INHBE predicted loss-of-function polypeptide, such subjects can be treated with an INHBE inhibitor, as described herein.

The present disclosure also provides methods of treating a subject with a therapeutic agent that treats or inhibits a cardiovascular disease, wherein the subject is suffering from the cardiovascular disease. In some embodiments, the methods comprise determining whether the subject has an INHBE variant nucleic acid molecule encoding an INHBE predicted loss-of-function polypeptide by obtaining or having obtained a biological sample from the subject, and performing or having performed a genotyping assay on the biological sample to determine if the subject has a genotype comprising the INHBE variant nucleic acid molecule. When the subject is INHBE reference, the therapeutic agent that treats or inhibits the cardiovascular disease is administered or continued to be administered to the subject in a standard dosage amount, and an INHBE inhibitor is administered to the subject. When the subject is heterozygous for an INHBE variant nucleic acid molecule, the therapeutic agent that treats or inhibits the cardiovascular disease is administered or continued to be administered to the subject in an amount that is the same as or lower than a standard dosage amount, and an INHBE inhibitor is administered to the subject. When the subject is homozygous for an INHBE variant nucleic acid molecule, the therapeutic agent that treats or inhibits the cardiovascular disease is administered or continued to be administered to the subject in an amount that is the same as or lower than a standard dosage amount. The presence of a genotype having an INHBE variant nucleic acid molecule encoding an INHBE predicted loss-of-function polypeptide indicates the subject has a decreased risk of developing a cardiovascular disease. In some embodiments, the subject is INHBE reference. In some embodiments, the subject is heterozygous for an INHBE variant nucleic acid molecule encoding an INHBE predicted loss-of-function polypeptide.

For subjects that are genotyped or determined to be either INHBE reference or heterozygous for an INHBE variant nucleic acid molecule encoding an INHBE predicted loss-of-function polypeptide, such subjects can be treated with an INHBE inhibitor, as described herein.

Detecting the presence or absence of an INHBE variant nucleic acid molecule encoding an INHBE predicted loss-of-function polypeptide in a biological sample from a subject and/or determining whether a subject has an INHBE variant nucleic acid molecule encoding an INHBE predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when the subject is INHBE reference, the subject is also administered a therapeutic agent that treats or inhibits a metabolic disorder in a standard dosage amount. In some embodiments, when the subject is heterozygous or homozygous for an INHBE variant nucleic acid molecule encoding an INHBE predicted loss-of-function polypeptide, the subject is also administered a therapeutic agent that treats or inhibits the metabolic disorder in a dosage amount that is the same as or lower than a standard dosage amount.

In some embodiments, when the subject is INHBE reference, the subject is also administered a therapeutic agent that treats or inhibits a cardiovascular disease in a standard dosage amount. In some embodiments, when the subject is heterozygous or homozygous for an INHBE variant nucleic acid molecule encoding an INHBE predicted loss-of-function polypeptide, the subject is also administered a therapeutic agent that treats or inhibits the cardiovascular disease in a dosage amount that is the same as or lower than a standard dosage amount.

In some embodiments, the treatment methods further comprise detecting the presence or absence of an INHBE predicted loss-of-function polypeptide in a biological sample from the subject. In some embodiments, when the subject does not have an INHBE predicted loss-of-function polypeptide, the subject is also administered a therapeutic agent that treats or inhibits a metabolic disorder in a standard dosage amount. In some embodiments, when the subject has an INHBE predicted loss-of-function polypeptide, the subject is also administered a therapeutic agent that treats or inhibits the metabolic disorder in a dosage amount that is the same as or lower than a standard dosage amount.

In some embodiments, the treatment methods further comprise detecting the presence or absence of an INHBE predicted loss-of-function polypeptide in a biological sample from the subject. In some embodiments, when the subject does not have an INHBE predicted loss-of-function polypeptide, the subject is also administered a therapeutic agent that treats or inhibits a cardiovascular disease in a standard dosage amount. In some embodiments, when the subject has an INHBE predicted loss-of-function polypeptide, the subject is also administered a therapeutic agent that treats or inhibits the cardiovascular disease in a dosage amount that is the same as or lower than a standard dosage amount.

The present disclosure also provides methods of treating a subject with a therapeutic agent that treats or inhibits a metabolic disorder, wherein the subject is suffering from the metabolic disorder. In some embodiments, the method comprises determining whether the subject has an INHBE predicted loss-of-function polypeptide by obtaining or having obtained a biological sample from the subject, and performing or having performed an assay on the biological sample to determine if the subject has an INHBE predicted loss-of-function polypeptide. When the subject does not have an INHBE predicted loss-of-function polypeptide, the therapeutic agent that treats or inhibits the metabolic disorder is administered or continued to be administered to the subject in a standard dosage amount, and an INHBE inhibitor is administered to the subject. When the subject has an INHBE predicted loss-of-function polypeptide, the therapeutic agent that treats or inhibits the metabolic disorder is administered or continued to be administered to the subject in an amount that is the same as or lower than a standard dosage amount, and an INHBE inhibitor is administered to the subject. The presence of an INHBE predicted loss-of-function polypeptide indicates the subject has a decreased risk of developing a metabolic disorder. In some embodiments, the subject has an INHBE predicted loss-of-function polypeptide. In some embodiments, the subject does not have an INHBE predicted loss-of-function polypeptide.

The present disclosure also provides methods of treating a subject with a therapeutic agent that treats or inhibits a cardiovascular disease, wherein the subject is suffering from the cardiovascular disease. In some embodiments, the method comprises determining whether the subject has an INHBE predicted loss-of-function polypeptide by obtaining or having obtained a biological sample from the subject, and performing or having performed an assay on the biological sample to determine if the subject has an INHBE predicted loss-of-function polypeptide. When the subject does not have an INHBE predicted loss-of-function polypeptide, the therapeutic agent that treats or inhibits the cardiovascular disease is administered or continued to be administered to the subject in a standard dosage amount, and an INHBE inhibitor is administered to the subject. When the subject has an INHBE predicted loss-of-function polypeptide, the therapeutic agent that treats or inhibits the cardiovascular disease is administered or continued to be administered to the subject in an amount that is the same as or lower than a standard dosage amount, and an INHBE inhibitor is administered to the subject. The presence of an INHBE predicted loss-of-function polypeptide indicates the subject has a decreased risk of developing a cardiovascular disease. In some embodiments, the subject has an INHBE predicted loss-of-function polypeptide. In some embodiments, the subject does not have an INHBE predicted loss-of-function polypeptide.

Detecting the presence or absence of an INHBE predicted loss-of-function polypeptide in a biological sample from a subject and/or determining whether a subject has an INHBE predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the polypeptide can be present within a cell or blood sample obtained from the subject, or maybe imputed from other information about the subject that has previously been generated from collection of a cell or blood sample from the subject or biological relatives of the subject. In any of these embodiments, determination by quantification of the amount of INHBE polypeptide can be included as a determination of loss of function due to the effective absence or reduction in the amount of the INHBE polypeptide. In any of these embodiments, detection, sequencing, and/or quantification of INHBE DNA and RNA can serve as methods for determining INHBE loss of function or absence of INHBE entirely.

Examples of therapeutic agents that treat or inhibit type 2 diabetes include, but are not limited to: metformin, insulin, sulfonylureas (such as glyburide, glipizide, and glimepiride), meglitinides (such as repaglinide and nateglinide), thiazolidinediones (such as rosiglitazone and pioglitazone), DPP-4 inhibitors (such as sitagliptin, saxagliptin, and linagliptin), GLP-1 receptor agonists (such as exenatide, liraglutide, and semaglutide), and SGLT2 inhibitors (such as canagliflozin, dapagliflozin, and empagliflozin). In some embodiments, the therapeutic agent is metformin, insulin, glyburide, glipizide, glimepiride, repaglinide, nateglinide, rosiglitazone, pioglitazone, sitagliptin, saxagliptin, linagliptin, exenatide, liraglutide, semaglutide, canagliflozin, dapagliflozin, or empagliflozin. In some embodiments, the therapeutic agent is metformin. In some embodiments, the therapeutic agent is insulin. In some embodiments, the therapeutic agent is glyburide. In some embodiments, the therapeutic agent is glipizide. In some embodiments, the therapeutic agent is glimepiride. In some embodiments, the therapeutic agent is repaglinide. In some embodiments, the therapeutic agent is nateglinide. In some embodiments, the therapeutic agent is rosiglitazone. In some embodiments, the therapeutic agent is pioglitazone. In some embodiments, the therapeutic agent is sitagliptin. In some embodiments, the therapeutic agent is saxagliptin. In some embodiments, the therapeutic agent is linagliptin. In some embodiments, the therapeutic agent is exenatide. In some embodiments, the therapeutic agent is liraglutide. In some embodiments, the therapeutic agent is semaglutide. In some embodiments, the therapeutic agent is canagliflozin. In some embodiments, the therapeutic agent is dapagliflozin. In some embodiments, the therapeutic agent is empagliflozin.

Examples of therapeutic agents that treat or inhibit obesity include, but are not limited to: orlistat, phentermine, topiramate, bupropion, naltrexone, and liraglutide. In some embodiments, the therapeutic agent is orlistat. In some embodiments, the therapeutic agent is phentermine. In some embodiments, the therapeutic agent is topiramate. In some embodiments, the therapeutic agent is bupropion. In some embodiments, the therapeutic agent is naltrexone. In some embodiments, the therapeutic agent is liraglutide.

Examples of therapeutic agents that treat or inhibit elevated triglyceride include, but are not limited to: statins (such as rosuvastatin, simvastatin, and atorvastatin), fibrates (such as fenofibrate, gemfibrozil, and fenofibric acid), nicotinic acid (such as niacin), and fatty acids (such as omega-3 fatty acids). In some embodiments, the therapeutic agent is a statin.

Examples of therapeutic agents that treat or inhibit lipodystrophy include, but are not limited to: EGRIFTA® (tesamorelin), GLUCOPHAGE® (metformin), SCULPTRA® (poly-L-lactic acid), RADIESSE® (calcium hydroxyapatite), polymethylmethacrylate (e.g., PMMA), ZYDERM® (bovine collagen), COSMODERM® (human collagen), silicone, glitazones, and hyaluronic acid. In some embodiments, the therapeutic agent that treats or inhibits lipodystrophy include, but are not limited to: tesamorelin, metformin, poly-L-lactic acid, a calcium hydroxyapatite, polymethylmethacrylate, a bovine collagen, a human collagen, silicone, and hyaluronic acid.

Examples of therapeutic agents that treat or inhibit liver inflammation include, but are not limited to hepatitis therapeutics and hepatitis vaccines.

Examples of therapeutic agents or procedures that treat or inhibit fatty liver disease include, but are not limited to, bariatric surgery and/or dietary intervention.

Examples of therapeutic agents that treat or inhibit hypercholesterolemia include, but are not limited to: statins (e.g., LIPITOR® (atorvastatin), LESCOL® (fluvastatin), lovastatin, LIVALO® (pitavastatin), PRAVACHOL® (pravastatin), CRESTOR® (rosuvastatin calcium), and ZOCOR® (simvastatin)); bile acid sequestrants (e.g., PREVALITE® (cholestyramine), WELCHOL® (colesevelam), and COLESTID® (colestipol)); PCSK9 Inhibitors (e.g., PRALUENT® (alirocumab) and REPATHA® (evolocumab); niacin (e.g., niaspan and niacor); fibrates (e.g., fenofibrate and LOPID® (gemfibrozil)); and ATP Citrate Lyase (ACL) Inhibitors (e.g., NEXLETOL® (bempedoic)). In some embodiments, the therapeutic agent that treats or inhibits hypercholesterolemia include, but are not limited to: statins (e.g., atorvastatin, fluvastatin, lovastatin, pitavastatin, pravastatin, rosuvastatin calcium, and simvastatin); bile acid sequestrants (e.g., cholestyramine, colesevelam, and colestipol); PCSK9 Inhibitors (e.g., alirocumab and evolocumab; niacin (e.g., niaspan and niacor); fibrates (e.g., fenofibrate and gemfibrozil); and ACL Inhibitors (e.g., bempedoic). In some embodiments, the therapeutic agent that treats or inhibits hypercholesterolemia is alirocumab or evolocumab. In some embodiments, the therapeutic agent that treats or inhibits hypercholesterolemia is alirocumab. In some embodiments, the therapeutic agent that treats or inhibits hypercholesterolemia is evolocumab.

Examples of therapeutic agents that treat or inhibit elevated liver enzymes (such as, for example, ALT and/or AST) include, but are not limited to, coffee, folic acid, potassium, vitamin B6, a statin, and fiber, or any combination thereof.

Examples of therapeutic agents that treat or inhibit NASH include, but are not limited to, OCALIVA® (obeticholic acid), Pioglitazone or other glitazones, Selonsertib, Elafibranor, Cenicriviroc, GR_MD_02, MGL_3196, IMM124E, arachidyl amido cholanoic acid (ARAMCHOL™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

In some embodiments, the therapeutic agent that treats or metabolic disorders is a melanocortin 4 receptor (MC4R) agonist. In some embodiments, the MC4R agonist comprises a protein, a peptide, a nucleic acid molecule, or a small molecule. In some embodiments, the protein is a peptide analog of MC4R. In some embodiments, the peptide is setmelanotide. In some embodiments, the therapeutic agent that treats or inhibits type 2 diabetes and/or reduces BMI is a combination of setmelanotide and one or more of sibutramine, orlistat, phentermine, lorcaserin, naltrexone, liraglutide, diethylpropion, bupropion, metformin, pramlintide, topiramate, and zonisamide. In some embodiments, the MC4R agonist is a peptide comprising the amino acid sequence His-Phe-Arg-Trp. In some embodiments, the small molecule is 1,2,3R,4-tetrahydroisoquinoline-3-carboxylic acid. In some embodiments, the MC4R agonist is ALB-127158(a).

Examples of therapeutic agents that treat or inhibit cardiomyopathy include, but are not limited to: 1) blood pressure lowering agents, such as ACE inhibitors, angiotensin II receptor blockers, beta blockers, and calcium channel blockers; 2) agents that slow heart rate, such as beta blockers, calcium channel blockers, and digoxin; 3) agents that keep the heart beating with a normal rhythm, such as antiarrhythmics; 4) agents that balance electrolytes, such as aldosterone blockers; 5) agents that remove excess fluid and sodium from the body, such as diuretics; 6) agents that prevent blood clots from forming, such as anticoagulants or blood thinners; and 7) agents that reduce inflammation, such as corticosteroids.

Examples of therapeutic agents that treat or inhibit heart failure include, but are not limited to: ACE inhibitors, angiotensin-2 receptor blockers, beta blockers, mineralocorticoid receptor antagonists, diuretics, ivabradine, sacubitril valsartan, hydralazine with nitrate, and digoxin.

Examples of therapeutic agents that treat or inhibit high blood pressure include, but are not limited to: diuretics (such as, chlorthalidone, chlorothiazide, hydrochlorothiazide, indapamide, and metolazone), beta-blockers (such as acebutolol, atenolol, betaxolol, bisoprolol fumarate, carteolol hydrochloride, metoprolol tartrate, metoprolol succinate, nadolol, etc.), ACE inhibitors (such as benazepril hydrochloride, captopril, enalapril maleate, fosinopril sodium, lisinopril, moexipril, perindopril, quinapril hydrochloride, ramipril, and trandolapril), angiotensin II receptor blockers (such as candesartan, eprosartan mesylate, irbesartan, losartan potassium, telmisartan, and valsartan), calcium channel blockers (such as amlodipine besylate, bepridil, diltiazem hydrochloride, felodipine, isradipine, nicardipine, nifedipine, nisoldipine, and verapamil hydrochloride), alpha blockers (such as doxazocin mesylate, prazosin hydrochloride, and terazosin hydrochloride), Alpha-2 Receptor Agonists (such as methyldopa), combined alpha and beta-blockers (such as carvedilol and labetalol hydrochloride), central agonists (such as alpha methyldopa, clonidine hydrochloride, guanabenz acetate, and guanfacine hydrochloride), peripheral adrenergic inhibitors (such as guanadrel, guanethidine monosulfate, and reserpine), and vasodilators (such as hydralazine hydrochloride and minoxidil).

In some embodiments, the dose of the therapeutic agents that treat or inhibit metabolic disorders and/or cardiovascular diseases can be reduced by about 10%, by about 20%, by about 30%, by about 40%, by about 50%, by about 60%, by about 70%, by about 80%, or by about 90% for subjects that are heterozygous for an INHBE predicted loss-of-function variant (i.e., a lower than the standard dosage amount) compared to subjects that are INHBE reference (who may receive a standard dosage amount). In some embodiments, the dose of the therapeutic agents that treat or inhibit metabolic disorders and/or cardiovascular diseases can be reduced by about 10%, by about 20%, by about 30%, by about 40%, or by about 50%. In addition, the subjects that are heterozygous for an INHBE predicted loss-of-function variant can be administered less frequently compared to subjects that are INHBE reference.

In some embodiments, the dose of the therapeutic agents that treat or a metabolic disorder and/or a cardiovascular disease can be reduced by about 10%, by about 20%, by about 30%, by about 40%, by about 50%, for subjects that are homozygous for a predicted loss-of-function variant INHBE nucleic acid molecule compared to subjects that are heterozygous for a predicted loss-of-function variant INHBE nucleic acid molecule. In some embodiments, the dose of the therapeutic agents that treat or inhibit a metabolic disorder and/or a cardiovascular disease can be reduced by about 10%, by about 20%, by about 30%, by about 40%, or by about 50%. In addition, the dose of therapeutic agents that treat or inhibit metabolic disorder and/or a cardiovascular disease in subjects that are homozygous for a predicted loss-of-function variant INHBE nucleic acid molecule can be administered less frequently compared to subjects that are heterozygous for a predicted loss-of-function variant INHBE nucleic acid molecule.

Administration of the therapeutic agents that treat or inhibit metabolic disorders and/or cardiovascular diseases and/or INHBE inhibitors can be repeated, for example, after one day, two days, three days, five days, one week, two weeks, three weeks, one month, five weeks, six weeks, seven weeks, eight weeks, two months, or three months. The repeated administration can be at the same dose or at a different dose. The administration can be repeated once, twice, three times, four times, five times, six times, seven times, eight times, nine times, ten times, or more. For example, according to certain dosage regimens a subject can receive therapy for a prolonged period of time such as, for example, 6 months, 1 year, or more.

Administration of the therapeutic agents that treat or inhibit metabolic disorders and/or cardiovascular diseases and/or INHBE inhibitors can occur by any suitable route including, but not limited to, parenteral, intravenous, oral, subcutaneous, intra-arterial, intracranial, intrathecal, intraperitoneal, topical, intranasal, or intramuscular. Pharmaceutical compositions for administration are desirably sterile and substantially isotonic and manufactured under GMP conditions. Pharmaceutical compositions can be provided in unit dosage form (i.e., the dosage for a single administration). Pharmaceutical compositions can be formulated using one or more physiologically and pharmaceutically acceptable carriers, diluents, excipients or auxiliaries. The formulation depends on the route of administration chosen. The term "pharmaceutically acceptable" means that the carrier, diluent, excipient, or auxiliary is compatible with the other ingredients of the formulation and not substantially deleterious to the recipient thereof.

The terms "treat", "treating", and "treatment" and "prevent", "preventing", and "prevention" as used herein, refer to eliciting the desired biological response, such as a therapeutic and prophylactic effect, respectively. In some embodiments, a therapeutic effect comprises one or more of a decrease/reduction in metabolic disorders and/or cardiovascular diseases, a decrease/reduction in the severity of metabolic disorders and/or cardiovascular diseases (such as, for example, a reduction or inhibition of development or metabolic disorders and/or cardiovascular diseases), a decrease/reduction in symptoms and metabolic disorder-related effects and/or cardiovascular disease-related effects, delaying the onset of symptoms and metabolic disorder-related effects and/or cardiovascular disease-related effects, reducing the severity of symptoms of metabolic disorder-related effects and/or cardiovascular disease-related effects, reducing the number of symptoms and metabolic disorder-related effects and/or cardiovascular disease-related effects, reducing the latency of symptoms and metabolic disorder-related effects and/or cardiovascular disease-related effects, an amelioration of symptoms and metabolic disorder-related effects and/or cardiovascular disease-related effects, reducing secondary symptoms, reducing secondary infections, preventing relapse to metabolic disorders and/or cardiovascular diseases, decreasing the number or frequency of relapse episodes, increasing latency between symptomatic episodes, increasing time to sustained progression, speeding recovery, or increasing efficacy of or decreasing resistance to alternative therapeutics, and/or an increased survival time of the affected host animal, following administration of the agent or composition comprising the agent. A prophylactic effect may comprise a complete or partial avoidance/inhibition or a delay of metabolic disorders and/or cardiovascular disease development/progression (such as, for example, a complete or partial avoidance/inhibition or a delay), and an increased survival time of the affected host animal, following administration of a therapeutic protocol. Treatment of metabolic disorders encompasses the treatment of subjects already diagnosed as having any form of metabolic disorders and/or cardiovascular diseases at any clinical stage or manifestation, the delay of the onset or evolution or aggravation or deterioration of the symptoms or signs of metabolic disorders and/or cardiovascular diseases, and/or preventing and/or reducing the severity of metabolic disorders and/or cardiovascular diseases.

The present disclosure also provides methods of identifying a subject having an increased risk for developing a metabolic disorder. In some embodiments, the method comprises determining or having determined in a biological sample obtained from the subject the presence or absence of an INHBE variant nucleic acid molecule (such as a genomic nucleic acid molecule, mRNA molecule, and/or cDNA molecule) encoding an INHBE predicted loss-of-function polypeptide. When the subject lacks an INHBE variant nucleic acid molecule encoding an INHBE predicted loss-of-function polypeptide (i.e., the subject is genotypically categorized as an INHBE reference), then the subject has an increased risk for developing a metabolic disorder. When the subject has an INHBE variant nucleic acid molecule encoding an INHBE predicted loss-of-function polypeptide (i.e., the subject is heterozygous or homozygous for an INHBE variant nucleic acid molecule encoding an INHBE predicted loss-of-function polypeptide), then the subject has a decreased risk for developing a metabolic disorder. In some embodiments, liver expression quantitative trait loci (eQTL) can be analyzed.

The present disclosure also provides methods of identifying a subject having an increased risk for developing a cardiovascular disease. In some embodiments, the method comprises determining or having determined in a biological sample obtained from the subject the presence or absence of an INHBE variant nucleic acid molecule (such as a genomic nucleic acid molecule, mRNA molecule, and/or cDNA molecule) encoding an INHBE predicted loss-of-function polypeptide. When the subject lacks an INHBE variant nucleic acid molecule encoding an INHBE predicted loss-of-function polypeptide (i.e., the subject is genotypically categorized as an INHBE reference), then the subject has an increased risk for developing a cardiovascular disease. When the subject has an INHBE variant nucleic acid molecule encoding an INHBE predicted loss-of-function polypeptide (i.e., the subject is heterozygous or homozygous for an INHBE variant nucleic acid molecule encoding an INHBE predicted loss-of-function polypeptide), then the subject has a decreased risk for developing a cardiovascular disease. In some embodiments, liver expression quantitative trait loci (eQTL) can be analyzed.

Having a single copy of an INHBE variant nucleic acid molecule encoding an INHBE predicted loss-of-function polypeptide is more protective of a subject from developing a metabolic disorder and/or a cardiovascular disease than having no copies of an INHBE variant nucleic acid molecule encoding an INHBE predicted loss-of-function polypeptide. Without intending to be limited to any particular theory or mechanism of action, it is believed that a single copy of an INHBE variant nucleic acid molecule (i.e., heterozygous for an INHBE variant nucleic acid molecule) is protective of a subject from developing a metabolic disorder and/or a cardiovascular disease, and it is also believed that having two copies of an INHBE variant nucleic acid molecule (i.e., homozygous for an INHBE variant nucleic acid molecule) may be more protective of a subject from developing a metabolic disorder and/or a cardiovascular disease, relative to a subject with a single copy. Thus, in some embodiments, a single copy of an INHBE variant nucleic acid molecule may not be completely protective, but instead, may be partially or incompletely protective of a subject from developing a metabolic disorder and/or a cardiovascular disease. While not desiring to be bound by any particular theory, there may be additional factors or molecules involved in the development of metabolic disorders and/or cardiovascular diseases that are still present in a subject having a single copy of an INHBE variant nucleic acid molecule, thus resulting in less than complete protection from the development of metabolic disorders and/or cardiovascular diseases.

Determining whether a subject has an INHBE variant nucleic acid molecule encoding an INHBE predicted loss-of-function polypeptide in a biological sample from a subject and/or determining whether a subject has an INHBE variant nucleic acid molecule encoding an INHBE predicted loss-of-function polypeptide can be carried out by any of the methods described herein. In some embodiments, these methods can be carried out in vitro. In some embodiments, these methods can be carried out in situ. In some embodiments, these methods can be carried out in vivo. In any of these embodiments, the nucleic acid molecule can be present within a cell obtained from the subject.

In some embodiments, when a subject is identified as having an increased risk of developing a metabolic disorder, the subject is further treated with a therapeutic agent that treats or inhibits metabolic disorders and/or an INHBE inhibitor, as described herein. For example, when the subject is INHBE reference, and therefore has an increased risk for developing a metabolic disorder, the subject is administered an INHBE inhibitor. In some embodiments, such a subject is also administered a therapeutic agent that treats or inhibits metabolic disorders. In some embodiments, when the subject is heterozygous for an INHBE variant nucleic acid molecule encoding an INHBE predicted loss-of-function polypeptide, the subject is administered the therapeutic agent that treats or inhibits metabolic disorders in a dosage amount that is the same as or lower than a standard dosage amount, and is also administered an INHBE inhibitor. In some embodiments, such a subject is also administered a therapeutic agent that treats or inhibits metabolic disorders. In some embodiments, when the subject is homozygous for an INHBE variant nucleic acid molecule encoding an INHBE predicted loss-of-function polypeptide, the subject is administered the therapeutic agent that treats or inhibits metabolic disorders in a dosage amount that is the same as or lower than a standard dosage amount. In some embodiments, the subject is INHBE reference. In some embodiments, the subject is heterozygous for an INHBE variant nucleic acid molecule encoding an INHBE predicted loss-of-function polypeptide. In some embodiments, the subject is homozygous for an INHBE variant nucleic acid molecule encoding an INHBE predicted loss-of-function polypeptide.

In some embodiments, when a subject is identified as having an increased risk of developing a cardiovascular disease, the subject is further treated with a therapeutic agent that treats or inhibits cardiovascular diseases and/or an INHBE inhibitor, as described herein. For example, when the subject is INHBE reference, and therefore has an increased risk for developing a cardiovascular disease, the subject is administered an INHBE inhibitor. In some embodiments, such a subject is also administered a therapeutic agent that treats or inhibits cardiovascular diseases. In some embodiments, when the subject is heterozygous for an INHBE variant nucleic acid molecule encoding an INHBE predicted loss-of-function polypeptide, the subject is administered the therapeutic agent that treats or inhibits cardiovascular diseases in a dosage amount that is the same as or lower than a standard dosage amount, and is also administered an INHBE inhibitor. In some embodiments, such a subject is also administered a therapeutic agent that treats or inhibits cardiovascular diseases. In some embodiments, when the subject is homozygous for an INHBE variant nucleic acid molecule encoding an INHBE predicted loss-of-function polypeptide, the subject is administered the therapeutic agent that treats or inhibits cardiovascular diseases in a dosage amount that is the same as or lower than a standard dosage amount. In some embodiments, the subject is INHBE reference. In some embodiments, the subject is heterozygous for an INHBE variant nucleic acid molecule encoding an INHBE predicted loss-of-function polypeptide. In some embodiments, the subject is homozygous for an INHBE variant nucleic acid molecule encoding an INHBE predicted loss-of-function polypeptide.

In some embodiments, any of the methods described herein can further comprise determining the subject's gene burden of having an INHBE variant nucleic acid molecule encoding an INHBE predicted loss-of-function polypeptide, and/or an INHBE predicted loss-of-function variant polypeptide associated with a decreased risk of developing a metabolic disorder and/or a cardiovascular disease. The gene burden is the aggregate of all variants in the INHBE gene, which can be carried out in an association analysis with metabolic disorders and/or cardiovascular diseases. In some embodiments, the subject is homozygous for one or more INHBE variant nucleic acid molecules encoding an INHBE predicted loss-of-function polypeptide associated with a decreased risk of developing a metabolic disorder and/or a cardiovascular disease. In some embodiments, the subject is heterozygous for one or more INHBE variant nucleic acid molecules encoding an INHBE predicted loss-of-function polypeptide associated with a decreased risk of developing a metabolic disorder and/or a cardiovascular disease. The result of the association analysis suggests that INHBE variant nucleic acid molecules encoding an INHBE predicted loss-of-function polypeptide are associated with decreased risk of developing a metabolic disorder and/or a cardiovascular disease. When the subject has a lower gene burden, the subject is at a higher risk of developing a metabolic disorder and/or a cardiovascular disease and the subject is administered or continued to be administered the therapeutic agent that treats, prevents, or inhibits a metabolic disorder and/or a cardiovascular disease in a standard dosage amount, and/or an INHBE inhibitor. When the subject has a greater gene burden, the subject is at a lower risk of developing a metabolic disorder and/or a cardiovascular disease and the subject is administered or continued to be administered the therapeutic agent that treats, prevents, or inhibits a metabolic disorder and/or a cardiovascular disease in an amount that is the same as or less than the standard dosage amount. The greater the gene burden, the lower the risk of developing a metabolic disorder and/or a cardiovascular disease.

In some embodiments, the subject's gene burden of having any one or more INHBE variant nucleic acid molecules encoding an INHBE predicted loss-of-function polypeptide represents a weighted sum of a plurality of any of the INHBE variant nucleic acid molecules encoding an INHBE predicted loss-of-function polypeptide. In some embodiments, the gene burden is calculated using at least about 2, at least about 3, at least about 4, at least about 5, at least about 10, at least about 20, at least about 30, at least about 40, at least about 50, at least about 60, at least about 70, at least about 80, at least about 100, at least about 120, at least about 150, at least about 200, at least about 250, at least about 300, at least about 400, at least about 500, at least about 1,000, at least about 10,000, at least about 100,000, or at least about or more than 1,000,000 genetic variants present in or around (up to 10 Mb) the INHBE gene where the gene burden is the number of alleles multiplied by the association estimate with a metabolic disorder or related outcome for each allele (e.g., a weighted burden score). This can include any genetic variants, regardless of their genomic annotation, in proximity to the INHBE gene (up to 10 Mb around the gene) that show a non-zero association with a metabolic disorder-related traits and/or a cardiovascular disease-related traits in a genetic association analysis. In some embodiments, when the subject has a gene burden above a desired threshold score, the subject has a decreased risk of developing a metabolic disorder and/or a cardiovascular disease. In some embodiments, when the subject has a gene burden below a desired threshold score, the subject has an increased risk of developing a metabolic disorder and/or a cardiovascular disease.

In some embodiments, the gene burden may be divided into quintiles, e.g., top quintile, intermediate quintile, and bottom quintile, wherein the top quintile of the gene burden corresponds to the lowest risk group and the bottom quintile of the gene burden corresponds to the highest risk group. In some embodiments, a subject having a greater gene burden comprises the highest weighted gene burdens, including, but not limited to the top 10%, top 20%, top 30%, top 40%, or top 50% of gene burdens from a subject population. In some embodiments, the genetic variants comprise the genetic variants having association with a metabolic disorder and/or a cardiovascular disease in the top 10%, top 20%, top 30%, top 40%, or top 50% of p-value range for the association. In some embodiments, each of the identified genetic variants comprise the genetic variants having association with a metabolic disorder and/or a cardiovascular disease with p-value of no more than about $10^{-2}$, about $10^{-3}$, about $10^{-4}$, about $10^{-5}$, about $10^{-6}$, about $10^{-7}$, about $10^{-8}$, about $10^{-9}$, about $10^{-10}$, about $10^{-11}$, about $10^{-12}$, about $10^{-13}$, about $10^{-14}$, about or $10^{-15}$. In some embodiments, the identified genetic variants comprise the genetic variants having association with a metabolic disorder and/or a cardiovascular disease with p-value of less than $5 \times 10^{-8}$. In some embodiments, the identified genetic variants comprise genetic variants having association with a metabolic disorder and/or a cardiovascular disease in high-risk subjects as compared to the rest of the reference population with odds ratio (OR) about 1.5 or greater, about 1.75 or greater, about 2.0 or greater, or about 2.25 or greater for the top 20% of the distribution; or about 1.5 or greater, about 1.75 or greater, about 2.0 or greater, about 2.25 or greater, about 2.5 or greater, or about 2.75 or greater. In some embodiments, the odds ratio (OR) may range from about 1.0 to about 1.5, from about 1.5 to about 2.0, from about 2.0 to about 2.5, from about 2.5 to about 3.0, from about 3.0 to about 3.5, from about 3.5 to about 4.0, from about 4.0 to about 4.5, from about 4.5 to about 5.0, from about 5.0 to about 5.5, from about 5.5 to about 6.0, from about 6.0 to about 6.5, from about 6.5 to about 7.0, or greater than 7.0. In some embodiments, high-risk subjects comprise subjects having gene burdens in the bottom decile, quintile, or tertile in a reference population. The threshold of the gene burden is determined on the basis of the nature of the intended practical application and the risk difference that would be considered meaningful for that practical application.

In some embodiments, when a subject is identified as having an increased risk of developing a metabolic disorder, the subject is further administered a therapeutic agent that treats, prevents, or inhibits a metabolic disorder, and/or an INHBE inhibitor, as described herein. For example, when the subject is INHBE reference, and therefore has an increased risk of developing a metabolic disorder, the subject is administered an INHBE inhibitor. In some embodiments, such a subject is also administered a therapeutic agent that treats, prevents, or inhibits a metabolic disorder. In some embodiments, when the subject is heterozygous for an INHBE variant nucleic acid molecule encoding an INHBE predicted loss-of-function polypeptide, the subject is administered the therapeutic agent that treats, prevents, or inhibits a metabolic disorder in a dosage amount that is the same as or less than a standard dosage amount, and is also administered an INHBE inhibitor. In some embodiments, the subject is INHBE reference. In some embodiments, the subject is heterozygous for an INHBE variant nucleic acid molecule encoding an INHBE predicted loss-of-function polypeptide. Furthermore, when the subject has a lower gene burden for having an INHBE variant nucleic acid molecule encoding an INHBE predicted loss-of-function polypeptide, and therefore has an increased risk of developing a metabolic disorder, the subject is administered a therapeutic agent that treats, prevents, or inhibits a metabolic disorder. In some embodiments, when the subject has a lower gene burden for having an INHBE variant nucleic acid molecule encoding an INHBE predicted loss-of-function polypeptide, the subject is administered the therapeutic agent that treats, prevents, or inhibits a metabolic disorder in a dosage amount that is the same as or greater than the standard dosage amount administered to a subject who has a greater gene burden for having an INHBE variant nucleic acid molecule encoding an INHBE predicted loss-of-function polypeptide.

In some embodiments, when a subject is identified as having an increased risk of developing a cardiovascular disease, the subject is further administered a therapeutic agent that treats, prevents, or inhibits a cardiovascular disease, and/or an INHBE inhibitor, as described herein. For example, when the subject is INHBE reference, and therefore has an increased risk of developing a cardiovascular disease, the subject is administered an INHBE inhibitor. In some embodiments, such a subject is also administered a therapeutic agent that treats, prevents, or inhibits a cardiovascular disease. In some embodiments, when the subject is heterozygous for an INHBE variant nucleic acid molecule encoding an INHBE predicted loss-of-function polypeptide, the subject is administered the therapeutic agent that treats, prevents, or inhibits a cardiovascular disease in a dosage amount that is the same as or less than a standard dosage amount, and is also administered an INHBE inhibitor. In some embodiments, the subject is INHBE reference. In some embodiments, the subject is heterozygous for an INHBE variant nucleic acid molecule encoding an INHBE predicted loss-of-function polypeptide. Furthermore, when the subject has a lower gene burden for having an INHBE variant nucleic acid molecule encoding an INHBE predicted loss-of-function polypeptide, and therefore has an increased risk of developing a cardiovascular disease, the subject is administered a therapeutic agent that treats, prevents, or inhibits a cardiovascular disease. In some embodiments, when the subject has a lower gene burden for having an INHBE variant nucleic acid molecule encoding an INHBE predicted loss-of-function polypeptide, the subject is administered the therapeutic agent that treats, prevents, or inhibits a cardiovascular disease in a dosage amount that is the same as or greater than the standard dosage amount administered to a subject who has a greater gene burden for having an INHBE variant nucleic acid molecule encoding an INHBE predicted loss-of-function polypeptide.

The present disclosure also provides methods of diagnosing a metabolic disorder in a subject. The methods comprise determining or having determined whether the subject has any one or more of the INHBE variant nucleic acid molecules or polypeptides produced therefrom described herein. When the subject is INHBE reference, and has one or more symptoms of a metabolic disorder, the subject is diagnosed as having a metabolic disorder. In some embodiments, the subject is homozygous for a reference INHBE nucleic acid molecule. In some embodiments, the subject is homozygous or heterozygous for an INHBE variant nucleic acid molecule encoding a predicted loss-of-function INHBE polypeptide. In some embodiments, when a subject is identified as having metabolic disorder (such as having one or more symptoms of metabolic disorder and being homozygous or heterozygous for an INHBE variant nucleic acid molecule encoding a predicted loss-of-function INHBE polypeptide), the subject is further treated with a therapeutic agent that treats or inhibits the metabolic disorder, such as any of those described herein.

The present disclosure also provides methods of diagnosing a cardiovascular disease in a subject. The methods comprise determining or having determined whether the subject has any one or more of the INHBE variant nucleic acid molecules or polypeptides produced therefrom described herein. When the subject is INHBE reference, and has one or more symptoms of a cardiovascular disease, the subject is diagnosed as having a cardiovascular disease. In some embodiments, the subject is homozygous for a reference INHBE nucleic acid molecule. In some embodiments, the subject is homozygous or heterozygous for an INHBE variant nucleic acid molecule encoding a predicted loss-of-function INHBE polypeptide. In some embodiments, when a subject is identified as having cardiovascular disease (such as having one or more symptoms of cardiovascular disease and being homozygous or heterozygous for an INHBE variant nucleic acid molecule encoding a predicted loss-of-function INHBE polypeptide), the subject is further treated with a therapeutic agent that treats or inhibits the cardiovascular disease, such as any of those described herein.

The present disclosure also provides methods of identifying a subject having an increased risk for developing a metabolic disorder, wherein the method comprises determining or having determined in a biological sample obtained from the subject the presence or absence of an INHBE predicted loss-of-function polypeptide. In some embodiments, the method is a blood based quantitative assay, such as a somalogic assay to quantify inhibin E.

The present disclosure also provides methods of identifying a subject having an increased risk for developing a cardiovascular disease, wherein the method comprises determining or having determined in a biological sample obtained from the subject the presence or absence of an INHBE predicted loss-of-function polypeptide. In some embodiments, the method is a blood based quantitative assay, such as a somalogic assay to quantify inhibin E.

The presence of INHBE polypeptides in suitable fluid samples, such as blood, plasma, and/or serum, can be determined by detecting the INHBE polypeptide using numerous methods for measuring INHBE or INHBE activity. For example, INHBE polypeptide can be detected by immunoassays using antibodies specific for INHBE. The antibody being capable of binding selectively to an INHBE polypeptide and/or CEA. The antibody can be used, for example, in Western blots of one- or two-dimensional gels, in high throughput methods such as enzyme linked immunoassay and/or in dot blot (Antibody Sandwich) assays of total cellular protein, or partially purified protein. In some embodiments, the concentration of INHBE in a suitable fluid is measured by an enzyme-linked immunosorbent assay (ELISA). In one example of the assay, a serum sample is diluted 400-fold and applied to a plate to which INHBE polypeptide antibodies from one animal origin (primary antibody) are attached. If enough INHBE is present in the serum, the INHBE may bind to these INHBE antibodies. The plate is then washed to remove all other components of the serum. A specially prepared "secondary antibody", such as from an animal origin different from that of the primary antibody, an antibody that binds to the primary antibody—is then applied to the plate, followed by another wash. This secondary antibody is chemically linked in advance to, for example, an enzyme. Thus, the plate will contain enzyme in proportion to the amount of secondary antibody bound to the plate. A substrate for the enzyme is applied, and catalysis by the enzyme leads to a change in color or fluorescence. Samples that generate a signal that is stronger than the known healthy sample are "positive". Those that generate weaker signal than the known healthy sample are "negative."

Alternately, the concentration of INHBE polypeptide in a suitable fluid can be determined by detecting the INHBE polypeptide using spectrometric methods, such as LC-MS/MS mass spectrometer, GCMS mass spectrometer, SDS PAGE methods later quantified with densitometry or mass spectrometry methods or any similar methods of quantifying proteins. Additional methods of quantifying polypeptide levels include, but are not limited to, HPLC (high performance liquid chromatography), SEC (size exclusion chromatography), modified Lowry assay, spectrophotometry, SEC-MALLS (size exclusion chromatography/multi-angle laser light scattering), and NMR (nuclear magnetic resonance).

Aptamers specific for INHBE polypeptides can also be used. A suitable aptamer is capable of binding selectively an INHBE polypeptide for measuring blood, plasma or serum concentration of INHBE polypeptide, or for detecting the presence of a variant INHBE. An INHBE polypeptide produced recombinantly or by chemical synthesis, and fragments or other derivatives or analogs thereof, including fusion proteins, may be used as an immunogen to generate aptamers that recognize the INHBE polypeptide. The term "aptamer" refers to a non-naturally occurring oligonucleotide chain or peptide molecule that has a specific action on a target compound (such as a specific epitope, therapeutic drug marker or surrogate marker). A specific action includes, but is not limited to, binding of the target compound, catalytically changing the target compound, and/or reacting with the target compound in a way that modifies/alters the target compound or the functional activity of the target compound. Aptamers can be engineered through repeated rounds of in vitro selection or SELEX™ (systematic evolution of ligands by exponential enrichment) to bind to various molecular targets such as small molecules. Methods for production/synthesis are described in, for example: Ellington et al., Nature, 1990, 346, 818-822; and Tuerk et al., Science, 1990, 249, 505-510. The "SELEX™" methodology involves the combination of selected nucleic acid ligands, which interact with a specific epitope in a desired action, for example binding to a protein, with amplification of those selected nucleic acids. Optional iterative cycling of the selection/amplification steps allows selection of one or a small number of nucleic acids, which interact most strongly with the specific epitope from a pool, which contains a very large number of nucleic acids. Cycling of the selection/amplification procedure is continued until a selected goal is achieved. The SELEX methodology is described in the following U.S. Pat. Nos. 5,475,096 and 5,270,163.

The present disclosure also provides methods of identifying a subject having a disease, such as a metabolic disorder, who may respond differentially to treatment with an INHBE inhibitor or other therapeutic agent affecting fat distribution. In some embodiments, the method comprises determining or having determined in a biological sample (liver, plasma, serum, and/or whole blood) obtained from the subject the presence or absence of an INHBE pLOF or pGOF or that are associated with liver expression of INHBE or measurement of INHBE in circulation or expression in liver. When the subject lacks such an INHBE variant (i.e., the subject is genotypically categorized as an INHBE reference), then the subject has an increased risk for developing a metabolic disorder and may be amenable to treatment with an INHBE inhibitor or other therapeutic agent affecting fat distribution. When the subject has such an INHBE variant nucleic acid molecule (i.e., the subject is heterozygous for an INHBE pLOF/pGOF or homozygous for an INHBE pLOF/pGOF), then the subject has a decreased risk for developing a metabolic disorder.

The present disclosure also provides methods of detecting the presence or absence of an INHBE variant nucleic acid molecule (genomic, mRNA, or cDNA) encoding a predicted loss-of-function INHBE polypeptide in a biological sample from a subject. It is understood that gene sequences within a population and mRNA molecules encoded by such genes can vary due to polymorphisms such as single-nucleotide polymorphisms.

The biological sample can be derived from any cell, tissue, or biological fluid from the subject. The sample may comprise any clinically relevant tissue, such as a bone marrow sample, a tumor biopsy, a fine needle aspirate, or a sample of bodily fluid, such as blood, gingival crevicular fluid, plasma, serum, lymph, ascitic fluid, cystic fluid, or urine. In some cases, the sample comprises a buccal swab. The sample used in the methods disclosed herein will vary based on the assay format, nature of the detection method, and the tissues, cells, or extracts that are used as the sample. A biological sample can be processed differently depending on the assay being employed. For example, when detecting any predicted loss-of-function variant INHBE nucleic acid molecule, preliminary processing designed to isolate or enrich the sample for the genomic DNA can be employed. A variety of techniques may be used for this purpose. When detecting the level of any predicted loss-of-function variant INHBE mRNA, different techniques can be used enrich the biological sample with mRNA. Various methods to detect the presence or level of an mRNA or the presence of a particular variant genomic DNA locus can be used.

In some embodiments, detecting an INHBE variant nucleic acid molecule encoding a predicted loss-of-function INHBE polypeptide in a subject comprises assaying or genotyping a biological sample obtained from the subject to determine whether an INHBE genomic nucleic acid molecule in the biological sample, and/or an INHBE mRNA molecule in the biological sample, and/or an INHBE cDNA molecule produced from an mRNA molecule in the biological sample, comprises one or more variations that cause a loss-of-function (partial or complete) or are predicted to cause a loss-of-function (partial or complete), such as any of the INHBE variant nucleic acid molecules encoding a predicted loss-of-function INHBE polypeptide described herein.

In some embodiments, the methods of detecting the presence or absence of an INHBE variant nucleic acid molecule (such as, for example, a genomic nucleic acid molecule, an mRNA molecule, and/or a cDNA molecule produced from an mRNA molecule) in a subject, comprise performing an assay on a biological sample obtained from the subject. The assay determines whether a nucleic acid molecule in the biological sample comprises a particular nucleotide sequence.

In some embodiments, the biological sample comprises a cell or cell lysate. Such methods can further comprise, for example, obtaining a biological sample from the subject comprising an INHBE genomic nucleic acid molecule or mRNA molecule, and if mRNA, optionally reverse transcribing the mRNA into cDNA. Such assays can comprise, for example determining the identity of these positions of the particular INHBE nucleic acid molecule. In some embodiments, the method is an in vitro method.

In some embodiments, the determining step, detecting step, or genotyping assay comprises sequencing at least a portion of the nucleotide sequence of the INHBE genomic nucleic acid molecule, the INHBE mRNA molecule, or the INHBE cDNA molecule in the biological sample, wherein the sequenced portion comprises one or more variations that cause a loss-of-function (partial or complete) or are predicted to cause a loss-of-function (partial or complete), such as any of the predicted loss-of-function variant INHBE nucleic acid molecules described herein.

In some embodiments, the determining step, detecting step, or genotyping assay comprises sequencing at least a portion of the nucleotide sequence of the INHBE genomic nucleic acid molecule in the biological sample, the nucleotide sequence of the INHBE mRNA molecule in the biological sample, or the nucleotide sequence of the INHBE cDNA molecule produced from the INHBE mRNA in the biological sample. In some embodiments, the determining step, detecting step, or genotyping assay comprises sequencing at least a portion of the nucleotide sequence of the INHBE genomic nucleic acid molecule in the biological sample. In some embodiments, the determining step, detecting step, or genotyping assay comprises sequencing at least a portion of the nucleotide sequence of the INHBE mRNA molecule in the biological sample. In some embodiments, the determining step, detecting step, or genotyping assay comprises sequencing at least a portion of the nucleotide sequence of the INHBE cDNA molecule produced from the INHBE mRNA molecule in the biological sample.

In some embodiments, the assay comprises sequencing the entire nucleic acid molecule. In some embodiments, only an INHBE genomic nucleic acid molecule is analyzed. In some embodiments, only an INHBE mRNA is analyzed. In some embodiments, only an INHBE cDNA obtained from INHBE mRNA is analyzed.

In some embodiments, the determining step, detecting step, or genotyping assay comprises: a) amplifying at least a portion of the nucleic acid molecule that encodes the INHBE polypeptide; b) labeling the amplified nucleic acid molecule with a detectable label; c) contacting the labeled nucleic acid molecule with a support comprising an alteration-specific probe; and d) detecting the detectable label.

In some embodiments, the nucleic acid molecule is mRNA and the determining step further comprises reverse-transcribing the mRNA into a cDNA prior to the amplifying step.

In some embodiments, the determining step, detecting step, or genotyping assay comprises: contacting the nucleic acid molecule in the biological sample with an alteration-specific probe comprising a detectable label, wherein the alteration-specific probe comprises a nucleotide sequence which hybridizes under stringent conditions to the nucleotide sequence of the amplified nucleic acid molecule; and detecting the detectable label. Alteration-specific polymerase chain reaction techniques can be used to detect mutations such as SNPs in a nucleic acid sequence. Alteration-specific primers can be used because the DNA polymerase will not extend when a mismatch with the template is present.

In some embodiments, the nucleic acid molecule in the sample is mRNA and the mRNA is reverse-transcribed into a cDNA prior to the amplifying step. In some embodiments, the nucleic acid molecule is present within a cell obtained from the subject.

In some embodiments, the assay comprises contacting the biological sample with a primer or probe, such as an alteration-specific primer or alteration-specific probe, that specifically hybridizes to an INHBE variant nucleic acid molecule (genomic, mRNA, or cDNA) and not the corresponding INHBE reference sequence under stringent conditions, and determining whether hybridization has occurred. In some embodiments, the assay comprises RNA sequencing (RNA-Seq). In some embodiments, the assays also comprise reverse transcribing mRNA into cDNA, such as by the reverse transcriptase polymerase chain reaction (RT-PCR).

In some embodiments, the methods utilize probes and primers of sufficient nucleotide length to bind to the target nucleotide sequence and specifically detect and/or identify a polynucleotide comprising an INHBE variant nucleic acid molecule (genomic, mRNA, or cDNA) encoding a predicted loss-of-function INHBE polypeptide. The hybridization conditions or reaction conditions can be determined by the operator to achieve this result. The nucleotide length may be any length that is sufficient for use in a detection method of choice, including any assay described or exemplified herein. Such probes and primers can hybridize specifically to a target nucleotide sequence under high stringency hybridization conditions. Probes and primers may have complete nucleotide sequence identity of contiguous nucleotides within the target nucleotide sequence, although probes differing from the target nucleotide sequence and that retain the ability to specifically detect and/or identify a target nucleotide sequence may be designed by conventional methods. Probes and primers can have about 80%, about 85%, about 90%, about 91%, about 92%, about 93%, about 94%, about 95%, about 96%, about 97%, about 98%, about 99%, or 100% sequence identity or complementarity with the nucleotide sequence of the target nucleic acid molecule.

Illustrative examples of nucleic acid sequencing techniques include, but are not limited to, chain terminator (Sanger) sequencing and dye terminator sequencing. Other methods involve nucleic acid hybridization methods other than sequencing, including using labeled primers or probes directed against purified DNA, amplified DNA, and fixed cell preparations (fluorescence in situ hybridization (FISH)). In some methods, a target nucleic acid molecule may be amplified prior to or simultaneously with detection. Illustrative examples of nucleic acid amplification techniques include, but are not limited to, polymerase chain reaction (PCR), ligase chain reaction (LCR), strand displacement amplification (SDA), and nucleic acid sequence based amplification (NASBA). Other methods include, but are not limited to, ligase chain reaction, strand displacement amplification, and thermophilic SDA (tSDA).

In hybridization techniques, stringent conditions can be employed such that a probe or primer will specifically hybridize to its target. In some embodiments, a polynucleotide primer or probe under stringent conditions will hybridize to its target sequence to a detectably greater degree than to other non-target sequences, such as, at least 2-fold, at least 3-fold, at least 4-fold, or more over background, including over 10-fold over background. In some embodiments, a polynucleotide primer or probe under stringent conditions will hybridize to its target nucleotide sequence to a detectably greater degree than to other nucleotide sequences by at least 2-fold. In some embodiments, a polynucleotide primer or probe under stringent conditions will hybridize to its target nucleotide sequence to a detectably greater degree than to other nucleotide sequences by at least 3-fold. In some embodiments, a polynucleotide primer or probe under stringent conditions will hybridize to its target nucleotide sequence to a detectably greater degree than to other nucleotide sequences by at least 4-fold. In some embodiments, a polynucleotide primer or probe under stringent conditions will hybridize to its target nucleotide sequence to a detectably greater degree than to other nucleotide sequences by over 10-fold over background. Stringent conditions are sequence-dependent and will be different in different circumstances.

Appropriate stringency conditions which promote DNA hybridization, for example, 6× sodium chloride/sodium citrate (SSC) at about 45° C., followed by a wash of 2×SSC at 50° C., are known or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (such as, for example, 10 to 50 nucleotides) and at least about 60° C. for longer probes (such as, for example, greater than 50 nucleotides). Stringent conditions may also be achieved with the addition of destabilizing agents such as formamide. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The present disclosure also provides methods of detecting the presence of a human INHBE predicted loss-of-function polypeptide comprising performing an assay on a sample obtained from a subject to determine whether an INHBE polypeptide in the subject contains one or more variations that causes the polypeptide to have a loss-of-function (partial or complete) or predicted loss-of-function (partial or complete).

In some embodiments, the detecting step comprises sequencing at least a portion of the polypeptide. In some embodiments, the detecting step comprises an immunoassay for detecting the presence of a polypeptide.

In some embodiments, when the subject does not have an INHBE predicted loss-of-function polypeptide, then the subject has an increased risk for developing a metabolic disorder or any of type 2 diabetes, lipodystrophy, liver inflammation, fatty liver disease, hypercholesterolemia, elevated liver enzymes (such as, for example, ALT and/or AST), obesity, high blood pressure, NASH, and/or elevated triglyceride level. In some embodiments, when the subject has an INHBE predicted loss-of-function polypeptide, then the subject has a decreased risk for developing a metabolic disorder or any of type 2 diabetes, obesity, lipodystrophy, liver inflammation, fatty liver disease, hypercholesterolemia, elevated liver enzymes (such as, for example, ALT and/or AST), high blood pressure, NASH, and/or elevated triglyceride level.

In some embodiments, when the subject does not have an INHBE predicted loss-of-function polypeptide, then the subject has an increased risk for developing a cardiovascular disease or any of cardiomyopathy, heart failure, and high blood pressure. In some embodiments, when the subject has an INHBE predicted loss-of-function polypeptide, then the subject has a decreased risk for developing a cardiovascular disease or any of cardiomyopathy, heart failure, and high blood pressure.

The present disclosure also provides uses of isolated nucleic acid molecules that hybridize to INHBE variant genomic nucleic acid molecules, INHBE variant mRNA molecules, and/or INHBE variant cDNA molecules (such as any of the genomic variant nucleic acid molecules, mRNA variant molecules, and cDNA variant molecules disclosed herein) in any of the methods described herein.

In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, at least about 100, at least about 200, at least about 300, at least about 400, at least about 500, at least about 600, at least about 700, at least about 800, at least about 900, at least about 1000, at least about 2000, at least about 3000, at least about 4000, or at least about 5000 nucleotides. In some embodiments, such isolated nucleic acid molecules comprise or consist of at least about 5, at least about 8, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, or at least about 25 nucleotides. In some embodiments, the isolated nucleic acid molecules comprise or consist of at least about 18 nucleotides. In some embodiments, the isolated nucleic acid molecules comprise or consists of at least about 15 nucleotides. In some embodiments, the isolated nucleic acid molecules consist of or comprise from about 10 to about 35, from about 10 to about 30, from about 10 to about 25, from about 12 to about 30, from about 12 to about 28, from about 12 to about 24, from about 15 to about 30, from about 15 to about 25, from about 18 to about 30, from about 18 to about 25, from about 18 to about 24, or from about 18 to about 22 nucleotides. In some embodiments, the isolated nucleic acid molecules consist of or comprise from about 18 to about 30 nucleotides. In some embodiments, the isolated nucleic acid molecules comprise or consist of at least about 15 nucleotides to at least about 35 nucleotides.

In some embodiments, such isolated nucleic acid molecules hybridize to INHBE variant nucleic acid molecules (such as genomic nucleic acid molecules, mRNA molecules, and/or cDNA molecules) under stringent conditions. Such nucleic acid molecules can be used, for example, as probes, primers, alteration-specific probes, or alteration-specific primers as described or exemplified herein, and include, without limitation primers, probes, antisense RNAs, shRNAs, and siRNAs, each of which is described in more detail elsewhere herein, and can be used in any of the methods described herein.

In some embodiments, the isolated nucleic acid molecules hybridize to at least about 15 contiguous nucleotides of a nucleic acid molecule that is at least about 70%, at least about 75%, at least about 80%, at least about 85%, at least about 90%, at least about 95%, at least about 96%, at least about 97%, at least about 98%, at least about 99%, or 100% identical to INHBE variant genomic nucleic acid molecules, INHBE variant mRNA molecules, and/or INHBE variant cDNA molecules. In some embodiments, the isolated nucleic acid molecules consist of or comprise from about 15 to about 100 nucleotides, or from about 15 to about 35 nucleotides. In some embodiments, the isolated nucleic acid molecules consist of or comprise from about 15 to about 100 nucleotides. In some embodiments, the isolated nucleic acid molecules consist of or comprise from about 15 to about 35 nucleotides.

In some embodiments, the alteration-specific probes and alteration-specific primers comprise DNA. In some embodiments, the alteration-specific probes and alteration-specific primers comprise RNA.

In some embodiments, the probes and primers described herein (including alteration-specific probes and alteration-specific primers) have a nucleotide sequence that specifically hybridizes to any of the nucleic acid molecules disclosed herein, or the complement thereof. In some embodiments, the probes and primers specifically hybridize to any of the nucleic acid molecules disclosed herein under stringent conditions.

In some embodiments, the primers, including alteration-specific primers, can be used in second generation sequencing or high throughput sequencing. In some instances, the primers, including alteration-specific primers, can be modified. In particular, the primers can comprise various modifications that are used at different steps of, for example, Massive Parallel Signature Sequencing (MPSS), Polony sequencing, and 454 Pyrosequencing. Modified primers can be used at several steps of the process, including biotinylated primers in the cloning step and fluorescently labeled primers used at the bead loading step and detection step. Polony sequencing is generally performed using a paired-end tags library wherein each molecule of DNA template is about 135 bp in length. Biotinylated primers are used at the bead loading step and emulsion PCR. Fluorescently labeled degenerate nonamer oligonucleotides are used at the detection step. An adaptor can contain a 5'-biotin tag for immobilization of the DNA library onto streptavidin-coated beads.

The probes and primers described herein can be used to detect a nucleotide variation within any of the INHBE variant genomic nucleic acid molecules, INHBE variant mRNA molecules, and/or INHBE variant cDNA molecules disclosed herein. The primers described herein can be used to amplify INHBE variant genomic nucleic acid molecules, INHBE variant mRNA molecules, or INHBE variant cDNA molecules, or a fragment thereof.

In the context of the disclosure "specifically hybridizes" means that the probe or primer (such as, for example, the alteration-specific probe or alteration-specific primer) does not hybridize to a nucleic acid sequence encoding an INHBE reference genomic nucleic acid molecule, an INHBE reference mRNA molecule, and/or an INHBE reference cDNA molecule.

In some embodiments, the probes (such as, for example, an alteration-specific probe) comprise a label. In some embodiments, the label is a fluorescent label, a radiolabel, or biotin.

The present disclosure also provides supports comprising a substrate to which any one or more of the probes disclosed herein is attached. Solid supports are solid-state substrates or supports with which molecules, such as any of the probes disclosed herein, can be associated. A form of solid support is an array. Another form of solid support is an array detector. An array detector is a solid support to which multiple different probes have been coupled in an array, grid, or other organized pattern. A form for a solid-state substrate is a microtiter dish, such as a standard 96-well type. In some embodiments, a multiwell glass slide can be employed that normally contains one array per well.

The nucleotide sequence of an INHBE reference genomic nucleic acid molecule is set forth in SEQ ID NO:1 (ENST00000266646.3 encompassing chr12:57455307-57458025 in the GRCh38/hg38 human genome assembly).

The nucleotide sequence of an INHBE reference mRNA molecule is set forth in SEQ ID NO:2. The nucleotide sequence of another INHBE reference mRNA molecule is set forth in SEQ ID NO:3. The nucleotide sequence of another INHBE reference mRNA molecule is set forth in SEQ ID NO:4.

The nucleotide sequence of an INHBE reference cDNA molecule is set forth in SEQ ID NO:5. The nucleotide sequence of another INHBE reference cDNA molecule is set forth in SEQ ID NO:6. The nucleotide sequence of another INHBE reference cDNA molecule is set forth in SEQ ID NO:7.

The amino acid sequence of an INHBE reference polypeptide is set forth in SEQ ID NO:8. Referring to SEQ ID NO:8, the INHBE reference polypeptide is 350 amino acids in length.

The genomic nucleic acid molecules, mRNA molecules, and cDNA molecules can be from any organism. For example, the genomic nucleic acid molecules, mRNA molecules, and cDNA molecules can be human or an ortholog from another organism, such as a non-human mammal, a rodent, a mouse, or a rat. It is understood that gene sequences within a population can vary due to polymorphisms such as single-nucleotide polymorphisms. The examples provided herein are only exemplary sequences. Other sequences are also possible.

The isolated nucleic acid molecules disclosed herein can comprise RNA, DNA, or both RNA and DNA. The isolated nucleic acid molecules can also be linked or fused to a heterologous nucleic acid sequence, such as in a vector, or a heterologous label. For example, the isolated nucleic acid molecules disclosed herein can be within a vector or as an exogenous donor sequence comprising the isolated nucleic acid molecule and a heterologous nucleic acid sequence. The isolated nucleic acid molecules can also be linked or fused to a heterologous label. The label can be directly detectable (such as, for example, fluorophore) or indirectly detectable (such as, for example, hapten, enzyme, or fluorophore quencher). Such labels can be detectable by spectroscopic, photochemical, biochemical, immunochemical, or chemical means. Such labels include, for example, radiolabels, pigments, dyes, chromogens, spin labels, and fluorescent labels. The label can also be, for example, a chemiluminescent substance; a metal-containing substance; or an enzyme, where there occurs an enzyme-dependent secondary generation of signal. The term "label" can also refer to a "tag" or hapten that can bind selectively to a conjugated molecule such that the conjugated molecule, when added subsequently along with a substrate, is used to generate a detectable signal. For example, biotin can be used as a tag along with an avidin or streptavidin conjugate of horseradish peroxidate (HRP) to bind to the tag, and examined using a calorimetric substrate (such as, for example, tetramethylbenzidine (TMB)) or a fluorogenic substrate to detect the presence of HRP. Exemplary labels that can be used as tags to facilitate purification include, but are not limited to, myc, HA, FLAG or 3×FLAG, 6×His or polyhistidine, glutathione-S-transferase (GST), maltose binding protein, an epitope tag, or the Fc portion of immunoglobulin. Numerous labels include, for example, particles, fluorophores, haptens, enzymes and their calorimetric, fluorogenic and chemiluminescent substrates and other labels.

The disclosed nucleic acid molecules can comprise, for example, nucleotides or non-natural or modified nucleotides, such as nucleotide analogs or nucleotide substitutes. Such nucleotides include a nucleotide that contains a modified base, sugar, or phosphate group, or that incorporates a non-natural moiety in its structure. Examples of non-natural nucleotides include, but are not limited to, dideoxynucleotides, biotinylated, aminated, deaminated, alkylated, benzylated, and fluorophor-labeled nucleotides.

The nucleic acid molecules disclosed herein can also comprise one or more nucleotide analogs or substitutions. A nucleotide analog is a nucleotide which contains a modification to either the base, sugar, or phosphate moieties. Modifications to the base moiety include, but are not limited to, natural and synthetic modifications of A, C, G, and T/U, as well as different purine or pyrimidine bases such as, for example, pseudouridine, uracil-5-yl, hypoxanthin-9-yl (I), and 2-aminoadenin-9-yl. Modified bases include, but are not limited to, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo (such as, for example, 5-bromo), 5-trifluoromethyl and other 5-substituted uracils and cytosines, 7-methylguanine, 7-methyladenine, 8-azaguanine, 8-azaadenine, 7-deazaguanine, 7-deazaadenine, 3-deazaguanine, and 3-deazaadenine.

Nucleotide analogs can also include modifications of the sugar moiety. Modifications to the sugar moiety include, but are not limited to, natural modifications of the ribose and deoxy ribose as well as synthetic modifications. Sugar modifications include, but are not limited to, the following modifications at the 2' position: OH; F; O-, S-, or N-alkyl; O-, S-, or N-alkenyl; O-, S- or N-alkynyl; or O-alkyl-O-alkyl, wherein the alkyl, alkenyl, and alkynyl may be substituted or unsubstituted $C_{1-10}$alkyl or $C_{2-10}$alkenyl, and $C_{2-10}$alkynyl. Exemplary 2' sugar modifications also include, but are not limited to, $—O[(CH_2)_nO]_mCH_3$, $—O(CH_2)_nOCH_3$, $—O(CH_2)_nNH_2$, $—O(CH_2)_nCH_3$, $—O(CH_2)_n—ONH_2$, and $—O(CH_2)_nON[(CH_2)_nCH_3)]_2$, where n and m are from 1 to about 10. Other modifications at the 2' position include, but are not limited to, $C_{1-10}$alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars can also include those that contain modifications at the bridging ring oxygen, such as $CH_2$ and S. Nucleotide sugar analogs can also have sugar mimetics, such as cyclobutyl moieties in place of the pentofuranosyl sugar.

Nucleotide analogs can also be modified at the phosphate moiety. Modified phosphate moieties include, but are not limited to, those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. These phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts, and free acid forms are also included. Nucleotide substitutes also include peptide nucleic acids (PNAs).

The present disclosure also provides therapeutic agents that treat or inhibit a metabolic disorder for use in the treatment of the metabolic disorder in a subject having: an INHBE variant genomic nucleic acid molecule encoding a predicted loss-of-function INHBE polypeptide; an INHBE variant mRNA molecule encoding a predicted loss-of-function INHBE polypeptide; or an INHBE variant cDNA molecule encoding a predicted loss-of-function INHBE polypeptide.

In some embodiments, the metabolic disorder is type 2 diabetes, and the therapeutic agent is chosen from metformin, insulin, glyburide, glipizide, glimepiride, repaglinide, nateglinide, thiazolidinediones, rosiglitazone, pioglitazone, sitagliptin, saxagliptin, linagliptin, exenatide, liraglutide, semaglutide, canagliflozin, dapagliflozin, and empagliflozin.

In some embodiments, the metabolic disorder is obesity, and the therapeutic agent is chosen from orlistat, phentermine, topiramate, bupropion, naltrexone, and liraglutide.

In some embodiments, the metabolic disorder is high blood pressure, and the therapeutic agent is chosen from chlorthalidone, chlorothiazide, hydrochlorothiazide, indapamide, metolazone, acebutolol, atenolol, betaxolol, bisoprolol fumarate, carteolol hydrochloride, metoprolol tartrate, metoprolol succinate, nadolol, benazepril hydrochloride, captopril, enalapril maleate, fosinopril sodium, lisinopril, moexipril, perindopril, quinapril hydrochloride, ramipril, trandolapril, candesartan, eprosartan mesylate, irbesartan, losartan potassium, telmisartan, valsartan, amlodipine besylate, bepridil, diltiazem hydrochloride, felodipine, isradipine, nicardipine, nifedipine, nisoldipine, verapamil hydrochloride, doxazosin mesylate, prazosin hydrochloride, terazosin hydrochloride, methyldopa, carvedilol labetalol hydrochloride, alpha methyldopa, clonidine hydrochloride, guanabenz acetate, guanfacine hydrochloride, guanadrel, guanethidine monosulfate, reserpine, hydralazine hydrochloride, and minoxidil.

In some embodiments, the metabolic disorder is elevated triglyceride, and the therapeutic agent is chosen from rosuvastatin, simvastatin, atorvastatin, fenofibrate, gemfibrozil, fenofibric acid, niacin, and an omega-3 fatty acid.

In some embodiments, the metabolic disorder is lipodystrophy, and the therapeutic agent is chosen from EGRIFTA® (tesamorelin), GLUCOPHAGE® (metformin), SCULPTRA® (poly-L-lactic acid), RADIESSE® (calcium hydroxyapatite), polymethylmethacrylate (e.g., PMMA), ZYDERM® (bovine collagen), COSMODERM® (human collagen), silicone, and hyaluronic acid. In some embodiments, the therapeutic agent that treats or inhibits lipodystrophy include, but are not limited to: tesamorelin, metformin, poly-L-lactic acid, a calcium hydroxyapatite, polymethylmethacrylate, a bovine collagen, a human collagen, silicone, and hyaluronic acid.

In some embodiments, the metabolic disorder is liver inflammation, and the therapeutic agent is chosen from hepatitis therapeutics and hepatitis vaccines.

In some embodiments, the metabolic disorder is fatty liver disease include, and the therapeutic agent or procedure is bariatric surgery and/or dietary intervention.

In some embodiments, the metabolic disorder is hypercholesterolemia, and the therapeutic agent is chosen from: statins (e.g., LIPITOR® (atorvastatin), LESCOL® (fluvastatin), lovastatin, LIVALO® (pitavastatin), PRAVACHOL® (pravastatin), CRESTOR® (rosuvastatin calcium), and ZOCOR® (simvastatin)); bile acid sequestrants (e.g., PREVALITE® (cholestyramine), WELCHOL® (colesevelam), and COLESTID® (colestipol)); PCSK9 Inhibitors (e.g., PRALUENT® (alirocumab) and REPATHA® (evolocumab); niacin (e.g., niaspan and niacor); fibrates (e.g., fenofibrate and LOPID® (gemfibrozil)); and ATP Citrate Lyase (ACL) Inhibitors (e.g., NEXLETOL® (bempedoic)). In some embodiments, the therapeutic agent that treats or inhibits hypercholesterolemia include, but are not limited to: statins (e.g., atorvastatin, fluvastatin, lovastatin, pitavastatin, pravastatin, rosuvastatin calcium, and simvastatin); bile acid sequestrants (e.g., cholestyramine, colesevelam, and colestipol); PCSK9 Inhibitors (e.g., alirocumab and evolocumab; niacin (e.g., niaspan and niacor); fibrates (e.g., fenofibrate and gemfibrozil); and ACL Inhibitors (e.g., bempedoic). In some embodiments, the therapeutic agent that treats or inhibits hypercholesterolemia is alirocumab or evolocumab. In some embodiments, the therapeutic agent that treats or inhibits hypercholesterolemia is alirocumab. In some embodiments, the therapeutic agent that treats or inhibits hypercholesterolemia is evolocumab.

In some embodiments, the metabolic disorder is elevated liver enzymes (such as, for example, ALT and/or AST), and the therapeutic agent is chosen from coffee, folic acid, potassium, vitamin B6, a statin, and fiber, or any combination thereof.

In some embodiments, the metabolic disorder is NASH and the therapeutic agent is obeticholic acid, Selonsertib, Elafibranor, Cenicriviroc, GR_MD_02, MGL_3196, IMM124E, arachidyl amido cholanoic acid, GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

In some embodiments, the therapeutic agent that treats or inhibits the metabolic disorder is a melanocortin 4 receptor (MC4R) agonist. In some embodiments, the MC4R agonist comprises a protein, a peptide, a nucleic acid molecule, or a small molecule. In some embodiments, the protein is a peptide analog of MC4R. In some embodiments, the peptide is setmelanotide. In some embodiments, the MC4R agonist is a peptide comprising the amino acid sequence His-Phe-Arg-Trp. In some embodiments, the small molecule is 1,2,3R,4-tetrahydroisoquinoline-3-carboxylic acid. In some embodiments, the MC4R agonist is ALB-127158(a).

The present disclosure also provides therapeutic agents that treat or inhibit a cardiovascular disease for use in the treatment of the cardiovascular disease in a subject having: an INHBE variant genomic nucleic acid molecule encoding a predicted loss-of-function INHBE polypeptide; an INHBE variant mRNA molecule encoding a predicted loss-of-function INHBE polypeptide; or an INHBE variant cDNA molecule encoding a predicted loss-of-function INHBE polypeptide.

In some embodiments, the cardiovascular disease is high blood pressure, and the therapeutic agent is chosen from chlorthalidone, chlorothiazide, hydrochlorothiazide, indapamide, metolazone, acebutolol, atenolol, betaxolol, bisoprolol fumarate, carteolol hydrochloride, metoprolol tartrate, metoprolol succinate, nadolol, benazepril hydrochloride, captopril, enalapril maleate, fosinopril sodium, lisinopril, moexipril, perindopril, quinapril hydrochloride, ramipril, trandolapril, candesartan, eprosartan mesylate, irbesartan, losartan potassium, telmisartan, valsartan, amlodipine besylate, bepridil, diltiazem hydrochloride, felodipine, Isradipine, nicardipine, nifedipine, nisoldipine, verapamil hydrochloride, doxazosin mesylate, prazosin hydrochloride, terazosin hydrochloride, methyldopa, carvedilol labetalol hydrochloride, alpha methyldopa, clonidine hydrochloride, guanabenz acetate, guanfacine hydrochloride, guanadrel, guanethidine monosulfate, reserpine, hydralazine hydrochloride, and minoxidil.

In some embodiments, the cardiovascular disease is cardiomyopathy, and the cardiovascular agent is chosen from: 1) blood pressure lowering agents, such as ACE inhibitors, angiotensin II receptor blockers, beta blockers, and calcium channel blockers; 2) agents that slow heart rate, such as beta blockers, calcium channel blockers, and digoxin; 3) agents that keep the heart beating with a normal rhythm, such as antiarrhythmics; 4) agents that balance electrolytes, such as aldosterone blockers; 5) agents that remove excess fluid and sodium from the body, such as diuretics; 6) agents that prevent blood clots from forming, such as anticoagulants or blood thinners; and 7) agents that reduce inflammation, such as corticosteroids.

In some embodiments, the cardiovascular disease is heart failure, and the therapeutic agent is chosen from: an ACE inhibitor, an angiotensin-2 receptor blocker, a beta blocker, a mineralocorticoid receptor antagonist, a diuretic, ivabradine, sacubitril valsartan, hydralazine with nitrate, and digoxin.

The present disclosure also provides INHBE inhibitors that treat or inhibit a metabolic disorder for use in the treatment of the metabolic disorder in a subject having: an INHBE variant genomic nucleic acid molecule encoding a predicted loss-of-function INHBE polypeptide; an INHBE variant mRNA molecule encoding a predicted loss-of-function INHBE polypeptide; or an INHBE variant cDNA molecule encoding a predicted loss-of-function INHBE polypeptide.

The present disclosure also provides INHBE inhibitors that treat or inhibit a cardiovascular disease for use in the treatment of the cardiovascular disease in a subject having: an INHBE variant genomic nucleic acid molecule encoding a predicted loss-of-function INHBE polypeptide; an INHBE variant mRNA molecule encoding a predicted loss-of-function INHBE polypeptide; or an INHBE variant cDNA molecule encoding a predicted loss-of-function INHBE polypeptide.

In some embodiments, the INHBE inhibitor comprises an antisense nucleic acid molecule, a small interfering RNA (siRNA), or a short hairpin RNA (shRNA) that hybridizes to an INHBE mRNA. In some embodiments, the INHBE inhibitor comprises a Cas protein and guide RNA (gRNA) that hybridizes to a gRNA recognition sequence within an INHBE genomic nucleic acid molecule. In some embodiments, the Cas protein is Cas9 or Cpf1. In some embodiments, the gRNA recognition sequence is located within SEQ ID NO:1. In some embodiments, a Protospacer Adjacent Motif (PAM) sequence is about 2 to 6 nucleotides downstream of the gRNA recognition sequence. In some embodiments, the gRNA comprises from about 17 to about 23 nucleotides. In some embodiments, the gRNA recognition sequence comprises a nucleotide sequence according to any one of SEQ ID NOs:9-27.

All patent documents, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the present disclosure can be used in combination with any other feature, step, element, embodiment, or aspect unless specifically indicated otherwise. Although the present disclosure has been described in some detail by way of illustration and example for purposes of clarity and understanding, it will be apparent that certain changes and modifications may be practiced within the scope of the appended claims.

The following examples are provided to describe the embodiments in greater detail. They are intended to illustrate, not to limit, the claimed embodiments. The following examples provide those of ordinary skill in the art with a disclosure and description of how the compounds, compositions, articles, devices and/or methods described herein are made and evaluated, and are intended to be purely exemplary and are not intended to limit the scope of any claims. Efforts have been made to ensure accuracy with respect to numbers (such as, for example, amounts, temperature, etc.), but some errors and deviations may be accounted for. Unless indicated otherwise, parts are parts by weight, temperature is in ° C. or is at ambient temperature, and pressure is at or near atmospheric.

EXAMPLES

Figure 2:
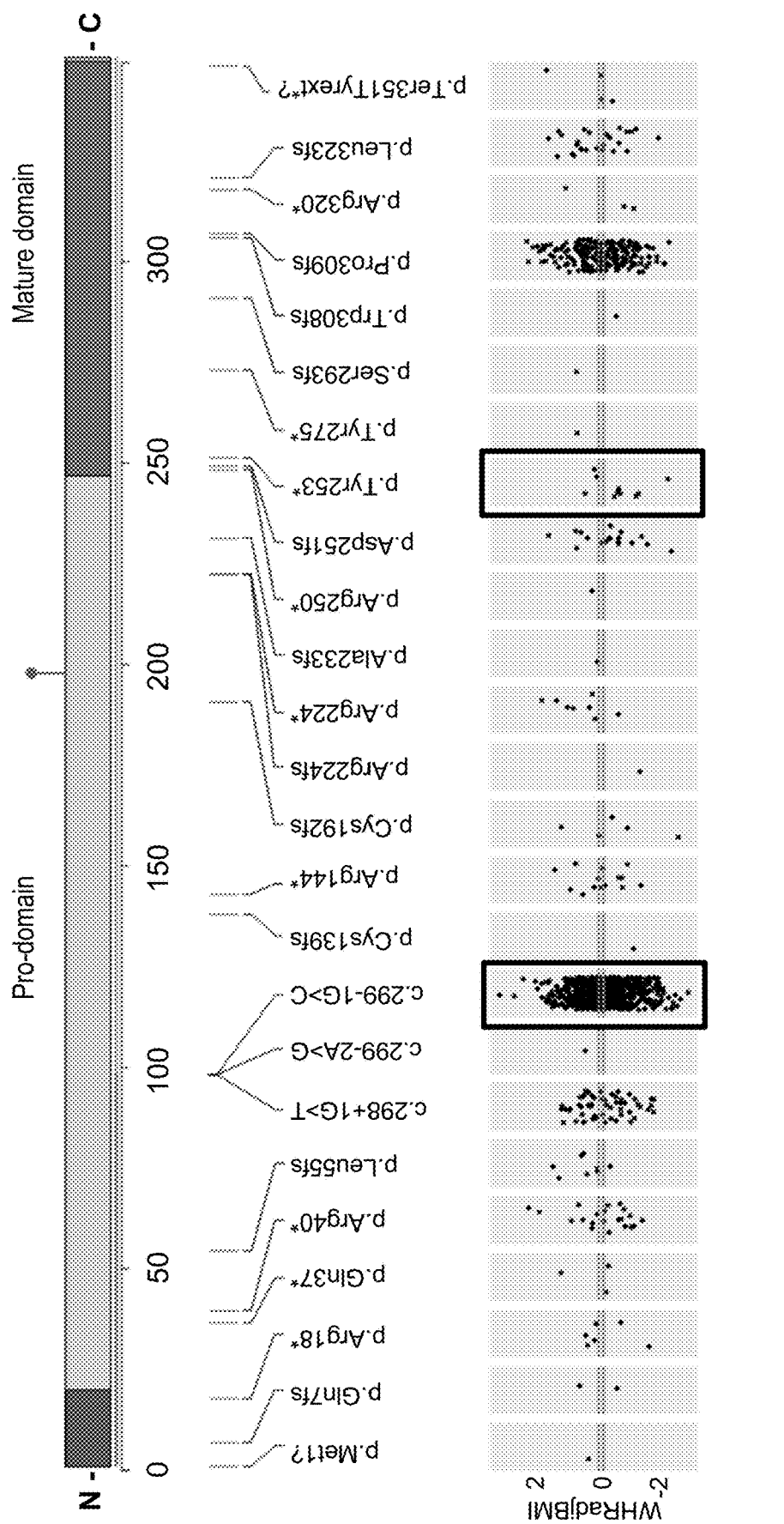
FIG. 2 depicts a gene model for INHBE showing the location of pLOF variants (top panel) and the phenotypic distribution of BMI-adjusted WHR in carriers of each variant; the top bar shows the median BMI-adjusted WHR in non-carriers, while the bottom bar shows the median BMI-adjusted WHR in carriers; two variants highlighted in boxes were individually associated with lower BMI-adjusted WHR; data are from the UK Biobank (UKB) and Mexico City Prospective Study (MCPS) cohorts; abbreviations: body mass index, BMI; waist-hip ratio, WHR.

Example 1: Loss of Function in INHBE is Associated with a More Favorable Fat Distribution and Protection Against Type 2 Diabetes in Humans An exome-wide association analysis for fat distribution, measured by the waist-to-hip circumference ratio adjusted for body mass index (BMI-adjusted WHR), was performed. BMI-adjusted WHR is a measure of body fat distribution independent of overall adiposity. For each gene in the genome, associations with BMI-adjusted WHR for the burden of rare predicted loss-of-function genetic variants (pLOF variants with alternative allele frequency [AAF] <1%) were estimated. In this analysis, the burden of rare (AAF<1%) predicted loss-of-function (pLOF) variants in INHBE was associated with a more favorable fat distribution (i.e., lower WHR adjusted for BMI; see, FIG. 1 and FIG. 2) at the exome-wide level of statistical significance ($p<3.6\times10^{-7}$, corresponding to a Bonferroni correction for the number of tests). Table 6 shows results of associations with fat distribution for pLOF variants in INHBE in 285,605 European ancestry participants in the UKB cohort (associations with BMI-adjusted WHR; genetic exposure is the burden of pLOF variants with AAF<1%). INHBE pLOF were strongly associated with lower BMI-adjusted WHR (see, Table 6). This statistically significant association was further replicated in a meta-analysis of additional data including a second tranche of UKB data (over 140,000 European ancestry participants) and over 95,000 admixed American participants from the MCPS study (see, FIG. 1).

TABLE 6

| INHBE gene-burden association result for BMI adjusted WHR in the UKB ||||| 
|---|---|---|---|---|
| AAF | Per allele effect (95% CI) in SD units | P-value | Genotype counts, RR\|RA\|AA genotypes | Per allele beta (95% CI) in BMI adjusted WHR units |
| 0.0012 | −0.21 (−0.29, −0.14) | 2.80E−08 | 285,605: 284,942\|663\|0 | −0.02 (−0.02, −0.01) |

Abbreviations: UKB=UK biobank study population, AAF=frequency of pLOF alleles across pLOF variants in the gene, RR=count of individuals having no heterozygous or homozygous observations of pLOFs variants in the gene, RA=count of individuals with at least one heterozygous pLOF and no homozygotes pLOF variants in the gene, AA=count of individuals with at least one homozygous pLOF variants in the gene, CI=confidence interval, pLOF=predicted loss-of-function, SD=standard deviation.

Table 6 shows the association of INHBE pLOF with BMI-adjusted WHR in the European ancestry individuals of the UK Biobank study population. The effect of INHBE pLOF variants was estimated in standard deviation (SD) units and in the ratio units of WHR. Table 6 shows that INHBE pLOF carriers have a lower BMI adjusted WHR compared to the average of individuals not carrying these genetic variants in analyses adjusting for covariates, ancestry and relatedness. Genotype counts display the number of individuals in the population studies carrying no variants leading to pLOF of INHBE (RR), one or more variants resulting in pLOF of a single INHBE allele (RA), or one or more pLOF variants in both INHBE alleles (AA).

This association of INHBE pLOF variants with lower BMI-adjusted WHR was consistent in men and women from the UK Biobank cohort (see, Table 7; genetic exposure is the burden of pLOF variants with AAF<1%).

TABLE 7

Sex-stratified INHBE pLOF variants association in the UKB

| Cohort (Sub-population) | AAF | Per allele effect (95% CI) in SD units | P-value | Genotype counts, RR\|RA\|AA genotypes | Per allele beta (95% CI) in BMI adjusted waist-hip ratio units |
|---|---|---|---|---|---|
| UKB (EUR women) | 0.001 | −0.19 (−0.27, −0.11) | 2.8E−06 | 232,890: 232,329\|561\|0 | −0.01 (−0.02, −0.01) |
| UKB (EUR men) | 0.001 | −0.16 (−0.25, −0.07) | 3.6E−04 | 196,500: 196,056\|444\|0 | −0.01 (−0.01, 0.005) |

Abbreviations: UKB=UK biobank study population, AAF=frequency of pLOF alleles across pLOF variants in the gene, RR=count of individuals having no heterozygous or homozygous observations of pLOFs variants in the gene, RA=count of individuals with at least one heterozygous pLOF and no homozygotes pLOF variants in the gene, AA=count of individuals with at least one homozygous pLOF variants in the gene, CI=confidence interval, pLOF=predicted loss of function, SD=standard deviation.

Table 7 shows the association of INHBE pLOF with BMI-adjusted WHR in European ancestry individuals from the UK Biobank study stratified by sex. The effect of INHBE pLOF variants was estimated in standard deviation (SD) units and in ratio units of WHR. Genotype counts display the number of individuals in the population studies carrying no variants leading to pLOF of INHBE (RR), one or more variants resulting in pLOF of a single INHBE allele (RA), or one or more pLOF variants in both INHBE alleles (AA). The association of INHBE pLOF variants with lower BMI-adjusted WHR was similarly strong in men and women included in this analysis.

Among pLOF variants in INHBE, the variant with the strongest association with BMI-adjusted WHR was a c.299-1G>C (12:57456093:G:C according to GRCh38/hg38 human genome assembly coordinates) mutation, predicted to affect the intron 1 acceptor splice site shortening exon 2 by 12 nucleotides at the 5' end (see, FIG. 3 and Table 8) and result in an in-frame deletion within the pro-domain of the INHBE protein (see, FIG. 4).

TABLE 8

Effect on splicing for the 12:57456093:G:C acceptor splice-site variant as predicted by the SpliceAI software.

| VARIANT | SPLICE CHANGE | DELTA SCORE |
|---|---|---|
| 12:57456093:G:C | Acceptor loss | 0.98 |
| | Acceptor gain | 0.9 |

Delta score: Value between 0-1, interpreted as the probability of the variant having a splice-change effect on the INHBE gene.

Table 8 shows the predicted effect of the variant 12:57456093:G:C on splicing of the INHBE gene.

In Chinese hamster ovary (CHO) cells, the c.299-1G>C splice variant was expressed and was found to result in a lower molecular weight protein that is not secreted outside the cell, indicating a loss-of-function (see, FIG. 5).

pLOF variants in INHBE were associated with larger hip circumference, higher arm and leg fat mass, suggestive of greater ability to store calories in peripheral adipose tissue (see, FIG. 6 and Table 9).

TABLE 9

Association of pLOF genetic variants in INHBE with adiposity phenotypes meta-analyzed across the UKB, Geisinger Health System (GHS) and MCPS studies

| Outcome (Clinical Units) | Genetic exposure | Per allele effect (95% CI) in SD units | P-value | Genotype counts RR\|RA\|AA genotypes | Per allele beta (95% CI) in clinical units |
|---|---|---|---|---|---|
| BMI (kg/m$^2$) | INHBE pLOF; AAF <1% | 0.06 (0.01, 0.11) | 0.02 | 645,626: 644,402\|1,224\|0 | 0.33 (0.04, 0.61) |
| Waist (cm) | | −0.03 (−0.09, 0.03) | 0.26 | 526,076: 525,034\|1,042\|0 | −0.45 (−1.22, 0.33) |
| Hip (cm) | | 0.07 (0.01, 0.13) | 0.03 | 526,031: 524,989\|1,042\|0 | 0.63 (0.08, 1.19) |

Abbreviations: UKB=UK biobank study population, GHS=Geisinger Health System study population, MCPS=Mexico City Prospective Study population, AAF=frequency of pLOF alleles across pLOF variants in the gene, RR=count of individuals having no heterozygous or homozygous observations of pLOFs variants in the gene, RA=count of individuals with at least one heterozygous pLOF and no homozygotes pLOF variants in the gene, AA=count of individuals with at least one homozygous pLOF variants in the gene, CI=confidence interval, pLOF=predicted loss-of-function, SD=standard deviation, kg/m$^2$=kilograms per meter square, cm=centimeters. Genotype counts display the number of individuals in the population studies carrying no variants leading to pLOF of INHBE (RR), one or more variants resulting in pLOF of a single INHBE allele (RA), or one or more pLOF variants in both INHBE alleles (AA).

Table 9 shows the association of INHBE pLOF with BMI, waist circumference, and hip circumference. The effect of INHBE pLOF is quantified in units of standard deviation, or in the respective clinical units of each anthropometric variable.

Rare pLOF variants in INHBE were also associated with protection against type 2 diabetes in humans. It was also found that INHBE pLOF variants were associated with lower risk of type 2 diabetes (T2D) (see, Table 10; genetic exposure is the burden of pLOF variants with AAF<1%), constituting the first evidence linking LOF in INHBE with type 2 diabetes in humans.

TABLE 10

Association of pLOF genetic variants in INHBE with T2D in the UKB, GHS and MCPS studies

| Cohort | AAF | Per allele OR (95% CI) | P-value | Genotype counts RR\|RA\|AA genotypes (cases) | Genotype counts RR\|RA\|AA genotypes (controls) |
|---|---|---|---|---|---|
| UKB | 0.001 | 0.82 (0.62, 1.08) | 0.15 | 23,907: 23,862\|45\|0 | 402,934: 401,981\|953\|0 |
| GHS | 0.001 | 0.44 (0.28, 0.70) | 0.0006 | 25,846: 25,828\|18\|0 | 63,749: 63,639\|110\|0 |

TABLE 10-continued

Association of pLOF genetic variants in INHBE with T2D in the UKB, GHS and MCPS studies

| Cohort | AAF | Per allele OR (95% CI) | P-value | Genotype counts RR\|RA\|AA genotypes (cases) | Genotype counts RR\|RA\|AA genotypes (controls) |
|---|---|---|---|---|---|
| MCPS | 0.0002 | 0.38 (0.13, 1.11) | 0.08 | 13,739: 13,738\|1\|0 | 83,278: 83,243\|35\|0 |
| Meta-analysis | 0.001 | 0.68 (0.54, 0.85) | 0.00097 | 63,492: 63,428\|64\|0 | 549,961: 548,863\|1,098\|0 |

Abbreviations: Meta-analysis=Joint analysis of all listed study populations, AAF=frequency of pLOF alleles across pLOF variants in the gene, RR=count of individuals having no heterozygous or homozygous observations of pLOFs variants in the gene, RA=count of individuals with at least one heterozygous pLOF and no homozygotes pLOF variants in the gene, AA=count of individuals with at least one homozygous pLOF variants in the gene, CI=confidence interval, pLOF=predicted loss-of-function, SD=standard deviation. Genotype counts display the number of individuals in the population studies either being cases of T2D or not in the T2D category carrying no variants leading to pLOF of INHBE (RR), one or more variants resulting in pLOF of a single INHBE allele (RA), or one or more pLOF variants in both INHBE alleles (AA).

Table 10 shows the association with T2D for pLOF variants in INHBE from an analysis of the UK Biobank (UKB), Geisinger Health System (GHS), and Mexico City Prospective study (MCPS) populations. The results show that, within each study population, INHBE pLOF variants were associated with lower risk of T2D and this was confirmed in a meta-analysis which combines results across all three study populations.

Furthermore, INHBE pLOF variants were associated with a favorable metabolic profile in an analysis across multiple cohorts (see, Table 11; genetic exposure is the burden of INHBE pLOF variants with AAF<1%), including lower HbA1c, ALT, triglycerides and LDL-C and higher HDL-C.

TABLE 11

Association of pLOF genetic variants in INHBE with metabolic meta-analyzed across the UKB, GHS and MCPS studies

| Outcome (Clinical Units) | AAF | Per allele effect (95% CI) in SD units | P-value | Genotype counts RR\|RA\|AA genotypes | Per allele beta (95% CI) in Clinical Units |
|---|---|---|---|---|---|
| Glucose (mg/dL) | 0.001 | 0.04 (−0.02, 0.10) | 0.24 | 460,195\|1,023\|0 | 0.76 (−0.51, 2.03) |
| HbA1c (%) | 0.001 | −0.06 (−0.11, −0.003) | 0.038 | 574,104\|1,086\|0 | −0.05 (−0.10, −0.003) |
| AST (U/L) | 0.001 | 0.0028 (−0.05, 0.06) | 0.92 | 514,592\|1,122\|0 | 0.03 (−0.5, 0.6) |
| ALT (U/L) | 0.001 | −0.07 (−0.13, −0.01) | 0.014 | 517,194\|1,123\|0 | −1.0 (−1.7, −0.2) |
| Triglycerides (mg/dL) | 0.001 | −0.11 (−0.16, −0.05) | 0.00017 | 500,594\|1,092\|0 | −9.2 (−14.1, −4.4) |
| HDL-C (mg/dL) | 0.001 | 0.13 (0.08, 0.19) | $3.1 \times 10^{-06}$ | 466,201\|1,024\|0 | 2.0 (1.1, 2.8) |
| LDL-C (mg/dL) | 0.001 | −0.06 (−0.11, −0.003) | 0.04 | 499,334\|1,092\|0 | −1.9 (−3.7, −0.1) |

Abbreviations: UKB=UK biobank study population, GHS=Geisinger Health System study population, MCPS=Mexico City Prospective Study, AAF=frequency of pLOF alleles across pLOF variants in the gene, RR=count of individuals having no heterozygous or homozygous observations of pLOFs variants in the gene, RA=count of individuals with at least one heterozygous pLOF and no homozygotes pLOF variants in the gene, AA=count of individuals with at least one homozygous pLOF variants in the gene, CI=confidence interval, pLOF=predicted loss-of-function, SD=standard deviation, mg/dL=milligrams per deciliter, U/L=Units per liter. Genotype counts display the number of individuals in the population studies carrying no variants leading to pLOF of INHBE (RR), one or more variants resulting in pLOF of a single INHBE allele (RA), or one or more pLOF variants in both INHBE alleles (AA).

Table 11 shows the association of INHBE pLOF variants with a range of metabolic phenotypes as estimated in a meta-analysis of the UKB, GHS, and MCPS study populations. Results are shown both in units of standard deviation, and in the original clinical units of the relevant metabolic phenotype.

In addition, INHBE pLOF variants were associated with reduced liver inflammation indices at magnetic resonance imaging (see, Table 12; genetic exposure is the burden of INHBE pLOF variants with AAF<1%).

TABLE 12

Association of pLOF genetic variants in INHBE with liver imaging phenotypes in the UKB

| Outcome (Clinical Units) | Effect (95% CI) in SD units | Effect (95% CI) in Clinical units | P-value | Allele count cases | AAF | ALT allele carriers % |
|---|---|---|---|---|---|---|
| ECF (Fraction of sampled pixels) | −0.25 (−0.47, −0.03) | −0.012 (−0.029, −0.002) | 0.026 | 36,690\|70\|0 | 0.00095 | 0.19% |

TABLE 12-continued

Association of pLOF genetic variants in INHBE with liver imaging phenotypes in the UKB

| Outcome (Clinical Units) | Effect (95% CI) in SD units | Effect (95% CI) in Clinical units | P-value | Allele count cases | AAF | ALT allele carriers % |
|---|---|---|---|---|---|---|
| ECF adjusted[a] (Fraction of sampled pixels) | −0.29 (−0.50, −0.08) | −0.018 (−0.031, −0.005) | 0.0060 | 35,205\|69\|0 | 0.00098 | 0.20% |
| PDFF (Fraction of sampled pixels) | 0.06 (−0.15, 0.27) | 0.29 (−0.72, 1.31) | 0.560 | 36,690\|70\|0 | 0.00095 | 0.19% |
| PDFF adjusted[a] (Fraction of sampled pixels) | 0.05 (−0.12, 0.22) | 0.24 (−0.58, 1.06) | 0.569 | 35,205\|69\|0 | 0.00098 | 0.20% |
| cT1 (time in milliseconds) | −0.23 (−0.45, −0.00) | −10.4 (−21.3, −0.00) | 0.047 | 36,690\|70\|0 | 0.00095 | 0.19% |
| cT1 adjusted[a] (time in milliseconds) | −0.26 (−0.47, −0.06) | −11.83 (−21.38, −2.73) | 0.012 | 35,205\|69\|0 | 0.00098 | 0.20% |
| T1 (time in milliseconds) | −0.33 (−0.56, −0.11) | −15.3 (−25.95, −5.10) | 0.0035 | 36,690\|70\|0 | 0.00095 | 0.19% |
| T1 adjusted[a] (time in milliseconds) | −0.36 (−0.57, −0.14) | −16.68 (−26.41, −6.49) | 0.00097 | 35,205\|69\|0 | 0.00098 | 0.20% |

[a]Adjusted for technical covariates including BMI, alcohol usage, and diabetes.

Abbreviations: PDFF=Proton density fat fraction (defined as the ratio of density of mobile protons from fat (triglycerides) and the total density of protons from mobile triglycerides and mobile water and reflects the concentration of fat within a tissue), ECF=extracellular fluid, T1=time constant for recovery of longitudinal magnetization. It's a relaxation time which measures how quickly the net magnetization recovers to its ground state. It can differ significantly based on the strength of the magnetic field and based on tissue composition. Furthermore, it increases with increased magnetic field, while it decreases with presence of fat and/or iron in the tissue, cT1=T1 corrected for the effects of liver iron content which result in T1 values being underestimated, UKB=UK biobank study population, AAF=frequency of pLOF alleles across pLOF variants in the gene, RR=count of individuals having no heterozygous or homozygous observations of pLOFs variants in the gene, RA=count of individuals with at least one heterozygous pLOF and no homozygotes pLOF variants in the gene, AA=count of individuals with at least one homozygous pLOF variants in the gene, CI=confidence interval, pLOF=predicted loss-of-function, SD=standard deviation.

Table 12 shows the association of INHBE pLOF variants with a range of liver imaging phenotypes in European ancestry individuals from the UK Biobank study population. The results show that INHBE pLOF variants are associated with lower levels of ECF and cT1 which are measures of liver inflammation, as defined by magnetic resonance imaging.

It was additionally investigated whether INHBE pLOF variants were associated with liver histopathology phenotypes in 3,565 bariatric surgery patients from the GHS cohort who underwent exome sequencing and a perioperative wedge biopsy of the liver. There were only three carriers for pLOF variants in INHBE in that set, but carrier status was associated with lower nonalcoholic fatty liver disease activity score (see, Table 13), a measure of the severity of liver disease at biopsy that sums steatosis, lobular inflammation and ballooning grades (Kleiner et al., Hepatology, 2005, 41, 1313-21).

TABLE 13

Association with lower nonalcoholic fatty liver disease activity score for rare pLOF variants in INHBE

| Outcome | Beta in SD of NAFLD activity score per allele (95% CI) | P-value | INHBE pLOF genotypes (Ref/Het/Hom) |
|---|---|---|---|
| NAFLD activity score | −1.05 (−1.98, −0.12) | 0.026 | 3,565\|3\|0 |

The association with NAFLD activity score (outcome) for rare pLOF variants in INHBE was reported. The association was estimated in 3,565 bariatric surgery patients from GHS.

Finally, it was found that a common variant near INHBE (12:57259799:A:C; rs57966846; AAF, 0.28) is associated with higher liver expression levels of INHBE mRNA (per-allele beta, 0.3 SDs of INHBE transcript abundance as quantified by RNASeq in over 2,000 participants to GHS who underwent a liver biopsy as part of bariatric surgery). It was also found that the 12:57259799:A:C variant is associated with higher BMI-adjusted WHR, triglycerides and risk of type 2 diabetes. The expression raising allele C was associated with higher BMI-adjusted WHR (p-value=1.5× $10^{-4}$), higher triglycerides (p-value=2.0× $10^{-11}$), higher T2D risk (p-value=0.03) (see, Table 14). This shows that genetically-determined overexpression of INHBE is associated with higher metabolic disease risk, while a loss of function is associated favorable metabolic profile and lower diabetes risk (as noted above from the pLOF variants associations).

TABLE 14

Association of an INHBE eQTL, 12:57259799:A:C, with various metabolic phenotypes in the UKB and GHS cohorts

| Genetic exposure | Outcome (Clinical Units) | AAF | Per allele effect (95% CI) in SD units or odds ratio | Per allele beta (95% CI) in Clinical Units | P-value | Genotype counts, RR\|RA\|AA genotypes |
|---|---|---|---|---|---|---|
| 12:57259799: A:C, Count of INHBE liver expression raising allele C | Triglycerides (mg/dL) | 0.285 | 0.01 SDs (0.009, 0.02) | 0.9 (0.9, 1.0) | $2.0 \times 10^{-11}$ | 274,658\|216,943\| 43,388 |
| | BMI-adj WHR (ratio units) | 0.285 | 0.008 SDs (0.004, 0.012) | 0.00064 (0.00032, 0.00080) | $1.5 \times 10^{-4}$ | 235,613\|187,407\| 37,740 |
| | T2D | 0.285 | $1.02^a$ ($1.00^a$, $1.04^a$) | — | 0.037 | T2D Controls: 255,408\|201,524\| 40,210 T2D Cases: 27,105\|21,053\|4,295 |

$^a$Estimates are in odds ratios.

Abbreviations: AAF=allele frequency of INHBE liver expression raising allele (i.e., alternate allele), CI=confidence interval, SD=standard deviation, RR=reference-reference allele, RA=reference-alternative allele, AA=alternative-alternative allele, mg/dL=milligrams per deciliter. Genotype counts display the number of individuals in the population studies having no copies of the INHBE liver expression raising allele (RR), having only one copy of the INHBE liver expression raising allele (RA), and having 2 copies of the INHBE liver expression raising allele (AA). Genotype counts are further stratified within individuals classified as T2D cases in the study population.

The association of 12:57259799:A:C with triglyceride levels, WHRadjBMI, and T2D risk was studied in all European ancestry participants from the UK Biobank and Geisinger Health studies. The results show that 12:57259799:A:C was significantly associated with higher triglyceride levels and higher BMI-adjusted WHR; in addition, there was an association with higher T2D risk.

Figure 7:
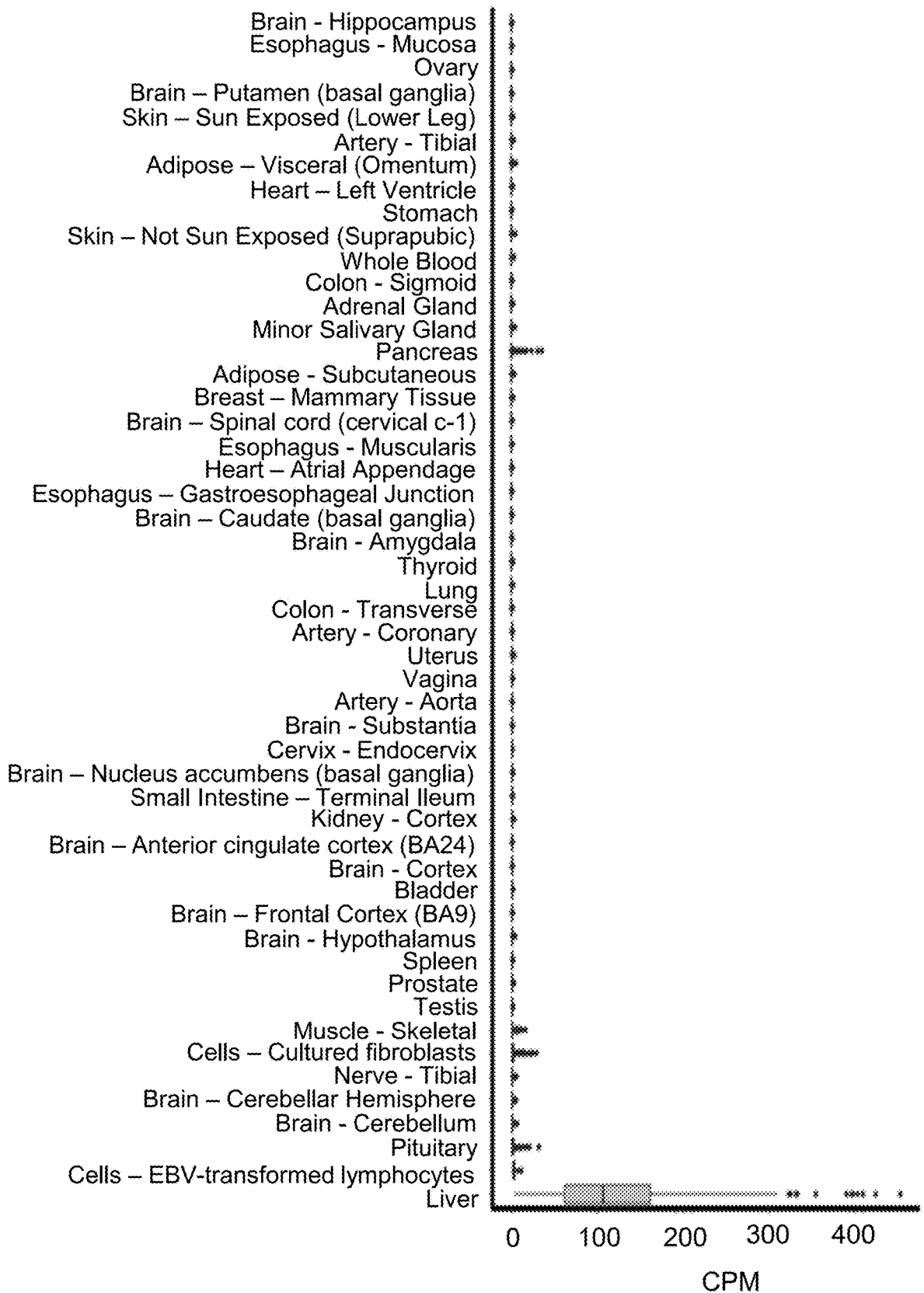
FIG. 7 shows INHBE expression patterns across tissues (left) and liver cell-types (right). The first panel shows, per tissue, the normalized mRNA expression values for INHBE in counts per million (CPM) using data from genotype tissue expression (GTEx) consortium (GTEx Portal 2021. Accessed 2021, June 1$^{st}$ via world wide web at "gtexportal.org/"). The second panel shows normalized cell-type specific expression levels within liver, in transcripts per million protein coding genes (pTPM), obtained from the human protein atlas (HPA) (Uhlen et al., Nat. Biotechnol. 2010, 28, 1248-50). Box plots depict the median (thick black vertical bar), the interquartile range, and minimum and maximum CPM values across individuals per tissue.
Figure 7:
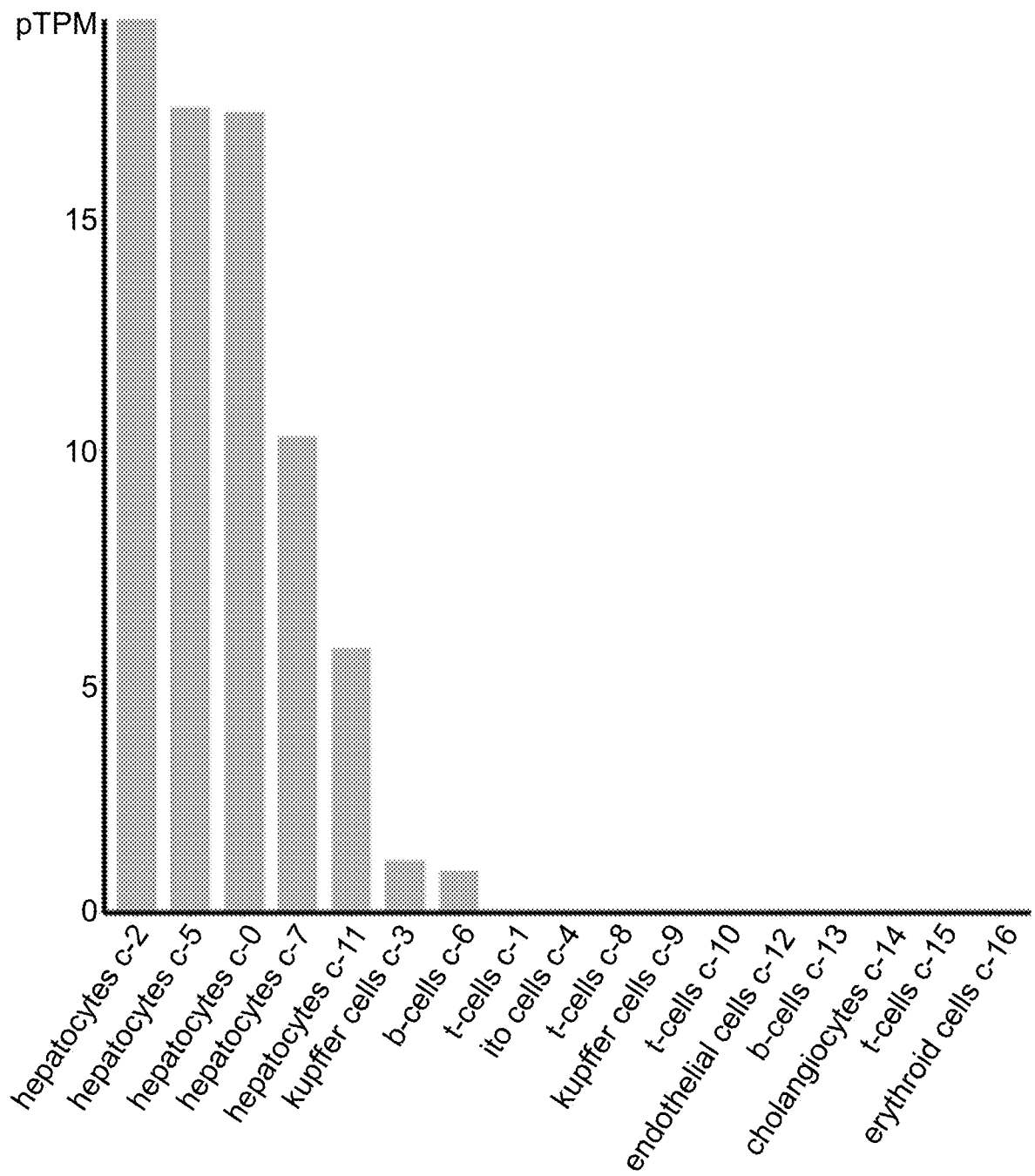
Figure 8:
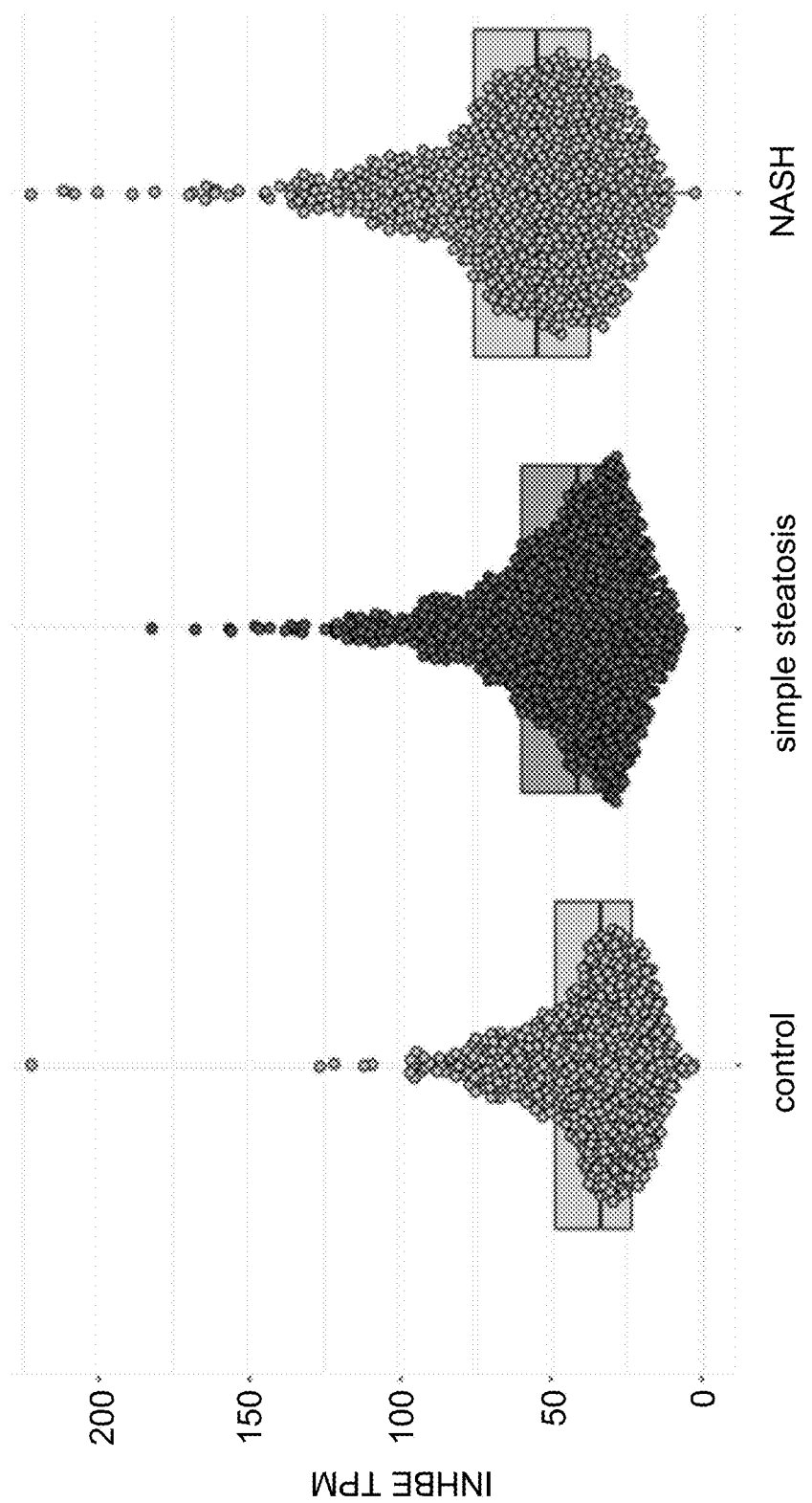
FIG. 8 shows liver mRNA expression of INHBE is upregulated in patients with steatosis and nonalcoholic steatohepatitis (NASH) compared to individuals with normal liver in bariatric surgery patients from GHS. In the top panel, the Figure shows liver mRNA expression levels of INHBE in transcripts per million (TPM; a normalization of RNA molecules for every 1 million molecules detected in a certain experiment) in patients with normal liver (control), steatosis of the liver (simple steatosis) and nonalcoholic steatohepatitis (NASH). In the bottom panel are statistics for comparisons between groups. The simple steatosis group showed higher expression of INHBE in the liver than the control group. The NASH group showed higher expression both when compared to the control and when compared to the simple steatosis groups. All differences in expression between groups were statistically significant.

Example 2: INHBE is Highly Expressed in Human Hepatocytes and its Expression was Upregulated in Patients with Steatosis and Nonalcoholic Steatohepatitis The mRNA expression of INHBE across tissues in humans from the Genotype Tissue Expression consortium (GTEx) was examined and it was found that INHBE is most highly expressed in liver among the GTEx tissues (see, FIG. 7). The mRNA expression of INHBE among cell types was also examined in data from the Human Protein Atlas (HPA) and it was found that INHBE was most highly expressed in hepatocytes (see, FIG. 7). The level of expression of INHBE in the liver of over 2,000 bariatric surgery patients in GHS who underwent liver RNASeq was also estimated. It was discovered that INHBE expression was upregulated in patients with steatosis of the liver compared to individuals with normal liver, in patients with nonalcoholic steatohepatitis compared to individuals with normal liver, and in patients with nonalcoholic steatohepatitis compared to patients with steatosis (see, FIG. 8).

Example 3: Associations with Visceral to Gluteofemoral Fat Ratio as Measured by MRI for INHBE Identified in the BMI-Adjusted WHR Discovery Analysis A subset of approximately 46,000 participants in UKB underwent two-point Dixon (Dixon, Radiology, 1984, 153, 189-194) MRI using Siemens MAGNETOM Aera 1.5T clinical MRI scanners (Littlejohns et al., Nat. Commun., 2020, 11, 2624), split into six different imaging series. This subset included 38,880 people with available exome sequencing. Stitching of the six different scan positions corrected for overlapping slices, partial scans, repeat scans, fat-water swaps, misalignment between imaging series, bias-field, artificially dark slices and local hotspots, similar to what has previously been performed (Basty et al., Image Processing and Quality Control for Abdominal Magnetic Resonance Imaging in the UK Biobank, 2020, ArXiv abs/2007.01251). A total of 52 subjects had their whole-body Dixon MRI manually annotated into six different classes of fat: upper body fat, abdominal fat, visceral fat, mediastinal fat, gluteofemoral fat and lower-leg fat. Special care was taken to tailor the training dataset to attempt to span the phenotypic diversity expected by specifically including training subjects that have genetic mutations that predispose them to abnormal fat and muscle phenotypes such as PPARG (Ludtke et al., J. Med. Genet., 2007, 44, e88), PLIN1 (Gandotra et al., N. Engl. J. Med., 2011, 364, 740-748), LMNA (Jeru et al., J. Med. Genet., 2017, 54, 413-416), LIPE (Zolotov et al., Am. J. Med. Genet., 2017, A 173, 190-194) and MC4R (Akbari et al., Science, 2021, 373). These annotations were then used to train a multi-class segmentation deep neural-net which employed a UNet (Weng et al., IEEE Access, 2021, 9, 16591-16603) architecture with a ResNet34 (He et al., in 2016 IEEE Conference on Computer Vision and Pattern Recognition (CVPR), 2016, 770-778) backbone, and a loss function of a sum of the Jaccard Index and categorical focal loss (Lin et al., IEEE Transactions on Pattern Analysis and Machine Intelligence, 2020, 42, 318-327). Fat volume phenotypes were calculated by summing the resulting segmentation maps from the neural net for each corresponding fat class. The visceral-to-gluteofemoral fat ratio was then calculated as the ratio of visceral to gluteofemoral fat volume for a given individual.

Rare coding variants in INHBE associated with BMI-adjusted WHR showed highly consistent associations with visceral-to-gluteofemoral fat ratio at MRI, a refined measure of fat distribution, in a subset of 38,880 people (i.e., ~6% of the discovery sample) who had undergone a whole-body MRI in UKB (see, Table 15). There was a nominally-significant association with lower MRI-defined visceral-to-gluteofemoral fat ratio for INHBE pLOF variants in the subset of UKB with MRI data (beta in SD units of fat ratio per allele, −0.24; 95% CI, −0.45 to −0.02; p=0.03; see, Table 15).

TABLE 15

| Beta (95% CI) per allele in SD units of visceral to gluteofemoral fat ratio from MRI | P | Genotype counts, RR\|RA\|AA genotypes | AAF, fraction of 1 |
|---|---|---|---|
| −0.238 (−0.453, −0.023) | 3.0E−02 | 38802\|78\|0 | 0.0010 |

Each gene-burden result in the table was analyzed in a model that accounted for the sex specific effects of age, body mass index, and height on visceral to gluteofemoral fat ratio. Abbreviations: pLOF, predicted loss of function; AAF, alternative allele frequency; CI, confidence intervals; SD, standard deviation; BMI, body mass index; p, P-value; RR, reference homozygote genotype; RA, reference-alternative genotype; AA, alternative homozygote genotype.

Example 4: INHBE Predicted Loss-of-Function Association with Increased Left Ventricular Ejection Fraction and Protection of Cardiomyopathy Cases in the present example were any study participant without heart disease. The results were based on meta-analyses of UKB, GHS, SINAI, UPENN-PMBB, MDCS, Indiana-Chalasani. Predicted loss-of-function in INHBE associated with increased left ventricular ejection fraction and protection of cardiomyopathy are shown in Table 16 (Burden of INHBE rare pLoF variants (M1.1)).

TABLE 16

| Outcome | Beta$_{SD}$ or OR [95% CI] | Clin. unit | P-value | Case allele count (RR\|RA\|AA) | Control allele count (RR\|RA\|AA) | AA carriers |
|---|---|---|---|---|---|---|
| 1 | 0.26 (0.04, 0.47) | 1.57% | 0.019 | 38,651\|80\|0 | — | 0.21% |
| 2 | 0.46 (0.23, 0.95) | — | 0.034 | 5,111\|2\|0 | 342,838\|650\|0 | 0.19% |

Outcome 1 is left ventricular ejection fraction*.
Outcome 2 is non-ischemic cardiomyopathy**.
*Left ventricular ejection fraction obtained by cardiac MRI in participants of the UK Biobank.
**Non-ischemic cardiomyopathy cases were defined as study participants with one or more of the following ICD10 codes: I420 (Dilated Cardiomyopathy), I425 (Other restrictive cardiomyopathy), I428 (Other noncompaction cardiomyopathies), I429 (primary cardiomyopathy\|unspecified), and absence of one or more of any ICD10 code indicative of myocardial infarction (I21\|I22\|I23\|I252\|I256) and hypertrophic cardiomyopathy (I421, I422).

Association of pLOF variants with lower blood pressure (see, Table 17; burden of INHBE rare pLOF variants—M1.1) is consistent with beneficial effect on hemodynamic traits.

TABLE 17

| Trait | Beta (95% CI) per allele in SD units | Effect in mmHg (95% CI) per allele | P-value | AAF, fraction of 1 | Genotype Counts (RR\|RA\|AA) |
|---|---|---|---|---|---|
| 1 | −0.06 (−0.11, −0.01) | −0.56 (−1.07, −0.05) | 0.03 | 0.00102 | 599,306\|1,224\|0 |
| 2 | −0.05 (−0.10, 0.00) | −0.84 (−1.72, 0.04) | 0.0614 | 0.00102 | 599,608\|1,224\|0 |

Trait 1 is diastolic blood pressure (treatment corrected).
Trait 2 is systolic blood pressure (treatment corrected).

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety and for all purposes.

SEQUENCE LISTING

The patent contains a lengthy sequence listing. A copy of the sequence listing is available in electronic form from the USPTO web site (https://seqdata.uspto.gov/?pageRequest=docDetail&DocID=US11759476B2). An electronic copy of the sequence listing will also be available from the USPTO upon request and payment of the fee set forth in 37 CFR 1.19(b)(3).

What is claimed is:

1. A method of treating a subject with a therapeutic agent that treats or inhibits type 2 diabetes, wherein the subject is suffering from type 2 diabetes, the method comprising the steps of:
    determining whether the subject has an Inhibin Subunit Beta E (INHBE) variant nucleic acid molecule encoding an INHBE predicted loss-of-function polypeptide by:
        obtaining or having obtained a biological sample from the subject; and
        performing or having performed a genotyping assay on the biological sample to determine if the subject has a genotype comprising the INHBE variant nucleic acid molecule; and
    when the subject is INHBE reference, then administering or continuing to administer to the subject the therapeutic agent that treats or inhibits type 2 diabetes in a standard dosage amount, and/or administering to the subject an INHBE inhibitor; and
    when the subject is heterozygous for an INHBE variant nucleic acid molecule, then administering or continuing to administer to the subject the therapeutic agent that treats or inhibits type 2 diabetes in an amount that is the same as or lower than a standard dosage amount, and/or administering to the subject an INHBE inhibitor;
    when the subject is homozygous for an INHBE variant nucleic acid molecule, then administering or continuing to administer to the subject the therapeutic agent that treats or inhibits type 2 diabetes in an amount that is the same as or lower than a standard dosage amount;
    wherein the presence of a genotype having the INHBE variant nucleic acid molecule encoding an INHBE predicted loss-of-function polypeptide indicates the subject has a decreased risk of developing type 2 diabetes.

2. The method according to claim 1, wherein the subject is INHBE reference, and the subject is administered or continued to be administered the therapeutic agent that treats or inhibits type 2 diabetes in a standard dosage amount, and/or is administered an INHBE inhibitor.

3. The method according to claim 1, wherein the subject is heterozygous for an INHBE variant nucleic acid molecule, and the subject is administered or continued to be administered the therapeutic agent that treats or inhibits type 2 diabetes in an amount that is the same as or lower than a standard dosage amount, and/or is administered an INHBE inhibitor.

4. The method according to claim 1, wherein the INHBE variant nucleic acid molecule is a missense variant, a splice-site variant, a stop-gain variant, a start-loss variant, a stop-loss variant, a frameshift variant, or an in-frame indel variant, or a variant that encodes a truncated INHBE polypeptide.

5. The method according to claim 1, wherein the INHBE inhibitor comprises an antisense nucleic acid molecule that hybridizes to an INHBE mRNA.

6. The method according to claim 1, wherein the INHBE inhibitor comprises an siRNA that hybridizes to an INHBE mRNA.

7. The method according to claim 1, wherein the INHBE inhibitor comprises an shRNA that hybridizes to an INHBE mRNA.

8. The method according to claim 1, wherein the therapeutic agent is chosen from metformin, insulin, glyburide, glipizide, glimepiride, repaglinide, nateglinide, thiazolidinediones, rosiglitazone, pioglitazone, sitagliptin, saxagliptin, linagliptin, exenatide, liraglutide, semaglutide, canagliflozin, dapagliflozin, and empagliflozin, or any combination thereof.

9. A method of treating a subject with a therapeutic agent that treats or inhibits liver inflammation, wherein the subject is suffering from liver inflammation, the method comprising the steps of:
    determining whether the subject has an Inhibin Subunit Beta E (INHBE) variant nucleic acid molecule encoding an INHBE predicted loss-of-function polypeptide by:
        obtaining or having obtained a biological sample from the subject; and
        performing or having performed a genotyping assay on the biological sample to determine if the subject has a genotype comprising the INHBE variant nucleic acid molecule; and
    when the subject is INHBE reference, then administering or continuing to administer to the subject the therapeutic agent that treats or inhibits liver inflammation in a standard dosage amount, and/or administering to the subject an INHBE inhibitor; and
    when the subject is heterozygous for an INHBE variant nucleic acid molecule, then administering or continuing to administer to the subject the therapeutic agent that treats or inhibits liver inflammation in an amount that is the same as or lower than a standard dosage amount, and/or administering to the subject an INHBE inhibitor;
    when the subject is homozygous for an INHBE variant nucleic acid molecule, then administering or continuing to administer to the subject the therapeutic agent that treats or inhibits liver inflammation in an amount that is the same as or lower than a standard dosage amount;
    wherein the presence of a genotype having the INHBE variant nucleic acid molecule encoding an INHBE predicted loss-of-function polypeptide indicates the subject has a decreased risk of developing liver inflammation.

10. The method according to claim 9, wherein the subject is INHBE reference, and the subject is administered or continued to be administered the therapeutic agent that treats or inhibits liver inflammation in a standard dosage amount, and/or is administered an INHBE inhibitor.

11. The method according to claim 9, wherein the subject is heterozygous for an INHBE variant nucleic acid molecule, and the subject is administered or continued to be administered the therapeutic agent that treats or inhibits liver inflammation in an amount that is the same as or lower than a standard dosage amount, and/or is administered an INHBE inhibitor.

12. The method according to claim 9, wherein the INHBE variant nucleic acid molecule is a missense variant, a splice-site variant, a stop-gain variant, a start-loss variant, a stop-loss variant, a frameshift variant, or an in-frame indel variant, or a variant that encodes a truncated INHBE polypeptide.

13. The method according to claim 9, wherein the INHBE inhibitor comprises an antisense nucleic acid molecule that hybridizes to an INHBE mRNA.

14. The method according to claim 9, wherein the INHBE inhibitor comprises an siRNA that hybridizes to an INHBE mRNA.

15. The method according to claim 9, wherein the INHBE inhibitor comprises an shRNA that hybridizes to an INHBE mRNA.

16. The method according to claim 9, wherein the therapeutic agent is a hepatitis therapeutic or a hepatitis vaccine.

* * * * *